US010993987B2

(12) United States Patent
Coulter et al.

(10) Patent No.: US 10,993,987 B2
(45) Date of Patent: May 4, 2021

(54) COMPOSITIONS COMPRISING CYCLOSPORIN

(71) Applicant: Sublimity Therapeutics Limited, Dublin (IE)

(72) Inventors: Ivan Coulter, Dublin (IE); Vincenzo Aversa, Dublin (IE); Mónica Torres Rosa, Dublin (IE); Dáire O'Donnell, Limerick (IE); Wyatt Renaud of Calhane, Donegal (IE)

(73) Assignee: Sublimity Therapeutics Limited, Dublin (IE)

( * ) Notice: Subject to any disclaimer, the term of this patent is extended or adjusted under 35 U.S.C. 154(b) by 0 days.

(21) Appl. No.: 15/525,031

(22) PCT Filed: Nov. 6, 2015

(86) PCT No.: PCT/EP2015/075984
§ 371 (c)(1),
(2) Date: May 5, 2017

(87) PCT Pub. No.: WO2016/071515
PCT Pub. Date: May 12, 2016

(65) Prior Publication Data
US 2018/0147254 A1    May 31, 2018

(30) Foreign Application Priority Data

Nov. 7, 2014  (GB) ........................................ 1419849
Nov. 7, 2014  (WO) ................. PCT/EP2014/074054
May 5, 2015  (GB) ........................................ 1507673

(51) Int. Cl.
*A61K 38/13*    (2006.01)
*A61K 9/107*    (2006.01)
(Continued)

(52) U.S. Cl.
CPC ............ *A61K 38/13* (2013.01); *A61K 9/0053* (2013.01); *A61K 9/107* (2013.01); *A61K 9/1617* (2013.01);
(Continued)

(58) Field of Classification Search
CPC ..... A61K 38/13; A61K 9/5073; A61K 9/1617
See application file for complete search history.

(56) References Cited

U.S. PATENT DOCUMENTS 3,971,852 A    7/1976  Brenner et al.
4,279,632 A    7/1981  Frosch et al.
(Continued)

FOREIGN PATENT DOCUMENTS

AU    1977031116    11/1977
CA    2170748    3/1995
(Continued)

OTHER PUBLICATIONS

"Nimotop® (nimiodipine) Capsules for Oral Use," FDA approved label text, Bayer Health Care: 2005.
(Continued)

*Primary Examiner* — Lakshmi S Channavajjala
(74) *Attorney, Agent, or Firm* — Klarquist Sparkman, LLP

(57) ABSTRACT

The present invention relates to a formulation comprising a pharmaceutically active ingredient and a coating. The invention also relates to the use of the formulation in the treatment and prevention of disorders of the gastrointestinal tract. Also disclosed are methods for preparing the formulations.

33 Claims, 18 Drawing Sheets

(51) Int. Cl.
    *A61K 9/16*           (2006.01)
    *A61K 9/50*           (2006.01)
    *A61K 9/00*           (2006.01)
    *A61K 45/06*          (2006.01)

(52) U.S. Cl.
    CPC .......... *A61K 9/1658* (2013.01); *A61K 9/5047* (2013.01); *A61K 9/5073* (2013.01); *A61K 45/06* (2013.01)

(56) References Cited

U.S. PATENT DOCUMENTS

| | | | |
|---|---|---|---|
| 4,379,454 A | 4/1983 | Campbell et al. |
| 4,388,307 A | 6/1983 | Cavanak |
| 4,422,985 A | 12/1983 | Morishita et al. |
| 4,460,563 A | 7/1984 | Calanchi |
| 4,481,157 A | 11/1984 | Morishita et al. |
| 4,597,959 A | 7/1986 | Barr |
| 4,601,894 A | 7/1986 | Hanna et al. |
| 4,652,441 A | 3/1987 | Okada et al. |
| 4,656,161 A | 4/1987 | Herr |
| 4,695,466 A | 9/1987 | Morishita et al. |
| 4,748,023 A | 5/1988 | Tamas et al. |
| 4,749,574 A | 6/1988 | Ueda et al. |
| 4,751,241 A | 6/1988 | Motoyama et al. |
| 4,857,335 A | 8/1989 | Bohm |
| 4,891,223 A | 1/1990 | Ambegaonkar et al. |
| 5,091,184 A | 2/1992 | Khanna |
| 5,102,668 A | 4/1992 | Eichel et al. |
| 5,145,684 A | 9/1992 | Liversidge et al. |
| 5,330,835 A | 7/1994 | Kikuchi et al. |
| 5,342,625 A | 8/1994 | Hauer et al. |
| 5,350,741 A | 9/1994 | Takada |
| 5,362,564 A | 11/1994 | Suzuki et al. |
| 5,385,737 A | 1/1995 | Shigeno et al. |
| 5,401,502 A | 3/1995 | Wunderlich et al. |
| 5,411,952 A | 5/1995 | Kaswan |
| 5,418,010 A | 5/1995 | Janda et al. |
| 5,478,508 A | 12/1995 | Suzuki et al. |
| 5,480,655 A | 1/1996 | Jizomoto et al. |
| 5,492,701 A | 2/1996 | Cervos et al. |
| 5,498,439 A | 3/1996 | Bonner et al. |
| 5,500,224 A | 3/1996 | Vranckx et al. |
| 5,510,118 A | 4/1996 | Bosch et al. |
| 5,529,777 A | 6/1996 | Andrianov et al. |
| 5,529,783 A | 6/1996 | Burke et al. |
| 5,571,533 A | 11/1996 | Santus et al. |
| 5,589,455 A | 12/1996 | Woo et al. |
| 5,645,856 A | 7/1997 | Lacy et al. |
| 5,650,232 A | 7/1997 | Glenn et al. |
| 5,665,386 A | 9/1997 | Benet et al. |
| 5,674,495 A | 10/1997 | Bowersock et al. |
| 5,795,590 A | 8/1998 | Kiefer et al. |
| 5,827,531 A | 10/1998 | Morrison et al. |
| 5,843,347 A | 12/1998 | Nguyen |
| 5,851,275 A | 12/1998 | Amidon |
| 5,858,401 A | 1/1999 | Bhalani et al. |
| 5,871,774 A | 2/1999 | Lemelson |
| 5,882,680 A | 3/1999 | Suzuki et al. |
| 5,914,132 A | 6/1999 | Kelm et al. |
| 5,958,876 A | 9/1999 | Woo et al. |
| 5,961,970 A | 10/1999 | Lowell et al. |
| 6,022,562 A | 2/2000 | Autant et al. |
| 6,113,936 A | 9/2000 | Takebayashi et al. |
| 6,146,663 A | 11/2000 | Bissery et al. |
| 6,174,466 B1 | 1/2001 | Kiefer et al. |
| 6,190,692 B1 | 2/2001 | Busetti et al. |
| 6,251,661 B1 | 6/2001 | Urabe et al. |
| 6,267,985 B1 | 7/2001 | Chen et al. |
| 6,284,271 B1 | 9/2001 | Lundberg et al. |
| 6,309,663 B1 | 10/2001 | Patel et al. |
| 6,361,298 B1 | 3/2002 | Kiefer et al. |
| 6,429,089 B1 | 8/2002 | Matsuki |
| 6,436,441 B1 | 8/2002 | Sako et al. |
| 6,451,339 B2 | 9/2002 | Patel et al. |
| 6,531,150 B1 | 3/2003 | Sunohara et al. |
| 6,569,463 B2 | 5/2003 | Patel et al. |
| 6,585,997 B2 | 7/2003 | Moro et al. |
| 6,620,788 B1 | 9/2003 | Tanida et al. |
| 6,761,903 B2 | 7/2004 | Chen et al. |
| 6,916,785 B2 * | 7/2005 | Patel .................. A61K 9/0095 424/456 |
| 6,923,988 B2 | 8/2005 | Patel et al. |
| 6,972,132 B1 | 12/2005 | Kudo et al. |
| 7,097,857 B2 | 8/2006 | Tracy et al. |
| 7,115,565 B2 * | 10/2006 | Gao .................... A61K 9/1075 424/461 |
| 7,267,813 B2 | 9/2007 | Watanabe et al. |
| 7,374,779 B2 | 5/2008 | Chen et al. |
| 7,727,551 B2 | 6/2010 | Massironi |
| 8,663,692 B1 | 3/2014 | Muller et al. |
| 2001/0003589 A1 | 6/2001 | Neuer |
| 2001/0024658 A1 | 9/2001 | Chen et al. |
| 2002/0009457 A1 | 1/2002 | Bowersock et al. |
| 2002/0098242 A1 | 7/2002 | Darder |
| 2003/0045516 A1 | 3/2003 | Luly et al. |
| 2003/0078194 A1 | 4/2003 | Cho et al. |
| 2003/0104048 A1 | 6/2003 | Patel et al. |
| 2003/0119797 A1 | 6/2003 | Chibout et al. |
| 2003/0124061 A1 | 7/2003 | Roberts |
| 2003/0180352 A1 | 9/2003 | Patel et al. |
| 2003/0193102 A1 | 10/2003 | Yan |
| 2003/0232076 A1 | 12/2003 | Makino et al. |
| 2003/0235595 A1 | 12/2003 | Chen et al. |
| 2004/0028619 A1 | 2/2004 | Watanabe et al. |
| 2004/0029855 A1 | 2/2004 | Klaveness et al. |
| 2004/0062802 A1 | 4/2004 | Hermelin |
| 2004/0126428 A1 | 7/2004 | Hughes et al. |
| 2004/0258701 A1 | 12/2004 | Dominowski et al. |
| 2004/0258702 A1 | 12/2004 | Blonder et al. |
| 2005/0095288 A1 | 5/2005 | Honea |
| 2005/0249807 A1 | 11/2005 | Brown et al. |
| 2006/0034937 A1 | 2/2006 | Patel |
| 2006/0135441 A1 | 6/2006 | Khodadoust et al. |
| 2006/0022270 A1 | 10/2006 | Kulkarni |
| 2007/0154554 A1 | 7/2007 | Burgermeister et al. |
| 2007/0292523 A1 | 12/2007 | Moodley et al. |
| 2008/0107694 A1 | 5/2008 | Trogden et al. |
| 2008/0124279 A1 | 5/2008 | Andremont et al. |
| 2008/0124389 A1 | 5/2008 | Jenkins et al. |
| 2008/0311201 A1 | 12/2008 | Der-Yang et al. |
| 2008/0317769 A1 | 12/2008 | Kang et al. |
| 2008/0318912 A1 | 12/2008 | Fox et al. |
| 2010/0136105 A1 | 6/2010 | Chen et al. |
| 2010/0215737 A1 | 8/2010 | Coulter |
| 2010/0239665 A1 | 9/2010 | Coulter |
| 2011/0020438 A1 * | 1/2011 | Andrysek ............... A61P 37/00 424/452 |
| 2013/0243873 A1 | 9/2013 | Aversa et al. |
| 2014/0242168 A1 | 8/2014 | Schiller et al. |
| 2015/0132374 A1 * | 5/2015 | Coulter ................ A61K 9/4808 424/452 |
| 2016/0310561 A1 * | 10/2016 | Coulter ................ A61K 9/1658 |

FOREIGN PATENT DOCUMENTS

| | | |
|---|---|---|
| CA | 2 069 485 | 4/2000 |
| CA | 2376261 | 12/2000 |
| CA | 2 570 184 | 12/2005 |
| CN | 1557283 | 12/2004 |
| CN | 1736369 | 2/2006 |
| DE | 19848849 | 4/2000 |
| EP | 0 348 910 | 6/1989 |
| EP | 0 396 425 | 5/1990 |
| EP | 0 550 067 | 12/1992 |
| EP | 0 525 731 | 2/1993 |
| EP | 0 670 163 | 8/1994 |
| EP | 0 650 721 | 5/1995 |
| EP | 0694308 | 1/1996 |
| EP | 0 709 087 | 5/1996 |
| EP | 0 760 237 | 3/1997 |
| EP | 0 778 083 | 6/1997 |
| EP | 0 813 876 | 6/1997 |

(56) References Cited

FOREIGN PATENT DOCUMENTS

| | | |
|---|---|---|
| EP | 0922451 | 6/1999 |
| EP | 1 184 038 | 3/2002 |
| EP | 2 105 129 | 9/2009 |
| FR | 2636534 | 3/1990 |
| GB | 2257359 | 1/1993 |
| GB | 2391743 | 2/2004 |
| IT | 109070 | 11/1977 |
| JP | 58-013508 | 1/1983 |
| JP | 58-077810 | 5/1983 |
| JP | S59088420 | 5/1984 |
| JP | S61126016 | 6/1986 |
| JP | 61-151119 | 7/1986 |
| JP | S64000015 | 1/1989 |
| JP | H5049899 | 3/1993 |
| JP | H06254382 | 9/1994 |
| JP | 2000-302654 | 10/2000 |
| WO | WO 93/00063 | 1/1993 |
| WO | WO 93/13753 | 7/1993 |
| WO | WO 94/15636 | 7/1994 |
| WO | WO 96/36322 | 11/1996 |
| WO | WO 97/02017 | 1/1997 |
| WO | WO 97/02042 | 1/1997 |
| WO | WO 97/07787 | 3/1997 |
| WO | WO 98/18610 | 5/1998 |
| WO | WO 98/50018 | 5/1998 |
| WO | WO 98/40051 | 9/1998 |
| WO | WO 98/50033 | 11/1998 |
| WO | WO 99/06024 | 2/1999 |
| WO | WO 99/13914 | 3/1999 |
| WO | WO 00/00179 | 1/2000 |
| WO | WO 00/33862 | 6/2000 |
| WO | WO 2000/069420 | 11/2000 |
| WO | WO 01/08666 | 2/2001 |
| WO | WO 01/32142 | 5/2001 |
| WO | WO 01/37808 | 5/2001 |
| WO | WO 2001/051008 | 7/2001 |
| WO | WO 02/064162 | 8/2002 |
| WO | WO 03/009812 | 2/2003 |
| WO | WO 03/018134 | 3/2003 |
| WO | WO 03/020243 | 3/2003 |
| WO | WO 03/030878 | 4/2003 |
| WO | WO 03/056938 | 7/2003 |
| WO | WO 2003/053404 | 7/2003 |
| WO | WO 03/092741 | 11/2003 |
| WO | WO 2004/022220 | 3/2004 |
| WO | WO 2004/042024 | 5/2004 |
| WO | WO 2004/064997 | 8/2004 |
| WO | WO 2004/084870 | 10/2004 |
| WO | WO 2004/108121 | 12/2004 |
| WO | WO 2005/020993 | 3/2005 |
| WO | WO 2005/020994 | 3/2005 |
| WO | WO 2005/030205 | 4/2005 |
| WO | WO 2005/048998 | 6/2005 |
| WO | WO 2005/072088 | 8/2005 |
| WO | WO 2005/074913 | 8/2005 |
| WO | WO 2005/100454 | 10/2005 |
| WO | WO 2005/107721 | 11/2005 |
| WO | WO 2006/018119 | 2/2006 |
| WO | WO 2006/026592 | 3/2006 |
| WO | WO 2006/027685 | 3/2006 |
| WO | WO 2006/035416 | 4/2006 |
| WO | WO 2006/035418 | 4/2006 |
| WO | WO 2006/110802 | 10/2006 |
| WO | WO 2007/007946 | 1/2007 |
| WO | WO 2007/012478 | 2/2007 |
| WO | WO 2007/014445 | 2/2007 |
| WO | WO 2007/018943 | 2/2007 |
| WO | WO 2007/095092 | 8/2007 |
| WO | WO 2008/122965 | 10/2008 |
| WO | WO 2008/122966 | 10/2008 |
| WO | WO 2008/122967 | 10/2008 |
| WO | WO 2008/132707 | 11/2008 |
| WO | WO 2009/002533 | 12/2008 |
| WO | WO 2009/014774 | 1/2009 |
| WO | WO 2009/060305 | 5/2009 |
| WO | WO 2010/005980 | 1/2010 |
| WO | WO 2010/043630 | 4/2010 |
| WO | WO 2010/133609 | 11/2010 |
| WO | WO 2015/067762 | 5/2015 |
| WO | WO 2015/067763 | 5/2015 |
| WO | WO 2015/078936 | 6/2015 |
| WO | WO 2015/104414 | 7/2015 |

OTHER PUBLICATIONS

Al-Meshal et al., "Oral administration of liposomes containing cyclosporine: a pharmacokinetic study," *International Journal of Pharmaceutics* 168:163-168, 1998.

Anderberg et al., "Sodium Caprate Elicits Dilatations in Human Intestinal Tight Junctions and Enhances Drug Absorption by the Paracellular Route," *Pharmaceutical Research* 10(6):857-864, 1993.

Bacigalupo et al., "Management of acute graft-versus-host disease," *British Journal of Haematology*, vol. 137, pp. 87-98, 2007.

Barnes et al., "Theophylline: New Perspectives for an Old Drug," *AM J Respir Crit Care Med* 167:813-818, 2003.

Borel et al., "Carotenoids in biological emulsions: solubility, surface-to-core distribution, and release from lipid droplets," *Journal of Lipid Research* 37:250-261, 1996.

Cannon, "Oral Solid Dosage Forms of Lipid-based Drug Delivery Systems," *AM Pharm Rev* 8(1):108-115, 2005.

Chourasia et al., "Pharmaceutical approaches to colon targeted drug delivery systems," *J. Pharm. Pharmaceut. Sci.* 6(1):33-66-2003.

Chowdary et al., "Controlled Nifedipine Release from Microcapsules of its Dispersions in PVP-MCC and HPC-MCC," *Drug Development and Industrial Pharmacy* 21(10):1183-1192, 1995.

Dhara et al., "Stability of Sodium Dodecyl Sulfate Micelles in the Presence of a Range of Water-Soluble Polymers: A Pressure-Jump Study," *J. Phys. Chem.*, vol. 105, pp. 7133-7138, 2000.

Drewe et al., "The absorption site of cyclosporine in the human gastro-intestinal tract," *Br. J. clin. Pharmac.* 33:39-43, 1992.

Drug Bank, www.drugbank.ca/drugs/DB00244, 12 pages.

Emmel et al., "Cyclosporin A Specifically Inhibits Function of Nuclear Proteins Involved in T Cell Activation,".

Gao et al., "Physiochemical characterization and evaluation of a microemulsion system for oral delivery of cyclosporine A," *International Journal of Pharmaceutics* 161:75-86, 1998.

Greener et al., "Interaction of Anionic Surfactants with Gelatin: Viscosity Effects," *Macromolecules*, vol. 20, pp. 2490-2498, 1987.

Gursoy et al., "Self-emulsifying drug delivery systems (SEDDS) for improved oral delivery of lipophilic drugs," *Biomedicine & Pharmacotherapy* 58:173-182, 2004.

Holmberg et al., *Surfactants and Polymers in Aqueous Solution, Second Ed.*, John Wiley and Sons Ltd., 2003.

Ikegawa et al., Inhibition of P-glycoprotein by flavonoid derivatives in Adriamycin-resistant human myelogenous leukemia (K562/ADM)cells, *Cancer Letters* 177:89-93, 2002.

Ismailos et al. "Unusual solubility behavior of cyclosporine A in aqueous media," *J. Pharm. Pharmacol.* 43:287-289, 1991.

Keck, "Cyclosporine Nanosuspensions: Optimised Size Characterisation & Oral Formulations," Doctoral Disssertation, Freien Universitat Berlin, 2006.

Kim et al., "Once-a-Day Oral Dosing Regimen of Cyclosporin A: Combined Therapy of Cyclosporin A Premicroemulsion Concentrates and Enteric Coated Solid-State Premicroemulsion Concentrates," *Pharmaceutical Research* 18(4):454-459, 2001.

LABRAFIL® M1944CS http://www.gattefosse.com/en/applications/labrafil-m1994cs.html.

Lawrance "Novel topical therapies for distal colitis," *World Journal of Gastrointestinal Pharmacology and Therapeutics* 1(5):87-93, 2010.

Liu et al., "Gelatin-Stabilised Microemulsion-Based Organogels Facilitates Percutaneous Penetration of Cyclosporin A In Vitro and Dermal Pharmacokinetics In Vivo," *Journal of Pharmaceutical Sciences* 96(11):3000-3009, Nov. 2007.

Loufrani, et al. "Vasodilator treatment with hydralazine increases blood flow in mdx mice resistance arteries without vascular wall remodeling or endothelium function improvement," *Journal of Hypertension* 23(10):1855-1860, 2005.

(56) References Cited

OTHER PUBLICATIONS

Madene et al., "Flavour encapsulation and controlled release—a review," *International Journal of Food Science and Technology* 41:1-21, 2006.
Manakova et al., "Failure of FK506 (tacrolimus) to alleviate apomorphine-induced circling in rat Parkinson model in spite of some cytoprotective effects in SH-SYSY dopaminergic cells," *Brain Research* 1038:83-91, 2005.
McGinity et al., "Aqueous Polymeric Coatings for Pharmaceuticals Dosage Forms," *Marcel Dekker, Inc.*, 1997.
McGinity et al., "Enteric Film Coating of Soft Gelatin Capsules," *Drug Development & Delivery* 3(6), Sep. 6, 2003.
Miller et al., "Controlled Trial of Nimodipine in Amyotrophic Lateral Sclerosis," *Neuromusc. Disord.*, 6(2):101-104, 1996.
Milojevic et al., "Amylose as a coating for drug delivery to the colon: Preparation and in vitro evaluation using 5-aminosalicylic acid pellets," *Journal of Controlled Release* 38:75-84, 1996.
Muller et al., "Competitive Adsorption of Gelatin and Sodium Dodecylbenzenesulfonate at Hydrophobic Surfaces," *Langmuir*, vol. 14, pp. 3107-3114, Mar. 17, 1998.
Murthy et al., "Treatment of Dextran Sulfate Sodium-Induced Murine Colitis by Intracolonic Cyclosporin," *Digestive Diseases and Sciences* 38(9):1722-1734, Sep. 1993.
Newman, et al. "Use of Nonionic Block Copolymers in Vaccines and Therapeutics," *Critical Reviews™ in Therapeutic Drug Carrier Systems* 15(2):89-142, 1998.
Non-Final Office Action issued by U.S. Patent and Trademark Office for U.S. Appl. No. 14/536,503 dated Jan. 15, 2016, 55 pages.
Office Action issued by Japan Patent Office for Japanese Patent Application No. 2006-507572 dated Sep. 24, 2014, 15 pages (with English translation).
Onoue et al., "Inhalable dry-emulsion formulation of cyclosporine A with improved anti-inflammatory effects in experimental asthma/COPD-model rats," *European Journal of Pharmaceutics and Biopharmaceutics*, 80(1): 54-60, Jan. 2012.
Pelkonen et al., "In vitro prediction of gastrointestinal absorption and bioavailability: an experts' meeting report," *European Journal of Clinical Pharmacology*, 57(9): 621-629, Nov. 2001.
Qiu et al., "Developing Solid Oral Dosage Forms: Pharmaceutical Theory & Practice," *Academic Press* p. 445 only, 2009.
Reich, "Formulation and physical properties of soft capsules," *Chapter 11, Pharmaceutical Capsules, 2nd edition*, Edited by Fridrun Podczeck and Brian E Jones, p. 208, 2004.
Ribeiro et al., "Microencapsulation of lipophilic drugs in chitosan-coated alginate microspheres," *International Journal of Pharmaceutics* 187:115-123, 1999.
Riviere, et al. "Effects of Vasoactive Drugs on Transdermal Lidocaine Iontophoresis," *Journal of Pharmaceutical Sciences* 80(7):615-620, 1991.
Rodriguez et al., "Colonic budenoside delivery from ph-dependent microcapsules containing lipidic cores," *Acia Technologiae et Legis Medicamenti*, vol. XI, N. 1, 2000.
Sandborn et al., "The Pharmacokinetics and Colonic Tissue Concentrations of Cyclosporine After IV, Oral, and Enema Administration," *J. Clin. Pharmacol.*, vol. 31, pp. 76-80, 1991.
Strickley, "Solubilizing Excipients in Oral and Injectable Formulations," *Pharmaceutical Research*, 21(2): 201-230, Feb. 2004.
Strowig et al., Comparison of Insulin Monotherapy and Combination Therapy with Insulin and Metformin or Insulin and Troglitazone in Type 2 Diabetes, *Diabetes Care* 25(10):1691-1698, 2002.
Sweetman and Martindale, "Nimodipine," *Cardiovascular Drugs* p. 946, 2002.
Takatsuka et al., "Intestinal Graft-Versus-Host Disease: Mechanisms and Management," *Drugs*, 63(1): 1-15, 2003.
U.S. Appl. No. 10/398,373, filed Aug. 14, 2003.
Wesley et al., "Structure of Polymer Surfactant Complexes Formed by Poly(2-(dimethylamino)ethyl methacrylate) and Sodium Dodecyl Sulfate," *Langmiur*, vol. 18, pp. 5704-5707, Apr. 30, 2002.
Westerink et al. "ProJuvant™ (Pluronic F127®/chitosan) enhances the immune response to intranasally administered tetanus toxoid," *Vaccine* 20:711-723, 2002.
Xu et al., "Effect of anionic surfactants on grafting density of gelatin modified with PDMS-E," *Colloids and Surfaces B: Biointerfaces*, vol. 114, pp. 310-315, Oct. 24, 2013.
Xu et al., "Structure Evolution of Gelatin Particles Induced by Ph and Ionic Strength," *Microscopy Research and Technique*, vol. 76, pp. 272-281, 2013.
Yang et al., "Transport and uptake characteristics of a new derivative of berberine (CPU-86017) by human intestinal epithelial cell line: Caco-2," *Acta Pharmacol Sin* 24(12):1185-1191, 2003.
Yeh et al., "Effect of Medium-Chain Glycerides on Physiological Properties of Rabbit Intestinal Epithelium in Vitro," *Pharmaceutical Research* 11(8):1148-1154, 1994.
Zhang et al., "P-glycoprotein restricted transport of nimodipine across blood-brain barrier," *Acta Pharmacol Sin* 24(9):903-906, 2003.
Zuber et al., "Reversible cerebral angiopathy," *J. Neurol.* 253:1585-1588, 2006.
Stack et al., "Short- and long-term outcome of patients treated with cyclosporin for severe acute ulcerative colitis," *Aliment. Pharmacol. Ther.*, vol. 12, pp. 973-978, Jun. 1, 1998.
Non-Final Office Action issued for U.S. Appl. No. 15/034,844 dated Aug. 23, 2017.
Rolfsen et al., "Oil-in-water biocompatible microemulsion as a carrier for the antitumor drug compound methyl dihydrojasmonate," *International Journal of Nanomedicine*, vol. 10, pp. 585-594, Jan. 12, 2015.
Cho et al., "Preparation and Evaluation of Solid-Self-Emulsifying Drug Delivery System Containing Paclitaxel for Lymphatic Delivery," *Journal of Nanomaterials*, vol. 2016, 15 pages, May 5, 2016.
Aguirre et al., "In vitro and in vivo preclinical evaluation of a minisphere emulsion-based formulation (SmPill®) of salmon calcitonin," *European Journal of Pharmaceutical Sciences*, vol. 79, pp. 102-111, Sep. 6, 2015.
Zhu et al., "Development and mathematical simulation of theophylline pulsatile release tablets," *Drug Development and Industrial Pharmacy*, vol. 31, pp. 1009-1017, Sep. 26, 2008.
Actis et al., "Oral microemulsion cyclosporin to reduce steroids rapidly in chronic active ulcerative colitis," *European Journal of Gastroenterology & Hepatology*, 11(8): 905-908, Aug. 1, 1999.
Campbell et al., "Combination immunomodulatory therapy with cyclosporine and azathioprine in corticosteroid-resistant severe ulcerative colitis: the Edinburgh experience of outcome," *Digestive and Liver Disease*, vol. 35, pp. 546-551, 2003.

* cited by examiner

Cremophor formulation

Capmul formulation (t0)  (t = 2 hours)  (t = 2 hours 30 mins)

(t0)  (t = 2 hours)  (t = 2 hours 30 mins)

(t=0)  (t = 1 hour)  (t = 1 hour 30 mins)

(t=0)  (t = 3 hours 30 mins)  (t = 4 hours 30 mins)

(t0)　　　(t = 1 hour 30 mins)　　　(t = 3 hours 30 mins)

(t=0)　　　(t = 30 mins)　　　(t = 1 hour)

(t=0)　　　(t = 2 hours 30 mins)　　　(t = 4 hours)

(t=0)　　　(t = 4 hours)　　　(t = 4 hours 30 mins)

(t=0)  (t = 2 hours)  (t = 3 hours 30 mins)

(t=0)  (t = 3 hours)  (t = 5 hours 30 mins)

(t=0)  (t = 2 hours)  (t = 4 hours 30 mins)

(t=0)  (t = 2 hours)  (t = 5 hours)

(t=0)　　(t = 1 hour 30 mins)　　(t = 3 hours)

(t=0)　　(t = 2 hours 30 mins)　　(t = 4 hours 30 mins)

(t=0)　　(t = 1 hour 30 mins)　　(t = 3 hours 30 mins)

(t0)　　(t = 1 hour 30 mins)　　(t = 3 hours)

(t=0) (t = 1 hour) (t = 2 hours)

(t0) (t = 1 hour) (t = 2 hours)

(t0) (t = 1 hour) (t = 1 hour 30 mins)

(t0) (t = 1 hour) (t = 2 hours 30 mins)

COMPOSITIONS COMPRISING CYCLOSPORIN

CROSS REFERENCE TO RELATED APPLICATIONS

This is the U.S. National Stage of International Application No. PCT/EP2015/075984, filed Nov. 6, 2015, which was published in English under PCT Article 21(2), which in turn claims the benefit of GB Application No. 1419849.3, filed Nov. 7, 2014, International Application No. PCT/EP2014/074054, filed Nov. 7, 2014, and GB Application No. 1507673.0, filed May 5, 2015.

This invention relates to a composition comprising a pharmaceutically active ingredient and a surfactant. The invention also relates to the use of the composition in the treatment and prevention of disorders, for example disorders of the gastrointestinal tract. Also disclosed are methods for preparing the compositions.

BACKGROUND

Cyclosporin A is a cyclic polypeptide which has immunosuppressive and anti-inflammatory properties. The compound has been approved for the prevention of organ rejection following kidney, liver, heart, combined heart-lung, lung or pancreas transplantation, for the prevention of rejection following bone marrow transplantation; the treatment and prophylaxis of Graft Versus Host Disease (GVHD); psoriasis; atopic dermatitis, rheumatoid arthritis and nephrotic syndrome (Neoral™ Summary of Product Characteristics 24 Feb. 2012). Cyclosporin A may also be useful for the treatment of a range of other diseases including for the treatment of severe recalcitrant plaque psoriasis Bechet's disease, anemia, myasthenia gravis and various conditions affecting the GI tract, including irritable bowel syndrome, Crohn's disease, colitis, including ulcerative colitis, diverticulitis, pouchitis, proctitis, Gastro-Intestinal Graft Versus Host Disease (GI-GVHD), colorectal carcinoma and adenocarcinoma as well as ischemia induced disease. A range of other diseases may benefit from treatment with cyclosporin A (Landford et al. (1998) Ann Intern Med; 128: 1021-1028) the entirety of which is incorporated herein by reference. Cyclosporin A has been used to treat a number of gastrointestinal conditions including inflammatory bowel disease (Sandborn W J, a critical review of cyclosporin therapy in inflammatory bowel disease, Inflamm Bowel Dis. 1995; 1:48-63), including ulcerative colitis (Lichtiger et al, preliminary report (cyclosporine in the treatment of severe ulcerative colitis), Lancet. 1990; 336:16-19; Cohen et al, Intravenous cyclosporine in ulcerative colitis (a five-year experience), Am J Gastroenterol. 1999; 94:1587-1592).

However cyclosporin A has a number of undesirable side effects including hypertension, impaired renal function, and neurotoxicity (Feutren et al, Risk factors for cyclosporine-induced nephropathy in patients with auto-immune diseases, International kidney biopsy registry of cyclosporine for autoimmune diseases, N Engl J Med. 1992; 326:1654-1660; Wijdicks et al., Neurotoxicity in liver transplant recipients with cyclosporine immunosuppression, Neurology. 1995; 45:1962-1964; and Porter et al, Cyclosporine-associated hypertension, National High Blood Pressure Education Program. Arch Intern Med. 1990; 150:280-283).

Cyclosporin A is available as an intravenous formulation; Sandimmun™, which is a solution of 50 mg/ml of cyclosporin A in ethanol and polyethoxylated castor oil (for example Kolliphor™ EL). The product is also available as orally administered formulations, including a soft gelatin capsule containing a solution of cyclosporin A in ethanol, corn oil and lineoyl macrogolglycerides (Sandimmune™ Soft Gelatin capsules) and as an orally administered solution containing the cyclosporin dissolved in olive oil, ethanol, and labrafil M 1944 CS (polyethoxylated oleic glycerides) (Sandimmune™ Oral Solution). More recently a microemulsion concentrate formulation has been approved containing cyclosporin A dissolved in DL-α-tocopherol, absolute ethanol, propylene glycol, corn oil-mono-di-triglycerides, polyoxyl 40 hydrogenated castor oil (Neoral™). Following oral administration the Neoral™ formulation results in the formation of a microemulsion and is stated to have an improved bioavailability compared to orally administered Sandimmune™. These orally administered cyclosporin A compositions are all instant release compositions and cyclosporin A will be present at high concentration in the stomach and small intestine from where it is systemically absorbed.

Sandborn et al. (J Clin Pharmacol. 1991; 31:76-80) determined the relative systemic absorption of cyclosporin following oral and intravenous as well as oil- and water-based enemas. Based on negligible plasma cyclosporin concentrations observed following enema administration, it was suggested that cyclosporin, even when solubilised, is poorly absorbed from the colon. The enemas however demonstrated considerable efficacy in the treatment of inflammatory bowel disease (Ranzi T, et al, Lancet 1989; 2:97). Intravenous or orally administered cyclosporin efficacy in the treatment of inflammatory bowel disease is dose dependent, requiring high doses to ensure adequate concentration reaches the colon. Systemic toxicity is known to be dose and duration dependent.

Formulating pharmaceutically active ingredients into a form suitable for administration to a patient is a developed area of science. It is also a key consideration for the efficacy of a drug. There are many examples of methods for formulating drugs and other active ingredients. The aim of these formulations are varied and can range from increasing systemic absorption, allowing for a new route of administration, improving bioavilability, reducing metabolism of the active, or avoiding undesirable routes of administration.

WO 2008/122965 discloses oral cyclosporin minicapsule compositions with modified release properties which release cyclosporin in at least the colon. WO2010/133609 discloses compositions comprising a water-soluble polymer matrix in which are dispersed droplets of oil, the compositions comprising a modified release coating. The disclosed compositions also contain an active principle.

There remains a need for orally administered cyclosporin A compositions which provide high levels of cyclosporin A in the lower GI tract, particularly in the colon and absorption of the cyclosporin A from the luminal contents into the tissues of the GI tract, particularly into the colonic tissue, for the treatment of conditions of the lower GI tract such as ulcerative colitis. Such compositions desirably minimise the systemic blood exposure to cyclosporin A thereby minimising the undesirable side effect associated with systemic exposure to cyclosporin A. Particularly there is a need for orally administered compositions which have a low exposure/area under the curve (AUC) and/or low peak blood concentration (Cmax) compared to the orally administered product Neoral™ and/or cyclosporin A administered intravenously as for example Sandimmune™.

Cyclosporin A is oil soluble; it is hydrophobic. Upon contact of a cyclosporin solution with water, the cyclosporin can form a solid by precipitating or crystalising out of solution. Precipitation or crystallisation of cyclosporin from solution can occur when the cyclosporin solution is present in an oil-in-water emulsion. Prior art oil-in-water emulsions comprising cyclosporin in solution have been found to have low emulsion stability and to precipitate or crystalise cyclosporin over time. Solid cyclosporin formation in an emulsion is undesirable. Therefore, there is a need for emulsions comprising cyclosporin in solution which have a higher emulsion stability. For example, there is a need for emulsions where the length of time for crystal formation or precipitation to occur is longer.

Formulating an active ingredient into a bead by passing a composition comprising a water-soluble polymer matrix in which are dispersed droplets of oil through a single orifice nozzle is disclosed in WO2010/133609. Solid cyclosporin formation in an emulsion is particularly undesirable whilst forming beads from an emulsion comprising solid cyclosporin. This is because solid cyclosporin is less active at an intended therapeutic site, for example the gastrointestinal tract, than solubilised cyclosporin. The problem of cyclosporin crystallising or precipitating is particularly relevant in scale up production of beads from the emulsion. Scaling up production of beads results in batches of the emulsion being kept for longer periods and the propensity for crystallisation or precipitation to happen increasing. Therefore, there is a need for an emulsion with a high stability to reduce the amount of solid in the emulsion whilst being processed into beads and consequently to reduce the amount of solid in the bead.

Similarly there is a need for a component of the emulsion to inhibit crystallisation or precipitation.

BRIEF SUMMARY OF THE DISCLOSURE

It has surprisingly been found that a surfactant has a stabilising effect on an emulsion comprising cyclosporin in solution. The surfactant may comprise or may be a medium chain or long chain fatty acid mono- or di-glyceride or a combination thereof, optionally wherein the surfactant does not comprise or is not a polyethyleneglycol ether or ester. The surfactant may have an HLB of up to 10, preferably of up to 7 or up to 5. Specifically, it has been found that a medium chain or long chain fatty acid mono- or di-glyceride or a combination thereof, optionally not comprising or being a polyethyleneglycol ether or ester, has a stabilising effect on an emulsion comprising cyclosporin in solution. The emulsion may be an oil-in-water emulsion.

A medium chain or long chain fatty acid mono- or di-glyceride is an ester of such a fatty acid and glycerol, wherein there may be one (mono-) or two (di-) fatty acids esterified to glycerol. The glycerol may consist of one glycerol for example mono glycerol (a mono-glycerol ester is also be referred to as a glyceride).

It has been found that the use of certain surfactants during the manufacture of the compositions are particularly effective in stabilising the colloid (for example emulsion), resulting from the mixing of an aqueous solution comprising a hydrogel forming polymer and an oil phase comprising cyclosporin A. When the colloid comprises an oil-in-water emulsion, it has been found that the presence of a surfactant having an HLB of up to 8 (particularly up to 6 or from 2 to 6) in the oil phase is particularly effective in stabilising the emulsion in particular during the preparation of the composition. The presence of such surfactants has been found to inhibit the formation of cyclosporin A crystals after the formation of the colloid (oil-in-water emulsion). The presence of a surfactant with an HLB of up to 10 maintains the cyclosporin A in solution in the oil phase during manufacture and may also provide favourable release of the cyclosporin A in a solubilised form from the composition following oral administration of the composition to a subject. Compositions comprising a surfactant of the invention with an HLB of up to 8 in at least the oil phase may exhibit high rates of release and/or extent of release of cyclosporin A from the composition compared to the use of surfactants with a higher HLB value in the oil phase. The presence of a surfactant with an HLB of up to 8 in at least the oil phase in the composition may inhibit the precipitation of cyclosporin A after release of the cyclosporin from the composition thereby retaining higher levels of cyclosporin in a solubilised form within the GI tract, for example in the colon. The compositions described herein wherein the composition comprises an oil phase and a surfactant having an HLB of up to 10 form a further independent aspect of the invention.

Accordingly, there is provided a use of a surfactant for stabilising an emulsion. Preferably, the emulsion is an oil in water emulsion. The surfactant preferably is or comprises a medium chain or long chain fatty acid mono- or di-glyceride or a combination thereof, optionally not comprising or being a polyethyleneglycol ether or ester.

By the phrase "the surfactant stabilises the emulsion", it is meant that the surfactant increases the length of time for solid particles (for example precipitation or crystallisation) to occur in an emulsion comprising cyclosporin in solution.

It has also been found that a surfactant inhibits crystallisation of cyclosporin from a cyclosporin solution in an oil phase in an oil-in-water emulsion. The surfactant is or comprises a medium chain or long chain fatty acid mono- or di-glyceride or a combination thereof, optionally wherein the surfactant does not comprise or is not a polyethyleneglycol ether or ester. Accordingly, the use of the surfactant provides an emulsion that is free of crystals or precipite for a longer period than prior art emulsions. An emulsion that takes longer for crystallisation or precipitation to occur is beneficial for large-scale bead production. Consequently, the invention contemplates a process utilising an emulsion comprising the surfactant to produce beads, particularly in scale up of the bead production process.

Ordinarily surfactants with a low HLB value, for example up to 8, are used as water-in-oil emulsifiers. As part of the invention it has been found that a surfactant is an emulsifier for oil-in-water emulsions comprising dissolved cyclosporin, wherein the surfactant has a HLB value of up to 8 and is or comprises a medium chain or long chain fatty acid mono- or di-glyceride or a combination thereof, optionally not comprising or being a polyethyleneglycol ether or ester.

In an aspect of the invention there is provided a liquid composition comprising an aqueous phase, a surfactant and an oil phase in which cyclosporin is dissolved. The surfactant may comprise or be a medium chain or long chain fatty acid mono- or di-glyceride or a combination thereof and does not comprise or is not a polyethyleneglycol ether or ester. The aqueous phase may comprise a hydrogel forming polymer. The oil phase may be dispersed in the aqueous phase. The oil phase may be dispersed in the aqueous phase in the form of a colloid, for example a liquid-liquid colloid. The oil phase may be dispersed in the aqueous phase in the form of an emulsion. Accordingly, the liquid composition may be a liquid emulsion composition.

The liquid composition may be converted into a solid form by allowing the hydrogel forming polymer to form a hydrogel matrix. There is also provided a process for converting the liquid composition into a bead, wherein the liquid composition is ejected through a single orifice nozzle.

In an aspect of the invention there is provided a composition comprising cyclosporin, a hydrogel forming polymer matrix, a surfactant and an oil phase being dispersed in the hydrogel forming polymer matrix. The surfactant may be or may comprise a medium chain or long chain fatty acid mono- or di-glyceride or a combination thereof and may not comprise or may not be a polyethyleneglycol ether or ester. The composition may be a solid composition. The composition may be in the form of a dried bead. The composition may be in the form of a dried colloid.

Advantageously an enhanced release profile is provided by the presence of the surfactant being or comprising a medium chain or long chain fatty acid mono- or di-glyceride or a combination thereof that does not comprise or is not a polyethyleneglycol ether or ester in compositions of the invention compared to compositions with a different surfactant. A solid composition of the invention exhibits a release profile with higher release of cyclosporin and maintenance of high cyclosporin levels in solution when compared to compositions with a different surfactant (Kolliphor EL, a polyethoxylated castor oil). The dissolution may be measured in deionised water.

Optionally, the cyclosporin, the hydrogel forming polymer matrix, the surfactant and the oil phase are comprised within a core. Thus, the composition may comprise a core. Accordingly, the composition may comprise a core, wherein the core comprises cyclosporin, a hydrogel forming polymer matrix, a surfactant and an oil phase being dispersed in the hydrogel forming polymer matrix, wherein the surfactant may be or comprise a medium chain or long chain fatty acid mono- or di-glyceride or a combination thereof and does not comprise or is not a polyethyleneglycol ether or ester.

The liquid composition may be a colloid, i.e. it may be a colloidal liquid composition. The composition may be a solid colloid or the composition may be in the form of a solid colloid, i.e. it may be a solid colloidal composition. The colloidal liquid composition of the invention may comprise a continuous phase which is or comprises a hydrogel-forming polymer and a disperse phase which is or comprises cyclosporin A and an oil phase, wherein the colloidal liquid composition or the solid colloidal composition further comprise a surfactant (also referred to as a first surfactant) comprising or being a medium chain or long chain fatty acid mono- or di-glyceride or a combination thereof and not comprising or not being a polyethyleneglycol ether or ester.

The solid colloidal composition of the invention may comprise a continuous phase which is or comprises a hydrogel-forming polymer matrix and a disperse phase which is or comprises cyclosporin A and an oil phase, wherein the colloidal liquid composition or the solid colloidal composition further comprise a surfactant (also referred to as a first surfactant) comprising or being a medium chain or long chain fatty acid mono- or di-glyceride or a combination thereof and not comprising or not being a polyethyleneglycol ether or ester.

Throughout the specification both the liquid composition and the composition are referred to by "composition". Furthermore, where an embodiment or aspect is referred to as a "composition" this may optionally be referring to a liquid composition (for example a colloidal liquid composition) and/or to a solid composition (for example a solid colloidal composition).

In an embodiment the oil phase comprises a solution of the cyclosporin. As such, the cyclosporin may be dissolved in the oil phase, for example completely dissolved, substantially completely dissolved, or partially dissolved. Thus, the oil phase may comprise a solution of cyclosporin and some undissolved cyclosporin.

Throughout this specification the term cyclosporin may be referring to the class of compounds or to cyclosporin A. Preferably, the use of cyclosporin is in reference to cyclosporin A.

The cyclosporin is suitably present in the composition in an amount of from about 5% to about 20%, from about 8% to about 15%, or from about 9% to about 14% by weight based upon the dry weight of the core or of the composition.

The cyclosporin is suitably present in the liquid composition in an amount of up to 10%, optionally from about 1% to about 10%, from about 2% to about 8%, from about 3% to about 6%, from about 3% to about 5% by weight of the liquid composition. Optionally the cyclosporin may be present in the liquid composition in about 4% by weight of the liquid composition.

A medium chain fatty acid mono-ester or di-ester comprises a fatty acid having 8 to 12 in chain carbon atoms. A long chain fatty acid mono-ester or di-ester comprises a fatty acid having at least 13 in chain carbon atoms, preferably 13 to 26 in chain carbon atoms. The long chain fatty acid may optionally have from 14 to 22 in chain carbon atoms or 16 to 20 in chain carbon atoms.

Preferably, the surfactant is a medium chain or long chain fatty acid mono- or di-glyceride or a combination thereof that does not comprise or is not a polyethyleneglycol ether or ester. Where the surfactant comprises a medium chain or long chain fatty acid mono- or di-glyceride or a combination thereof that does not comprise or is not a polyethyleneglycol ether or ester, the medium chain or long chain fatty acid mono- or di-glyceride or a combination thereof is substantially all of the surfactant. For example, the surfactant may comprise medium chain or long chain fatty acid mono- or di-glyceride or a combination thereof that does not comprise or is not a polyethyleneglycol ether or ester in an amount of greater than 80% of the surfactant, optionally greater than 85%, 90%, 95%, 97%, 98% or 99%. Suitably, the surfactant is substantially free of a triglyceride. For example, the surfactant may comprise less than 10%, 8%, 5%, 3%, 2% or 1% of a triglyceride.

The presence of the surfactant may enhance the rate and or extent of release of cyclosporin from the composition following oral administration. The presence of the surfactant may act to maintain a high proportion of the cyclosporin in a solubilised form after it has been released from the composition into an aqueous medium such as that found in the lower GI tract, particularly the colon.

The surfactant may have an HLB value of up to 8, up to 6, or up to 5. Alternatively the surfactant may have an HLB value selected from: up to 7, 1-8, 1-7, 2-6, 1-5, 2-5, 1-4, 1-3, 1-2, 2-4, 3-4, 3-6, 5-8, 6-8 and 6-7. Preferably, the surfactant has an HLB value of up to 6, 2-6 or 3-6.

The cyclosporin A may be soluble in the surfactant, for example the cyclosporin A may have a solubility of more than 200 mg/g in the surfactant. Thus, the surfactant may have a cyclosporin solubility of more than 200 mg/g. The surfactant may have a cyclosporin solubility of from 200 mg/g to 500 mg/g, optionally from 250 mg/g to 500 mg/g.

The surfactant may have a cyclosporin solubility of from 200 mg/g to 400 mg/g, from 225 mg/g to 375 mg/g, from 200 mg/g to 300 mg/g, from 300 mg/g to 400 mg/g, from 225 mg/g to 275 mg/g, from 350 mg/g to 400 mg/g. Preferably, the surfactant has a cyclosporin solubility of from 200 mg/g to 400 mg/g or from 225 mg/g to 375 mg/g. The surfactant may have a cyclosporin solubility of from 250 mg/g to 400 mg/g, from 250 mg/g to 375 mg/g, from 250 mg/g to 300 mg/g, from 300 mg/g to 400 mg/g, from 250 mg/g to 275 mg/g, from 350 mg/g to 400 mg/g. Preferably, the surfactant has a cyclosporin solubility of from 250 mg/g to 400 mg/g or from 250 mg/g to 375 mg/g. The solubility of cyclosporin in a surfactant may be determined by techniques known to those skilled in the art, for example by following the protocol described in Development of a Self Micro-Emulsifying Tablet of Cyclosporine-A by the Liquisolid Compact Technique, Zhao et al (International Journal of Pharmaceutical Sciences and Research, 2011, Vol. 2(9), 2299-2308) which is incorporated herein by reference.

The surfactant may have an HLB of up to 6 and a cyclosporin solubility of from 200 mg/g to 400 mg/g. The surfactant may have an HLB value of 2-6 (optionally 3-6) and a cyclosporin solubility of from 200 mg/g to 400 mg/g. The surfactant may have an HLB value of 2-6 (optionally 3-6) and a cyclosporin solubility of from 225 mg/g to 275 mg/g. The surfactant may have an HLB value of 2-6 (optionally 3-6) and a cyclosporin solubility of from 250 mg/g to 300 mg/g.

The surfactant may have an HLB of up to 6 and a cyclosporin solubility of from 250 mg/g to 400 mg/g. The surfactant may have an HLB value of 2-6 (optionally 3-6) and a cyclosporin solubility of from 250 mg/g to 400 mg/g. The surfactant may have an HLB value of 2-6 (optionally 3-6) and a cyclosporin solubility of from 250 mg/g to 375 mg/g. The surfactant may have an HLB value of 2-6 (optionally 3-6) and a cyclosporin solubility of from 250 mg/g to 300 mg/g.

The surfactant may be or comprise a medium chain or long chain fatty acid mono- or di-glyceride or a combination thereof and may not comprise or may not be a polyethyleneglycol ether or ester, wherein the fatty acid ester is saturated or unsaturated. Preferably, the fatty acid is unsaturated. The unsaturated fatty acid may contain only one or only two double bonds.

Where the surfactant is a medium chain or long chain fatty acid di-glyceride (by which it is meant that there are two fatty acids esterified to a glycerol) the surfactant may comprise two fatty acids which are the same or different. For example the two fatty acids may both be unsaturated or may both be saturated. Alternatively, one of the two fatty acids may be saturated and the other fatty acid may be unsaturated.

Preferably the surfactant is a long chain mono- or di-glyceride or a combination thereof and does not comprise or is not a polyethyleneglycol ether or ester. A further preferred surfactant is a long chain mono- or di-glyceride or a combination thereof and does not comprise or is not a polyethyleneglycol ether or ester, wheren the fatty acid has a chain length of 13 to 22 carbon atoms, optionally 16 to 20 carbon atoms. In particular the fatty acid may have a chain length of 18 carbon atoms.

In an embodiment the surfactant is selected from: glyceryl monocaprate, glyceryl dicaprate, glyceryl monocaprylate, glyceryl dicaprylate, glyceryl caprate, glyceryl monocaprylate/caprate, glyceryl caprylate/caprate glyceryl dicaprylate/caprate, glyceryl monooleate/dioleate, glyceryl monooleate, glyceryl dioleate, glyceryl monostearate, glyceryl distearate, glyceryl monopalmitostearate, glyceryl dipalmitostearate, glyceryl monobehenate, glyceryl dibehenate, glycerol monolinoleate, glyceryl dilinoleate, polyglyceryl dioleate, propylene glycol monoheptanoate, and a combination thereof.

A preferred surfactant may be or comprise a surfactant selected from: glyceryl monocaprylate/caprate, glyceryl dicaprylate/caprate, glyceryl monooleate, glycerol monolinoleate, glyceryl dioleate, glyceryl monostearate, glyceryl distearate, glyceryl monopalmitostearate, glyceryl dipalmitostearate, glyceryl monobehenate, glyceryl dibehenate, glyceryl monolinoleate, glyceryl dilinoleate, polyglyceryl dioleate and a combination thereof.

Accordingly, there is provided a composition comprising cyclosporin, a hydrogel forming polymer matrix, a surfactant and an oil phase being dispersed in the hydrogel forming polymer matrix, wherein the surfactant may be or may comprise a surfactant selected from: glyceryl monocaprylate/caprate, glyceryl dicaprylate/caprate, glyceryl monooleate, glycerol monolinoleate, glyceryl dioleate, glyceryl monostearate, glyceryl distearate, glyceryl monopalmitostearate, glyceryl dipalmitostearate, glyceryl monobehenate, glyceryl dibehenate, glyceryl monolinoleate, glyceryl dilinoleate, polyglyceryl dioleate and a combination thereof.

The surfactant may comprise or be a surfactant selected from: glyceryl caprylate, glyceryl caprate, glyceryl monooleate, glyceryl dioleate, glycerol monolinoleate or a combination thereof.

A particularly preferred surfactant may be or comprise a surfactant selected from: glyceryl caprylate/caprate (Capmul MCM), glyceryl monooleate/dioleate (Capmul GMO-50) and glycerol monolinoleate (Maisine 35-1).

Optionally, the surfactant is not a mixture of glyceryl monostearate EP/NF and PEG-75 palmitostearate (for example Gelto™ 64). Suitably, the surfactant may not be or comprise a mixture of glyceryl monostearate.

In an embodiment the oil phase comprises an oil or liquid lipid and the surfactant is present in an amount greater than the oil or liquid lipid. Optionally, the surfactant may be present in an amount of more than 6 wt % of the dry weight of the composition. This refers to the uncoated composition or the core. The surfactant may comprise more than 12 wt % of the oil phase, for example in the liquid composition. The surfactant may be present in the composition in an amount of from about 5% to about 20%, from about 8% to about 20%, from about 8% to about 15%, or from about 10% to about 14% by weight based upon the dry weight of the core. It is to be understood that reference to the "dry weight of the core" means the weight of the components present in the uncoated core other than water.

The weight ratio of the surfactant:oil may be from about 5:1 to about 1:5, from about 3:1 to about 1:2, from about 3:1 to about 1:1 or from about 2.5:1 to 1.5:1. Suitably the weight ratio may be about 1:1, about 2:1, about 2.5:1, about 3:1, about 1:1.5 or about 1:2.

Accordingly, in a preferred embodiment there is provided a liquid composition comprising an aqueous phase, a surfactant and an oil phase in which cyclosporin is dissolved, wherein the aqueous phase comprises a hydrogel forming polymer, the oil phase is dispersed in the aqueous phase and the surfactant comprises or is a surfactant selected from: glyceryl caprylate/caprate (Capmul MCM), glyceryl monooleate/dioleate (Capmul GMO-50), glycerol monolinoleate (Maisine 35-1) and a combination thereof. The oil phase may be dispersed in the aqueous phase in the form of a colloid, for example a liquid-liquid colloid. The oil phase may be dispersed in the aqueous phase in the form of an emulsion. Accordingly, the liquid composition may be a liquid emulsion composition.

There is provided a composition comprising cyclosporin, a hydrogel forming polymer matrix, a surfactant and an oil phase being dispersed in the hydrogel forming polymer matrix, wherein the surfactant comprises or is a surfactant selected from: glyceryl caprylate/caprate (Capmul MCM), glyceryl monooleate/dioleate (Capmul GMO-50), glycerol monolinoleate (Maisine 35-1) and a combination thereof. The composition may be a solid composition. The composition may be in the form of a dried bead. The composition may be in the form of a dried colloid.

Optionally, the surfactant is or comprises glyceryl monooleate, glyceryl dioleate or a combination thereof. Capmul GMO-50 is an example of a commercially available surfactant that comprises a combination of glyceryl monooleate and glyceryl dioleate. Thus, the surfactant may be Capmul GMO-50. Where Capmul GMO-50 is mentioned in the specification it will be understood that it is referring to a mixture of glyceryl monooleate and glyceryl dioleate. Capmul GMO-50 may also refer to glyceryl monooleate alone.

Similarly, the skilled person would understand that a surfactant that is described as, for example glyceryl monooleate/dioleate, contemplates a combination of glyceryl monooleate and glyceryl dioleate. In other words a "/" in a surfactant name indicates that the surfactant is a mixture of two components.

The composition may comprise a coating to control or modulate release of the cyclosporin from the composition. Advantageously the coating is a polymeric coating to provide delayed and/or sustained release of the cyclosporin from the composition. Suitably such coatings are described in more detail below and include a coating which is or comprises a coating selected from a controlled release polymer, a sustained release polymer, an enteric polymer, a pH independent polymer, a pH dependent polymer and a polymer specifically susceptible to degradation by bacterial enzymes in the gastrointestinal tract, or a combination of two or more such polymers. In a particular embodiment the coating is or comprises a pH-independent polymer, for example a coating which is or comprises ethyl cellulose. In a further specific embodiment the coating is or comprises a pH-independent polymer, for example ethyl cellulose, and optionally a water-soluble polysaccharide, for example pectin or chitosan, or a combination thereof, particularly pectin.

In an embodiment the coating that is referred to in the preceding paragraph is an outer coating, also referred to as a second coating. The composition may optionally comprise a further coating, referred to as a sub-coat or a first coating. The respective polymers of the first coating and the second coating are different. Often the second coating does not have any polymer found in the first coating; for example, if the first coating comprises (e.g. is) a hydroxypropylmethyl cellulose, then the second coating will not also comprise a hydroxypropylmethyl cellulose. In addition the situation is contemplated where the first coating is or comprises a water-soluble ether or ester of a cellulose ether, the major component(s) (e.g. more than 50%) of the second coating is or comprises a different polymer to that of the first coating. Accordingly, the first and second coatings suitably provide two layers of material as part of the composition. It is to be understood that when the second coating comprises a mixture of components, minor components of the outer second coating may be the same as the material of the sub-coating. By way of example, when the first coating is or comprises HPMC and the second coating comprises ethyl cellulose, the ethyl cellulose may optionally further comprise a minor amount (e.g. less than 50%, 40%, 30% or 20%) of the first coating material, HPMC in this example. In such embodiments the first coating and the second coating are considered to be different.

The composition of the invention may comprise cyclosporin, a hydrogel forming polymer matrix, a surfactant and an oil phase being dispersed in the hydrogel forming polymer matrix, wherein the surfactant may be a medium chain or long chain fatty acid mono- or di-glyceride or a combination thereof and may not comprise or may not be a polyethyleneglycol ether or ester. Optionally, the composition may further comprise a first coating, wherein the first coating is or comprises a water-soluble cellulose ether as described above and elsewhere herein. In addition to the first coating or alternatively to the first coating the composition may comprise a second coating. Optionally, the second coating is or comprises a coating, suitably a polymeric coating, to control or modulate release of the active ingredient from the composition. The polymeric coating may be as further described elsewhere in this specification.

Where the composition comprises a first coating and a second coating the second coating may be outside the first coating.

The composition may comprise: a core, wherein the core comprises cyclosporin, a hydrogel forming polymer matrix, a surfactant and an oil phase being dispersed in the hydrogel forming polymer matrix; a first coating outside the core, wherein the first coating is a water-soluble cellulose ether as described above and elsewhere herein; and a second coating outside the first coating, wherein the surfactant is as described herein, the surfactant being, for example, a medium chain or long chain fatty acid mono- or di-glyceride or a combination thereof and not comprising or not being a polyethyleneglycol ether or ester. Throughout this specification "core" may refer to a core comprising cyclosporin, a hydrogel forming polymer matrix, a surfactant, as described herein, and an oil phase being dispersed in the hydrogel forming polymer matrix.

According to an embodiment of the invention, the surfactant optionally is a medium chain or long chain fatty acid mono-glyceride, di-glyceride or a combination thereof, the first coating is or comprises a water-soluble cellulose ether, and the composition further comprises a second coating outside the first coating wherein the second coating is or comprises a coating, suitably a polymeric coating, to control or modulate release of the active ingredient from the composition. The polymeric coating may be as further described elsewhere in this specification.

The first coating suitably may be or comprise a water-soluble cellulose ether. The water-soluble cellulose ether may be any cellulose ether or derivative of a cellulose ether, for example an ester of a cellulose ether that is soluble in water. Therefore, the water-soluble cellulose ether may be selected from: an alkyl cellulose; a hydroxyalkyl cellulose; a hydroxyalkyl alkyl cellulose; and a carboxyalkyl cellulose. Suitably the first coating is or comprises one or more water-soluble cellulose ethers selected from: methyl cellulose, hydroxyethyl cellulose, hydroxypropyl cellulose and hydroxypropylmethyl cellulose, and combinations thereof. In particular embodiments the first coating is or comprises a water-soluble hydroxypropyl methylcellulose. The water-soluble cellulose ethers and water-soluble derivatives thereof (e.g. water-soluble esters of a cellulose ether) present in the first coating (sub-coat) suitably form at least 20%, 40%, 50%, 60%, 70%, 80%, 85% or 90% by weight of the dry weight of the first coating.

In accordance with the present invention there is provided a pharmaceutical composition comprising a core and a first coating, wherein the core comprises cyclosporin, a hydrogel forming polymer matrix, a surfactant and an oil phase being dispersed in the hydrogel forming polymer matrix and the first coating comprises or is a water soluble cellulose ether and the first coating is present in an amount corresponding to a weight gain due to the first coating of from 0.5% to 20% by weight of the core, wherein the surfactant is as described herein, for example a medium chain or long chain fatty acid mono- or di-glyceride or a combination thereof and not comprising or not being a polyethyleneglycol ether or ester.

The first coating of the present invention modifies the release of the active ingredient from the composition. There would be an expectation that a coating on a composition would slow the rate of release of the active ingredient within a composition. One might reasonably expect this as coating the composition with additional material would provide an additional barrier to a dissolution medium coming into contact with the active ingredient in the composition. In contrast to this expected outcome, the compositions of the present invention comprise a coating comprising or being a water soluble cellulose ether that increases the rate of release of the active ingredient compared to a composition without the coating. In addition the coating of the present invention has the beneficial effect of maintaining the active ingredient in solution, whereas a comparable composition lacking the coating of the invention provides less of the active ingredient in solution as time progresses. Without wishing to be bound by theory, it is believed that the coating prevents precipitation of the active ingredient from solution, thereby maintaining a higher amount of the active in solution.

Throughout the present application active ingredient, active, and pharmaceutically active ingredient are used interchangeably and all refer to cyclosporin, preferably cyclosporin A.

The composition of the present invention may take any form known to the person skilled in the art. Preferably, the composition is an oral composition. The composition may be in the form of a single minibead or a multiplicity of minibeads. Accordingly the invention provides a minibead comprising cyclosporin, a hydrogel forming polymer matrix, a surfactant and an oil phase being dispersed in the hydrogel forming polymer matrix, wherein the surfactant is or comprises a medium chain or long chain fatty acid mono- or di-glyceride or a combination thereof and does not comprise or is not a polyethyleneglycol ether or ester. The invention also provides a composition comprising a multiplicity of minibeads. Similarly, the invention provides a multiple minibead formulation comprising a unit dosage form comprising a multiplicity of minibeads.

The invention also provides for a pharmaceutical composition comprising a core and a first coating, wherein the core comprises cyclosporin, a hydrogel forming polymer matrix, a surfactant and an oil phase being dispersed in the hydrogel forming polymer matrix and the first coating comprises or is a water-soluble cellulose ether and the first coating has a thickness of from 1 µm to 1 mm wherein the surfactant is as described herein, for example a medium chain or long chain fatty acid mono- or di-glyceride or a combination thereof and not comprising or not being a polyethyleneglycol ether or ester.

Any of the pharmaceutical compositions of the invention may comprise a further coating, referred to herein as a second coating. The second coating may be outside the first coating. The second coating may be or comprise a delayed release polymer. In any embodiment and any aspect of the invention the first and second coating may be different.

The invention therefore, contemplates a pharmaceutical composition comprising a core, a first coating and a second coating outside of the first coating, wherein the core comprises cyclosporin, a hydrogel forming polymer matrix, a surfactant and an oil phase being dispersed in the hydrogel forming polymer matrix, the first coating comprises or is a water soluble cellulose ether (for example HPMC), and the second coating comprises or is a delayed release polymer (for example ethylcellulose), wherein the surfactant is a medium chain or long chain fatty acid mono- or di-glyceride or a combination thereof and does not comprise or is not a polyethyleneglycol ether or ester.

The composition of any aspect or embodiment of the invention may be in the form of a solid colloid. Furthermore, the core of a composition may be in the form of a solid colloid. The colloid comprises a continuous phase and a disperse phase. Suitable continuous phases and disperse phases which may be used to form the core are defined in more detail below and in the detailed description of the invention. The continuous phase may comprise or be the hydrogel forming polymer matrix. Hence, where the continuous phase is the hydrogel forming polymer matrix, the composition of the invention may take the form of a solid unit of the hydrogel forming polymer comprising a disperse phase. The disperse phase may be droplets dispersed in the continuous phase, or the hydrogel forming polymer matrix. The disperse phase may comprise or be the oil phase.

Thus, the invention provides a composition in the form of a solid colloid comprising a continuous phase and a dispersed phase, wherein the continuous phase comprises or is a hydrogel forming polymer matrix and the continuous phase is or comprises oil phase, wherein the composition further comprises cyclosporin and a surfactant. Preferably, the surfactant is a medium chain or long chain fatty acid mono- or di-glyceride or a combination thereof and does not comprise or is not a polyethyleneglycol ether or ester. The oil phase may comprise the cyclosporin in solution.

The composition may comprise a core in the form of a solid colloid comprising a continuous phase and a dispersed phase, wherein the continuous phase comprises or is a hydrogel forming polymer matrix and the continuous phase is or comprises oil phase, wherein the core further comprises cyclosporin and a surfactant, wherein the surfactant is a medium chain or long chain fatty acid mono- or di-glyceride or a combination thereof and does not comprise or is not a polyethyleneglycol ether or ester. The oil phase may comprise the cyclosporin in solution.

The continuous phase of a solid colloid composition or core is or comprises a hydrogel-forming polymer matrix. In embodiments the hydrogel-forming polymer matrix is or comprises a hydrocolloid, a non-hydrocolloid gum or chitosan. In a particular embodiment the hydrogel-forming polymer matrix is or comprises gelatin, agar, a polyethylene glycol, starch, casein, chitosan, soya bean protein, safflower protein, alginates, gellan gum, carrageenan, xanthan gum, phthalated gelatin, succinated gelatin, cellulosephthalate-acetate, oleoresin, polyvinylacetate, polymerisates of acrylic or methacrylic esters and polyvinylacetate-phthalate and any derivative of any of the foregoing; or a mixture of two or more such polymers. In a further embodiment the hydrogel-forming polymer matrix is or comprises a hydrocolloid selected from carrageenan, gelatin, agar and pectin, or a combination thereof optionally selected from gelatin and agar or a combination thereof. Particularly, the polymer of the hydrogel-forming polymer matrix is or comprises gelatin. In an embodiment, the hydrogel-forming polymer does not comprise a cellulose or a cellulose derivative, e.g. does not comprise a cellulose ether.

In this aspect of the invention the composition may be in the form of a solid colloid the colloid comprising a continuous phase and a disperse phase and the cyclosporin may be in solution or suspended in the disperse phase. For example, the cyclosporin may be in solution in the disperse phase.

It is to be understood that the individual embodiments described above may be combined with one or more of the other embodiments described to provide further embodiments of the invention.

The first coating may be in contact with the core. The second coating may be on the first coating. In embodiments the first coating is in contact with the core and the second coating is on the first coating.

The second coating may be or may comprise a delayed release polymer and the delayed release polymer may be selected from an enteric polymer, a pH independent polymer, a pH dependent polymer and a polymer specifically susceptible to degradation by bacterial enzymes in the gastrointestinal tract, or a combination of two or more such polymers. Hence, the second coating may be any of the aforementioned delayed release polymers or any may be or possess the characteristics mentioned in relation to the delayed release polymer mentioned below.

In embodiments the delayed release polymer may be water-soluble or water-permeable in an aqueous medium with a pH greater than 6.5. The delayed release polymer may be or comprise a pH-independent polymer, for example ethyl cellulose.

In any aspect and any embodiment of the invention the water-soluble cellulose ether may be selected from any one or a combination of: methyl cellulose, hydroxyethyl cellulose, hydroxypropyl cellulose and hydroxypropyl methylcellulose. The water-soluble cellulose ether may preferably be hydroxylpropyl methylcellulose (HPMC).

In embodiments the first coating may be or comprise hydroxypropyl methyl cellulose and the second coating may be or comprise ethyl cellulose.

The disclosure of the weight gain of the first coating is given as a % by weight of the core. Similarly, the weight gain of the second coating is given as a % by weight of the core, where there is no first coating (sub-coat) on the core. Where the composition comprises a first coating, the weight gain of the second coating is given as a % by weight of the composition that is coated by the second coating, for example the core and the first coating.

The hydrogel forming polymer or the hydrogel forming polymer matrix may be or comprise a hydrocolloid, a non-hydrocolloid gum or chitosan. The hydrogel forming polymer or the hydrogel forming polymer matrix may be a reversible hydrocolloid, for example a thermoreversible hydrocolloid or a thermoreversible hydrogel forming polymer. Alternatively, the hydrogel forming polymer or the hydrogel forming polymer matrix may be or comprise an irreversible hydrocolloid. The hydrogel forming polymer or the hydrogel forming polymer matrix may be or comprise gelatin, agar, a polyethylene glycol, starch, casein, chitosan, soya bean protein, safflower protein, alginates, gellan gum, carrageenan, xanthan gum, phthalated gelatin, succinated gelatin, cellulosephthalate-acetate, oleoresin, polyvinylacetate, polymerisates of acrylic or methacrylic esters and polyvinylacetate-phthalate and any derivative of any of the foregoing; or a mixture of one or more such a hydrogel forming polymers. The hydrogel forming polymer or the hydrogel forming polymer matrix may be or comprise a hydrocolloid selected from carrageenan, gelatin, agar and pectin, or a combination thereof optionally selected from gelatin and agar or a combination thereof, more optionally the hydrogel forming polymer or the or the hydrogel forming polymer matrix forming polymer matrix is or comprises gelatin. The hydrogel forming polymer matrix is or comprises a non-hydrocolloid gum optionally selected from a cross-linked salt of alginic acid. In preferred embodiments the hydrogel forming polymer or the hydrogel forming polymer matrix is or comprises gelatin.

In embodiments the hydrogel forming polymer or the hydrogel forming polymer matrix further comprising a plasticiser, optionally a plasticiser selected from glycerin, a polyol for example sorbitol, polyethylene glycol and triethyl citrate or a mixture thereof, particularly sorbitol.

The hydrogel forming polymer matrix may encapsulate the cyclosporin. The cyclosporin may be encapsulated in solution. The cyclosporin may be in solution or suspended in another component, for example the oil phase or the disperse phase discussed elsewhere, of the composition that is also encapsulated by the hydrogel forming polymer matrix.

The disperse phase may be solid, semi-solid or liquid. In particular, the disperse phase may be liquid. In other particular instances the disperse phase may be semi-solid, for example it may be waxy.

The disperse phase may be or comprise the oil phase, for example the oil phase may be a solid, a semi-solid or a liquid. Suitably the disperse phase or the oil phase is or comprises a liquid lipid and optionally a solvent miscible therewith. The liquid lipid is optionally a medium chain mono- di- or triglyceride (particularly a medium chain triglyceride).

Suitably, cyclosporin is soluble in the solvent. The solvent may be an alcohol (for example ethanol or isopropanol), a glycol (for example propylene glycol or a polyethylene glycol) or a glycol ether. The solvent may be a glycol ether, for example an ethylene glycol ether, more particularly an alkyl, aryl or aralkyl ethylene glycol ether. The solvent may be a glycol ether selected from 2-methoxyethanol; 2-ethoxyethanol; 2-propoxyethanol; 2-isopropoxyethanol; 2-butoxyethanol; 2-phenoxyethanol; 2-benzyloxyethanol; 2-(2-methoxyethoxy)ethanol; 2-(2-ethoxyethoxy)ethanol; and 2-(2-butoxyethoxy)ethanol. More particularly the solvent is 2-(2-ethoxyethoxy)ethanol or 2-phenoxyethanol. A particular solvent is 2-(2-ethoxyethoxy)ethanol.

The cyclosporin may be dissolved in the disperse phase. The cyclosporin may be suspended in the disperse phase. The disperse phase may be as described elsewhere herein, for example it may be as described in the immediately preceding two paragraphs.

The oil phase or disperse phase may be or may comprise a liquid lipid. Particularly, the oil phase or disperse phase may comprise or be a short-, medium- or long-chain triglyceride formulation, or a combination thereof, for example a caprylic/capric triglyceride, i.e. a caprylic/capric triglyceride formulation.

Accordingly, in an embodiment the liquid composition comprises an aqueous phase, a surfactant and an oil phase in which cyclosporin is dissolved, wherein the surfactant may comprise or be a medium chain or long chain fatty acid mono- or di-glyceride or a combination thereof and does not comprise is not a polyethyleneglycol ether or ester, the aqueous phase may comprise a hydrogel forming polymer, and the oil phase comprises a short-, medium- or long-chain triglyceride formulation, or a combination thereof (optionally a caprylic/capric triglyceride, i.e. a caprylic/capric triglyceride formulation) and is dispersed in the aqueous phase. The oil phase may be dispersed in the aqueous phase in the form of a colloid, for example a liquid-liquid colloid. The oil phase may be dispersed in the aqueous phase in the form of an emulsion. Accordingly, the liquid composition may be a liquid emulsion composition.

Additionally, in an embodiment the composition comprises cyclosporin, a hydrogel forming polymer matrix, a surfactant and an oil phase comprising a short-, medium- or long-chain triglyceride formulation, or a combination thereof (optionally a caprylic/capric triglyceride, i.e. a caprylic/capric triglyceride formulation) and being dispersed in the hydrogel forming polymer matrix, wherein the surfactant may be or may comprise a medium chain or long chain fatty acid mono- or di-glyceride or a combination thereof and does not comprise or is not a polyethyleneglycol ether or ester. The composition may be in the form of a dried colloid. The composition may be in the form of a bead.

In a particular embodiment the disperse phase or the oil phase further comprises a solvent, thus optionally the disperse phase or the oil phase may be or comprise a liquid lipid and a solvent. The solvent may be miscible with the liquid lipid and water, optionally wherein the solvent is selected from 2-(2-ethoxyethoxy)ethanol and a poly(ethylene glycol), particularly wherein the solvent is 2-(2-ethoxyethoxy) ethanol. In a further embodiment the disperse phase or oil phase is or comprises a medium chain mono- di- or triglyceride (particularly a medium chain triglyceride), 2-(ethoxyethoxy)ethanol and the surfactant. The disperse phase or oil phase as described in this paragraph may contain the cyclosporin, the cyclosporin may optionally be in solution.

Preferably, the oil phase or disperse phase comprises a short-, medium- or long-chain triglyceride formulation, or a combination thereof (optionally a caprylic/capric triglyceride, i.e. a caprylic/capric triglyceride formulation). Where the oil phase or disperse phase comprises a short-, medium- or long-chain triglyceride formulation, or a combination thereof, the triglyceride is substantially all of the disperse phase or oil phase (optionally the liquid lipid). For example, the oil phase or disperse phase may comprise short-, medium- or long-chain triglyceride formulation in an amount of greater than 80% of the oil phase or disperse phase (optionally the liquid lipid), optionally greater than 85%, 90%, 95%, 97%, 98% or 99%. Suitably, the short-, medium- or long-chain triglyceride formulation is substantially free of mono- or di-glycerides. For example, the surfactant may comprise less than 10%, 8%, 5%, 3%, 2% or 1% of a mono- or di-glycerides.

In embodiments the composition further comprises one or more additional surfactants, preferably one additional surfactant. The additional surfactant may be referred to as a second surfactant or further surfactant throughout the specification and these terms are used interchangeably. Where the compositions of the invention comprise a second surfactant the surfactant that may be or may comprise a medium chain or long chain fatty acid mono- or di-glyceride or a combination thereof and does not comprise or is not a polyethyleneglycol ether or ester is referred to as a first surfactant.

Suitable surfactants for the second surfactant are described in more detail in the detailed description of the invention. The second surfactant may be an anionic or non-ionic surfactant. The second surfactant may be a sucrose monoester, an alkyl sulfate or a polyethylene glycol alkyl ether. The second surfactant may be sucrose laurate, sucrose palmitate, sodium octyl sulfate, sodium octadecyl sulfate, sodium dodecyl sulphate, polyethylene glycol hexadecyl ether, polyoxyethylene glycol octadecyl ether, or polyethylene glycol dodecyl ether. Optionally, the second surfactant may be sodium octyl sulfate, sodium octadecyl sulfate, sodium dodecyl sulphate or polyethylene glycol dodecyl ether.

Preferably the second surfactant is an anionic surfactant. For example, the second surfactant may be an alkyl sulphate, for example sodium octyl sulfate, sodium octadecyl sulfate, or sodium dodecyl sulphate (preferably sodium dodecyl sulphate).

In those embodiments where the liquid composition is in the form of a colloid, the composition is in the form of a solid colloid or the composition comprises a core in the form of a solid colloid, the colloid comprises a continuous phase and a disperse phase, wherein the continuous phase comprises the hydrogel-forming polymer matrix and the second surfactant may be present in the continuous phase, the disperse phase or both. Preferably the second surfactant is present in the continuous phase and the first surfactant is present in the disperse phase. Accordingly, the aqueous phase of the liquid composition may comprise the second surfactant and the oil phase may comprise the first surfactant. In one embodiment the core further comprises one additional surfactant present in at least the continuous phase, the surfactant having an HLB value of greater than 10, for example greater than 20.

The composition may have the characteristics of a composition formed by mixing a disperse phase with a continuous phase to form a colloid, wherein the continuous phase is an aqueous phase comprising hydrogel forming polymer and the disperse phase is a oil phase, wherein the pharmaceutically active ingredient is in the continuous phase or the disperse phase, wherein the colloid is gelled to form the composition. The composition is thus in the form of a solid colloid.

Furthermore, the composition may comprise a core having the characteristics of a core formed by mixing a disperse phase with a continuous phase to form a colloid, wherein the continuous phase is an aqueous phase comprising hydrogel forming polymer and the disperse phase is a oil phase, wherein the pharmaceutically active ingredient is in the continuous phase or the disperse phase, wherein the colloid is gelled to form the core. The core is thus in the form of a solid colloid.

The cyclosporin may be present in the composition in solution or in suspension. In the aspect where the invention provides a liquid composition the cyclosporin is in solution.

The liquid composition comprises an aqueous phase, a surfactant and an oil phase in which cyclosporin is dissolved and may have the characteristics of a liquid composition obtained by a process comprising:
(i) dissolving a hydrogel-forming polymer in an aqueous liquid to form an aqueous phase solution;
(ii) dissolving the cyclosporin in the oil phase to form a solution; and
(iii) mixing the aqueous phase solution (i) and the oil phase solution (ii) to form a colloid (optionally an emulsion).

The composition or core of the invention may have the characteristics of a composition obtained by a process comprising:
(a) ejecting the liquid composition through a nozzle to form droplets;
(b) causing or allowing the a hydrogel-forming polymer to gel or solidify to form a hydrogel-forming polymer matrix; and
(c) drying the solid.

The composition or core comprises cyclosporin, a hydrogel forming polymer matrix, a surfactant and an oil phase and may have the characteristics of a composition obtained by a process comprising:
(i) dissolving a hydrogel-forming polymer in an aqueous liquid to form an aqueous phase solution;
(ii) dissolving the cyclosporin in the oil phase to form a solution;

(iii) mixing the aqueous phase solution (i) and the oil phase solution (ii) to form a colloid (optionally an emulsion);
(iv) ejecting the colloid through a nozzle to form droplets;
(v) causing or allowing the a hydrogel-forming polymer to gel or solidify to form a hydrogel-forming polymer matrix; and
(vi) drying the solid.

The aqueous phase and oil phase may be mixed (for example in step (iii)) in an oil phase to aqueous phase ratio of from 1:4 to 1:10, optionally from 1:4 to 1:8, from 1:5 to 1:7. For example, the oil phase to aqueous phase ratio may be 1:4, 1:5, 1:6 or 1:7.

The oil phase solution (ii) may be prepared by dissolving or dispersing the cyclosporin A in a suitable hydrophobic liquid. The hydrophobic liquid may be for example, any of the oils or liquid lipids described herein. By way of example the hydrophobic liquid may be, or comprise, saturated or unsaturated fatty acids or a triglyceride, or an ester or ether thereof with polyethylene glycols. A particular oil for the oil phase is or comprises a triglyceride, for example an oil comprising a medium chain triglyceride, optionally wherein the oil comprises a triglyceride of at least one fatty acid selected from fatty acids having 6, 7, 8, 9, 10, 11 or 12 carbon atoms, e.g. $C_8$-$C_{10}$ fatty acids.

The aqueous phase solution (i) may further comprise a surfactant selected from: sucrose monoester, an alkyl sulfate and a polyethylene glycol alkyl ether, optionally the sselected from: sucrose laurate, sucrose palmitate, sodium octyl sulfate, sodium octadecyl sulfate, sodium dodecyl sulphate, polyethylene glycol hexadecyl ether, polyoxyethylene glycol octadecyl ether, and polyethylene glycol dodecyl ether. The aqueous phase solution (i) may further comprise a surfactant selected from: sodium octyl sulfate, sodium octadecyl sulfate, sodium dodecyl sulphate or polyethylene glycol dodecyl ether. Preferably, the aqueous phase solution (i) further comprises an anionic surfactant, e.g. as described elsewhere herein, for example sodium dodecyl sulphate (SDS).

In one embodiment the liquid composition or composition having the characteristics of a liquid composition or composition obtained by the process above is a composition or liquid composition comprising an oil phase dispersed in the aqueous phase solution, wherein the liquid composition or composition is or comprises cyclosporin, glyceryl monooleate/dioleate, gelatin, SDS, sorbitol, caprylic/capric triglyceride, 2-(ethoxyethoxy)ethanol; wherein the aqueous phase solution (i) is or comprises gelatin, sorbitol and SDS; and the oil phase solution (ii) is or comprises cyclosporin, glyceryl monooleate/dioleate, caprylic/capric triglyceride, 2-(ethoxyethoxy)ethanol and the active ingredient.

Cores having the characteristics of cores obtained by the above-described processes, for example cores obtained by the processes, may be coated to provide a coating that comprises or is a water-soluble cellulose ether, optionally with a second coating to control or modify release, preferably a polymeric coating as described above and herein. The coated composition may be obtained by applying to the core the coating, e.g. applying to the core first and second coatings as described. Before the coating is applied, the core may be made by a process having steps (i) to (vi) or (i) to (v) described above. Suitable methods for applying the coating(s) are described below and include applying the coatings by spray coating a coating composition onto the core. The processes having steps (i) to (vi) or (i) to (v) themselves form aspects of the invention.

The composition or core may further comprise a second surfactant (also referred to as a further surfactant), optionally wherein the second surfactant is an anionic surfactant, optionally selected from alkyl sulphates, carboxylates or phospholipids, or a non-ionic surfactant, optionally selected from sorbitan-based surfactants, PEG-fatty acids, fatty alcohol ethoxylates, alkylphenol ethoxylate, fatty acid ethoxylates, fatty amide ethoxylates, alkyl glucosides or glyceryl fatty acids, or poloxamers, or a combination thereof. Hence the liquid composition of the invention may comprise at least the following features, an aqueous phase comprising a hydrogel forming polymer, a first surfactant and an oil phase being dispersed in the aqueous phase in which cyclosporin is dissolved and a second surfactant. Similarly, the composition of the invention may comprise at least the following features, cyclosporin, a hydrogel forming polymer matrix, a first surfactant and an oil phase being dispersed in the hydrogel forming polymer matrix and a second surfactant.

In embodiments where the composition is in the form of a solid colloid, the second surfactant may be in the disperse phase or the continuous phase. The second surfactant may be in the continuous phase and may be an anionic surfactant, for example at least one surfactant selected from fatty acid salts and bile salts, particularly an alkyl sulphate, for example sodium dodecyl sulphate. The surfactant in the disperse phase may be a non-ionic surfactant.

In embodiments the composition comprises a second surfactant which is or comprises an anionic surfactant, for example sodium dodecyl sulphate, which is in the continuous phase.

In embodiments the composition further comprises a combination of excipients selected from: an anionic surfactant and a solvent; an anionic surfactant and an oil; and an anionic surfactant, a solvent and an oil. Preferably, the anionic surfactant is an alkyl sulphate, for example sodium dodecyl sulphate, the oil is a medium chain mono-, di- and/or tri-glyceride (optionally a medium chain triglyceride, for example caprylic/capric triglyceride, and the solvent is 2-(ethoxyethoxy)ethanol.

The composition may further comprise an excipient selected from: a surfactant, a solubiliser, a permeability enhancer, a disintegrant, a crystallisation inhibitor, a pH modifier, a stabiliser, or a combination thereof.

The composition of the invention or, where the composition comprises a core, the core may comprise a disperse phase or oil phase, wherein the disperse phase or oil phase is or comprises:

cyclosporin;

a medium or long chain fatty acid mono- or di-ester or a combination thereof which does not comprise is not a polyethyleneglycol ether or ester, such as a medium or long chain fatty acid mono- or di-glyceride or a combination thereof, for example glyceryl monooleate/dioleate;

a medium chain mono- di- or tri-glyceride, for example caprylic/capric triglyceride; and a solvent, for example 2-(ethoxyethoxy)ethanol and the composition or the core may further comprise a continuous phase or aqueous phase being or comprising:

an anionic surfactant, for example at least one surfactant selected from fatty acid salts and bile salts, particularly an alkyl sulphate, for example sodium dodecyl sulphate a hydrogel forming polymer matrix which is or comprises a hydrocolloid selected from carrageenan, gelatin, agar and pectin, or a combination thereof optionally selected from gelatin and agar or a combination thereof, more optionally the polymer of the a hydrogel forming polymer matrix is or comprises gelatin; and optionally a plasticiser, for example a plasticiser selected from glycerin, a polyol for example sorbitol, polyethylene glycol and triethyl citrate or a mixture thereof, particularly sorbitol.

In one embodiment the composition comprises a core and a coating outside the core, wherein the core is in the form of a solid colloid, the colloid comprising a continuous phase and a disperse phase, wherein the disperse phase is or comprises:
  cyclosporin A;
  a medium or long chain fatty acid mono- or di-glyceride or a combination thereof which does not comprise is not a polyethyleneglycol ether or ester, for example glyceryl monooleate/dioleate;
  a medium chain mono- di- and/or tri-glyceride, for example caprylic/capric triglyceride; and
  a co-solvent, for example 2-(ethoxyethoxy)ethanol;
and wherein the continuous phase is or comprises:
  a hydrogel-forming polymer matrix which is or comprises a hydrocolloid selected from carrageenan, gelatin, agar and pectin, or a combination thereof optionally selected from gelatin and agar or a combination thereof, more optionally the polymer of the water-soluble polymer matrix is or comprises gelatin;
  optionally a plasticiser, optionally a plasticiser selected from glycerin, a polyol for example sorbitol, polyethylene glycol and triethyl citrate or a mixture thereof, particularly sorbitol; and
  an anionic surfactant, for example at least one surfactant selected from fatty acid salts and bile salts, particularly an alkyl sulphate, for example sodium dodecyl sulphate;
and wherein the coating on the core is a first coating or a second coating, as described herein.

Suitably the coating comprises a first coating and a second coating outside the first coating; and wherein
  the first coating is the coating which is or comprises a water-soluble cellulose ether as described above; and
  the second coating is or comprises a coating, suitably a polymeric coating, as defined above to control or modulate release of cyclosporin A from the composition.

In embodiments comprising a first coating and/or a second coating, for example as mentioned in the immediately preceding paragraph, a particular first coating is or comprises hydroxypropylmethyl cellulose and a particular second coating outside the first coating is or comprises a pH independent polymer, for example ethyl cellulose; more particularly the second coating is or comprises ethyl cellulose and optionally a polysaccharide selected from water soluble and naturally occurring polysaccharides, for example pectin or another water-soluble naturally occurring polysaccharide. The second coating may therefore contain pectin or another said polysaccharide or it may be substantially free of pectin and other said polysaccharides. There are therefore disclosed second coatings which comprise ethylcellulose as a controlled release polymer and which further comprise pectin or another said polysaccharide as well as second coatings which comprise ethylcellulose as a controlled release polymer and which do not further comprise pectin or another said polysaccharide.

The hydrogel forming polymer, optionally comprising gelatin, may be present in an amount of 300 to 700 mg/g (optionally 380 to 500 mg/g). The medium chain mono, di and/or tri-glycerides, may be present in an amount of 20 to 200 mg/g (optionally 40 to 80 mg/g). The solvent, for example 2-(ethoxyethoxy)ethanol, may be present in an amount of 100 to 250 mg/g (optionally 160 to 200 mg/g). The medium or long chain fatty acid mono- or di-ester or a combination thereof which does not comprise or is not a polyethyleneglycol ether or ester, for example glyceryl monooleate/dioleate, may be present in an amount of 80 to 200 mg/g (optionally 100 to 150 mg/g). The anionic surfactant, for example sodium dodecyl sulphate, may be present in an amount of up to 100 mg/g or up to 50 mg/g (optionally 10-70 mg/g, 15-60 mgm/g or 15-50 mg/g, preferably 25-50 mg/g or 25-45 mg/g).

The composition or the core may comprise a hydrogel forming polymer comprising gelatin, optionally in an amount of 300 to 700 mg/g, the core further comprising medium chain mono, di and/or tri-glycerides, optionally in an amount of 20 to 200 mg/g, wherein the composition or core further comprises the following components:
  solvent, for example 2-(ethoxyethoxy)ethanol, optionally in an amount of 100 to 250 mg/g;
  a medium or long chain fatty acid mono- or di-ester or a combination thereof which does not comprise or is not a polyethyleneglycol ether or ester, for example glyceryl monooleate/dioleate,
optionally in an amount of 80 to 200 mg/g; and
  anionic surfactant, for example sodium dodecyl sulphate, optionally in an amount of up to 70 mg/g or up to 50 mg/g.

As will be recognised the composition or core further comprises cyclosporin.

The composition or the core may comprise:
  a hydrogel forming polymer, for example which is, or comprises, gelatin in an amount of 300 to 700 mg/g;
  cyclosporin in an amount of up to about 250 mg/g, for example 50 to 250 mg/g;
  medium chain triglycerides, for example Miglyol 810 in an amount of 20 to 200 mg/g, optionally a solvent, for example 2-(ethoxyethoxy)ethanol, which when present is in an amount of 100 to 250 mg/g;
  a surfactant comprising a medium or long chain fatty acid mono- or di-ester or a combination thereof which does not comprise or is not a polyethyleneglycol ether or ester, for example glyceryl monooleate/dioleate, in an amount of 80 to 200 mg/g; and
  anionic surfactant, for example sodium dodecyl sulphate, in an amount of up to 60 mg/g or up to 50 mg/g, for example 10 to 50 mg/g, or optionally 20 to 45 mg/g.

The composition or the core may comprise:
  gelatin in an amount of 380-500 mg/g;
  cyclosporin in an amount of 90-250 mg/g (optionally 90-200 mg/g or 90-160 mg/g); and
  caprylic/capric triglyceride in an amount of 40-80 mg/g;
  2-(2-ethoxyethoxy) ethanol in an amount of 160-200 mg/g;
  glyceryl monooleate and/or glyceryl dioleate in an amount of 100-150 mg/g; and
  SDS in an amount of 15-60 mg/g or 15-50 mg/g (optionally 25-50 mg/g or 25-45 mg/g);
  and
optionally D-sorbitol in an amount of 30-80 mg/g.

The composition or the core may comprise:
  gelatin in an amount of 380-500 mg/g;
  cyclosporin in an amount of 90-140 mg/g; and
  caprylic/capric triglyceride in an amount of 40-80 mg/g;
  2-(2-ethoxyethoxy) ethanol in an amount of 160-200 mg/g;
  glyceryl monooleate and/or glyceryl dioleate in an amount of 100-150 mg/g; and
  SDS in an amount of 15-50 mg/g (optionally 25-50 mg/g or 25-45 mg/g); and
  optionally D-sorbitol in an amount of 30-80 mg/g.

The composition or core may be a colloid. Where the composition or the core is a colloid, the cyclosporin may be dissolved in the disperse phase of the colloid.

The composition or core may be a colloid; thus, the composition or core may comprise a continuous phase and a disperse phase wherein the continuous phase comprises:
gelatin in an amount of 380-500 mg/g; and
optionally D-sorbitol in an amount of 30-80 mg/g;
the disperse phase comprises:
cyclosporin in an amount of 90-140 mg/g; and
caprylic/capric triglyceride in an amount of 40-80 mg/g;
and the composition further comprises:
2-(2-ethoxyethoxy)ethanol in an amount of 160-200 mg/g;
glyceryl monooleate and/or glyceryl dioleate in an amount of 100-150 mg/g; and
SDS in an amount of 15-50 mg/g.

A colloidal composition or core comprising a continuous phase comprising:
a hydrogel forming polymer matrix comprising gelatin in an amount of 300 to 700 mg/g;
a disperse phase comprising:
cyclosporin in an amount of up to 200 mg/g; and
a medium chain tri-glyceride in an amount of 20 to 200 mg/g;
and the composition further comprising:
solvent in an amount of 100 to 250 mg/g;
surfactant (a first surfactant) being or comprising a medium or long chain fatty acid mono- or di-ester or a combination thereof which does not comprise is not a polyethyleneglycol ether or ester, for example glyceryl monooleate/dioleate; and
anionic surfactant (a second surfactant) in an amount of up to 50 mg/g.

In the embodiments above which refer to mg/g of a component, the concentration is based upon the dry weight of the composition.

Suitably in the six compositions or cores described immediately above, the composition is a colloid comprising a disperse phase and a continuous phase; wherein the disperse phase comprises cyclosporin, medium-chain triglyceride and medium or long chain fatty acid mono- or di-ester surfactant; and the continuous phase comprises the hydrogel forming polymer (e.g. gelatin) and an anionic surfactant (e.g. SDS).

The invention includes within its scope compositions wherein the core is a colloid having a disperse phase and the continuous phase (matrix phase) of the colloid further includes dispersed particles of a pharmaceutically active ingredient, for example microparticles or nanoparticles. The disperse phase and continuous phase may otherwise be as described elsewhere in this specification.

The composition of the invention and/or the core may be in the form of a minibead. It may be that the core is a minibead and the first coating and, where applicable, the second coating in conjunction with the core are in the form of a minibead. However, it may be possible for the core to be a minibead and the composition not to be a minibead. The composition may additionally comprise a multiplicity of minibeads. Hence the invention contemplates a minibead with the features of the pharmaceutical compositions disclosed herein.

The composition or the minibead may have a largest cross sectional dimension of a core of from about 0.01 mm to about 5 mm, for example from 1 mm to 5 mm, as in the case of from 1 mm to 3 mm or 1 mm to 2 mm. The minibead may be spheroidal. The spheroidal minibeads may have an aspect ratio of no more than 1.5, for example from 1.1 to 1.5.

The composition of the invention may be for oral administration. The composition may be formulated into a unit dosage form for oral administration comprising from 0.1 mg to 1000 mg, optionally from 1 mg to 500 mg, for example 10 mg to 300 mg, or 25 to 250 mg suitably about 25 mg, about 35 mg, about 37.5 mg, about 75 mg, about 150 mg, about 180 mg, about 210 mg, about 250 mg or about 300 mg of cyclosporin. Suitably the composition is in a multiple minibead unit dosage form selected from multiple minibeads in, for example, soft or hard gel capsules, gelatin capsules, HPMC capsules, compressed tablets or sachets. The minibeads may be as described elsewhere herein.

The compositions described herein may be used to deliver cyclosporin A locally to specific locations in the GIT, for example the solid compositions described herein, may be adapted to provide release of cyclosporin A in at least the colon. The compositions may be used to provide the cyclosporin A locally in the GIT in a solubilised form, thereby providing high concentrations of cyclosporin in an active (available) form within the GIT where it acts to provide a therapeutic benefit in a number of medical conditions, particularly conditions affecting the GIT as described in more detail herein, such as ulcerative colitis. The release of cyclosporin A in an active form, for example a solubilised form, enables high concentrations of cyclosporin A to be absorbed directly into the local tissues of the GIT, such as the colon. However, as described above, systemic exposure cyclosporin A has a number of undesirable side effects. Therefore, a cyclosporin A composition which minimises systemic exposure to cyclosporin whilst maintaining therapeutically beneficial concentrations in the tissues of the GIT would be desirable.

The major pathways of cyclosporin A metabolism in humans are via cytochrome P450 3A4 (CYP 3A4) and cytochrome P450 2J2 (CYP 2J2), with three major metabolites being formed (two hydroxylated metabolites AM1, AM9 and one N-demethylated metabolite, AM4N). These metabolites have minimal, if any immunosuppressive activity. Therefore minimising the metabolism of cyclosporin is desirable, because this minimises the formation of inactive metabolites and maximises the quantity of cyclosporin available to interact locally with the tissues in the GIT. The primary metabolism of cyclosporin is via CYP 3A4, which is mainly found in the liver and the small intestine.

The total mass of CYP3A in the entire small intestine has been estimated to be 1% of that in the liver. However, despite the relatively low mass of CYP3A in the small intestine, enteric CYP3A can contribute significantly, and in some cases equally, with hepatic CYP3A, to the overall first-pass metabolism of several drugs including cyclosporin (Paine et al; Drug Metabolism and Disposition, Vol 34(5), 2006, 880-885). CYP 3A4 expression in the colon is lower than in the small intestine. Compositions which control the release of cyclosporin to limit or inhibit release in the upper GI tract, for example, by using one or more modified release coatings, may reduce enteric (i.e. non-systemic or "presystemic") P450 metabolism. However, some metabolism would still be expected resulting from the P450 expressed in the tissues in the lower GIT.

It has been found that certain compositions described herein, particularly compositions which release cyclosporin in the lower GI tract, especially in the colon, provide very low levels of cyclosporin metabolism following oral administration of the composition. The compositions therefore maximise the amount of active (solubilised) cyclosporin available to interact with the tissues of the GI tract following release of the cyclosporin from the composition. Without wishing to be bound by theory, it is thought that certain components present in the composition, for example the medium chain or long chain fatty acid mono- or di-glyceride surfactant present in the composition, may act to inhibit cyclosporin metabolism by CYP 3A4 present in the tissues of the GI tract. When the composition is provided in a modified release format which prevents or inhibits release of cyclosporin in the upper GI tract, systemic absorption and metabolism of cyclosporin in liver is also minimised. Therefore, the modified release compositions described herein minimise both systemic and enteric metabolism of cyclosporin. Low levels of cyclosporin metabolism may enable a lower dose of cyclosporin to be administered whilst maintaining a therapeutic benefit, thereby, widening the therapeutic window of the drug.

The relative degree of cyclosporin metabolism following oral administration of a composition may be assessed by, for example, measuring the concentration of cyclosporin and the concentration of cyclosporin metabolites present in a faecal sample collected from a patient following oral administration of a composition comprising cyclosporin. As will be illustrated in the Examples, modified release compositions comprising cyclosporin and the surfactant (for example Capmul GMO-50) resulted in very low levels of cyclosporin metabolism compared to a similar composition comprising a different surfactant (Cremophor). Compositions, particularly orally administered compositions, which exhibit low cyclosporin metabolism following release of cyclosporin from the composition, form a further aspect of the invention.

Accordingly, there is provided a composition comprising cyclosporin A, wherein after oral administration of the composition to a human, the mean concentration of cyclosporin A: the concentration of cyclosporin A metabolites in a faecal sample from the human is greater than 12:1. The mean concentration of cyclosporin A: the concentration of cyclosporin A metabolites in the faecal sample may be selected from: greater than 19:1; greater than 24:1; greater than 31:1 and greater than 50:1. The mean concentration of cyclosporin A: the concentration of cyclosporin A metabolites in the faecal sample may be selected from: from 20:1 to 30:1; from 20:1 to 35:1; from 20:1 to 40:1; from 20:1 to 60:1; from 30:1 to 50:1; and from 20:1 to 100:1. The mean concentration of cyclosporin A: the concentration of cyclosporin A metabolites in the faecal sample may be selected from 12.5:1 to 90:1; from 13:1 to 85:1; from 15:1 to 85:1; from 16:1 to 85:1; from 20:1 to 83:1; and from 65:1 to 79:1; optionally wherein the ratio is about 76:1.

The mean concentration of cyclosporin A: the concentration of cyclosporin A metabolites in the faecal sample may be determined from a faecal sample collected from 12 to 28 hours after oral administration of a single dose of the composition to the human. Alternatively the faecal sample may be collected after a more prolonged period of regular oral administration of the composition to the human, after which the cyclosporin and metabolite concentrations in the faeces may have reached a steady state, thereby reducing the variability in the measured ratio of cyclosporin:metabolites. For example, the faeces may be collected 4 to 6 hours after the oral administration of the last dose of a dosage regimen wherein the cyclosporin composition is orally administered once or twice per day for 2, 3 4, 5, 6 or 7 days. The faeces may, for example, be collected after oral administration of 75 mg of cyclosporin once or twice per day. Suitably, the faecal sample is collected 4 to 6 hours after oral administration of the last dose of a dosing regimen of the composition; the dosing regimen comprising once or twice daily oral administration of the composition to the human for seven days; optionally wherein the dosing regimen comprises once daily administration of the composition comprising 75 mg of cyclosporin A for seven days. In a further embodiment the composition comprising cyclosporin is orally administered once per day for two days (for example as a single 75 mg daily dose of cyclosporin) and the faecal sample is collected 4 to 6 hours after the last dose of the composition on the second day.

The main metabolites of cyclosporin are the AM1, AM4N and AM9 cyclosporin metabolites. The ratio of cyclosporin: cyclosporin metabolites in the faecal sample is suitably the ratio of cyclosporin:the total concentration of AM4N and AM9 cyclosporin metabolites. The ratio of cyclosporin: cyclosporin metabolites in the faecal sample may be the ratio of cyclosporin:the total concentration of AM1, AM4N and AM9 cyclosporin metabolites.

The concentration of cyclosporin and its metabolites in the faeces may be measured using any suitable analytical method, for example chromatography and mass spectrometry as illustrated in the Examples section.

Suitably the concentrations of cyclosporin and metabolites in the faeces are measured in faecal samples obtained from healthy male subjects so as to minimise the inter-patient variability in the measured values. The faecal samples are suitably obtained from healthy male subjects aged between 20 and 50 years, preferably weighing between 60 and 100 kg. Suitably the ratio is the arithmetic mean of the measured ratio of cyclosporin:cyclosporin metabolites in a representative number of subjects, for example at least 4, 5, 6, 7, 8, 9 or 10 subjects. Generally at least 4 subjects would be a sufficient number to provide a representative mean ratio.

The composition comprising cyclosporin A may be any composition comprising cyclosporin A which provides a ratio of cyclosporin:cyclosporin metabolites which is greater than 12:1 (or within any of the ranges described above in relation to this aspect of the invention). The composition is suitably a composition comprising cyclosporin A, wherein the composition releases cyclosporin A in a solubilised form when the composition is placed in an aqueous dissolution medium. By "solubilised" in meant that the cyclosporin in released in an active form, for example in a dissolved form such as a solution, when the composition is placed in an aqueous dissolution medium, for example an aqueous environment encountered in the lower GIT tract, particularly in the colon, following oral administration of the composition.

The composition may be, or comprise, cyclosporin A that is partially or completely dissolved in dissolved in a lipophilic substance. The lipophilic substance may be or comprise an oil, or a surfactant in which the cyclosporin is at least partially, or preferably fully dissolved. Suitable oils and surfactants which may be used include, but are not limited to any of the the oils and surfactants described herein.

In one embodiment the cyclosporin may be dissolved or dispersed in a low melting point lipophilic substance, suitably a substance with a melting point in the range of 30 to 70° C. Suitably the hydrophobic material is a wax like solid with a melting point in the range of 30 to 60° C., particularly suitable are lipophilic waxy material which are solid at room temperature, but which melt or soften at temperatures in the range of 30 to 50° C., or more preferably 30 to 40° C. The lipophilic material may be selected from one or more of unsaturated alcohols, hydrogenated alcohols, fatty acids, fatty acid esters, fatty acid amides, fatty acid mono- di- or triglycerides, polyethoxylated fatty acids and polyethyoxylated fatty acid esters, cholesterol derivatives and waxes. The wax may be a suitable animal or plant derived wax, for example carnauba wax or a synthetic wax such as paraffin wax. The lipophilic material may comprise a wax, a saturated of unsaturated fatty acid (for example palmitic, stearic, myristic, lauric, laurylic, or oleic acid), or a derivative thereof for example a mono-, di-, or triglyceride or a polyethylene glycol ester thereof. The lipophilic material comprising the dissolved or dispersed cyclosporin is suitably used in the form of a particulate composition, for example as a granule composition. Suitably the lipophilic substance comprising the dissolved or dispersed cyclosporin is itself dispersed, in a suitable carrier matrix. For example, granules comprising the the lipophilic substance and dissolved or dispersed cyclosporin are dispersed in a suitable carrier matrix. The carrier matrix may be a modified release matrix material, particularly a modified release polymer matrix. A modified release matrix may provide delayed or sustained release of the cyclosporin from the matrix, thereby providing a modified release composition. The carrier matrix is suitably a hydrophilic material. The matrix material may be, or comprise, acrylic or methacrylic acid polymers or copolymers, alkylvinyl polymers, hydroxyalkyl celluloses, carboxyalkyl celluloses, polysaccharides, dextrins, pectins, starches, starch derivatives, or natural or synthetic gums for example an alginate. The carrier matrix may be a hydrogel forming polymer such as those described herein, including gelatin.

The composition may comprise cyclosporin A and a surfactant. Suitably the surfactant is or comprises a medium chain or long chain fatty acid mono- or di-glyceride or a combination thereof as described herein. Suitably, the in this embodiment the weight ratio of cyclosporin to medium chain or long chain fatty acid mono- or di-glyceride or a combination is from about 3:1 to about 1:3, for example about 3:1 to about 1:2, or about 2.5:1 to about 1:1.8, about 1.5:1 to 1:1.5, about 1.2:1 to 1:1.2, about 1.2:1, about 1:1, or about 1:1.2. Suitably the cyclosporin composition in this embodiment further comprises an oil phase. The oil phase may be any suitable hydrophobic oil, for example an oil having a low HLB value (for example HLB less than 10). Particularly the oil phase may comprise any of the oil phases described herein, for example the oil phase may be or comprise triglycerides, for example a medium chain triglyceride. The weight ratio of oil to surfactant may be for example 12:1 to 1:5, for example from about 5:1 to about 1:5, from about 3:1 to about 1:2, from about 3:1 to about 1:1 or from about 2.5:1 to 1.5:1. The composition may further comprise a solvent. The solvent is suitably an organic solvent in which cyclosporin is soluble. More particularly suitable solvents include those in which both cyclosporin and the oil phase (when present) are soluble. For example the solvent may comprise 2-(ethoxyethoxy)ethanol. The cyclosporin may be partially or fully dissolved in the composition. Accordingly, the cyclosporin may be substantially dissolved in the composition. Suitably the cyclosporin is fully dissolved in the composition.

The composition is suitably formulated such that release of cyclosporin in the upper GI Tract, for example in the duodenum and jejunum, is minimised so as to minimise the systemic absorption of cyclosporin and both hepatic and enteric P450 metabolism. Accordingly a particular composition is a modified release composition. Suitably the release of cyclosporin from the composition is minimised for the first 4 hours after oral administration such that the composition can pass through the duodenum and jejunum and into the ileum before releasing large amounts of cyclosporin. Preferably the composition releases the majority (for example at least 50%) of the cyclosporin into the colon. Suitably the composition releases less than 40% (for example less than 35%, or less than 30%) of the cyclosporin from the composition 4 hours when measured in the two stage dissolution test described herein. Suitably the composition releases less than 15% (for example 0 to 10%) of the cyclosporin A after 2 hours; and releases 10% to 40% (for example 10% to 35%, or suitably 15% to 35%) of the cyclosporin A at 4 hours, when measured in the two stage dissolution test.

The composition may be formulated to provide the desired modified release profile by, for example, use of any of the coatings described herein, in particular coatings which are adapted to release cyclosporin in at least the colon. Suitable coatings include, for example, a modified release coating comprising a pH independent polymer such as ethyl cellulose. The coating may also comprise a first coating comprising a water soluble cellulose ether such as HPMC, as described herein. Other modified release coatings are also contemplated including but not limited to enteric coating systems and other delayed release coatings. Generally the modified release coatings comprise a polymeric coating.

In this aspect of the invention, when the composition comprises cyclosporin A and a surfactant which is or comprises a medium chain or long chain fatty acid mono- or di-glyceride or a combination thereof as described herein, the cyclosporin and surfactant are suitably dispersed within in matrix. The cyclosporin is released from the matrix when the composition is placed in an aqueous environment, for example as would be found in the lower GI tract such as in the colon. Suitable matrix materials which may be used to disperse the cyclosporin and surfactant may be any of the matrix materials described herein, for example those described under "Composition" in the detailed description. In certain embodiments the matrix material may be selected such that the matrix itself modifies the release of cyclosporin from the composition as described in more detail in the detailed description of the invention. In such compositions it may be possible to achieve the desired inhibition of release of cyclosporin in the first 4 hours following oral administration without the need for additional modified release coating(s). In other embodiments the matrix material may be coated with one or more of the modified release coatings, such as those described herein to provide the required cyclosporin release profile. In a particular, in this aspect of the invention the matrix is a hydrogel polymer, as described herein, more particularly the matrix is or comprises gelatin.

In a preferred embodiment in this aspect of the invention, the composition comprising cyclosporin may be any of the cyclosporin compositions described herein which comprise a surfactant wherein the surfactant is, or comprises, a medium chain or long chain fatty acid mono- or di-glyceride or a combination thereof.

The cyclosporin compositions described herein, more particularly the modified release compositions described herein, provide pharmacokinetic (PK) properties which minimise systemic exposure to cyclosporin compared to, for example, intravenous administration of cyclosporin and/or oral administration of instant release cyclosporin compositions such as Neoral™. The following paragraphs describing suitable PK properties of the compositions are applicable to any of the cyclosporin compositions described herein.

The composition may provide a low systemic whole blood exposure to cyclosporin following oral administration of the composition. The composition may provide a mean whole blood cyclosporin A $AUC_{0-inf}$ of less than about 450 ng·hr/ml, less than about 350 ng·hr/ml, or less than about 300 ng·hr/ml after oral administration of the composition as a single dose containing 75 mg cyclosporin A to a human in a fasted state, or an $AUC_{0-inf}$ directly proportional thereto for a total dose other than 75 mg. For example, the composition may provide a mean whole blood cyclosporin A $AUC_{0-inf}$ of from about 140 to about 420 ng·hr/ml, for example from about 150 to about 300 ng·hr/ml after oral administration of the composition as a single dose containing 75 mg cyclosporin A to a human in a fasted state, or an $AUC_{0-inf}$ directly proportional thereto for a total dose other than 75 mg.

A high peak blood concentration of cyclosporin A ($C_{max}$) may result in undesirable side effects and potentially reduce the therapeutic window available for a composition containing cyclosporin A. Accordingly, the compositions suitably provide a low $C_{max}$. The composition comprising cyclosporin A, may provide a mean maximum whole blood concentration of cyclosporin A (Cmax) of less than 100 ng/ml. The composition may for example provide a $C_{max}$ of from about 15 to about 60 ng/ml, for example about 20 to 50 ng/ml, wherein in each case the $C_{max}$ is that measured after oral administration of the composition as a single dose containing 75 mg of cyclosporin A to a human in a fasted state, or a $C_{max}$ directly proportional thereto for a total dose other than 75 mg.

The time taken to reach maximum whole blood concentration (Tmax) of the cyclosporin A suitably occurs between about 3 and about 10 hours after oral administration of the composition as a single dose to a human in a fasted state. The Tmax may occur between about 4 hours and about 10 hours, or between about 4 hours and about 8 hours, or between about 5 and about 6 hours after oral administration of the composition. For example a $T_{max}$ at about 5 hours, about 5.5 hours or about 6 hours.

An IV dose of 2 to 4 mg/kg/day cyclosporin is known to be efficacious in the treatment of ulcerative colitis patients (Lichtiger et al *N. Engl J Med* 1994; 330: 1841-1845). An IV dose of 2 mg/kg is approximates to a cyclosporin dose of approximately 150 mg (assuming an average weight of about 75 kg). As illustrated in the examples section it has been found that the AUC resulting from IV administration of cyclosporin as Sandimmun™ is significantly higher than the AUC resulting from the modified release compositions comprising the surfactant. IV administration of cyclosporin results in effectively 100% systemic bioavailability. Accordingly, a comparison of the AUC for IV administration with the orally administered cyclosporin compositions described herein enable the absolute oral bioavailability (F %) to be determined. As illustrated in the examples, the cyclosporin compositions described herein provide a low absolute oral bioavailability. The F % is calculated by calculating the relative % of the AUC following oral administration relative to the AUC observed following IV administration of 2 mg/kg Sandimmun™. As will be realised compensation for the actual dose of cyclosporin needs to be accounted for when calculating the F %. For example if the AUC for oral administration is that measured following a single dose of 75 mg of cyclosporin, the relative % needs to be multiplied by 2 to compensate for the fact that the effective total IV dose was 150 mg cyclosporin. Similarly, if a 37.5 mg dose of cyclosporin is administered orally, the relative % needs to be multiplied by 4.

The composition comprising cyclosporin A may provide a cyclosporin A absolute bioavailability following oral administration of the composition is less than 15%, for example less than 10%; optionally wherein the absolute bioavailability is from 0.5% to 15% suitably from 1% to 10%.

Suitably the composition releases the cyclosporin in at least the colon. The composition may also release cyclosporin in other parts of the GI tract for example in the duodenum, jejunum and/or ileum. Suitably however, release of cyclosporin in the upper GI tract such as the duodenum and jejunum is minimised so as to reduce systemic exposure to cyclosporin A and/or reduce P450 metabolism of the drug. The release profile of cyclosporin A from the composition may be assessed by measuring the release in an in vitro dissolution test. The composition comprising cyclosporin may release less than 15% (for example 0 to 10%) of the cyclosporin A after 2 hours; releases 10% to 40% (for example 10% to 35%, or suitably 15% to 35%) of the cyclosporin A at 4 hours; and releases from about 30% to 70% (for example 40% to 70%) of the cyclosporin A between 4 hours and 12 hours, when measured in a two stage dissolution test using a USP Apparatus II with a paddle speed of 75 rpm and a dissolution medium temperature of 37° C.; wherein for the first 2 hours of the dissolution test the dissolution medium is 750 ml of 0.1 N HCl, and at 2 hours 250 ml of 0.2M tribasic sodium phosphate containing 2% SDS is added to the dissolution medium and the pH is adjusted to pH 6.8 (herein referred to as "the two-stage dissolution test).

The composition may release less than 20% of the cyclosporin A after 2 hours; releases 10 to 40% of the cyclosporin A at 4 hours; and releases at least 60% of the cyclosporin A at 12 hours, when measured in the two stage dissolution test. The composition may release less than 10% of the cyclosporin A after 2 hours; releases 10 to 30% of the cyclosporin A at 4 hours; and releases at least 50% of the cyclosporin A at 12 hours, when measured in the two stage dissolution test. The composition may release from about 30 to about 75% of the cyclosporin A between 4 hours and 12 hours in the two stage dissolution test, for example the composition releases from about 40 to about 75%, particularly from about 45 to 70% of the cyclosporin A between 4 hours and 12 hours in the two stage dissolution test. The composition may release less than 15% (for example 0 to 10%) of the cyclosporin A after 2 hours; releases 10% to 40% (for example 10% to 35%, or suitably 15% to 35%) of the cyclosporin A at 4 hours; and releases from about 25% to 70% (for example 40% to 70%) of the cyclosporin A between 4 hours and 12 hours in the two stage dissolution test.

It is to be understood that any of the individual PK parameters and/or in-vitro or other release profiles described herein may be combined with the compositional features of the cyclosporin compositions described herein, for example relating to any one or a combination of AUC; Cmax; Tmax; cyclosporin A concentration in the luminal contents; cyclosporin A concentration in the GI tract tissue; the ratio of cyclosporin A in the luminal contents: cyclosporin A in GI tract tissues; the ratio of the concentration of cyclosporin A: the concentration of cyclosporin A metabolites in collected faeces; the concentration of cyclosporin A in intracolonic faeces: the concentration of cyclosporin A in colonic tissue; or the concentration of cyclosporin A in colonic tissue. By way of a non-limiting example of such a combination of features composition comprising cyclosporin A, provides a mean concentration of cyclosporin A: the concentration of cyclosporin A metabolites in a faecal sample from the human of greater than 12:1 after oral administration of the composition to the human; and wherein the composition provides an $AUC_{0\text{-}inf}$ of less than about 450 ng·hr/ml, (e.g. from about 140 to about 420 ng·hr/ml) after oral administration of the composition as a single dose containing 75 mg cyclosporin A to a human in a fasted state, or an $AUC_{0\text{-}inf}$ directly proportional thereto for a total dose other than 75 mg. Optionally this composition may release 0 to 10% of the cyclosporin A after 2 hours; 10% to 35% of the cyclosporin A at 4 hours; and releases from about 40% to 70% of the cyclosporin A between 4 hours and 12 hours, when measured in the two stage dissolution test.

In another embodiment the composition releases 0 to 10% of the cyclosporin A after 2 hours; and releases from 50 to 100% of the cyclosporin A after 12 hours, when measured in the two stage dissolution test. In another embodiment the composition releases less than 20% of the cyclosporin A after 2 hours; releases 5 to 40% of the cyclosporin A at 4 hours and releases at least 50% of the cyclosporin A at 12 hours, when measured in the two stage dissolution test.

The cyclosporin compositions described herein are expected to provide similar or higher levels of cyclosporin A in the colonic tissue compared to IV administration of Sandimmun™, but with a higher intracolonic faecal concentration of cyclosporin A as a result of the local release of the cyclosporin directly into the colon. The relatively high local concentration of cyclosporin in the colon is expected to provide beneficial therapeutic effects.

The composition comprising cyclosporin A described herein, may provide a ratio of the mean concentration of cyclosporin A present in intracolonic faeces: the mean concentration of cyclosporin A present in colonic tissue in an adult human patient after oral administration of the composition of from about 50:1 to about 500:1, optionally from about 80:1 to about 300:1, or optionally about 100:1 to about 250:1; wherein the concentration of the cyclosporin A is measured in samples of the intracolonic faeces and the colonic tissue taken substantially simultaneously 4 to 6 hours after oral administration of the last dose of a once daily oral dosing regimen of the composition, the dosing regimen comprising once daily oral administration of the composition for seven days. Optionally the once daily oral dosing regimen of the composition provides a single daily dose of 75 mg cyclosporin A. However, other doses may be administered for example any of the cyclosporin doses described herein including but not limted to 37.5 mg or 150 mg once per day. Optionally the dosage regimen may be a twice daily dosage regimen for seven days, for example 37.5 mg twice per day, 75 mg twice per day or 150 mg twice per day.

Reference herein to a sample being taken "substantially simultaneously" means that the samples are obtained close to the same time point, for example the colonic tissue and/or intracolonic faeces and/or blood samples are taken within about 2 hours, 1 hour or 30 minutes of each other, suitably the samples are all taken at the same time point.

In contrast to the compositions according to the invention, IV administration cyclosporin as Sandimmun™ results in a lower ratio of the mean concentration of cyclosporin A present in intracolonic faeces: the mean concentration of cyclosporin A present in colonic tissue. As illustrated in the Examples, when patients were treated with Sandimmun® IV (2 mg/kg) administered as an infusion over 24 hours (2 mg/kg/day) a ratio of about 3:1 was observed.

Accordingly, the orally administered cyclosporin compositions described herein are expected to provide a relatively high colonic tissue concentrations compared to IV administration of an equivalent dose of cyclosporin (e.g. as Sandimmun™ IV).

The composition comprising cyclosporin A may provide a concentration of cyclosporin A in colonic tissue of at least 250 ng/g following oral administration of the composition to a human, for example at least 300, 350, 400 or 450 ng/g. Accordingly, the composition may provide a cyclosporin A concentration of from about 250 to 6000 ng/g, for example from 400 ng/g to 6000 ng/g, from 500 to 5000 ng/g, from 600 to 4000 ng/g, or from 600 to 2000 ng/g. Particularly the composition provides a cyclosporin A concentration in colonic tissue of from about 1000 to about 1500 ng/g, for example about 1200 ng/g. Suitably the compositon is orally administered to provide a daily dose of cyclosporin A within the ranges described herein, suitably a total daily dose in the range of 15 to 300 mg cyclosporin. Optionally the composition provides a dose may be 37.5 mg, 75 mg or 150 mg cyclosporin A once or twice per day.

The colonic tissue samples described above may be obtained using conventional methods, for example by taking a tissue sample during endoscopy as described in the examples herein.

As described above, compositions comprising cyclosporin A and a surfactant, wherein the surfactant comprises, or is a medium chain or long chain fatty acid mono- or di-glyceride or a combination thereof may inhibit P450 metabolism of cyclosporin A. Such compositions may be useful for the preparation of modified release of cyclosporin in the lower GI tract as described above. Also contemplated are such compositions for administration of cyclosporin to any part of the GI tract, for example duodenum or jejunum as, for example, an instant release composition. The compositions may reduce the rate and or extent of cyclosporin metabolism and thereby maximise the amount of cyclosporin in the GI tract.

According to a further feature of the invention there is provided a composition comprising cyclosporin A and a surfactant, wherein the surfactant comprises, or is a medium chain or long chain fatty acid mono- or di-glyceride or a combination thereof. Suitably the composition does not comprise or is not a polyethyleneglycol ether or ester. Suitably the surfactant is present in an amount of at least 6% by weight of the composition, for example at least 10%, at least 15% or at least 20% by weight of the composition. Optionally the surfactant is present in an amount of from 10 to about 50% by weight.

The composition according to this aspect of the invention may further comprise an oil phase, for example any of the oil phases described herein.

The cyclosporin may be partially or completely dissolved in the composition. Suitably the cyclosporin is completely dissolved in the composition.

A particular composition comprises:
 (i) 10 to 60 parts cyclosporin A;
 (ii) 5 to 40 parts of a medium chain fatty acid triglyceride, for example a caprylic/capric triglyceride;
 (iii) 10 to 50 parts of the surfactant; and
 (iv) 0 to 60 parts solvent;
wherein all parts are parts by weight and the sum of the parts (i)+(ii)+(iii)+(iv)=100.

Another composition comprises:
 (i) 10 to 40 parts cyclosporin A;
 (ii) 5 to 25 parts of a medium chain fatty acid triglyceride, a caprylic/capric triglyceride;
 (iii) 15 to 30 parts of the surfactant; and
 (iv) 10 to 60 parts solvent (optionally 20 to 40 parts or 25-30 parts solvent), for example 2-(2-ethoxyethoxy) ethanol);

wherein all parts are parts by weight and the sum of the parts (i)+(ii)+(iii)+(iv)=100.

Optionally in this aspect the surfactant is selected from glyceryl caprylate, glyceryl caprate, glyceryl monooleate, glyceryl dioleate and glycerol monolinoleate, or a combination thereof.

The cyclosporin compositions according to this aspect may be administered orally, for example to provide an instant release composition. Also contemplated is the administration of the composition to the GI tract rectally, for example in the form of an enema or suppository. Other routes of administration of the composition are also contemplated, for example the composition may be administered directly to the GIT, by for example intra-duodenal administration, intra-jejunal or intra-ileal administration. Such routes of administration enable the compositon to bypass the stomach (and optionally other parts of the GI tract) for delivery to specific points in the lower GI tract. These routes of administration may be achieved using for example suitable tubing with an exit at the desired location within the GI tract. Suitably the tubing is inserted orally or nasally into the GI Tract. Alternatively, administration may be achieved by gastric tubing, or continuous or discontinuous percutaneous endoscopic gastrostomy (PEG) tubing. PEG is an endoscopic medical procedure in which a tube (PEG tube) is passed into a patient's stomach through the abdominal wall. This method of administration may be particularly suitable for patients that cannot take the drug orally due to for example dysphagia or sedation.

A further aspect of the invention provides a composition described herein for use as a medicament. The composition may comprise at least one further active ingredient, for example at least one further immunosuppressant. In particular there is provided a composition for use in the treatment, e.g. prevention, of a condition of the GIT. The composition may be for use in the treatment of an inflammatory bowel disease, irritable bowel syndrome, Crohn's disease, ulcerative colitis, celiac disease, graft-versus-host disease, gastrointestinal graft-versus-host disease, gastroenteritis, duodenitis, jejunitis, ileitis, peptic ulcer, Curling's ulcer, appendicitis, colitis, pseudomembraneous colitis, diverticulosis, diverticulitis, pouchitis, collagenous colitis, macorscopic colitis, diarrheal colitis, endometriosis, colorectal carcinoma and adenocarcinoma. The composition may also be for use in the treatment of proctitis. The composition may be for use in the prevention or treatment of primary sclerosing cholangitis, familial adenomatous polyposis, or perinanal Crohn's, including perianal fistulae.

In embodiments where the pharmaceutical composition does not comprise a second coating, the composition may be for use in the treatment of conditions that affect the small intestine. Such compositions may be able to treat conditions selected from celiac disease, GVHD or Crohn's disease.

The invention additionally provides a method for administering cyclosporin to a subject, comprising orally administering to the subject a composition described herein. The method may be performed in the treatment, e.g. prevention, of disease. The subject may be a mammal, in particular a human. Also provided is a method for treating a condition of the GI tract in a subject, preferably a human, in need thereof comprising orally administering to the mammal a therapeutically effective amount of a composition described herein. Conditions of the GI tract which may be treated or prevented include the conditions disclosed herein.

A further aspect of the invention provides the use of a composition described herein for use in the manufacture of a medicament for the treatment, e.g. prevention, of a condition of the GIT. Conditions of the GI tract include those disclosed herein.

The invention also contemplates a method of treating a condition selected from inflammatory bowel disease, irritable bowel disease, Crohn's disease, ulcerative colitis, celiac disease, graft vs host disease, gastrointestinal graft-versus-host disease, gastroenteritis, duodenitis, jejunitis, ileitis, peptic ulcer, Curling's ulcer, appendicitis, colitis, pseudomembraneous colitis, diverticulosis, diverticulitis, collagenous colitis, endometriosis, colorectal carcinoma and adenocarcinoma, wherein the method comprises administering a pharmaceutical composition of the invention.

In another aspect the invention provides a method of treating conditions that affect the small intestine, wherein the method comprises administering a composition of the invention which does not comprise a second coating. The conditions of the small intestine may be selected from celiac disease, GVHD or Crohn's disease.

In an aspect of the invention there is provided a process for making a liquid composition, the process comprising mixing an oil phase with an aqueous phase comprising a hydrogel forming polymer, wherein the oil phase has cyclosporin in solution and comprises a surfactant which is medium chain or long chain fatty acid mono- or di-glyceride or a combination thereof, wherein the surfactant does not comprise or is not a polyethyleneglycol ether or ester.

Optionally, the oil phase and the aqueous phase are mixed in an oil phase to aqueous phase ratio of from 1:2 to 1:12, optionally 1:4 to 1:10, 1:4 to 1:8, for example 1:5 or 1:7.

The process may further comprise the step of causing the emulsion to solidify.

The process may further comprise the step of:
coating a core with a coating comprising HPMC wherein the weight gain due to the coating is from 0.5% to 20% of the weight of the pharmaceutical composition. The core may comprise a pharmaceutically active ingredient and may be a core as described in this specification.

An additional advantage of the present application may be that a composition dissolved in a dissolution medium yields a uniform droplet size with low polydispersivity compared to formulations with a different first surfactant.

Accordingly, there is provided a composition comprising cyclosporin, a hydrogel forming polymer matrix, a surfactant and an oil phase being dispersed in the hydrogel forming polymer matrix, wherein the surfactant is or comprises a medium chain or long chain fatty acid mono- or di-glyceride or a combination thereof and does not comprise or is not a polyethyleneglycol ether or ester, wherein the composition releases droplets with a uniform size. Optionally the droplets may have low polydispersity. Optionally the uniform size may be a droplet size of from about 1 nm to about 350 nm.

The droplet size may be selected from: from about 20 nm to about 350 nm; from about 20 nm to about 300 nm; from about 20 nm to about 250 nm from about 100 nm to about 350 nm; from about 100 nm to about 300 nm; from about 100 nm to about 250 nm; from about 100 nm to about 200 nm; from about 150 nm to about 250 nm; from about 150 nm to about 200 nm; from about 150 nm to about 350 nm; and from about 150 nm to about 300 nm. Preferably, the droplet size may be selected from: from about 20 nm to about 250 nm; from about 100 nm to about 250 nm; and from about 100 nm to about 200 nm.

The size of the droplets may be measured using dynamic light scattering. The dynamic light scattering experiments were carried out by analysis of a liquid medium arrived at as follows. Minibeads of the invention (0.5 g) comprising Capmul GMO-50 as the first surfactant were added to a beaker containing 50 g of deionised water. The beaker contents were mixed at 250 rpm and at 37° C. throughout the study. Samples of the beaker contents were taken at 0, 1, 2, 3, 4, 5, 6 and 24 hours. Samples of the beaker contents were filtered 0.65 μm pore size filters (Merck Millipore Ultrafree-CL Centrifugal Filter). The particle size and zeta potential was measured using a Malvern Nano-Zetasiser.

For certain active ingredients it may be desirable to limit or delay release of the active from the composition until the composition has passed through the stomach and upper GI tract. The compositions of the invention comprising a second coat may be particularly suitable for such applications. The second coat acts to delay release from the composition, whilst the presence of the coating of the invention (e.g. HPMC) increases the amount of active released when the composition releases the active in the lower GI tract. The period of delay to the release of the active as a result of the presence of the second coating can be tailored by appropriate selection of the nature or amount of second coating used. For a given second coating material a higher weight gain of coating will generally increase the time period between administration of the composition and release of the active. The compositions of the invention can therefore be used to provide high levels of release of active agent at very specific parts of the GI tract to provide, for example, topical treatment to diseased tissue within the GI tract. Such delayed release compositions may be particularly beneficial when the active has undesirable side effects which may arise from systemic absorption higher in the GI tract.

Included in this description by reference are the subject matters of the appended claims. The description is therefore to be read together with the claims and features mentioned in the claims are applicable to the subject matters of the description. For example, a feature described in a process claim is applicable also to products mentioned in the description, where the feature is manifested in the product. For example, a feature mentioned in a product claim is applicable also to relevant process subject matters contained in this description. Similarly, a feature mentioned in the description in the context of a process is applicable also to products mentioned in the description, where the feature is manifested in the product. Also, a feature mentioned in the description in the context of a product is applicable also to relevant process subject matters contained in this description.

BRIEF DESCRIPTION OF THE DRAWINGS

Embodiments of the invention are further described hereinafter with reference to the accompanying drawings, in which:

FIG. 7 is a graph plotting % of cyclosporin released against time over 24 hours in deionised water and showing the release profiles of minibeads of Example 6a.

In FIGS. 11 and 12, BID=twice daily; OD=once daily. Values below the lower limit of quantification (<0.2 ng/mL) are presented as equal to zero.

In FIG. 14 "PK fast", "PK medium" and "PK slow" refer to the Fast Release Formulation, Formulation I and Formulation II used in Comparative Example 10. "CyCol 2014" refers to the formulation used in Example 9.

DETAILED DESCRIPTION

Figure 1:
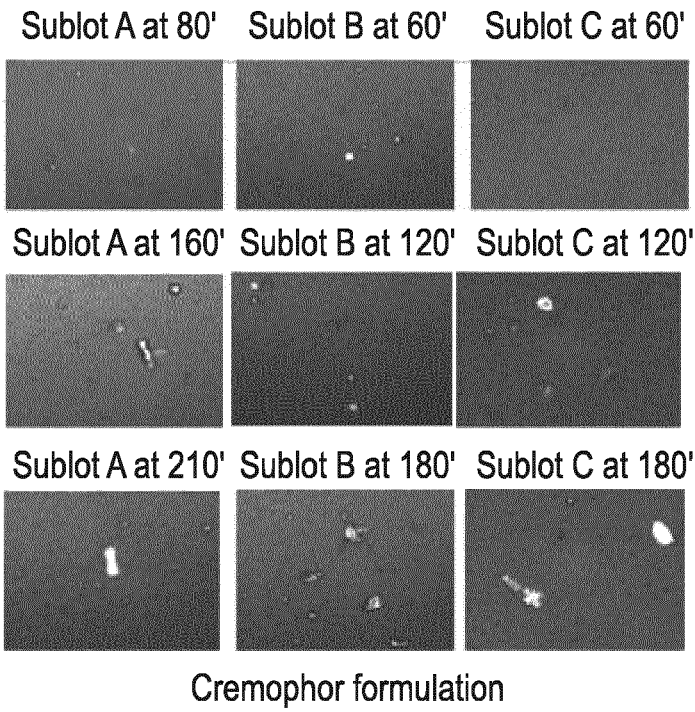
FIG. 1 is an image showing crystal formation over time of a comparative composition.

A mono-glyceride or di-glyceride of the present invention may comprise one glycerol esterified to one fatty acid or one glycerol esterified to two fatty acids the fatty acids may be the same or different, ordinarily the fatty acids will be the same. The surfactant of the invention is a surfactant that does not comprise or is not a polyethyleneglycol ether or ester; by this it is meant that there is no polyethyleneglycol component bonded to the surfactant molecule by an ether or ester linkage. For example a pegylated fatty acid glyceride such as oleoyl macrogol-6 glycerides (commercially available as Labrafil M1944CS). It is possible that a commercial surfactant of the invention is supplied with a small amount of polyethyleneglycol (PEG) contained within the supplied surfactant composition. The use of such commercial formulations of surfactants which contain non-bonded PEG, put another way free PEG) are not excluded by the limitation that the surfactant does not comprise or is not a polyethyleneglycol ether or ester.

Reference to "cyclosporin" herein is a reference to cyclosporin-A (also known as cyclosporine and the INN ciclosporin. It is contemplated that other forms of cyclosporin may be used in the compositions described herein, for example cyclosporin-B, -C, -D or -G and derivatives or pro drugs of any thereof.

The term "treatment", and the therapies encompassed by this invention, include the following and combinations thereof: (1) reducing the risk of or inhibiting, e.g. delaying, initiation and/or progression of, a state, disorder or condition; (2) preventing, e.g. reducing the risk of, or delaying the appearance of clinical symptoms of a state, disorder or condition developing in a patient (e.g. human or animal) that may be afflicted with or predisposed to the state, disorder or condition but does not yet experience or display clinical or subclinical symptoms of the state, disorder or condition; (3) inhibiting the state, disorder or condition (e.g., arresting, reducing or delaying the development of the disease, or a relapse thereof in case of maintenance treatment, of at least one clinical or subclinical symptom thereof); and/or (4) relieving the condition (e.g. causing regression of the state, disorder or condition or at least one of its clinical or subclinical symptoms). Where the composition of the invention is used in the treatment of a patient, treatment contemplates any one or more of: maintaining the health of the patient; restoring or improving the health of the patient; and delaying the progression of the disorder. The benefit to a patient to be treated may be either statistically significant or at least perceptible to the patient or to the physician. It will be understood that a medicament will not necessarily produce a clinical effect in every patient to whom it is administered, and this paragraph is to be understood accordingly. The compositions and methods described herein are of use for therapy and/or prophylaxis of disease.

The treatments may include maintenance therapy of patients who have suffered a disorder and whose condition has subsequently improved, e.g. because of treatment. Such patients may or may not suffer a symptomatic disorder. Maintenance therapy aims to arrest, reduce or delay (re-) occurrence or progression of a disorder.

"Effective amount" means an amount sufficient to achieve the desired treatment, e.g. result in the desired therapeutic or prophylactic response. The therapeutic or prophylactic response can be any response that a user (e.g., a clinician) will recognise as an effective response to the therapy. It is further within the skill of one of ordinary skill in the art to determine appropriate treatment duration, appropriate doses, and any potential combination treatments, based upon an evaluation of therapeutic or prophylactic response.

The terms "dry" and "dried" as applied to compositions or compositions of the disclosure may each include reference to compositions or compositions containing less than 5% free water by weight, e.g. less than 1% free water by weight. Primarily, however, "dry" and "dried" as applied to compositions of the disclosure mean that the hydrogel present in the initial solidified composition has dried sufficiently to form a rigid composition. Where a solid colloid is referred to this also refers to a dried colloid according to the definition herein.

Ingredients and excipients of the described compositions are suitable for the intended purpose. For example, pharmaceutical compositions comprise pharmaceutically acceptable ingredients.

If not otherwise stated, ingredients, components, excipients etc. of the compositions of the invention are suitable for one or more of the intended purposes discussed elsewhere herein.

For the avoidance of doubt, it is hereby stated that the information disclosed earlier in this specification under the heading "Background" is relevant to the invention and is to be read as part of the disclosure of the invention.

Where the invention is referred to as a formulation it takes the same meaning as the composition of the invention. Accordingly, formulation and composition are used interchangeably.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

Composition

The liquid composition comprises cyclosporin, a polymer capable of forming a matrix (a hydrogel forming polymer), a surfactant and an oil phase. The oil phase, cyclosporin and the surfactant are contained within the polymer capable of creating a matrix. The cyclosporin is dissolved in the oil phase. When the polymer forms a matrix the liquid composition is formed into a composition of the invention.

The composition comprises a matrix and cyclosporin. The matrix may be formed with a hydrogel-forming polymer, and may contain additional excipient(s) to the polymer. The active ingredient is contained within the matrix. The active ingredient may be in solution or in suspension, or in a combination thereof; however the invention is not limited to compositions comprising a solution or suspension of the active and it includes, for example, active ingredients encapsulated in liposomes or cyclodextrin. The matrix may contain inclusions in which the active ingredient is comprised; for example, the inclusions may comprise a hydrophobic medium in which the active ingredient is dissolved or suspended. An active ingredient may therefore be directly dissolved or suspended in the matrix, or it may be dissolved or suspended indirectly in the matrix by way of inclusions in which the active ingredient is dissolved or suspended.

The composition, therefore, comprises a matrix-forming polymer, in particular a hydrogel-forming polymer. The matrix of the composition may be or comprise a polymer matrix comprising a polymer selected from a water-permeable polymer, a water-swellable polymer and a biodegradable polymer. In particular, the matrix is or comprises a hydrogel-forming polymer described in more detail below.

Modified release of the active ingredient from the composition may be achieved by virtue of the properties of the matrix material. For example the matrix may be a permeable or erodible polymer within which the active ingredient is contained, e.g. dissolved or suspended; following oral administration the matrix is gradually dissolved or eroded thereby releasing the active ingredient from the matrix. Erosion may be achieved by biodegradation of a biodegradable polymer matrix. Where the matrix is permeable, water permeates the matrix enabling the drug to diffuse from the matrix. A matrix formed with a hydrogel-forming polymer may therefore include a modified release polymer. As such modified release polymers may be mentioned cellulose derivatives, for example hydroxypropylmethyl cellulose, poly(lactic acid), poly(glycoloic)acid, poly(lactic-co glycolic acid copolymers), polyethylene glycol block co-polymers, polyorthoesters, polyanhydrides, polyanhydride esters, polyanhydride imides, polyamides and polyphosphazines.

Water Soluble Cellulose Ether Coating

The invention provides pharmaceutical compositions that may have a first coating which is or comprises a water-soluble cellulose ether. The invention provides pharmaceutical compositions that have a first polymer coating, wherein the polymer is or comprises a water-soluble cellulose ether. The water-soluble cellulose ether may be, for example selected from methyl cellulose, hydroxyethyl cellulose, hydroxylpropyl cellulose and hydroxypropylmethyl cellulose.

Suitably the material of the first coating (i.e. the sub-coating) is different to the second coating on the composition. For example, where the first coating is or comprises a water-soluble ester of a cellulose ether, the major component(s) (e.g. more than 50%) of the second coating is or comprises a different polymer to that of the first coating. Accordingly, the first and second coatings suitably provide two layers of material as part of the composition. It is to be understood that when the second coating comprises a mixture of components, minor components of the outer second coating may the same as the material of the first coating. By way of example, when the first coating is or comprises HPMC and the second coating comprises ethyl cellulose, the ethyl cellulose may optionally further comprise a minor amount (e.g. less than 50%, 40%, 30% or 20%) of the first coating material, HPMC in this example. In such embodiments the sub-coat and the second coating are considered to be different.

The water-soluble cellulose ether may be a water-soluble cellulose ether selected from an alkyl cellulose, for example methyl cellulose, ethyl methyl cellulose; a hydroxyalkyl cellulose, for example hydroxyethyl cellulose (available as Cellosize™ and Natrosol™), hydroxypropyl cellulose (available as Klucel™) or hydroxymethyl cellulose; a hydroxyalkyl alkyl cellulose, for example hydroxyethyl methyl cellulose (NEMC), hydroxypropyl methyl cellulose (available as Methocel™, Pharmacoat™, Benecel™) or ethyl hydroxyethyl cellulose (EHEC); and a carboxyalkyl cellulose, for example carboxymethyl cellulose (CMC). Suitably the water-soluble cellulose ether may, for example be selected from methyl cellulose, hydroxyethyl cellulose, hydroxylpropyl cellulose and hydroxypropylmethyl cellulose.

The water-soluble cellulose ether may be a low viscosity polymer which is suitable for application as a film or coating to the composition. The viscosity of the polymer may be from about 2 to about 60 mPa·s, for example a viscosity of: about 2 to about 20 mPa·s; about 2 to about 8 mPa·s; more suitably a viscosity of about 4 to about 10 mPa·s, for example about 4 to about 6 mPa·s. Alternatively, the viscosity of the polymer may fall outside any or all of the just-mentioned ranges, for example be above 20 mPa·s. Alternatively, the viscosity of the polymer may fall outside any or all of the just-mentioned ranges, for example be above 20 mPa·s. The viscosity of the polymer may be determined by measuring the viscosity of a 2% solution of the polymer in water at 20° C. using a Ubbelode viscometer using ASTM standard methods (D1347 and D2363).

The water soluble cellulose ether may be a water-soluble hydroxypropylmethyl cellulose (HPMC or hypromellose). HPMC is prepared by modifying cellulose to substitute hydroxy groups with methoxy and hydroxypropyl groups. Each anhydroglucose unit in the cellulose chain has three hydroxyl groups. The amount of substituent groups on the anhydroglucose units may be expressed as the degree of substitution. If all three hydroxyl groups on each unit are substituted, the degree of substitution is 3. The number of substituent groups on the ring determines the properties of the HPMC. The degree of substitution may also be expressed as the weight % of the methoxy and hydroxypropyl groups present. Suitably the HPMC has from about 19 to about 30% methoxy substitution and from about 7 to about 12% hydroxypropyl substitution. Particularly the HPMC has 25 to 30% methoxy substitution and 7 to 12% hydroxypropyl substitution. Suitably the HPMC is a low viscosity HPMC which is suitable for application as a film or coating to the composition. The viscosity of the HPMC is suitably from about 2 to 60 mPa·s, for example about 2 to about 20 mPa·s, more suitably a viscosity of about 4 to about 10 mPa·s. The viscosity of the HPMC is determined by measuring the viscosity of a 2% solution of the HPMC in water at 20° C. using a Ubbelode viscometer using ASTM standard methods (D1347 and D2363). Such HPMC is available as for example Methocel™, for example Methocel™ E, including Methocel™ E5.

When the first coating is or comprises a water-soluble derivative of a cellulose ether, the derivative may, for example be a water-soluble ester of a cellulose ether. Water-soluble esters of cellulose ethers are well known and may comprise esters of a cellulose ether, formed with one or more suitable acylating agent(s). Acylation agents may be, for example suitable acids or acid anhydrides or acyl halides. Accordingly the ester of a cellulose ether may contain a single ester moiety or two or more ester moieties to give a mixed ester. Examples of water-soluble esters of cellulose ethers may be water-soluble phthalate, acetate, succinate, propionate or butyrate esters of a cellulose ether (for example HPMC). Suitably the water-soluble ester of a cellulose ether is a water-soluble phthalate, acetate-succinate, propionate, acetate-propionate or acetate-butyrate ester of a cellulose ether (for example HPMC).

In one embodiment the water-soluble ester of a cellulose ether may be or comprise a water-soluble ester of any of the water-soluble cellulose ethers described above in relation to the sub-coating.

Particular water-soluble esters of cellulose ethers are water-soluble esters of HPMC. Esters of HPMC which are soluble in water at a pH greater than 5.5 may be or comprise hydroxypropyl methylcellulose phthalate (HPMCP), or hydroxypropyl methylcellulose acetate succinate (HPMCAS) in which the presence of ionisable carboxyl groups causes the polymer to solubilize at high pH (>5.5 for the LF grade and >6.8 for the HF grade). These polymers are commercially available from Shin-Etsu Chemical Co. Ltd.

The cellulose ether-containing coating may comprise or be hypromellose, e.g. it may be made of a mixture of hypromellose, titanium dioxide and polyethylene glycol; the coating may comprise at least 20 wt % hypromellose and optionally at least 50% or at least 75 wt % hypromellose, e.g. at least 80 wt % or at least 85 wt % or 90 wt % hypromellose. The coating material used to form the coating may therefore comprise a dry weight percentage of hypromellose mentioned in the preceding sentence.

If it is desired for the coating to use a mixture of hypromellose, titanium dioxide and polyethylene glycol, commercial products corresponding to such mixtures are available including Opadry White, a product commercialised by Colorcon. More generally, there may be mentioned various products commercialised under the trade name Opadry and Opadry II. Further non limiting examples include Opadry YS-1-7706-G white, Opadry Yellow 03692357, Opadry Blue 03690842). These formulations are available as dry film coating formulations that can be diluted in water shortly before use. Opadry and Opadry II formulations comprise a cellulosic film forming polymer (e.g., HPMC and/or HPC), and may contain polydextrose, maltodextrin, a plasticizer (e.g., triacetin, polyethylene glycol), polysorbate 80, a colorant (e.g., titanium dioxide, one or more dyes or lakes), and/or other suitable film-forming polymers (e.g., acrylate-methacrylate copolymers). Suitable OPADRY or OPADRY II formulations may comprise a plasticizer and one or more of maltodextrin, and polydextrose (including but not limited to a) triacetin and polydextrose or maltodextrin or lactose, or b) polyethylene glycol and polydextrose or maltodextrin). Particularly preferred commercial products are Opadry White (HPMC/HPC-based) and Opadry II White (PVA/PEG-based).

The cellulose ether-containing coating may also be applied as a simple solution comprising water and the polymer of the first coating. For example when the polymer is an HPMC, for example such as Methocel, the first coating may be applied to the core as an aqueous solution or dispersion of the HPMC. Optionally the coating solution may include other solvents such as an alcohol. Alternatively the coating may be applied as a solution or dispersion in a volatile organic solvent.

Suitably the first coating that contains a water soluble cellulose ether is present in an amount corresponding to a weight gain of the composition due to the coating of from 0.5% to 40% (for example from 0.5% to 30%; from 0.5% to 20%; from 1% to 25%; from 1% to 15%; from 1% to 6%; from 1% to 4%; from 4% to 6%; from 6% to 10%; from 9% to 15%; or from 12% to 15%) by weight based upon the weight of the composition prior to applying the coating. The first coating that contains a water soluble cellulose ether is present in an amount corresponding to a weight gain of the composition due to the coating of from 1% to 10%; from 4% to 10%; from 4% to 8%; and from 5% to 8% by weight based upon the weight of the core or the composition prior to applying the coating.

In another embodiment the first coating that contains a water-soluble cellulose ether is present in an amount corresponding to a weight gain due to the first coating in a range selected from 9 to 30%, suitably 9% to 20%, or particularly 10% to 15% by weight based upon the weight of the composition prior to applying the coating.

Suitably the first coating that contains a water soluble cellulose ether provides a coating thickness on the composition of at least 5 μm, suitably from about 5 μm to about 1 mm, for example from about 10 μm to about 1 mm, from about 10 μm to about 500 μm, from about 50 μm to about 1 mm, or about from about 50 μm to about 500 μm. The thickness may therefore be from about 100 μm to about 1 mm, e.g. 100 μm to about 750 μm or about 100 μm to about 500 μm. The thickness may be from about 250 μm to about 1 mm, e.g. about 250 μm to about 750 μm or 250 μm to about 500 μm. The thickness may be from about 500 μm to about 1 mm, e.g. about 750 μm to about 1 mm or about 500 μm to about 750 μm. The thickness may therefore be from about 10 μm to about 100 μm, e.g. from about 10 μm to about 50 μm or about 50 μm to about 100 μm.

When the first coating comprises a water-soluble cellulose ether the cellulose ether(s) suitably forms at least 40%, 50%, 60%, 70%, 80%, 85% or 90% by weight of the dry weight of the first coating. Alternatively the water-soluble cellulose ether is the first coating.

It is preferred to dry the composition of the invention before the first coating that contains a water-soluble cellulose ether is applied, as is described in more detail below in relation to the coating process.

It has been found that applying to a core comprising a pharmaceutically active ingredient a sub-coating, referred to elsewhere in the application as the subcoat (hence the subcoat and the first coating are equivalent), that contains a water soluble cellulose ether prior to applying a delayed release coating provides unexpected advantages. The presence of such a sub-coating has been found to enhance the dissolution properties of the delayed release compositions according to the invention. In particular the presence of such a sub-coating has been found to increase the rate of release of the active ingredient from the composition and also to increase the amount of the active ingredient released in a set time period compared to compositions prepared without using such a sub-coating. These findings are unexpected, because it would have been expected that the presence of a sub-coating in addition to a delayed release outer coating would act to delay or inhibit release of drug from the composition and, at a given time, for there to be less drug released, because there is a thicker coating present. However, as illustrated in the Examples, contrary to these expectations both the extent and rate of release of active ingredient are increased compared to compositions without such a sub-coating. Accordingly, delayed release compositions according to the invention which comprise a sub-coat that comprises or is a water-soluble cellulose ether and a delayed release coating outside the sub-coat, provide a unique dissolution profile. The presence of such a sub-coating has also been found to reduce batch-to-batch variability, particularly when the core is in the form of a minibead. A sub-coating that comprises or is a water-soluble cellulose ether may therefore also reduce intra- and inter-patient variability as a result of a more consistent dissolution profile. The unique properties of sub-coated compositions according to the invention (particularly the dissolution profile) are expected to contribute to favourable pharmacokinetic properties of the compositions according to the invention.

Accordingly in an embodiment there is provided a composition comprising cyclosporin, a hydrogel forming polymer matrix, a surfactant and an oil phase being dispersed in the hydrogel forming polymer matrix, wherein the surfactant is a medium chain or long chain fatty acid mono- or di-glyceride or a combination thereof and does not comprise or is not a polyethyleneglycol ether or ester, the composition further comprising a first coating; and wherein the first coating is or comprises a water-soluble cellulose ether.

The composition may have a second coating comprising or being a delayed release polymer.

Accordingly in an embodiment there is provided a composition comprising cyclosporin, a hydrogel forming polymer matrix, a surfactant and an oil phase being dispersed in the hydrogel forming polymer matrix, wherein the surfactant is a medium chain or long chain fatty acid mono- or di-glyceride or a combination thereof and does not comprise or is not a polyethyleneglycol ether or ester, the composition further comprising a first coating and a second coating outside the first coating; and wherein the first coating is or comprises a water-soluble cellulose ether; and the second coating is or comprises a delayed release coating, e.g. is or comprises a delayed release polymer.

An aspect of the invention resides in a multiple minibead composition comprising at least two populations of active ingredient-containing minibeads, wherein members of at least one minibead population are minibeads as described herein (i.e. compositions of the invention in minibead format). It will be understood that the two populations are different. Such a plural minibead population composition may comprise or consist of the following two populations:
- a first population having a coating that is or comprises a water-soluble cellulose ether but having no outer coating, e.g. as described herein; and
- a second population having a first coating that is or comprises a water-soluble cellulose ether and a second coating that is or comprises a delayed release coating, for example as described herein e.g. a coating that is or comprises a delayed release polymer.

The respective minibeads of each population of a plural minibead composition may contain cyclosporin as the minibeads of some or all of the other populations, or one population may contain cyclosporin and another population may contain a different active ingredient(s) thereto, e.g. a different combination.

A multiple population composition may be for use in treating a disorder of the GI tract, for example as described herein. Such a composition may be for use in treating a disorder affecting multiple regions of the GIT, e.g. the upper intestine and the lower intestine, and may comprise an active ingredient selected from immunosuppressants (e.g. cyclosporin), hydroxylase inhibitors (e.g. hydralazine) and anti-inflammatories (e.g. mesalazine).

The minibeads of a multiple population composition may by way of example be contained in a gel capsule or a sachet.

The second coating is outside the first coating and may be any of the delayed release coatings described herein. In particular, the second coating is or comprises a pH independent polymer modified release coating described above. For example the second coating may be or comprise an enteric coating or a pH independent coating. The second coating may comprise a mixture of polymers including a polymer degradable by bacterial or other enzymes. In a particular embodiment the second coating comprises ethyl cellulose and optionally a water-soluble polysaccharide, in particular one susceptible to degradation by colonic bacteria, suitably pectin. Accordingly the second coating may comprise the Surelease-pectin mixture described above.

It is not a requirement that both the first and second coatings are present in the composition at the same time. For example, the composition may comprise second coating (outer coating) in the absence of a first coating. Conversely, the composition may comprise a first coating in the absence of a second coating.

The first and second coating may independently be aqueous-based coatings or may be solvent-based coatings. By this it is meant that the first and/or second coating may be formulated prior to being applied to the core or composition and/or applied to the core or composition as an aqueous-based composition or as a solvent-based (non-aqueous solvent-based) composition. The aqueous-based or solvent-based coating compositions may be a suspension or a solution of the coating material in water or in a solvent.

In an embodiment the composition comprises a core and an outer coating (also referred to as a second coating herein), the core comprising cyclosporin, a hydrogel forming polymer matrix, a surfactant and an oil phase being dispersed in the hydrogel forming polymer matrix, wherein the surfactant is a medium chain or long chain fatty acid mono- or di-glyceride or a combination thereof and does not comprise or is not a polyethyleneglycol ether or ester. The composition may optionally further comprise a sub-coat.

In one embodiment of the invention there is provided a composition comprising a core, a first coating and a second coating outside the first coating; and wherein:

the core comprises cyclosporin, a hydrogel forming polymer matrix, a surfactant and an oil phase being dispersed in the hydrogel forming polymer matrix, wherein the surfactant is a medium chain or long chain fatty acid mono- or di-glyceride or a combination thereof and does not comprise or is not a polyethyleneglycol ether or ester;

the first coating is or comprises a water-soluble cellulose ether, particularly hydroxypropylmethyl cellulose;

the second coating is or comprises a modified release coating or delayed release coating, particularly a pH independent modified release coating;

the first coating is present in an amount corresponding to a weight gain due to the first coating in a range selected from: (i) 8% to 15%; (ii) from 8% to 12%, for example about 10%; or (iii) from 2.5% to 6%, for example about 5% by weight based upon the weight of the composition prior to applying the first coating; and wherein the second coating is present in an amount corresponding to a weight gain of the composition due to the second coating selected from (a) from 4% to 20%; (b) from 7.5% to 20%; (C) from 10% to 12%, for example about 11% or about 11.5%; or (d) from 16% to 18%, for example about 17% by weight based upon the weight of the composition prior to applying the second coating.

The first and second coatings in the embodiment of the immediately preceding paragraph are suitably any of the first and second coatings described above or below. Accordingly it is intended that the coatings described in this section may be applied to any of the compositions described herein to provide a delayed release coating if required. The coatings are particularly useful to provide a modified release coating to the cores comprising a polymer matrix and pharmaceutically active ingredient described in this application.

Outer Barrier or Protective Coating

The compositions described herein may comprise a protective coating outside the first and/or second coating, for example outside the second coating, the modified release coating. The protective coating may help to protect the modified release coating from damage resulting from, for example formulating the composition into a final dosage form, or during the handling, transport or storage of the composition. The protective coating is suitably applied to the outer surface of the composition. The protective coating may be applied directly to the second coating (the modified release coating) such that the protective coating is in contact with the second coating (the modified release coating). The protective coating is suitably a water soluble coating which does not adversely affect the release of the cyclosporin A from the composition when in use. Suitably the protective coating is or comprises a water-soluble polymer. The protective coating may comprise a water-soluble cellulosic or PVA film-forming polymer. Suitably the protective coating may be or comprise Opadry (HPMC/HPC-based), Opadry II (PVA/PEG-based) or polyvinyl alcohol-polyethylene glycol graft copolymers (Kollicoat IR) as described herein. The protective coating may be present as a layer of from about 2 to about 50 µm. Suitably the protective coating is applied to give a weight-gain of from about 0.5 to about 10%, based upon the weight of the composition prior to applying the protective coating.

Polymer Matrix

The composition of the invention comprises cyclosporin, a hydrogel forming polymer matrix, a surfactant and an oil phase being dispersed in the hydrogel forming polymer matrix. In addition, in certain embodiments of the invention the composition of the invention comprises a core wherein the core comprises cyclosporin, a hydrogel forming polymer matrix, a surfactant and an oil phase being dispersed in the hydrogel forming polymer matrix. The composition or the core comprises a continuous phase or matrix phase, which may be or comprise the hydrogel forming polymer matrix, to provide mechanical strength. In embodiments the cyclosporin is comprised within a disperse phase or oil phase within the continuous phase or matrix. The cyclosporin may be present as a disperse phase within the hydrogel-forming polymer matrix (continuous phase or aqueous phase) of the core or composition. The disperse phase may be or comprise the oil phase. For example the disperse phase may comprise a lipid and cyclosporin A. The core or the composition may be prepared by dispersing the cyclosporin, dissolved in the oil phase within an aqueous phase comprising the hydrogel forming polymer matrix to form a colloid and then causing the composition to solidify (gel), thereby immobilising the cyclosporin within the hydrogel-forming polymer matrix.

The core may have the form of a solid colloid, the colloid comprising a continuous phase and a disperse phase, wherein the continuous phase is or comprises the hydrogel-forming polymer matrix and the disperse phase is or comprises an oil phase optionally comprising the cyclosporin. The disperse phase may comprise a vehicle containing the cyclosporin, for example containing it as a solution or a suspension or a combination of both. The vehicle may be an oil phase as described herein.

Such cores comprising a hydrogel-forming polymer and a disperse phase comprising cyclosporin A are described in more detail below.

Delayed Release Coatings

The invention provides compositions having a coating that comprises, or is, a coating-forming polymer, wherein the coating-forming polymer is a hydrogel-forming polymer; the coating may be a first coating outside which is a second coating. The second coating may be a delayed release coating, although the invention does not require that the second coating be a delayed release coating. The second coating may comprise or be a delayed release polymer.

The first coating may be present in an amount described elsewhere in this specification.

The first coating may be present in an amount corresponding to a weight gain due to the first coating of from 0.5% to 20% by weight of the core.

Furthermore, the composition may comprise a first coating present in an amount corresponding to a weight gain due to the coating selected from ranges of from: 0.5% to 15%; 1% to 15%; 1% to 12%; 1% to 10%; 1% to 8%; 1% to 6%; 1% to 4%, 2% to 10%; 2% to 8%; 2% to 6%; 2% to 7%; 2% to 4%; 4% to 8%; 4% to 7%, 4% to 6%, 5% to 7%; 7% to 20%; 7% to 16%; 9% to 20%; 9% to 16%; 10% to 15%; and 12% to 16%.

The invention provides for a pharmaceutical composition comprising a core, a first coating and a second coating outside of the first coating, wherein the core comprises cyclosporin, a hydrogel forming polymer matrix, a surfactant and an oil phase being dispersed in the hydrogel forming polymer matrix, the first coating comprises or is a water soluble cellulose ether, and the second coating comprises or is a delayed release polymer, and the first coating may be present in an amount corresponding to a weight gain due to the first coating of from 0.5% to 20% by weight of the core, wherein the surfactant is a medium chain or long chain fatty acid mono- or di-glyceride or a combination thereof and does not comprise or is not a polyethyleneglycol ether or ester.

The composition of the invention may comprise a first coating with a thickness of 1 µm to 1 mm. Thus, the % weight gain due to the coating specified above may correspond to a thickness of 1 µm to 1 mm.

The first coating may have a thickness selected from ranges of from: 1 µm to 500 µm; 10 µm to 250 µm; 10 µm to 100 µm; 10 µm to 50 µm; 10 µm to 20 µm; 50 µm to 100 µm; 100 µm to 250 µm; 100 µm to 500 µm; 50 µm to 500 µm; 50 µm to 250 µm; 100 µm to 1 mm; 500 µm to 1 mm. The coating having the thicknesses disclosed in this paragraph may be any of the coatings in the application. In particular the coating referred to in this paragraph may be the water-soluble cellulose ether coating.

The first coating may be present in a weight gain selected from a range of from: 1% to 20%, 4% to 7%, 5% to 7%, 4% to 15%, 8% to 15%, 4% to 12% and 8% to 12%. The second coating may be present in a weight gain selected from a range of from: 8% to 15% or 8% to 12%.

In addition, the invention provides for a pharmaceutical composition comprising a core, a first coating and a second coating outside of the first coating, wherein the core comprises cyclosporin, a hydrogel forming polymer matrix, a surfactant and an oil phase being dispersed in the hydrogel forming polymer matrix, the first coating comprises or is a water soluble cellulose ether, and the second coating comprises or is a delayed release polymer, and the first coating has a thickness of from 1 µm to 1 mm. The core may optionally further comprise a hydrogel forming polymer, wherein the surfactant is a medium chain or long chain fatty acid mono- or di-glyceride or a combination thereof and does not comprise or is not a polyethyleneglycol ether or ester.

The second coating may be present in an amount described elsewhere herein. Suitably the second coating provides a coating thickness on the composition of from about 10 µm to about 1 mm, for example, from about 10 µm to about 500 µm, from about 50 µm to about 1 mm, or about from about 50 µm to about 500 µm. The thickness may therefore be from about 100 µm to about 1 mm, e.g. 100 µm to about 750 µm or about 100 µm to about 500 µm. The thickness may be from about 250 µm to about 1 mm, e.g. about 250 µm to about 750 µm or 250 µm to about 500 µm. The thickness may be from about 500 µm to about 1 mm, e.g. about 750 µm to about 1 mm or about 500 µm to about 750 µm. The thickness may therefore be from about 10 µm to about 100 µm, e.g. from about 10 µm to about 50 µm or about 50 µm to about 100 µm.

It is contemplated within any aspect or embodiment where there is a second coating (also referred to as an outer coating) that the second coating may be present in a % weight gain of from 2% to 40%. In addition the second coating may be present in an amount corresponding to a weight gain due to the coating selected from ranges of from: 4% to 30%, 4% to 7%, 7% to 40%, 7% to 30%, 8% to 25%, 8% to 20%, 2% to 25%, 2% to 20%, 4% to 25%, 4% to 20%, 4% to 15%, 4% to 13%, 7% to 15%, 7% to 13%, 8% to 12%, 9% to 12% and 20% to 25%.

In any aspect and embodiment of the invention the first coating may be present in a % weight gain relative to the core of from 0.5% to 20%, preferably 1% to 16% or 4% to 16%, and the second coating may be present in a % weight gain of 4% to 24%, 7% to 24%, 22% to 24%, 7% to 15%, or 8% to 12%, preferably 22% to 24%, 7% to 15%, or 8% to 12%.

The core is preferably in the form of a minibead, for example as described hereafter in more detail, for example in the form of a solid colloid. The second coat may be a film or it may be a membrane. The second coat, e.g. film or membrane, may serve to delay release until after the stomach; the coat may therefore be an enteric coat. The delayed release coat may comprise one or more delayed release substances, preferably of a polymeric nature (e.g. methacrylates etc; polysaccharides etc as described in more detail below), or combination of more than one such substance, optionally including other excipients, for example, plasticizers. Preferred plasticizers, if they are used, include hydrophilic plasticizers for example triethyl citrate (TEC) which is particularly preferred when using the Eudragit® family of polymers as coatings as described below. Another preferred plasticiser, described in more detail below in relation to coating with ethyl cellulose, is dibutyl sebacate (DBS). Alternative or additional optionally included excipients are glidants. A glidant is a substance that is added to a powder or other medium to improve its flowability. A typical glidant is talc which is preferred when using the Eudragit® family of polymers as coatings.

The delayed release coating (the second coating) may be applied as described below and may vary as to thickness and density. The amount of coat is defined by the additional weight added to (gained by) the dry composition (e.g. the core) to which it is applied. Weight gain is preferably in the range 0.1% to 50%, preferably from 1% to 15% of the dry weight of the core, more preferably in the range 3% to 10% or in the range 5-12% or in the range 8-12%.

Polymeric coating material of a delayed release coating may comprise methacrylic acid co-polymers, ammonio methacrylate co-polymers, or mixtures thereof. Methacrylic acid co-polymers such as, for example, EUDRAGIT™ S and EUDRAGIT™ L (Evonik) are particularly suitable. These polymers are gastroresistant and enterosoluble polymers. Their polymer films are insoluble in pure water and diluted acids. They may dissolve at higher pHs, depending on their content of carboxylic acid. EUDRAGIT™ S and EUDRAGIT™ L can be used as single components in the polymer coating or in combination in any ratio. By using a combination of the polymers, the polymeric material can exhibit solubility at a variety of pH levels, e.g. between the pHs at which EUDRAGIT™ L and EUDRAGIT™ S are separately soluble. In particular, the coating may be an enteric coating comprising one or more co-polymers described in this paragraph. A particular coating material to be mentioned is Eudragit L 30 D-55.

The trade mark "EUDRAGIT" is used hereinafter to refer to methacrylic acid copolymers, in particular those sold under the trade mark EUDRAGIT by Evonik.

The delayed release coating, where present, can comprise a polymeric material comprising a major proportion (e.g., greater than 50% of the total polymeric coating content) of at least one pharmaceutically acceptable water-soluble polymer, and optionally a minor proportion (e.g., less than 50% of the total polymeric content) of at least one pharmaceutically acceptable water insoluble polymer. Alternatively, the membrane coating can comprise a polymeric material comprising a major proportion (e.g., greater than 50% of the total polymeric content) of at least one pharmaceutically acceptable water insoluble polymer, and optionally a minor proportion (e.g., less than 50% of the total polymeric content) of at least one pharmaceutically acceptable water-soluble polymer.

Ammonio methacrylate co-polymers such as, for example, EUDRAGIT™ RS and EUDRAGIT™ RL (Evonik) are suitable for use in the present invention. These polymers are insoluble in pure water, dilute acids, buffer solutions, and/or digestive fluids over the entire physiological pH range. The polymers swell in water and digestive fluids independently of pH. In the swollen state, they are then permeable to water and dissolved active agents. The permeability of the polymers depends on the ratio of ethylacrylate (EA), methyl methacrylate (MMA), and trimethylammonioethyl methacrylate chloride (TAMCI) groups in the polymer. For example, those polymers having EA:MMA:TAMCI ratios of 1:2:0.2 (EUDRAGIT™ RL) are more permeable than those with ratios of 1:2:0.1 (EUDRAGIT™ RS). Polymers of EUDRAGIT™ RL are insoluble polymers of high permeability. Polymers of EUDRAGIT™ RS are insoluble films of low permeability. A diffusion-controlled pH-independent polymer in this family is RS 30 D which is a copolymer of ethyl acrylate, methyl methacrylate and a low content of methacrylic acid ester with quaternary ammonium groups present as salts to make the polymer permeable. RS 30 D is available as an aqueous dispersion.

The amino methacrylate co-polymers can be combined in any desired ratio, and the ratio can be modified to modify the rate of drug release. For example, a ratio of EUDRAGIT™ RS: EUDRAGIT™ RL of 90:10 can be used. Alternatively, the ratio of EUDRAGIT™ RS: EUDRAGIT™ RL can be about 100:0 to about 80:20, or about 100:0 to about 90:10, or any ratio in between. In such compositions, the less permeable polymer EUDRAGIT™ RS generally comprises the majority of the polymeric material with the more soluble RL, when it dissolves, permitting gaps to be formed through which solutes can come into contact with the core allowing for the active to escape in a controlled manner.

The amino methacrylate co-polymers can be combined with the methacrylic acid co-polymers within the polymeric material in order to achieve the desired delay in the release of the drug and/or poration of the coating and/or exposure of the composition within the coating to allow egress of drug and/or dissolution of the immobilization or water-soluble polymer matrix. Ratios of ammonio methacrylate co-polymer (e.g., EUDRAGIT™ RS) to methacrylic acid co-polymer in the range of about 99:1 to about 20:80 can be used. The two types of polymers can also be combined into the same polymeric material, or provided as separate coats that are applied to the beads.

Eudragit™ FS 30 D is an anionic aqueous-based acrylic polymeric dispersion consisting of methacrylic acid, methyl acrylate, and methyl methacrylate and is pH sensitive. This polymer contains fewer carboxyl groups and thus dissolves at a higher pH (>6.5). The advantage of such a system is that it can be easily manufactured on a large scale in a reasonable processing time using conventional powder layering and fluidized bed coating techniques. A further example is EUDRAGIT® L 30D-55 which is an aqueous dispersion of anionic polymers with methacrylic acid as a functional group. It is available as a 30% aqueous dispersion.

In addition to the EUDRAGIT™ polymers described above, a number of other such copolymers can be used to control drug release. These include methacrylate ester co-polymers such as, for example, the EUDRAGIT™ NE and EUDRAGIT™ NM ranges. Further information on the EUDRAGIT™ polymers can be found in "Chemistry and Application Properties of Polymethacrylate Coating Systems," in Aqueous Polymeric Coatings for Pharmaceutical Dosage Forms, ed. James McGinity, Marcel Dekker Inc., New York, pg 109-114 the entirety of which is incorporated herein by reference.

Several derivatives of hydroxypropyl methylcellulose (HPMC) also exhibit pH dependent solubility and may be used in the invention for the delayed release coating. As examples of such derivatives may be mentioned HPMC esters, for example hydroxypropyl methylcellulose phthalate (HPMCP), which rapidly dissolves in the upper intestinal tract and hydroxypropyl methylcellulose acetate succinate (HPMCAS) in which the presence of ionisable carboxyl groups causes the polymer to solubilize at high pH (>5.5 for the LF grade and >6.8 for the HF grade). These polymers are commercially available from Shin-Etsu Chemical Co. Ltd. As with other polymers described herein as useful for delayed release coatings, HPMC and derivatives (e.g. esters) may be combined with other polymers e.g. EUDRAGIT RL-30 D.

Other polymers may be used to provide a coating in particular enteric, or pH-dependent, polymers. Such polymers can include phthalate, butyrate, succinate, and/or mellitate groups. Such polymers include, but are not limited to, cellulose acetate phthalate, cellulose acetate succinate, cellulose hydrogen phthalate, cellulose acetate trimellitate, hydroxypropyl-methylcellulose phthalate, hydroxypropylmethylcellulose acetate succinate, starch acetate phthalate, amylose acetate phthalate, polyvinyl acetate phthalate, and polyvinyl butyrate phthalate.

pH Independent Polymer Delayed Release Coatings

In a particular embodiment the second coating, where present, is or comprises a polymeric coating which is pH-independent in its dissolution profile and/or in its ability to release the active ingredient incorporated in the compositions of the invention. A pH-independent polymer delayed release coating comprises a delayed release polymer, optionally a plurality of delayed release polymers, and one or more other optional components. The other components may serve to modulate the properties of the composition. Examples have already been given (e.g., Eudragit RS and RL).

Another example of a pH-independent polymeric coating is a coating that comprises or is ethylcellulose; a pH-independent polymeric coating may have a delayed release polymer that is ethylcellulose, therefore. It will be understood that an ethylcellulose formulation for use in coating a dosage form may comprise, in addition to ethylcellulose and—in the case of a liquid formulation—a liquid vehicle, one or more other components. The other components may serve to modulate the properties of the composition, e.g. stability or the physical properties of the coating such as the flexibility of the film coating. The ethylcellulose may be the sole delayed release polymer in such a composition. The ethylcellulose may be in an amount of at least 50%, at least 60%, at least 70%, at least 80%, at least 90% or at least 95% by weight of the dry weight of a coating composition for use in coating a dosage form. Accordingly, an ethylcellulose coating may include other components in addition to the ethylcellulose. The ethylcellulose may be in an amount of at least 50%, at least 60%, at least 70%, at least 80%, at least 90% or at least 95% by weight of the ethylcellulose coating. Consequently, ethylcellulose may be in an amount of at least 50%, at least 60%, at least 70%, at least 80%, at least 90% or at least 95% by weight of the dry weight of the second coating. Suitably the ethyl cellulose coating further comprises a plasticizer as described below to improve the flexibility of the film and to improve the film-forming properties of the coating composition during application of the coating.

A particular ethylcellulose coating composition which may be applied to the composition, optionally to the core (i.e. in the absence of a first coating) or to the first coating is a dispersion of ethylcellulose in a sub-micron to micron particle size range, e.g. from about 0.1 to 10 μm in size, homogeneously suspended in water with the aid of an emulsification agent, e.g. ammonium oleate. The ethylcellulose dispersion may optionally and preferably contain a plasticizer. Suitably plasticisers include for example dibutyl sebacate (DBS), diethylphthalate, triethyl citrate, tributyl citrate, triacetin, or medium chain triglycerides. The amount of plasticizer present in the coating composition will vary depending upon the desired properties of the coating. Typically the plasticizer comprises from 1 to 50%, for example about 8 to about 50% of the combined weight of the plasticizer and ethyl cellulose. Such ethylcellulose dispersions may, for example, be manufactured according to U.S. Pat. No. 4,502,888, which is incorporated herein by reference. One such ethylcellulose dispersion suitable for use in the present invention and available commercially is marketed under the trademark Surelease®, by Colorcon of West Point, Pa. USA. In this marketed product, the ethylcellulose particles are, e.g., blended with oleic acid and a plasticizer, then optionally extruded and melted. The molten plasticized ethylcellulose is then directly emulsified, for example in ammoniated water optionally in a high shear mixing device, e.g. under pressure. Ammonium oleate can be formed in situ, for instance to stabilize and form the dispersion of plasticized ethylcellulose particles. Additional purified water can then be added to achieve the final solids content. See also U.S. Pat. No. 4,123,403, which is incorporated herein by reference.

The trademark "Surelease®" is used hereinafter to refer to ethylcellulose coating materials, for example a dispersion of ethylcellulose in a sub-micron to micron particle size range, e.g. from about 0.1 to 10 μm in size, homogeneously suspended in water with the aid of an emulsification agent, e.g. ammonium oleate. In particular, the trademark "Surelease®" is used herein to refer to the product marketed by Colorcon under the Surelease® trademark.

Surelease® dispersion is an example of a combination of film-forming polymer, plasticizer and stabilizers which may be used as a second coating to adjust rates of active principle release with reproducible profiles that are relatively insensitive to pH. The principal means of drug release is by diffusion through the Surelease® dispersion membrane and is directly controlled by film thickness. Use of Surelease® is particularly preferred and it is possible to increase or decrease the quantity of Surelease® applied as coating in order to modify the dissolution of the coated composition. Unless otherwise stipulated, use of the term "Surelease"

may apply to Surelease E-7-19020, E-7-19030, E-7-19040 or E-7-19050. An ethylcellulose coating formulation, for example Surelease E-7-19020, may comprise ethylcellulose blended with oleic acid and dibutyl sebacate, then extruded and melted. The molten plasticized ethylcellulose is then directly emulsified in ammoniated water in a high shear mixing device under pressure. Ammonium oleate is formed in situ to stabilize and form the dispersion of plasticized ethylcellulose particles. Additional purified water is then added to achieve the final solids content. An ethylcellulose coating formulation, for example Surelease E-7-19030, may additionally comprise colloidal anhydrous silica dispersed into the material. An ethylcellulose coating formulation, for example Surelease E-7-19040, may comprise medium chain triglycerides instead of dibutyl sebacate, in particular in a formulation comprising colloidal anhydrous silica and oleic acid. An ethylcellulose coating formulation, for example Surelease E-7-19050, may derive from blending ethylcellulose with oleic acid before melting and extrusion. The molten plasticized ethylcellulose is then directly emulsified in ammoniated water in a high shear mixing device under pressure. Ammonium oleate is formed in situ to stabilize and form the dispersion of plasticized ethylcellulose particles. However, formulations that comprise medium chain triglycerides, colloidal anhydrous silica and oleic acid are preferred. Surelease E-7-19040 is particularly preferred.

The invention also contemplates using combinations of ethylcellulose, e.g. a Surelease formulation, with other coating components, for example sodium alginate, e.g. sodium alginate available under the trade name Nutrateric™.

In addition to the EUDRAGIT™ and Surelease® polymers discussed above, where compatible, any combination of coating polymers disclosed herein may be blended to provide additional delayed-release profiles.

The delayed release coating can further comprise at least one soluble excipient to increase the permeability of the polymeric material. These soluble excipients can also be referred to or are pore formers. Suitably, the at least one soluble excipient or pore former is selected from among a soluble polymer, a surfactant, an alkali metal salt, an organic acid, a sugar, a polysaccharide, and a sugar alcohol. Such soluble excipients include, but are not limited to, polyvinyl pyrrolidone, polyvinyl alcohol (PVA), polyethylene glycol, a water-soluble hydroxypropyl methyl cellulose, sodium chloride, surfactants such as, for example, sodium lauryl sulfate and polysorbates, organic acids such as, for example, acetic acid, adipic acid, citric acid, fumaric acid, glutaric acid, malic acid, succinic acid, and tartaric acid, sugars such as, for example, dextrose, fructose, glucose, lactose, and sucrose, sugar alcohols such as, for example, lactitol, maltitol, mannitol, sorbitol, and xylitol, xanthan gum, dextrins, and maltodextrins; and a polysaccharide susceptible of degradation by a bacterial enzyme normally found in the colon, for example polysaccharides include chondroitin sulphate, pectin, dextran, guar gum and amylase, chitosan etc. and derivatives of any of the foregoing. In some embodiments, polyvinyl pyrrolidone, mannitol, and/or polyethylene glycol can be used as soluble excipients. The at least one soluble excipient can be used in an amount ranging from about 0.1% to about 15% by weight, based on the total dry weight of the polymer coating, for example from about 0.5% to about 10%, about 0.5% to about 5%, about 1% to about 3%, suitably about 2% based on the total dry weight of the polymer coating. The delayed release coating may be free from HPMC.

The modifications in the rates of release, such as to create a delay or extension in release, can be achieved in any number of ways. Mechanisms can be dependent or independent of local pH in the intestine, and can also rely on local enzymatic activity to achieve the desired effect. Examples of modified-release compositions are known in the art and are described, for example, in U.S. Pat. Nos. 3,845,770; 3,916, 899; 3,536,809; 3,598,123; 4,008,719; 5,674,533; 5,059, 595; 5,591,767; 5,120,548; 5,073,543; 5,639,476; 5,354, 556; and 5,733,566 all of which are incorporated herein by reference in their entirety.

The addition to Surelease® or other pH-independent polymer substance of a second polymer (e.g. a polysaccharide, especially a heteropolysaccharide) which is susceptible to degradation by colonic bacterial enzymes (and optionally or alternatively by pancreatic or other relevant enzymes), helps provide targeted release of the active ingredient to a site or sites within the GI tract where the second polymer is degraded. By varying the amount of second polymer added present in the coating the dissolution profile may be optimized to provide the required release of cyclosporin A from the composition.

In a particular embodiments the delayed release coating provides for release of the active agent in at least the colon. Accordingly in one embodiment the coating comprises a combination of ethylcellulose (preferably a described above, and particularly formulated with an emulsification agent such as, for example, ammonium oleate and/or a plasticizer such as, for example, dibutyl sebacate or medium chain triglycerides) and a polysaccharide susceptible of degradation by a bacterial enzyme normally found in the colon. Such polysaccharides include chondroitin sulphate, pectin, dextran, guar gum and amylase, chitosan etc. and derivatives of any of the foregoing. Chitosan may be used in connection with obtaining a colon-specific release profile; additionally or alternatively, pectin may be so used.

The use of polysaccharides by themselves for delayed release coating purposes has been tried with limited success. Most of the non-starch polysaccharides suffer from the drawback of lacking good film forming properties. Also, they tend to swell in the GI tract and become porous, resulting in the early release of the drug. Even amorphous amylose, which is resistant to degradation by pancreatic alpha amylase but capable of degradation by colonic bacterial enzymes, has the disadvantage of swelling in aqueous media although this can be controlled by incorporating insoluble polymer, for example ethyl cellulose and/or acrylate, into the amylose film. Amylose however is not water-soluble and although water-insoluble polysaccharides are not excluded, use of a water-soluble polysaccharide (WSP) susceptible to bacterial enzymatic degradation brings particularly advantageous results when used as a coating in accordance with this embodiment of the present invention. A particularly preferred polysaccharide in this embodiment of the present invention is pectin. Various kinds of pectin may be used including pectin of different grades available i.e. with differing degrees of methylation (DM), i.e. percentage of carbonyl groups esterified with methanol, for example pectins with a DM of more than 50%, known as High Methoxy (HM) Pectins or Low Methoxy (LM) pectins, or a pectin combination comprising an HM pectin and an LM pectin. It is also possible in this embodiment to use pectins having various degrees of acetylation (Dac). Taken together, the DM and Dac or the degree of substitution is known as Degree of Esterification (DE). Pectins of various DE's may be used according to the invention. As an alternative to pectin, sodium alginate may be used as a polysaccharide according to an embodiment of the invention. However, other embodiments may conveniently include amylose and/or starch which contains amylose. Various grades of starch, containing different percentages of amylose may be used including for example Hylon V (National Starch Food Innovation) which has an amylose percentage of 56% or Hylon VII which has an amylose percentage of 70%. The remaining percentage is amylopectin. The polysaccharides pectin, amylose and sodium alginate are particularly preferred for achieving colon delivery of the active ingredient.

It has been found that water-soluble polysaccharide, suitably pectin, can act as a former of pores in the coating otherwise provided by ethylcellulose (preferably Surelease). By "pores" is not meant shaft-like holes from the surface to the core of the composition, rather areas of weakness or absence of coating occurring stochastically on and within the coating of the invention.

Pore formers have been described before in connection with Surelease (see e.g. US 2005/0220878).

According to a particular embodiment of the invention the delayed release coating comprises ethylcellulose, e.g. Surelease™, and a water-soluble polysaccharide (WSP) wherein the proportion of ethylcellulose (in particular Surelease™) to WSP is ideally in the range 90:10 to 99:1, preferably, 95:5 to 99:1, more preferably 97:3 to 99:1, for example about 98:2 based upon the dry weight of the coating. Suitably in this embodiment the weight gain of the composition due to application of the coating comprising ethylcellulose, e.g. Surelease™, and the WSP is in the range of from 1 to 30% (for example from: 3% to 25%; 5% to 15%; 8% to 14%; 10% to 12%; 12% to 18%; or 16% to 18%, suitably the weight gain is about 11%, about 11.5%, or about 17%). It is particularly preferred that the WSP in this embodiment is pectin. Particularly favoured weight gains using coatings comprising ethylcellulose, e.g. Surelease™, are those in the range 5-12% or in the range 8-12%.

Accordingly in an embodiment the second coating comprises ethyl cellulose and a water soluble polysaccharide (particularly pectin) wherein the water-soluble polysaccharide (WSP) is present in an amount of 0.1% to about 10% by weight, based on the dry weight of the second coating. Suitably the WSP is present in an amount of from about 0.5% to about 10%, for example about 0.5% to about 5%, about 1% to about 3%, suitably about 2% based on the total dry weight of the second coating. In this embodiment the WSP is preferably pectin. In this embodiment the second composition suitably further comprises a plasticizer. Suitable plasticizers include these described above in relation to Surelease™. Suitably the weight gain of the composition due to application of the second coating in this embodiment is in the range of from 1 to 30% (for example from: 3% to 25%; 5% to 15%; 8% to 14%; 10% to 12%; 12% to 18%; or 16% to 18%, suitably the weight gain is about 11%, about 11.5%, or about 17%).

In an embodiment the delayed release polymer is not a water-soluble cellulose ether. Where the second coating comprises or is a delayed release polymer the delayed release polymer may not be the same as the water-soluble cellulose ether of the first coating. Accordingly the second coating may not be the same as the first coating.

Continuous Phase Polymer Matrix (Aqueous Phase)

This section of the specification refers to a polymer matrix and continuous phase both of which concern the hydrogel forming polymer matrix. Therefore, reference to a polymer matrix or continuous phase can be equated to the hydrogel forming polymer matrix. Furthermore, this section of the specification relating to the polymer matrix recites amounts of constituents in terms of percent by weight of the composition, in the context of this section of the specification, what is meant is percent by weight of the dry weight of the composition or core excluding coating(s).

The composition or the core may comprise a matrix or continuous phase and also a disperse phase or oil phase. Similarly the liquid composition of the invention comprises an aqueous phase comprising a hydrogel forming polymer. Suitably the continuous phase or matrix phase of the composition or core is or comprises a hydrogel-forming polymer. A hydrogel-forming polymer is a polymer capable of forming a hydrogel. A hydrogel may be described as a solid or semi-solid material, which exhibits no flow when at rest, comprising a network (matrix) of hydrophilic polymer chains that span the volume of an aqueous liquid medium. A hydrogel forming polymer matrix is a network of hydrogel forming polymer chains, thus a hydrogel forming polymer matrix is a hydrogel forming polymer that has been allowed or caused to form a matrix.

The composition or core may comprise a hydrogel-forming polymer matrix and the liquid composition may select a hydrogel-forming polymer selected from the group consisting of: gelatin; agar; agarose; pectin; carrageenan; chitosan; alginate; starch; xanthan gum; gum Arabic; guar gum; locust bean gum; polyurethane; polyether polyurethane; cellulose; cellulose ester, cellulose acetate, cellulose triacetate; cross-bonded polyvinyl alcohol; polymers and copolymers of acrylic acid, hydroxyalkyl acrylates, hydroxyethyl acrylate, diethylene glycol monoacrylate, 2-hydroxypropylacrylate, 3-hydroxypropyl acrylate; polymers and copolymers of methacrylic acid, hydroxyethyl methacrylate, diethyleneglycol monomethacrylate, 2-hydroxypropyl methacrylate, 3-hydroxypropyl methacrylate, dipropylene glycol monomethylacrylate; vinylpyrrolidone; acrylamide polymers and copolymers, N-methylacrylamide, N-propylacrylamide; methacrylamide polymers and copolymers, N-isopropylmethacrylamide, N-2-hydroxyethylmethacrylamide; and vinyl pyrrolidone; and combinations thereof. In specific embodiments binary or tertiary etc combinations of any of the above substances are foreseen.

In a further embodiment the hydrogel-forming polymer or the hydrogel forming polymer matrix is selected from the group consisting of gelatin, agar, a polyethylene glycol, starch, casein, chitosan, soya bean protein, safflower protein, alginates, gellan gum, carrageenan, xanthan gum, phthalated gelatin, succinated gelatin, cellulosephthalate-acetate, oleoresin, polyvinylacetate, polymerisates of acrylic or methacrylic esters and polyvinylacetate-phthalate and any derivative of any of the foregoing; or a mixture of one or more such hydrogel-forming polymers.

The hydrogel-forming polymer or the hydrogel forming polymer matrix may also be referred to as a hydrocolloid i.e. a colloid system wherein the colloid particles are disperse in water and the quantity of water available allows for the formation of a gel. In embodiments it is preferred to use reversible hydrocolloids preferably thermo-reversible hydrocolloids (e.g. agar, agarose, gelatin etc) as opposed to irreversible (single-state) hydrocolloids. Thermo-reversible hydrocolloids can exist in a gel and sol state, and alternate between states with the addition or elimination of heat. Gelatin, agar and agarose are thermo-reversible, rehydratable colloids and are particularly preferred. Gelatin derivatives such as, for example, succinated or phthalated gelatins are also contemplated. Thermoreversible hydrocolloids which may be used according to the invention, whether individually or in combination, include those derived from natural sources such as, for example, carrageenan (extracted from seaweed), gelatin (extracted from bovine, porcine, fish or vegetal sources), agar (from seaweed), agarose (a polysaccharide obtained from agar) and pectin (extracted from citrus peel, apple and other fruits). A non-animal based hydrocolloid may be preferred for certain applications e.g. administration to vegetarians or to individuals not wishing to ingest animal products for religious or health reasons. In relation to the use of carrageenan, reference is made to US patent application 2006/0029660 A1 (Fonkwe et al), the entirety of which is incorporated herein by reference. The hydrogel-forming polymer may comprise or be a combination of gelatin with one or more other thermoreversible hydrocolloids, e.g. with one or more other of the thermoreversible hydrocolloids just listed. The hydrogel-forming polymer may comprise or be a combination of gelatin with agar; optionally, at least one further thermoreversible hydrocolloid may be included in the combination, for example one just listed.

Thermo-reversible colloids present a benefit over other hydrogel-forming polymers. Gelation or hardening of thermo-reversible colloids occurs by cooling the colloid, e.g. in a liquid cooling bath or by air flow. Gelation of other hydrogel-forming polymers, which is chemically driven, can lead to leakage of the composition contents into the gelation medium as the hardening process can take time to occur. Leakage of the content of the composition may lead to an inaccurate quantity of the active ingredient within the composition. Thermo-reversible colloids are also known as thermo-reversible gels, and it is therefore preferred that the hydrogel former be a thermo-reversible gelling agent.

Another term which may be applied to hydrogel formers which are advantageous is "thermotropic": a thermotropic gelling agent (which the reader will infer is preferred as a hydrogel former used in the invention) is one caused to gel by a change in temperature and such gelling agents are able to gel more rapidly than those whose gelling is chemically induced, e.g. ionotropic gelling agents whose gelling is induced by ions, for example chitosan. In embodiments of the invention, therefore, the hydrogel former is a thermotropic gel-forming polymer or a combination of such polymers.

The manufacture of the composition to prepare a core may require that the hydrogel-forming polymer be present as a solution, which is preferably an aqueous solution. The hydrogel-forming polymer represents between 5% and 50%, preferably between 10% and 30%, still more preferably between 15% and 20% by weight of the aqueous phase during manufacture as described herein. In addition the hydrogel-forming polymer may comprise 8 to 35%, (for example 15-25%, preferably 17-18%) hydro-gel forming polymer; 65%-85% (preferably 77-82%) of water plus, optionally, from 1-5% (preferably 1.5 to 3%) sorbitol. When present surfactant (e.g. anionic surfactant) in the aqueous phase pre-mix may be present in an amount of 0.1 to 5% (preferably 0.5 to 4%) wherein all parts are by weight of the aqueous phase.

In the aspect of the invention where the liquid composition is provided the hydrogel forming polymer may be present as an aqueous solution in the aqueous phase. The amounts of hydrogel forming polymer recited in the immediately preceding paragraph are equally relevant to embodiments of the liquid composition.

In embodiments the composition comprises at least 25%, suitably at least 40% by weight based upon the dry weight of the composition of the hydrogel-forming polymer matrix. For example the hydrogel-forming polymer matrix is present from 25 to 70%, for example 40 to 70% suitably 45 to 60% of the composition, wherein the % is by weight based upon the dry weight of the composition.

In embodiments the hydrogel-forming polymer is a pharmaceutically acceptable polymer.

In certain embodiments the hydrogel-forming polymer is gelatin. In certain embodiments the hydrogel-forming polymer matrix is gelatin. In certain embodiments the hydrogel-forming polymer comprises gelatin. In certain embodiments the gelatin comprises at least 30%, for example 30 to 70% or 40 to 70% suitably 40 to 60% of the composition, wherein the % is by weight based upon the dry weight of the composition.

The hydrogel-forming polymer may optionally comprise a plasticiser for example sorbitol or glycerine, or a combination thereof. In particular one or more plasticisers may be combined with gelatin.

In embodiments in which the hydrogel-forming polymer comprises or is gelatin, reference is hereby made to "Bloom strength", a measure of the strength of a gel or gelatin developed in 1925 by O. T. Bloom. The test determines the weight (in grams) needed by a probe (normally with a diameter of 0.5 inch) to deflect the surface of the gel 4 mm without breaking it. The result is expressed in Bloom (grades) and usually ranges between 30 and 300 Bloom. To perform the Bloom test on gelatin, a 6.67% gelatin solution is kept for 17-18 hours at 10° C. prior to being tested.

When the hydrogel-forming polymer comprises or is gelatin the bloom strength of the gelatin may be in the range of 125 Bloom to 300 Bloom, 200 Bloom to 300 Bloom and preferably 225 Bloom to 300 Bloom. It should be appreciated that higher bloom strength gelatin can be replaced by lower bloom strength gelatin at higher concentrations.

According to the invention, in embodiments in which the hydrogel forming polymer or hydrogel-forming polymer matrix comprises or is gelatin, the gelatin may be sourced by a variety of means. For example, it can be obtained by the partial hydrolysis of collagenous material, such as the skin, white connective tissues, or bones of animals. Type A gelatin is derived mainly from porcine skins by acid processing, and exhibits an isoelectric point between pH 7 and pH 9, while Type B gelatin is derived from alkaline processing of bones and animal (bovine) skins and exhibits an isoelectric point between pH 4.7 and pH 5.2. Type A gelatin is somewhat preferred. Gelatin for use in the invention may also be derived from the skin of cold water fish. Blends of Type A and Type B gelatins can be used in the invention to obtain a gelatin with the requisite viscosity and bloom strength characteristics for bead manufacture.

Lower temperature gelatin (or gelatin derivatives or mixtures of gelatins with melting point reducers) or other polymer matrices able to be solidified at lower temperatures (e.g. sodium alginate) may also be used. It is therefore believed that polymer which comprises or is low temperature gelatin is a preferred matrix polymer.

According to the invention, in embodiments in which the hydrogel forming polymer or hydrogel forming polymer matrix comprises or is gelatin, the starting gelatin material is preferably modified before manufacture to produce "soft gelatin" by the addition of a plasticizer or softener to the gelatin to adjust the hardness of the composition of the invention. The addition of plasticizer achieves enhanced softness and flexibility as may be desirable to optimise dissolution and/or further processing such as, for example, coating. Useful plasticizers of the present invention for combination with gelatin or another hydrogel-forming polymer include glycerine (1,2,3-propanetriol), D-sorbitol (D-glucitol), sorbitol BP (a non-crystallizing sorbitol solution) or an aqueous solution of D-sorbitol, sorbitans (e.g. Andidriborb 85/70), mannitol, maltitol, gum arabic, triethyl citrate, tri-n-butyl citrate, dibutylsebacate. Other or similar low molecular weight polyols are also contemplated for example ethylene glycol and propylene glycol. Polyethylene glycol and polypropylene glycol may also be used although these are less preferred. Glycerine and D-sorbitol may be obtained from the Sigma Chemical Company, St. Louis, Mo. USA or Roquette, France. Some active agents and excipients included for other functions may act as plasticisers.

Softeners or plasticisers, if utilized, can be ideally incorporated in a proportion rising to 30%, preferably up to 20% and more preferably up to 10% by dry weight of the composition of the invention, even more preferably between 3 and 8%, and most preferably between 4% and 6%.

Although not essential, the hydrogel-forming polymer matrix may also optionally contain a disintegrant where it is particularly desired to enhance the rate of disintegration of the composition of the invention. Examples of disintegrants which may be included are alginic acid, croscarmellose sodium, crospovidone, low-substituted hydroxypropyl cellulose and sodium starch glycolate.

A crystallisation inhibitor (e.g. approximately 1% by dry weight of the composition) may also be included in the composition of the invention. An example is hydroxy propyl/methyl cellulose (HPC or HPMC, hypromellose etc) which may play other roles such as, for example, emulsifier.

In another embodiment, the hydrogel-forming polymer matrix is chitosan which can exist in the form of biogels with or without additives as described e.g. in U.S. Pat. No. 4,659,700 (Johnson & Johnson); by Kumar Majeti N. V. Ravi in Reactive and Functional Polymers, 46, 1, 2000; and by Paul et al. in ST.P. Pharma Science, 10, 5, 2000 the entirety of all 3 of which is incorporated herein by reference. Chitosan derivatives e.g. thiolated entities are also contemplated.

The hydrogel-forming polymer matrix may be a non-hydrocolloid gum. Examples are the cross-linked salts of alginic acid. For example, aqueous solutions of sodium alginate gums extracted from the walls of brown algae have the well known property of gelling when exposed to di- and trivalent cations. A typical divalent cation is calcium, often in the form of aqueous calcium chloride solution. It is preferred in this embodiment that the cross-linking or gelling have arisen through reaction with such a multivalent cation, particularly calcium.

The hydrogel-forming polymer matrix may have a low water content, therefore the composition may have a low water content. As described below, during manufacture of a core the disperse phase or oil phase, optionally comprising cyclosporin, is mixed with an aqueous solution of the hydrogel-forming polymer and the composition is gelled, for example to provide a composition or a core which are minibeads. Suitably the composition or cores are dried following formation to reduce the water content present therein.

In certain embodiments the composition does not comprise compounds containing a disulphide bond. In embodiments the hydrogel-forming polymer does not comprise compounds containing a disulphide bond.

The hydrogel-forming polymer matrix forming the continuous phase of the core (aqueous phase) may further comprise a surfactant. Surfactants which may be used in the composition are described in the section "surfactants" below.

Surfactant which may be present in the continuous phase, aqueous phase or the hydrogel forming polymer matrix of the composition or core include, for example a surfactant selected from the group consisting of: cationic; amphoteric (zwitterionic); anionic surfactants, for example perfluorooctanoate (PFOA or PFO), perfluoro-octanesulfonate (PFOS), sodium dodecyl sulfate (SDS), ammonium lauryl sulfate, and other alkyl sulfate salts, sodium laureth sulfate, also known as sodium lauryl ether sulfate (SLES) and alkyl benzene sulphonate; and non-ionic surfactants for example perfluorocarbons, polyoxyethyleneglycol dodecyl ether (e.g. Brij such as, for example, Brij 35), Myrj (e.g. Myrj 49, 52 or 59), fatty alcohol ethoxylates, alkylphenol ethoxylate, fatty acid ethoxylates, fatty amide ethoxylates, alkyl glucosides, Tween 20 or 80 (also known as Polysorbate) (Brij, Myrj and Tween products are available commercially from Croda), poloxamers which are nonionic triblock copolymers composed of a central hydrophobic chain of polyoxypropylene (poly(propylene oxide)) flanked by two hydrophilic chains of polyoxyethylene (poly(ethylene oxide)), or a combination of the foregoing. In particular, the surfactant may be selected from, or comprise, anionic surfactants and combinations thereof, the anionic surfactants optionally being those mentioned in this paragraph. A particular class of surfactant comprises sulfate salts. A preferred anionic surfactant in the aqueous phase is SDS. Mixtures of anionic surfactants may be used. Mixtures of further surfactants are also contemplated, e.g. mixtures comprising perfluorocarbons.

In embodiments of the invention, the core comprises a hydrophilic surfactant which, without being bound by theory, is believed at least partially to partition the aqueous phase (polymer matrix).

Such surfactants intended for such inclusion in the aqueous phase of the core are preferably readily diffusing or diffusible surfactants to facilitate manufacturing and processing of the composition of the invention.

The surfactant may have an HLB of at least 10 and optionally of at least 15, e.g. at least 20, or at least 30 and optionally of 38-42, e.g. 40. Such surfactants can be of any particular type (ionic, non-ionic, zwitterionic) and may comprise as a proportion of dry weight of the composition from 0.1% to 6%, e.g. 0.1% to 5%. 0.1% to 4% or 0.1% to 3%, more preferably in a proportion of at least 1% and in particular between 1.0 and 4.5 or 5%, ideally within or just outside the 2-4% range, for example from 2 to 3% or approximately 2% or approximately 4%.

Unless otherwise stated or required, all percentages and ratios are by weight.

In one embodiment the anionic surfactant which may be present in the continuous phase, aqueous phase or the hydrogel forming polymer matrix of the composition or core may be an anionic surfactant selected from alkyl sulphates, carboxylates or phospholipids, or combinations thereof.

The physical form of the surfactant at the point of introduction into the aqueous phase during preparation of the composition or core plays a role in the ease of manufacture of the composition or core. As such, although liquid surfactants can be employed, it is preferred to utilize a surfactant which is in solid form (e.g. crystalline, granules or powder) at room temperature, particularly when the aqueous phase comprises gelatin.

Disperse Phase

The polymer matrix or the continuous phase of the composition, or in embodiments where a core is present, the core described above (for example the hydrogel-forming polymer) may comprise a disperse phase. Similarly the aqueous phase of the liquid composition comprises a disperse phase which is or comprises the oil phase. Suitably the disperse phase, where present, may comprise the cyclosporin. In such embodiments the cyclosporin is preferably soluble in the disperse phase, i.e. the disperse phase comprises a vehicle in which the active is dissolved. Embodiments wherein the cyclosporin is solubilised in the disperse phase are preferred, because such compositions release the cyclosporin in a solubilised form, which may enhance the therapeutic effect of the drug at the site of release, for example by enhancing absorption into the colonic mucosa.

In embodiments the cyclosporin is or is comprised in the disperse phase. The disperse phase is or comprises the oil phase. Preferably, the disperse phase is the oil phase.

The disperse phase may comprise a water immiscible phase (also referred to herein as an oil phase). The water immiscible phase may be solid, semi-solid or liquid at ambient temperature (e.g. 25° C.), and therefore the oil phase may for example be waxy at ambient temperature. The oil phase may be or may comprise a liquid lipid and optionally a solvent miscible therewith. The cyclosporin may be present in the oil phase. Suitably the cyclosporin is soluble in the oil phase.

The disperse phase may comprise a combination of oils, for example liquid lipids. The liquid lipid may be a short-, medium- or long-chain triglyceride formulation, or a combination thereof. A medium chain triglyceride(s) (MCT) comprises one or more triglycerides of at least one fatty acid selected from $C_6$, $C_7$, $C_8$, $C_9$, $C_{10}$, $C_{11}$ and $C_{12}$ fatty acids. It will be understood that commercially available triglyceride, in particular MCT, formulations useful in the invention are mixtures derived from natural products and usually or always contain minor amounts of compounds which are not MCTs; the term "medium chain triglyceride formulation" is therefore to be interpreted to include such formulations. A short chain triglyceride(s) comprises one or more triglycerides of at least one short chain fatty acid selected from $C_2$-$C_5$ fatty acids. A long chain triglyceride(s) comprises one or more triglycerides of at least one long chain fatty acid having at least 13 carbon atoms.

The liquid lipid may comprise or be triglycerides and/or diglycerides. Such glycerides may be selected from medium chain triglycerides or short chain triglycerides or a combination thereof.

The liquid lipid may be a caprylic/capric triglyceride, i.e. a caprylic/capric triglyceride formulation (which it will be understood may contain minor amounts of compounds which are not caprylic/capric triglycerides).

The disperse phase may optionally comprise a solvent. Accordingly the oil phase may comprise a solvent. Said solvent which is optionally included in an oil phase may be miscible with both the liquid lipid and with water. Examples of suitable solvents are 2-(2-ethoxyethoxy)ethanol available commercially under trade names Carbitol™, Carbitol cellosolve, Transcutol™, Dioxitol™, Poly-solv DE™, and Dowanal DE™; or the purer Transcutol™ HP (99.9). Transcutol P or HP, which are available commercially from Gattefosse, are preferred. Another possible co-solvent is poly(ethylene glycol). PEGs of molecular weight 190-210 (e.g. PEG 200) or 380-420 (e.g. PEG 400) are preferred in this embodiment. Suitable PEGs can be obtained commercially under the name "Carbowax" manufactured by Union Carbide Corporation although many alternative manufacturers or suppliers are possible.

The disperse phase may represent from 10-85% by dry weight of the core.

As discussed above the disperse phase may be an oil phase comprising any pharmaceutically suitable oil, e.g. a liquid lipid. The oil phase may be present as oil drops. In terms of dry weight of the core, the oil phase may comprise a proportion from 10% to 85%, e.g. 15% to 50%, for example 20% to 30% or from 35% to 45%. The term "oil" means any substance that is wholly or partially liquid at ambient temperature or close-to-ambient temperature e.g. between 10° C. and 40° C. or between 15° C. and 35° C., and which is hydrophobic but soluble in at least one organic solvent. Oils include vegetable oils (e.g. neem oil) and petrochemical oils.

The oil may be present in the composition in an amount of from about 2% to about 25%, from about 3% to about 20%, from about 3% to about 10% or from about 5% to about 10% by weight based upon the dry weight of the core.

Oils which may be included in the oil phase include poly-unsaturated fatty acids such as, for example, omega-3 oils for example eicosapentanoic acid (EPA), docosohexaenoic acid (DHA), alpha-linoleic acid (ALA), conjugated linoleic acid (CLA). Preferably ultrapure EPA, DHA or ALA or CLA are used e.g. purity up to or above 98%. Omega oils may be sourced e.g. from any appropriate plant e.g. sacha inchi. Such oils may be used singly e.g. EPA or DHA or ALA or CLA or in any combination. Combinations of such components including binary, tertiary etc combinations in any ratio are also contemplated e.g. a binary mixture of EPA and DHA in a ratio of 1:5 available commercially under the trade name Epax 6000. The oil part of the oil phase may comprise or be an oil mentioned in this paragraph.

Oils which may be included in the oil phase are particularly natural triglyceride-based oils which include olive oil, sesame oil, coconut oil, palm kernel oil, neem oil. The oil may be or may comprise saturated coconut and palm kernel oil-derived caprylic and capric fatty acids and glycerin e.g. as supplied under the trade name Miglyol™ a range of which are available and from which one or more components of the oil phase of the invention may be selected including Miglyol™ 810, 812 (caprylic/capric triglyceride); Miglyol™ 818: (caprylic/capric/linoleic triglyceride); Miglyol™ 829: (caprylic/capric/succinic triglyceride; Miglyol™ 840: (propylene glycol dicaprylate/dicaprate). Note that Miglyol™ 810/812 are MCT formulations which differ only in $C_8/C_{10}$-ratio and because of its low $C_{10}$-content, the viscosity and cloud point of Miglyol™ 810 are lower. The Miglyol™ range is available commercially from Sasol Industries. As noted above, oils which may be included in the oil phase need not necessarily be liquid or fully liquid at room temperature. Waxy-type oils are also possible: these are liquid at manufacturing temperatures but solid or semi-solid at normal ambient temperatures. The oil part of the oil phase may comprise or be an oil mentioned in this paragraph.

Alternative or additional oils which may be included in the oil phase according to the invention are other medium chain triglyceride formulations such as for example Labrafac™ Lipophile manufactured by Gattefosse in particular product number WL1349. Miglyol™ 810, 812 are also medium chain triglyceride formulations.

Accordingly the oil phase may be or comprise medium chain mono- di- or tri-glycerides.

The medium chain glyceride(s) (eg mono- di- or tri-glyceride(s)) mentioned herein are those which comprise one or more triglycerides of at least one fatty acid selected from fatty acids having 6, 7, 8, 9, 10, 11 or 12 carbon atoms, e.g. $C_8$-$C_{10}$ fatty acids.

The oil phase may further comprise the surfactant as described above and elsewhere herein. The presence of the surfactant in the oil phase may also provide a stabilising effect on the liquid composition when the oil phase is dispersed in the aqueous phase. In addition the presence of the surfactant in the oil phase may inhibit crystallisation of cyclosporin from a cyclosporin solution in the oil phase. The surfactant may also provide enhanced emulsification when the disperse phase is mixed with the aqueous phase during preparation of the liquid composition, composition or core (i.e act as an emulsifier).

The liquid lipid or oil of the oil phase or disperse phase is suitably not a surfactant. However, certain oils, particularly those derived from natural sources will comprise components which may have surface active properties. For example many triglyceride oils also comprise mono and diglyceride components and may therefore exhibit some surfactant like properties. Accordingly the oil suitably has an HLB value of 0-10, however suitably the oil has an HLB which is close to 0 for example an HLB of 0 to 3, optionally about 0, about 1 or about 2.

Surfactant in the oil phase may for example be or comprise a medium chain or long chain fatty acid mono- or di-glyceride or a combination thereof, wherein the surfactant does not comprise or is not a polyethyleneglycol ether or ester. Optionally the surfactant is a medium chain or long chain fatty acid mono-glyceride, di-glyceride or a combination thereof, optionally wherein the surfactant does not comprise or is not a polyethyleneglycol ether or ester. Two particular surfactants contemplated by the invention are glyceryl caprylate/caprate and glyceryl monooleate/dioleate. Commercial preparations may also be used as a surfactant e.g. those commercial preparations which contain minor components. Preferred examples are Capmul GMO-50 (glyceryl monooleate/dioleate) and Capmul MCM (glyceryl caprylate/caprate).

Within embodiments, the HLB of the oil may be in the range 0-10 (optionally 1-8, e.g. 1-6 and sometimes 1-5).

In another embodiment the oil phase comprises an oil with an HLB in the range 0-10 (preferably 1-5) and the has an HLB of up to 10 and optionally up to 7, 1-8, 1-7, 1-5, 2-5, 1-4, 1-3, 1-2, 2-4, 3-4, 5-8, 6-8 and 6-7.

In another embodiment the oil phase comprises an oil and the surfactant wherein the oil and the surfactant both have an HLB in the range 0-10. For example the oil has an HLB of 1-5, for example 1 to 4 or 1-2 and the surfactant has an HLB 2-8, for example 3-7, 2-6, or 3-4).

Suitable oils which may comprise or be the oil phase or disperse phase with a low HLB (HLB less than 10) include medium chain triglycerides, caprylocaproyl macrogolglycerides and caprylic/capric triglyceride. In terms of commercial products, particularly preferred oils in the lower HLB range are Labrafac™ Lipophile (e.g. 1349 WL), Captex 355 and Miglyol 810.

It is to be understood that the oil phase or disperse phase in the embodiments above may further comprise one or more solvents, for example 2-(2-ethoxyethoxy)ethanol or low molecular weight PEG as mentioned above. The solvent may be present in the composition in an amount of form about 1% to 30%, for about 5% to about 30%, for about 10% to about 25%, or from about 12% to about 22% by weight based upon the dry weight of the uncoated composition or upon the dry weight of the core.

A particular oil phase comprises an oil (low HLB), the surfactant and a co-solvent. For example the following three commercial products: Transcutol P (as co-solvent), Myglyol 810 (as oil) and Capmul GMO-50 (surfactant). An oil phase may therefore comprise or consist of a combination of the following: 2-ethoxyethanol, an MCT and particularly a caprylic/capric triglyceride formulation, and glyceryl monooleate/dioleate. The oil phase may further comprise the cyclosporin.

Preferably, cyclosporin is soluble in the oil phase. As discussed below in relation to preparation of the composition, the cyclosporin is suitably dissolved in the oil phase and the oil phase is mixed with an aqueous phase comprising the hydrogel-forming polymer.

The disperse phase (oil phase) may be or comprise a glyceride formulation, optionally wherein the disperse phase is or comprises a fatty acid monoglyceride, diglyceride or triglyceride or a combination thereof, or the disperse phase is or comprises a caprylic/capric triglyceride formulation.

The disperse phase of the colloidal core may comprise self-assembly structures, for example micelles, vesicles, liposomes or nanoparticles, or at least the structures which result from drying aqueous colloids of such types (have the characteristics of structures which result from drying aqueous colloids of such types). The invention in particular includes formulations in which the disperse phase is micellar, i.e. formed of micelles and/or promicelles. The term "promicelle" refers to a part of a formulation which will form a micelle upon contact with water, e.g. gastrointestinal contents.

The following discussion for convenience refers to micelles but is applicable in general to other self-assembly structures. A micelle-forming surfactant is present as micelles dispersed within the hydrogel-forming polymer in a "wet" (not yet dried) composition made as an intermediate in the manufacturing process described herein. It is believed also to be present as micelles in the dried composition but observability of micelles or micelle-like structures in the dried composition is not a requirement of the invention. It is mentioned at this point that the presence of a surfactant in micelle form does not require that the entire surfactant content of a composition is in micelle form as it is considered more probable that a portion of the surfactant will be outside the micelles. Thus in the "wet" composition, whether the hydrogel-forming polymer is in the gel state or the sol (liquid) state may comprise the micelle-forming surfactant at a concentration above the critical micelle concentration.

The diameter of the dispersed micelles may be between 0.5 nm and 200 nm, 1 nm and 50 nm, or 5 nm and 25 nm. The size of the micelles may be determined by dynamic light scattering or diffusion NMR techniques known within the art. Although the size of the micelles is given as a diameter this does not imply that the micelles must be purely spherical species only that they may possess some approximately circular dimension.

The surfactant may be a non-ionic surfactant. The surfactant may be a polyoxyethylated surfactant. The surfactant has a hydrophilic head which may be a hydrophilic chain, for example a polyoxyethylene chain or a polyhydroxylated chain.

The surfactant of course has a hydrophobic part and in particular a hydrophobic chain. The hydrophobic chain may be a hydrocarbon chain, for example having at least 6 carbon atoms and optionally at least 10 carbon atoms, and particularly of at least 12 carbon atoms; some hydrocarbon chains have no more than 22 carbon atoms, for example $C_{10}$-$C_{20}$, $C_{12}$-$C_{20}$ or $C_{15}$-$C_{20}$ hydrocarbon chains. It may be an alkyl chain, e.g. having a number of carbon atoms just mentioned. It may be an alkenyl chain comprising one or more carbon-carbon double bonds, e.g. having a number of carbon atoms just mentioned. The surfactant may comprise a hydrocarbon chain, e.g. alkyl chain or alkenyl chain that is substituted provided that it maintains a hydrophobic characteristic. There may for example be one or two substituents, for example a single substituent, e.g. selected from halogen (e.g.

F or Cl), hydroxy, thiol oxo, nitro, cyano; hydroxy or thiol substituents may be esterified by for example a fatty acid. One class of surfactants comprise a hydrocarbon monosubstituted by hydroxy; optionally, at least a portion of the hydroxy groups of an aliquot of surfactant, e.g. of the surfactant in a bead, may be esterified by a fatty acid or mono-hydroxy fatty acid as disclosed herein or etherified by a fatty alcohol for example having at least 6 carbon atoms and optionally at least 10 carbon atoms, and particularly of at least 12 carbon atoms; some hydrocarbon chains have no more than 22 carbon atoms, for example $C_{10}$-$C_{20}$, $C_{12}$-$C_{20}$ or $C_{15}$-$C_{20}$ fatty alcohols.

The hydrophobic chain may be part of an esterified fatty acid $R^1$—COOH or of an etherified or esterified fatty ether $R^1$—COH where $R^1$ is the hydrophobic chain, e.g. as mentioned in the preceding paragraph. The ester-forming or, as the case may be, ether-forming group will typically comprise a hydrophilic chain.

As mentioned, the surfactant may have a hydrophilic chain and may be a non-ionic surfactant, and may satisfy both requirements. The hydrophilic chain may be a poly(ethyleneglycol), also known as poly(oxyethylene) or macrogol. The hydrophilic chain may be of the formula —(O—$CH_2$—$CH_2$)$_n$—OR where n is 5 or 6 to 50 and R is H or alkyl, e.g. ethyl or methyl. The invention includes implementations in which n is from 6 to 40, e.g. from 6 to 35. In some embodiments, n is from 6 to 25 and optionally is from 8 to 25 or from 8 to 15. In other embodiments, n is from 8 to 50 or from 8 to 40, e.g. is from 10 to 50, 10 to 40 or 10 to 35. In a particular embodiment, n is 15. For all hydrophilic chains of the formula —(O—$CH_2$—$CH_2$)$_n$—OR, in one class of embodiments R is H.

The hydrophilic chain may be a polyhydroxylated chain (for example a $C_5$-$C_{20}$ e.g. $C_5$-$C_{10}$ chain), e.g. having a hydroxy group on the carbon atoms of the chain, for example a glucamide.

The micelle-forming surfactant may comprise a combination of a hydrophobic chain as described above and a hydrophilic chain as described above. It may therefore be, or comprise, a macrogol ester of a fatty acid as described herein or a macrogol ether of a fatty alcohol as described herein.

Micelle-forming surfactants comprising a hydrophobic chain and a hydrophilic chain can be selected from the group consisting of: macrogol esters; macrogol ethers; diblock copolymers; triblock copolymers; and amphiphilic polymers. In certain embodiments of the invention any combinations of the group are included within the invention.

Examples of macrogol esters which are suitable for use in the present invention are macrogol esters of fatty acids having at least 6 carbon atoms and optionally at least 10 carbon atoms, and particularly of at least 12 carbon atoms; some fatty acids have no more than 22 carbon atoms, for example $C_{10}$-$C_{20}$, $C_{12}$-$C_{20}$ or $C_{15}$-$C_{20}$ fatty acids. The fatty acids may be saturated or unsaturated but are in particular saturated. To be mentioned are macrogol 25 cetostearyl ether (Cremophor® A25); macrogol 6 cetostearyl ether (Cremophor® A6); macrogol glycerol ricinoleate 35 (Cremophor® EL); macrogol-glycerol hydroxystearate 40 (Cremophor® RH 40); macrogol-15-hydroxystearate (Solutol® HS 15). Examples of macrogol ethers which are suitable for use in the present invention are macrogol ethers of fatty alcohols having at least 6 carbon atoms and optionally at least 10 carbon atoms, and particularly of at least 12 carbon atoms; some fatty alcohols have no more than 22 carbon atoms, for example $C_{10}$-$C_{20}$, $C_{12}$-$C_{20}$ or $C_{15}$-$C_{20}$ fatty alcohols. The fatty alcohols may be saturate or unsaturated but are in one embodiment saturated.

Examples of amphiphilic polymers which are suitable for use in the present invention are: alkyl glucamides; fatty alcohol poly(ethoxyl)ates also known as polyethoxylated alkyl ethers; poly(ethoxyl)ated fatty acid esters (Myrj or Solutol); fatty amide polyethoxylate; fatty amine ethoxylate; alkylphenol ethoxylate; polyethoxylated sorbitan esters (polysorbates); polyethoxylated glycerides; or poly-glycerol esters.

Examples of copolymers, which are suitable for use in the present invention are: pluronics(poloxamers); polyvinylpyrollidone-polyvinylacetate (Plasdone S630); aminoalkyl methacrylate copolymer (Eudragit EPO); methacrylic acid-methyl methacrylate copolymer (Eudragit S100, L100); polycaprolactone-PEG; polycaprolactone-methoxy-PEG; poly(aspartic acid)-PEG; poly(benzyl-L-glutamate)-PEG; poly(D,L-lactide)methoxy-PEG; poly(benzyl-L-aspartate-PEG; or poly(L-lysine)-PEG In a preferred embodiment the micelle-forming surfactant cis a macrogol ester, more preferably a macrogol ester that conforms to the European Pharmacopoeia monograph number 2052 macrogol-15-hydroxystearate, such as Kolliphor® HS 15 marketed by BASF.

Kolliphor® HS 15 consists of polyglycol mono- and di-esters of 12-hydroxystearic acid and about 30% of free polyethylene glycol. The main components of the ester part have the following chemical structures:

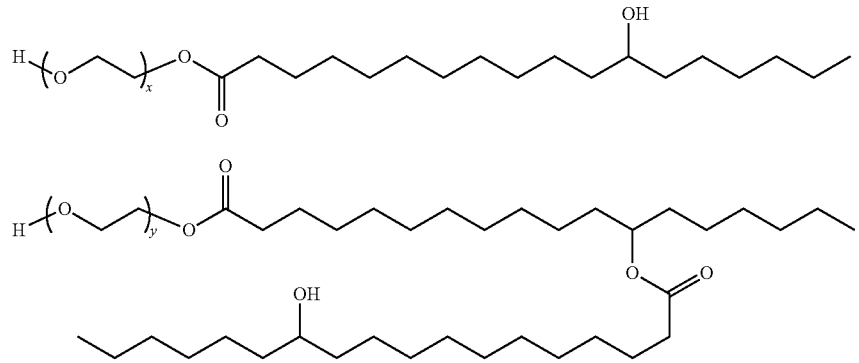

where x and y are integers and a small part of the 12-hydroxy group can be etherified with polyethylene glycol.

Suitable surfactants comprise those which during manufacture combine with the aqueous phase (including hydrogel-forming polymer) in an amount above their CMC to form a clear liquid. Kolliphor® HS 15 is such a surfactant.

In certain embodiments the weight ratio of the micelle-forming surfactant to the antigen is from 10:1 to 100:1, optionally from 50:1 to 100:1. In some embodiments, the ratio is from 80:1 to 90:1. In particular embodiments, the ratio is from 50:1 to 60:1.

In particular embodiments, the compositions of the invention comprise a combination of micelle-forming compounds. Such a combination of micelle-forming compounds may consist of two or more surfactants as mentioned in the preceding section of this specification. Alternatively, a surfactant may be combined with one or more other compounds at least potentially able to form micelles with the surfactant, optionally selected from cationic lipids and glycolipids, amongst others. As an additional option, a composition may comprise a plurality of surfactants as mentioned in the preceding section of this specification and one or more other compounds at least potentially able to form micelles with the surfactant, optionally selected from cationic lipids and glycolipids, amongst others.

The invention therefore includes compositions as described herein which comprise:

two or more micelle-forming surfactants, e.g. two or more surfactants having a hydrophobic chain and a hydrophilic chain;

a compound, e.g. a single compound or two or more compounds, selected from cationic lipids and glycolipids;

two or more micelle-forming surfactants and a compound, e.g. a single compound or two or more compounds, selected from cationic lipids and glycolipids.

A disperse phase which is or comprises a surfactant may enhance the absorption of an active ingredient, for example cyclosporin A, into the tissue of the GIT, for example by forming self-assembly structures, such as micelles, which are associated with the active ingredient and thus present the drug to the mucosa tissue of the GI tract in a form which enhances uptake/absorption into the tissue.

The oil phase may also include one or more volatile or non-volatile solvents, which may be the same or different from the solvent or co-solvent previously mentioned. Such solvents may for example remain in the formulation of the invention following processing e.g. initial dissolution of the components present in the core, and have no particular function in the core formulation. Alternatively, such solvents if present may function to maintain the cyclosporin a dissolved state (in solution) within the oil phase or to facilitate dispersion, egress etc. In other embodiments, the solvent may have partly or fully evaporated during processing and therefore be present in only minor quantities if at all. In a related embodiment, the solvent, particularly when a solvent which is both oil and water-soluble is used, may be partly or completely present in the aqueous phase of the core. An example of such a solvent is ethanol. Another example is transcutol which is already mentioned as a co-solvent.

Accordingly, the composition may comprise a hydrogel-forming polymer matrix which forms a continuous phase and a disperse phase comprising cyclosporin, a low HLB medium or long chain mono- or di-ester surfactant, a low HLB oil, and optionally a co-solvent. Optionally, the medium or long-chain mono- or di-ester surfactant is a medium- or long-chain mono- or di-glyceride surfactant.

In a particular embodiment the composition or the core is in the form of a solid colloid, the colloid comprising a continuous phase and a disperse phase, wherein the disperse phase is or comprises:
cyclosporin;
a medium chain mono-, di- and/or tri-glyceride, for example a medium chain triglyceride, particularly caprylic/capric triglyceride;
a medium- or long-chain mono- or di-glyceride, particularly glyceryl monooleate/dioleate; and
a co-solvent (for example 2-(ethoxyethoxy)ethanol);
and wherein the continuous phase is or comprises:
a hydrogel-forming polymer matrix which is or comprises a hydrocolloid selected from carrageenan, gelatin, agar and pectin, or a combination thereof optionally selected from gelatin and agar or a combination thereof, more particularly the polymer of the a hydrogel-forming polymer matrix is or comprises gelatin;
a plasticiser, optionally a plasticiser selected from glycerin, a polyol for example sorbitol, polyethylene glycol and triethyl citrate or a mixture thereof, particularly sorbitol; and
an anionic surfactant, for example at least one surfactant selected from fatty acid salts, alkyl sulphates and bile salts, particularly an alkyl sulphate, for example sodium dodecyl sulphate.

In a further specific embodiment the disperse phase comprises:
cyclosporin in an amount of 60-180 mg/g;
caprylic/capric triglyceride in an amount of 40-80 mg/g;
2-(2-ethoxyethoxy)ethanol in an amount of 100-200 mg/g; and
glyceryl monooleate and/or glyceryl dioleate in an amount of 100-150 mg/g, wherein
weights are based upon the dry weight of the composition.
The oil phase or disperse phase may comprise:
cyclosporin in an amount of 120-360 mg/g;
caprylic/capric triglyceride in an amount of 80-160 mg/g;
2-(2-ethoxyethoxy) ethanol in an amount of 200-400 mg/g; and
glyceryl monooleate and/or glyceryl dioleate in an amount of 200-300 mg/g,
wherein the weights are based on the weight of the wet composition.

The liquid composition may comprise an oil phase comprising:
cyclosporin in an amount of 20-60 mg/g;
caprylic/capric triglyceride in an amount of 13-27 mg/g;
2-(2-ethoxyethoxy) ethanol in an amount of 50-70 mg/g; and
glyceryl monooleate and/or glyceryl dioleate in an amount of 30-55 mg/g,
wherein weights are based upon the wet weight of the composition, i.e. the liquid composition, optionally wherein the oil phase to aqueous phase ratio may be 1:5.

In an embodiment the aqueous phase or continuous phase comprises a hydrogel-forming polymer matrix comprising gelatin in an amount of 300 to 700 mg/g, and SDS in an amount of 15-50 mg/g, wherein weights are based upon the dry weight of the composition.

In an embodiment the aqueous phase may comprise a hydrogel-forming polymer matrix comprising gelatin in an amount of 120 to 280 mg/g and SDS in an amount of 6-20 mg/g wherein the weights are based upon the weight of the aqueous phase. The aqueous phase may comprise a hydrogel-forming polymer matrix comprising gelatin in an amount of 100 to 230 mg/g and SDS in an amount of 5-16 mg/g, wherein the weights are based on the weight of the composition, i.e. the liquid composition, optionally wherein the oil phase to aqueous phase ratio may be 1:5.

Suitably in the embodiment of the immediately preceding two paragraphs the cyclosporin may be present in an amount of 90 to 140 mg/g, for example of 60 to 150 mg/g, 80 to 120 mg/g or particularly 80 to 100 mg/g. The anionic surfactants are as defined herein, for example an anionic surfactant selected from alkyl sulphates, carboxylates or phospholipids (particularly SDS).

The composition or the cores described above comprising hydrogel-forming polymer matrix may be coated as described herein. A particular coating for these embodiments is a coating comprising:

a first coating (sub-coating) which is or comprises a water-soluble cellulose ether, particularly hydroxypropylmethyl cellulose;

a second coating outside the first coating which is or comprises a modified release coating, particularly a pH independent modified release coating, more especially a coating comprising ethyl cellulose (e.g. Surelease) still more particularly a coating comprising ethyl cellulose and a water-soluble polysaccharide such as pectin (e.g. a Surelease-pectin coating as described herein); and wherein the first coating is present in an amount corresponding to a weight gain due to the first coating in a range selected from: (i) from 8% to 12%, for example about 10%; or (ii) from 4% to 6%, for example about 5% by weight based upon the weight of the formulation prior to applying the first coating; and wherein the second coating is present in an amount corresponding to a weight gain of the formulation due to the second coating selected from (a) from 10% to 12%, for example about 11% or about 11.5%; or (b) from 16% to 18%, for example about 17% by weight based upon the weight of the formulation prior to applying the second coating.

Equally, the composition or the cores described above comprising hydrogel-forming polymer matrix may be coated with a coating comprising:

a second coating which is or comprises a modified release coating, particularly a pH independent modified release coating, more especially a coating comprising ethyl cellulose (e.g. Surelease) still more particularly a coating comprising ethyl cellulose and a water-soluble polysaccharide such as pectin (e.g. a Surelease-pectin coating as described herein); and wherein the second coating is present in an amount corresponding to a weight gain of the formulation due to the second coating selected from (a) from 10% to 12%, for example about 11% or about 11.5%; or (b) from 16% to 18%, for example about 17% by weight based upon the weight of the formulation prior to applying the second coating.

Surfactant

The composition comprises a surfactant, as described above. The surfactant may be present in the composition or the core, for example in the hydrogel-forming polymer matrix, or in the disperse phase or both. The surfactant may also be present in one or more of the coatings comprised in the composition or applied to the core.

The composition may comprise a further surfactant. Where the composition comprises a further surfactant this surfactant can be referred to as a second surfactant and the surfactant present in the composition of the invention can be referred to as a first surfactant. Accordingly, the first surfactant is or comprises the medium chain or long chain fatty acid mono- or di-glyceride or a combination thereof, which does not comprise or is not a polyethyleneglycol ether or ester. The further surfactant may be present in the composition or the core, for example in the hydrogel-forming polymer matrix, or in the disperse phase or both. The further surfactant may also be present in one or more of the coatings comprised in the composition or applied to the core. Suitable further surfactants can be anionic, cationic, zwitterionic, or non-ionic.

In the description and claims of this specification, the term "surfactant" is employed as a contraction for "surface active agent". For the purposes of this description and claims, it is assumed that there are four major classifications of surfactants; therefore the further surfactant may be: anionic, cationic, non-ionic, and amphoteric (zwitterionic). The non-ionic surfactant remains whole, has no charge in aqueous solutions, and does not dissociate into positive and negative ions. Anionic surfactants are water-soluble, have a negative charge and dissociate into positive and negative ions when placed in water. The negative charge lowers the surface tension of water and acts as the surface-active agent. Cationic surfactants have a positive charge, and also dissociate into positive and negative ions when placed in water. In this case, the positive ions lower the surface tension of the water and act as the surfactant. The amphoteric (zwitterionic) surfactant assumes a positive charge in acidic solutions and performs as a cationic surfactant, or it assumes a negative charge in an alkaline solution and acts as an anionic surfactant.

The further surfactant(s) may be selected from: anionic surfactants and combinations thereof; from non-ionic surfactants and combinations thereof; and from combination of an anionic surfactant (e.g. a single such surfactant or a plurality thereof) and a non-ionic surfactant (e.g. a single such surfactant or a plurality thereof). Preferably the second surfactant is an anionic surfactant.

Accordingly, in an embodiment the liquid composition comprises an aqueous phase comprising a hydrogel forming polymer, a first surfactant and an oil phase being dispersed in the aqueous phase in which cyclosporin is dissolved, wherein the first surfactant is or comprises a medium chain or long chain fatty acid mono- or di-glyceride or a combination thereof and the first surfactant does not comprise or is not a polyethyleneglycol ether or ester, the liquid composition, further comprising a second surfactant, preferably wherein the second surfactant is an anionic surfactant. The second surfactant may be present in an amount of 10 to 70 mg/g or 15 to 60 mg/g.

Furthermore, in an embodiment the composition comprises cyclosporin, a hydrogel forming polymer matrix, a first surfactant and an oil phase being dispersed in the hydrogel forming polymer matrix, wherein the first surfactant is or comprises a medium chain or long chain fatty acid mono- or di-glyceride or a combination thereof and does not comprise or is not a polyethyleneglycol ether or ester, the composition further comprising a second surfactant, preferably wherein the second surfactant is an anionic surfactant.

Surfactants can also be classified according to their hydrophilic-lipophilic balance (HLB) which is a measure of the degree to which the surfactant is hydrophilic or lipophilic, determined by calculating values for the different regions of the molecule, as described (originally for non-ionic surfactants) by Griffin in 1949 and 1954 and later by Davies. The methods apply a formula to the molecular weight of the whole molecule and of the hydrophilic and lipophilic portions to give an arbitrary (semi-empirical) scale up to 40 although the usual range is between 0 and 20. An HLB value of 0 corresponds to a completely hydrophobic molecule, and a value of 20 would correspond to a molecule made up completely of hydrophilic components. The HLB value can be used to predict the surfactant properties of a molecule:

| HLB Value | Expected properties |
| --- | --- |
| 0 to 3 | antifoaming agent |
| from 4 to 6 | W/O emulsifier |
| from 7 to 9 | wetting agent |
| from 8 to 18 | an O/W emulsifier |
| from 13 to 15 | typical of detergents |
| 10 to 18 | solubiliser or hydrotrope |

Although HLB numbers are assigned to surfactants other than the non-ionic, for which the system was invented, HLB numbers for anionic, cationic, non-ionic, and amphoteric (zwitterionic) surfactants can have less significance and often represent a relative or comparative number and not the result of a mathematical calculation. This is why it is possible to have surfactants above the "maximum" of 20. HLB numbers can however be useful to describe the HLB requirement of a desired application for a given emulsion system in order to achieve good performance.

Non-Ionic Surfactants

The further surfactant (second surfactant) may be or comprise at least one surfactant selected from the following non-ionic surfactants.

PEG-fatty acid monoester surfactants, PEG-fatty acid diester surfactants, PEG-fatty acid monoester and diester surfactant mixtures, PEG glycerol fatty acid esters, transesterified products of oils and alcohols, lower alcohol fatty acid esters, polyglycerised fatty acids, propylene glycol fatty acid esters, mono and diglyceride surfactants, sterol and sterol derivative surfactants, PEG-sorbitan fatty acid esters, sorbitan fatty acid esters, polyethylene glycol alkyl ethers, sugar ester surfactants, polyethylene glycol alkyl phenol surfactants, POE-POP block copolymers, phospholipids.

A PEG-fatty acid mono ester surfactant for example PEG 4-100 monolaurate, PEG 4-100 monooleate, PEG 4-100 monostearate, PEG-laurate, PEG-oleate, PEG stearate, and PEG ricinoleate. A PEG-fatty acid diester surfactant for example PEG dilaurate; PEG dioleate, PEG distearate, PEG dipalmitate. A mixture of PEG-fatty acid mono- and diesters.

A PEG glycerol fatty acid ester for example PEG glyceryl laurate, PEG glyceryl stearate, PEG glyceryl oleate.

PEG-sorbitan fatty acid esters for example PEG sorbitan laurate, PEG sorbitan monolaurate, PEG sorbitan monopalmitate, PEG sorbitan monostearate, PEG sorbitan tristearate, PEG sorbitan tetrastearate, PEG sorbitan monooleate, PEG sorbitan oleate, PEG sorbitan trioleate, PEG sorbitan tetraoleate, PEG sorbitan monoisostearate, PEG sorbitol hexaoleate, PEG sorbitol hexastearate.

Propylene glycol fatty acid esters for example propylene glycol monocaprylate, propylene glycol monolaurate, propylene glycol oleate, propylene glycol myristate, propylene glycol monostearate, propylene glycol 72ydroxyl stearate, propylene glycol ricinoleate, propylene glycol isostearate, propylene glycol monooleate, propylene glycol dicaprylate/dicaprate, propylene glycol dioctanoate, propylene glycon caprylate/caprate, propylene glycol dilaurate, propylene glycol distearate, propylene glycol dicaprylate, propylene glycol dicaprate.

A sorbitan fatty acid ester for example sorbitan monolaurate, sorbitan monopalmitate, sorbitan monooleate, sorbitan monostearate, sorbitan trioleate, sorbitan sesquioleate, sorbitan tristearate, sorbitan monoisostearate, sorbitan sesquistearate.

Lower alcohol fatty acid esters for example ethyl oleate, isopropy myristate, isopropyl palmitate, ethyl linoleate, isopropyl linoleate.

Polyoxyethylene-polyoxypropylene block copolymers for example poloxamer 105, poloxamer 108, poloxamer 122, poloxamer 123, poloxamer 124, poloxamer 181, poloxamer 182, poloxamer 183, poloxamer 184, poloxamer 185, poloxamer 188, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, poloxamer 334, poloxamer 335, poloxamer 338, poloxamer 401, poloxamer 402, poloxamer 403, poloxamer 407.

Polyglycerised fatty acids for example polyglyceryl stearate, polyglyceryl oleate, polyglyceryl isostearate, polyglyceryl laurate, polyglyceryl ricinoleate, polyglyceryl linoleate, polyglyceryl pentaoleate, polyglyceryl dioleate, polyglyceryl distearate, polyglyceryl trioleate, polyglyceryl septaoleate, polyglyceryl tetraoleate, polyglyceryl decaisostearate, polyglyceryl decaoleate, polyglyceryl monooleate, dioleate, polyglyceryl polyricinoleate.

PEG alkyl ethers for example PEG oleyl ether, PEG lauryl ether, PEG cetyl ether, PEG stearyl ether.

PEG alkyl phenols for example PEG nonyl phenol, PEG octyl phenol ether.

Transesterification products of alcohol or polyalcohol with natural or hydrogenated oils for example PEG castor oil, PEG hydrogenated castor oil, PEG corn oil, PEG almond oil, PEG apricot kernel oil, PEG olive oil, PEG-6 peanut oil, PEG hydrogenated palm kernel oil, PEG palm kernel oil, PEG triolein, PEG corn glycerides, PEG almond glycerides, PEG trioleate, PEG caprylic/capric triglyceride, lauroyl macrogol glyceride, stearoyl macrogol glyceride, mono, di, tri, tetra esters of vegetable oils and sorbitol, pentaerythrityl tetraisostearate, pentaerythrityl distearate, pentaerythrityl tetraoleate, pentaerythrityl tetrastearate, pentaerythrityl tetracaprylate/tetracaprate, pentaerythrityl tetraoctanoate.

Oil-soluble vitamins for example vitamins A, D, E, K, and isomers, analogues, and derivatives thereof. The derivatives include, for example, organic acid esters of these oil-soluble vitamin substances, for example the esters of vitamin E or vitamin A with succinic acid. Derivatives of these vitamins include tocopheryl PEG-1000 succinate (Vitamin E TPGS) and other tocopheryl PEG succinate derivatives with various molecular weights of the PEG moiety, for example PEG 100-8000.

Sterols or sterol derivatives (e.g. esterified or etherified sterols as for example PEGylated sterols) for example cholesterol, sitosterol, lanosterol, PEG cholesterol ether, PEG cholestanol, phytosterol, PEG phytosterol.

Sugar esters for example sucrose distearate, sucrose distearate/monostearate, sucrose dipalmitate, sucrose monostearate, sucrose monopalmitate, sucrose monolaurate, alkyl glucoside, alkyl maltoside, alkyl maltotrioside, alkyl glycosides, derivatives and other sugar types: glucamides.

Carboxylates (in particular carboxylate esters) for example ether carboxylates, succinylated monoglycerides, sodium stearyl fumarate, stearoyl propylene glycol hydrogen succinated, mono/diacetylated tartaric acid esters of mono- and diglycerides, citric acid esters of mono-, diglycerides, glyceryl-lacto esters of fatty acids; acyl lactylates: lactylic esters of fatty acids, calcium/sodium stearoyl-2-lactylate calcium/sodium stearoyl lactylate, alginate salts, propylene glycol alginate.

A fatty acid monoglyceride, diglyceride or triglyceride or a combination thereof.

Anionic Surfactants

The further surfactant (second surfactant) may be or comprise at least one anionic surfactant.

The second surfactant may be a fatty acid salt or bile salt for example sodium caproate, sodium caprylate, sodium caprate, sodium laurate, sodium myristate, sodium myristoleate, sodium palmitate, sodium palmitoleate, sodium oleate, sodium ricinoleate, sodium linoleate, sodium linolenate, sodium stearate, sodium lauryl sulfate, sodium tetradecyl sulfate, sodium lauryl sarcosinate, sodium dioctyl sulfosuccinate; sodium cholate, sodium taurocholate, sodium glycocholate, sodium deoxycholate, sodium tau rodeoxycholate, sodium glycodeoxycholate, sodium ursodeoxycholate, sodium chenodeoxycholate, sodium taurochenodeoxycholate, sodium glyco chenodeoxycholate, sodium cholylsarcosinate and sodium N-methyl taurocholate. Preferably the second surfactant is sodium lauryl sulphate.

Phospholipids for example egg/soy lecithin, cardiolipin, sphingomyelin, phosphatidylcholine, phosphatidyl ethanolamine, phosphatidic acid, phosphatidyl glycerol, phosphatidyl serine.

Phosphoric acid esters having the general formula RO-P03-M+ where the R group is an ester forming group, e.g. an alkyl, alkenyl or aryl group optionally substituted by a PEG moiety through which the alkyl, alkenyl or aryl group is coupled to the phosphate moiety. R may be a residue of a long chain (e.g. >C9) alcohol or a phenol. Specific examples include diethanolammonium polyoxyethylene-10 oleyl ether phosphate, esterification products of fatty alcohols or fatty alcohol ethoxylates with phosphoric acid or anhydride.

Sulfates and sulfonates (in particular esters thereof) for example ethoxylated alkyl sulfates, alkyl benzene sulfones, α-olefin sulfonates, acyl isethionates, acyl taurates, alkly glyceryl ether sulfonates, octyl sulfosuccinate disodium, disodium undecylenamideo-MEA-sulfosuccinate, alkyl phosphates and alkyl ether phosphates.

Cationic Surfactants

The further surfactant (second surfactant) may be or comprise at least one cationic surfactant selected from the following cationic surfactants.

Hexadecyl triammonium bromide, dodecyl ammonium chloride, alkyl benzyldimethylammonium salts, diisobutyl phenoxyethoxydimethyl benzylammonium salts, alkylpyridinium salts; betains (trialkylglycine): lauryl betaine (N-lauryl,N,N-dimethylglycine); ethoxylated amines: polyoxyethylene-15 coconut amine, alkyl-amines/diamines/quaternaty amines and alkyl ester.

Emulsifiers

The surfactant may act as an emulsifier such surfactants include non-ionic emulsifiers, for example selected from: a mixture of triceteareth-4 phosphate, ethylene glycol palmitostearate and diethylene glycol palmitostearate (for example sold under the trade mark SEDFOS™ 75); sorbitan esters, e.g. sorbitan monooleate, sorbitan monolaurate, sorbitan monpalmitate, sorbitan monostearate (for example products sold under the trade mark Span®), PEG-8 beeswax e.g. sold under the trade mark Apifil®; a mixture of cetyl alcohol, ceteth-20 and steareth-20 (for example Emulcire™ 61 WL 2659); a mixture of PEG-6 stearate and PEG-32 stearate (for example Tefose® 1500); a mixture of PEG-6 palmitostearate, ethylene glycol palmitostearate, and PEG-32 palmitostearate (e.g. Tefose® 63); triglycerol diisostearate (for example products sold under the trade mark Plurol Diisoteariquel; polyglyceryl-3 dioleate (for example products sold under the trade mark Plural® Oleique).

Preferred Second Surfactants

Preferably the second surfactant is an anionic surfactant. For example, the second surfactant may be an alkyl sulphate, for example sodium dodecyl sulphate. The second surfactant may be present in an amount of 10 to 70 mg/g or 15 to 60 mg/g.

The second surfactant may be a fatty acid salt or bile salt for example sodium caproate, sodium caprylate, sodium caprate, sodium laurate, sodium myristate, sodium myristoleate, sodium palmitate, sodium palmitoleate, sodium oleate, sodium ricinoleate, sodium linoleate, sodium linolenate, sodium stearate, sodium lauryl sulfate, sodium tetradecyl sulfate, sodium lauryl sarcosinate, sodium dioctyl sulfosuccinate; sodium cholate, sodium taurocholate, sodium glycocholate, sodium deoxycholate, sodium tau rodeoxycholate, sodium glycodeoxycholate, sodium ursodeoxycholate, sodium chenodeoxycholate, sodium taurochenodeoxycholate, sodium glyco chenodeoxycholate, sodium cholylsarcosinate and sodium N-methyl taurocholate. Preferably the second surfactant is sodium lauryl sulphate.

Other Excipients

The composition optionally contains one or more of the following additional substances or categories of substances. For example, the composition may contain a protectant such as, for example, a proteolytic enzyme inhibitor or a protector against acid degradation or both (e.g. an alkali for example sodium hydroxide); an adhesive entity such as, for example, a muco- or bio-adhesive; excipients to maximize solubility of the active ingredient; excipients to maximize permeability of the active ingredient in the GIT. Typical excipients for enhancing the permeability of the epithelial barrier include but are not limited to sodium caprate, sodium dodecanoate, sodium palmitate, SNAG, chitosan and derivatives thereof, fatty acids, fatty acid esters, polyethers, bile salts, phospholipids, alkyl polyglucosides, sugar esters, hydroxylase inhibitors, antioxidants (e.g. ascorbic acid) and/or nitric oxide donors. The preceding list is of particular interest to enhance permeability in the ileum.

To enhance permeability in the colon, typical excipients include, but not limited to sodium caprate, sodium dodecanoate, sodium palmitate, SNAG, chitosan and derivatives thereof, fatty acids, fatty acid esters, polyethers, bile salts, phospholipids, alkyl polyglucosides, hydroxylase inhibitors, antioxidants (optionally selected from curcuminoids, flavonoids, curcumin, beta-carotene, α-tocopherol, ascorbic acid, ascorbate, lazaroid, carvedilol, butylated hydroxytoluene, propyl gallate, hydralazine, carnosic acid, vitamin E, lecithin Ovolecithin (vitelin), vegilecithin, fumaric acid or citric acid) and/or nitric oxide donors, including nitric oxide donor groups covalently attached to various pharmaceutically active ingredients. The composition may further comprise excipients or other active pharmaceutical or other ingredients to enhance local tissue bioavailability in the GIT, such as the small intestine or colon, including efflux pump inhibitors, including, but not limited to PgP pump inhibitors (optionally selected from NSAIDs, cimetidine, omeprazole, Vitamin E TPGS, verapimil, quinidine, PSC833, amprenavir (APV), indinavir (IDV), nelfinavir (NFV), ritonavir (RTV) and saquinavir (SQV)), and metabolism inhibitors, including, but not limited to, cytochrome P450 inhibitors, optionally selected from: essential oils, cimetidine, surfactants (for example cremophor), oils, omeprazole, verapamil, ritonavir and carbamazepine as well as plant extracts, e.g, from citrus fruits. The composition may therefore further comprise a P450 inhibitor to further reduce metabolism of cyclosporin following administration of the composition. The P450 inhibitor may act to inhibit enteric and/or hepatic metabolism of the cyclosporin. The composition may further comprise a PgP inhibitor. Optionally the composition may comprise a P450 inhibitor and a PgP inhibitor.

The composition may further comprise excipients to enhance the therapeutic potential of an active ingredient, for example cyclosporin A or another immunosuppressant, throughout the gastrointestinal tract, including in the ileum and colon including, but not limited to absorption limiters, essential oils such as, for example, omega 3 oils, natural plant extracts such as, for example, neem, ion-exchange resins, bacteria degradable conjugation linkers such as, for example, azo bonds, polysaccharides such as, for example, amylose, guar gum, pectin, chitosan, inulin, cyclodextrins, chondroitin sulphate, dextrans, guar gum and locust bean gum, nuclear factor kappa B inhibitors, acids such as, for example, fumaric acid, citric acid and others, as well as modifications thereof.

The composition may further comprise excipients to reduce systemic side effects associated with absorption of certain active, for example cyclosporin or other immunosuppressants, in the GIT, such as the small intestine, including, but not limited to, antioxidants, such as, for example, curcuminoids, flavanoids or more specifically including curcumin, beta-carotene, α-tocopherol, ascorbate or lazaroid.

The composition may further or separately comprise antioxidants (such as, for example, ascorbic acid or BHT—butyl hydroxy toluene) taste-masking or photosensitive components or photoprotective components. Antioxidants may be incorporated in the aqueous phase (e.g. hydrophilic antioxidants) or in the disperse phase of the core (e.g. hydrophobic antioxidants such as, for example, vitamin E) for example up to 1% by weight, preferably between 0.01 and 0.50% by weight, more preferably between 0.10 to 0.20% by weight.

The composition may further comprise immune-enhancing nutrients such as vitamins A/B/C/E; carotenoids/beta-carotene and iron, manganese, selenium, zinc, especially when the composition contains an immunosuppressant, as in the case of an immunosuppressant targeted to the ileum and/or colon, e.g. the colon. Such nutrients may be present in composition, or if the composition has a coating, for example if it is the form of a bead, the nutrients may be included in the coating.

The composition may also include other well know excipients used in pharmaceutical compositions including colorants, taste masking agents, diluents, fillers, binders etc. The presence of such optional additional components will of course depend upon the particular dosage form adopted.

Shape, Size and Geometry

The composition of the invention can be formed into a limitless number of shapes and sizes. In the section below describing the process for making the composition, various methods are given including pouring or introducing a fluid dispersion into a mould where it hardens or can be caused to harden. Thus the composition can be created in whichever form is desired by creating an appropriate mould (e.g. in the shape of a disc, pill or tablet). However, it is not essential to use a mould. For example, the composition may be formed into a sheet e.g. resulting from pouring a fluid dispersion onto a flat surface where it hardens or can be caused to harden.

Preferably, the composition may be in the form of spheres or spherical-like shapes made as described below. Preferably, the composition of the invention is in the form of substantially spherical, seamless minibeads. The absence of seams on the minibead surface is an advantage e.g. in further processing, for example coating, since it allows more consistent coating, flowability etc. The absence of seams on the minbeads also enhances consistency of dissolution of the beads.

The preferred size or diameter range of minibeads according to the invention can be chosen to avoid retention in the stomach upon oral administration of the minibeads. Larger dosage forms are retained for variable periods in the stomach and pass the pyloric sphincter only with food whereas smaller particles pass the pylorus independently of food. Selection of the appropriate size range (see below) thus makes the therapeutic effect post-dosing more consistent. Compared to a single large monolithic oral format such as, for example, a traditional compressed pill, a population of beads released into the GI tract (as foreseen by the dosage form of the present invention) permits greater intestinal lumen dispersion so enhancing absorption via exposure to greater epithelial area, and achieves greater topical coating in certain parts of the GI tract for example the colon). Reduction of residence time in the ileo-caecal junction is another potential advantage.

The composition of the invention is preferably monolithic meaning internally (i.e. cross-sectionally) homogeneous, excluding a possible thin skin of matrix material and excluding any coating layers.

The minibeads provided for by the formulation of the present invention generally range in diameter from 0.5 mm to 10 mm with the upper limit preferably 5 mm, e.g. 2.5 mm A particularly convenient upper limit is 2 mm or 1.7 mm. The lower limit can preferably be 1 mm, e.g. 1.2 mm, more preferably from 1.3 mm, most preferably from 1.4 mm. In one embodiment the diameter is from 0.5 to 2.5 mm, for example from 1 mm to 3 mm, 1 mm to 2 mm, 1.2 mm to 3 mm or 1.2 mm to 2 mm. The minibeads may have a diameter of no more than 2.5 mm, irrespective of their minimum size. The beads may have a diameter of no more than 2 mm, irrespective of their minimum size.

A minibead as described herein may have an aspect ratio of no more than 1.5, e.g. of no more than 1.3, for example of no more than 1.2 and, in particular, of from 1.1 to 1.5, 1.1 to 1.3 or, 1.1 to 1.2. A population of minibeads as described herein, e.g. at least 10 beads, may have an average aspect ratio of no more than 1.5, e.g. of no more than 1.3, for example of no more than 1.2 and, in particular, of from 1 to 1.5, 1 to 1.3 or 1 to 1.2. The aspect ratios mentioned in this paragraph optionally apply to coated minibeads and optionally apply to uncoated minibeads. Average aspect ratio is suitably determined for a population of minibeads, e.g. at least 10 minibeads, using a particle size analyser, for example an Eyecon™ particle characteriser of Innopharma Labs, Dublin 18, Ireland.

The minibeads of the disclosure may, therefore, have a size as disclosed above and an aspect ratio of from 1 to 1.5. The beads of the disclosure may have a size as disclosed above and an aspect ratio of no more than 1.3, for example of no more than 1.2 and, in particular, of from 1.1 to 1.5, 1.1 to 1.3 or, 1.1 to 1.2.

Bead size (diameter) may be measured by any suitable technique, for example microscopy, sieving, sedimentation, optical sensing zone method, electrical sensing zone method or laser light scattering. For the purposes of this specification, bead size is measured by analytical sieving in accordance with USP General Test <786> Method I (USP 24-NF 18, (U.S. Pharmacopeial Convention, Rockville, Md., 2000), pp. 1965-1967).

In embodiments, minibeads of the invention are monodisperse. In other embodiments, minibeads of the invention are not monodisperse. By "monodisperse" is meant that for a population of beads (e.g. at least 100, more preferably at least 1000) the minibeads have a coefficient of variation (CV) of their diameters of 35% or less, optionally 25% or less, for example 15% or less, such as e.g. of 10% or less and optionally of 8% or less, e.g. 5% or less. A particular class of polymer beads has a CV of 25% or less. CV when referred to in this specification is defined as 100 times (standard deviation) divided by average where "average" is mean particle diameter and standard deviation is standard deviation in particle size. Such a determination of CV is performable using a sieve.

The invention includes minibeads having a CV of 35% and a mean diameter of 1 mm to 2 mm, e.g. 1.5 mm. The invention also includes minibeads having a CV of 20% and a mean diameter of 1 mm to 2 mm, e.g. 1.5 mm, as well as minibeads having a CV of 10% and a mean diameter of 1 mm to 2 mm, e.g. 1.5 mm. In one class of embodiments, 90% of minibeads have a diameter of from 0.5 mm to 2.5 mm, e.g. of from 1 mm to 2 mm.

Dosage Forms

The composition of the invention may be prepared as an orally administrable dosage form suitable for pharmaceutical use. In those embodiments where the formulation is in the form of a minibead, the present invention provides for a dosage form comprising a plurality of the minibeads for example as a capsule, a tablet, a sprinkle or a sachet. The minibeads may also be administered rectally or vaginally administered compositon, for example as an enema or suppository. The composition, for example in the form of minibeads may be blended in a suitable medium to provide a suppository or enema compositons. Suitable media for suppositories and enemas are well known and include for example, a low melting point wax for a suppository or a suitable aqueous or oil based medium for an enema compositon.

The liquid composition of the invention may be formulated as an orally, rectally or vaginally administrable dosage form suitable for pharmaceutical use. The liquid composition may be formulated into a hard or soft gelatin capsule, a suppository or an enema. Deliverly of the liquid compositon to the stomach may also be achieved via a gastric feeding tube located in the stomach or by means of a percutaneous endoscopic gastrostomy tube (PEG tubing) as hereinabove described. The liquid composition may also be administered directly to specific points in the GI tract, for example the duodenum, jejunem or ileum via oral or intranasal tubing with an exit at the desired point in the GI tract. Delivery of the liquid composition via tubing may be under gravtity flow or under positive pressure using a pump or syringe drive etc.

In embodiments the dosage form comprising a population of beads may be presented in a single unit dosage form e.g. contained in a single hard gel capsule which releases the beads e.g. in the stomach. Alternatively the beads may be presented in a sachet or other container which permits the beads to be sprinkled onto food or into a drink or to be administered via a feeding tube for example a naso-gastric tube or a duodenal feeding tube. Alternatively, the beads may be administered as a tablet for example if a population of beads is compressed into a single tablet as described below. Alternatively, the beads may be filled e.g. compressed into a specialist bottle cap or otherwise fill a space in a specialised bottle cap or other element of a sealed container (or container to be sealed) such that e.g. on twisting the bottle cap, the beads are released into a fluid or other contents of the bottle or vial such that the beads are disperse (or dissolve) with or without agitation in such contents. The fluid or other contents of the bottle or vial may optionally contain one of more additional active agent(s) to facilitate the conventiaent co-administration of the cyclosporin composition with other active agents. An example is the Smart Delivery Cap manufactured by Humana Pharma International (HPI) S.p.A, Milan, Italy.

The dosage form may be formulated in such a way so that the beads of the invention can be further developed to create a larger mass of beads e.g. via compression (with appropriate oil or powder-based binder and/or filler known to persons skilled in the art. The larger (e.g. compressed) mass may itself take a variety of shapes including pill shapes, tablet shapes, capsule shapes etc. A particular problem which this version of the bead embodiment solves is the "dead space" (above the settled particulate contents) and/or "void space" (between the particulate content elements) typically found in hard gel capsules filled with powders or pellets. In such pellet- or powder-filled capsules with dead/void space, a patient is required to swallow a larger capsule than would be necessary if the capsules contained no such dead space. The beads of this embodiment of the invention may readily be compressed into a capsule to adopt the inner form of whichever capsule or shell may be desired leaving much reduced, e.g. essentially no, dead/void space. Alternatively the dead or void space can be used to advantage by suspending beads in a vehicle such as, for example, an oil which may be inert or may have functional properties such as, for example, permeability enhancement or enhanced dissolution or may comprise an active ingredient being the same or different from any active ingredients in the bead. For example, hard gelatin or HPMC capsules may be filled with a liquid medium combined with uncoated and/or coated beads. The liquid medium may be one or more of the surfactant phase constituents described herein or it may be one or more surfactants. Particularly preferred but non-limiting examples are corn oil, sorbitane trioleate (sold under the trade mark SPAN 85), propylene glycol dicaprylocaprate (sold under the trade mark Labrafac), 2-(2-ethoxyethoxy)ethanol (sold under the trade mark Transcutol P) and polysorbate 80 (sold under the trade mark Tween 80).

In a representative embodiment the bead of the dosage form is prepared as described herein for example by mixing together at least the following materials: a hydrogel-forming polymer; an oil phase, a surfactant being or comprising a medium chain or long chain fatty acid mono- or di-glyceride or a combination thereof, wherein the surfactant does not comprise or is not a polyethyleneglycol ether or ester, and cyclosporin A, suitably cyclosporin A being dissolved in the oil phase, such as a liquid lipid to form a dispersion of the cyclosporin A in the hydrogel-forming polymer. The dispersion is immobilized within the solidified bead by ejection from a single orifice nozzle into a suitable cooling liquid. Following removal of the cooling liquid the bead is coated with a modified release coating (the second coating) (suitably with a sub-coat under the modified release coating), the coated bead is then optionally filled into a gelatin or HPMC capsule suitable for pharmaceutical use.

Suitably the dosage form is prepared as a unit dosage form containing from for oral administration comprising from 0.1 mg to 1000 mg, optionally from 1 mg to 500 mg, for example 10 mg to 300 mg, 15 mg to 300 mg, or 25 to 250 mg, suitably about 15 mg, about 25 mg, about 35 mg, about 50 mg, about 75 mg, about 100 mg, about 150 mg, about 180 mg, about 200 mg, about 210 mg or about 250 mg cyclosporin A Determination of Contents and Distribution of Formulations The identity and/or distribution of one or more of the components of a composition according to the invention can be determined by any method known to those skilled in the art. The distribution of one or more components of a composition can, for example, be determined by near-infrared (NIR) chemical imaging technology. NIR chemical imaging technology can be used to generate images of the surface or cross section of a composition, for example a minibead. The image produced by this technique shows the distribution of one or more components of the composition. In addition to NIR chemical imaging technology, the distribution of one or more components of a composition such as minibead, for example, be determined by time-of-flight secondary ion mass spectrometry (ToFSIMS). ToFSIMS imaging can reveal the distribution of one or more components within the composition. The images produced by ToFSIMS analysis or NIR analysis can show the distribution of components across a surface of the composition or a cross section of the composition. The methods described in this paragraph are applicable, for example, to composition comprising a polymer matrix, e.g. a dried, colloid, solution or dispersion.

Pharmacokinetics

The orally administered compositions comprising cyclosporin A described herein may provide, amongst other features, a favourable pharmacokinetic profile compared to orally administered Neoral and/or to intravenously administered cyclosporin A as for example Sandimmun™.

The compositions according to the invention provide lower mean whole blood exposure to cyclosporin A following oral administration compared to oral administration of Neoral™ at the same dose of cyclosporin A. The whole blood exposure to cyclosporin A may be determined by measuring the area under the Curve (AUC) of the whole blood cyclosporin A concentration-time curve following administration of a single dose of a composition containing cyclosporin A. The area under the concentration-time curve (AUC), calculated from the start of dosing (t=0) to the last measured concentration (t) is designated to be "$AUC_{0-t}$". Accordingly reference to "$AUC_{0-24\ hr}$" is the AUC between t=0 and the last measurement point at 24 hours following administration. The $AUC_{0-t}$ may be calculated using well known methods for example by linear trapezoidal analysis. The area under the concentration-time curve extrapolated to infinity is "$AUC_{0-inf}$". The $AUC_{0-inf}$ is calculated using known methods as:

$$AUC_{0-t} + \frac{C_t}{K_{el}}$$

Where: Ct=the fitted last non-zero concentration for that treatment, $AUC_{0-t}$ is as defined above; and $K_{el}$=the elimination rate constant. $K_{el}$ is calculated by regression analysis of the natural log (Ln) of whole blood concentration values—time profile.

The term "Cmax" refers to the maximum concentration of cyclosporin in whole blood following administration of a single dose of a composition containing cyclosporin A.

The term "Tmax" refers to the time taken to reach Cmax following oral administration of a composition containing cyclosporin A.

For statistical analysis, the PK data is log-transformed prior to conducting statistical testing. In general, statistical tests are carried out using an analysis of variance procedure (ANOVA) and calculating a 90% confidence interval for each pharmacokinetic parameter (Cmax and AUC).

The measurement and analysis of AUC, Cmax and Tmax are well known in the art and can be carried out using methods and techniques described in further detail in the examples or by reference to standard textbooks such as Remington, The Science and Practice of Pharmacy $22^{nd}$ edition, or Basic Pharmacokinetics and Pharmacodynamics: An integrated Textbook and Computer Simulations, Sara E. Rosenbaum, 2011 John Wiley& Sons. In all cases references to AUC, Cmax and Tmax are the mean values measured following administration of a composition containing cyclosporin A to a human, preferably a healthy male human in a fasted state. Suitably the subjects used in the PK study are adult male humans with weighing about 70 kg (for example 70 kg±12 kg). Suitably the subjects have a body mass index of about 25 $kg/m^2$ (for example 25 $kg/m^2$±2.5 $kg/m^2$).

In some embodiments the composition of the invention provides an AUC and/or a Cmax value as the AUC or Cmax "following oral administration of a single dose of 75 mg cyclosporin A". It is known that cyclosporin A exhibits an approximately linear pharmacokinetic profile EU HMA's Public Assessment Report on Ciclosporin "Docpharma" soft capsules DK/H/968/1-3/MR, page 4.

Accordingly reference to an "AUC or Cmax of a particular value after oral administration of the composition as a single dose containing 75 mg cyclosporin A to a human in a fasted state, or an AUC or Cmax directly proportional thereto for a total dose other than 75 mg" is to be understood to mean that the AUC or Cmax value is directly proportional to mass of the cyclosporin A dose administered. By way of example, if a single dose of 150 mg cyclosporin A were to be administered the corresponding AUC and Cmax values will be approximately twice that obtained with a single dose of 75 mg cyclosporin A. Similarly administration of a single dose of 37.5 mg of cyclosporin A would be expected to provide a AUC and Cmax values approximately half those observed following administration of 75 mg cyclosporin A. The dose proportionality for cyclosporin A is applicable over a broad range of dosages of cyclosporin A for example from 0.1 to 1000 mg, suitably between about 1 mg and about 500 mg, more particularly between about 5 mg and about 350 mg.

In one embodiment the composition provides a mean whole blood $AUC_{0-inf}$ of from about 140 to about 420 ng·hr/ml, for example from about 140 to about 350 ng·hr/ml, about 140 to about 400 ng·hr/ml about 150 to about 350 ng·hr/ml, about 150 to about 300 ng·hr/ml about 180 to about 350 ng·hr/ml, about 200 to about 400 ng·hr/ml or about 180 to about 320 ng·hr/ml and a mean whole blood Cmax of from about 25 to about 45 ng/ml after oral administration of the composition as a single dose containing 75 mg cyclosporin A to a human in a fasted state, or a $AUC_{0-inf}$ and Cmax directly proportional thereto for a total dose other than 75 mg. Suitably the composition provides a Tmax of from about 4 hours to about 8 hours, suitably from about 4 hours to about 6 hours and particularly at about 5 hours; or about 5.5 hours; or about 6 hours.

Cyclosporin A concentration in Faecal Samples

The cyclosporin composition may release cyclosporin A (preferably in a solubilised form for example as a solution in an oil droplet or as micelles containing cyclosporin A) in the lower GI tract and particularly the colon. Accordingly, the composition provides high local cyclosporin A concentrations in the luminal contents and further results in absorption of cyclosporin A into the tissue of the GI tract. The luminal and tissue concentration of cyclosporin A following oral administration of a composition of the invention is higher relative to that resulting from oral administration of Neoral™ or IV administration as Sandimmun™. However, as discussed above, the composition according to the invention results in a relatively low systemic blood exposure to the cyclosporin A. The cyclosporin compositions described herein comprising the surfactant may also reduce the cyclosporin A metabolism following release of the cyclosporin from the composition into the GI tract.

The cyclosporin composition may provide a ratio of the mean concentration of cyclosporin A: the concentration of cyclosporin A metabolites (for example the sum of the mean AM4N and AM9 metabolite concentrations, or the sum of the mean AM1, AM9, and AM4N metabolite concentrations of greater than 12:1. Suitably the metabolite concentration is measured as the sum of the mean concentration of each metabolite present in the faecal sample. In one embodiment "the concentration of cyclosporin A metabolites" refers to the sum of the mean concentrations of the AM4N+AM9 metabolites present in the sample. In another embodiment "the concentration of cyclosporin A metabolites" refers to the sum of the mean concentrations of the AM4N+AM9+AM1 metabolites present in the sample. Accordingly In one embodiment ratio of the mean concentration of cyclosporin A: the concentration of AM1, AM9, and AM4N metabolites is greater than 12:1, for example, from 20:1 to 40:1, from 20:1 to 35:1, Suitably the ratio of cyclosporin A: metabolite concentration in the faecal sample is determined after orally administering a single dose of 75 mg cyclosporin A. However, other doses and dose regimens such as twice daily dosing may also be used. As described above the concentrations may be determined in a faecal sample collected 12 to 28 hours after dosing the composition. However, the concentrations may be determined in faeces collected at other time points following oral administration of the composition provided sufficient time has elapsed after oral administration of the composition for transit through the gut such that cyclosporin and its metabolites to be present in the collected faecal sample. It is expected that the ratios of cyclosporin to metabolites measured in a collected faecal samples will be approximately the same irrespective of the specific time point at which the faeces is collected. Accordingly, reference herein to collection of a faecal sample at 12 to 28 hours is not intended to be limiting. Suitably, the ratios of cyclosporin to metabolites are measured in samples of faeces taken from subjects that have been exposed to a regular daily dose of the composition. After a prolonged period of daily dosing it is expected that steady-state concentrations of cyclosporin and metabolites will be achieved and as such there may be less variability in the measured concentrations of cyclosporin and metabolites in the faeces. Accordingly, the concentration of cyclosporin:metabolites may, for example, be measured in a faecal sample collected 4 to 6 hours after oral administration of the last dose of a once daily oral dosing regimen of the composition, the dosing regimen comprising once daily oral administration of the composition (for example containing 75 mg cyclosporin A) for seven days.

By way of comparison to the compositions according to the invention, the examples herein show that oral administration of Neoral™ results in a ratio of cyclosporin A:Cyclosporin metabolites (AM4N+AM9) of approximately 0.6:1, reflecting the relatively high systemic exposure and relatively low local tissue exposure in the lower GI tract, particularly in the colon. Similarly IV administration of 2 mg/Kg of cyclosporin resulted in a ratio of about 0.3:1 to about 0.45:1.

Cyclosporin A in Luminal Contents and GI Tissue

The high concentration of cyclosporin A in the luminal contents of the lower GI tract and the concentration of cyclosporin A in the tissue of the GI tract may be determined by measuring cyclosporin A concentration in luminal content and tissue samples taken at specific points along the GI tract. Cyclosporin A concentrations in intracolonic faeces and colonic tissue may be measured in human patients as described in the protocols described in the Examples. The composition comprising cyclosporin provides high concentrations of cyclosporin A in the mucosa and sub-mucosa (i.e. the inner tissues) of for example the colon. The cyclosporin A concentration in the colonic tissues may be measured by taking a section of the colonic tissue, separating the layers of tissue (for example the mucosa, sub-mucosa and muscularis externa), and measuring the cyclosporin concentration in each of the respective tissue layers.

The presence of a high colonic luminal cyclosporin A concentration provided by the composition of the invention is expected to provide a concentration gradient which acts to promote absorption of the cyclosporin A (preferably in a solubilised form) into the lamina propria of the colon, where the main target dysregulated immune cells associated with many inflammatory diseases of the colon predominate. The compositions of the invention therefore provide a local topical treatment of diseased colonic tissue and are expected to be useful in the treatment of conditions such as ulcerative colitis and other inflammatory diseases affecting the at least the colon. In contrast oral administration of Neoral™ provides relatively low luminal concentration of cyclosporin A to the inner colonic tissues. Intravenous administration of cyclosporin A as Sandimmun™ reduces the metabolism in the intestine and may provide similar faecal metabolite concentrations as an orally administered composition according to the invention. However, the IV administration of cyclosporin results in significantly higher systemic exposure and moreover, relatively high doses of IV cyclosporin may be required to provide therapeutic concentrations of cyclosporin in the colonic tissue compared to oral administration of a composition according to the invention.

The composition comprising cyclosporin may therefore be expected to provide a therapeutic benefit at lower doses than Neoral and/or Sandimmun™, thus further minimising side effects associated with systemic exposure to cyclosporin A. Some release or cyclosporin A from the composition may occur as the composition passes through the GI tract and release of cyclosporin may not be exclusive to the colon. As such the composition of the invention may provide locally acting cyclosporin A in at least the colon and in other parts of the GI tract, for example the rectum and ileum, the composition may therefore provide therapeutic benefit in the treatment or prevention of conditions affecting not just the colon, but also other parts of the GI tract as described herein.

Measurement of cyclosporin concentration in the colonic tissue and intracolonic faeces in humans may be performed as described in the Examples. Suitably samples of colonic tissue are obtained from a patient who has been orally treated with a composition containing cyclosporin by sigmoidoscopy using, for example pinch biopsy forceps, to obtain samples of colonic tissue. Suitably sigmoidoscopy is a flexible sigmoidoscopy. The sigmoidoscopy is preferably carried out in the unprepared bowel (except for air and water) such that the tissue samples obtained replicate as closely as possible the in-vivo tissue status, which might otherwise be disturbed by extensive bowel preparation. Biopsies are suitably about 5 mm in size and ideally at least 5 biopsies are taken approximately 1 cm apart from the subject. Preferably the biopsies are obtained as close to the splenic flexure as possible. Alternatively, biopsies may also be obtained from within the sigmoid colon. Each biopsy should be rinsed with saline, blot dried and then stored at low temperature, suitably at about −70° C., prior to analysis. The tissue samples may be analysed directly for the concentration of cyclosporin A present in the tissue. However, preferably the mucous layer present on the tissue surface is first removed from the sample such that the cyclosporin concentration measured is the concentration of cyclosporin present in the epithelial and musosal tissue. The mucous layer may be removed by washing with a suitable solvent such as N-acetyl cysteine in water. Removal of the mucose layer ensures that the concentration of cyclosporin measured is representative of the concentration which has been absorbed into the tissue, rather than the mucosal layer. The cyclosporin present in the mucosal layer can be determined by analysing the mucosal washings. Suitable methods for the preparation and analysis of the colonic tissue are set out in the examples section.

Samples of intracolonic faeces are suitably collected from approximately the same location within the colon as the tissue biopsies such that the measurement of cyclosporin concentration in the tissue and intra-colonic faeces represents the concentrations present at approximately the same position within the colon.

The tissue biopsies and intra-colonic faecal samples should be obtained after a sufficient duration of cyclosporin dosing to reach steady-state concentrations in the colon. For example, the biopsies and faecal samples are suitably may be carried out after 7 days of daily oral dosing with the composition. The biopsies and intracolonic faecal samples are suitably obtained simultaneously within 4 to 6 hours after the last dose in the 7 day dosage regimen.

The ratio of the mean concentration of cyclosporin A present in intracolonic faeces: the mean concentration of cyclosporin A present in colonic tissue in an adult human patient after oral administration of the composition is greater than 30:1, for example, greater than about 40:1 or greater than about 50:1. The mean concentration of cyclosporin A present in intracolonic faeces: the mean concentration of cyclosporin A present in colonic tissue may be about 30:1 to about 500:1, about 50:1 to about 500:1, optionally from about 80:1 to about 300:1, or optionally about 100:1 to about 250:1. In contrast the Examples show that IV administration of Sandimmun results in an intracolonic faecal: tissue ratio of cyclosporin A of about 3:1.

References to a "mean" value in relation of the PK, tissue and faecal analysis described herein is unless specified otherwise a reference to the arithmetic mean value of the measured values.

Dissolution Profile

The compositions comprising cyclosporin provide compositions with a specific in-vitro dissolution profile for the release cyclosporin A from the composition. The compositions show minimal release of cyclosporin A in the stomach and upper GI tract such as the duodenum and jejunum and higher release in at least the colon. The in-vivo release may be modelled using a two stage in-vitro dissolution test in which a composition is exposed to 0.1 N HCl for two hours to simulate pH of the gastric environment and is then exposed to pH 6.8 for twenty two hours (by adding a sufficient quantity of 0.2M tribasic sodium phosphate solution containing 2% sodium dodecyl sulfate (SDS)) to simulate pH in the small intestine and lower GI tract.

Reference to "a two stage dissolution test using a USP Apparatus II with a paddle speed of 75 rpm and a dissolution medium temperature of 37° C.; wherein for the first 2 hours of the dissolution test the dissolution medium is 750 ml of 0.1 N HCl, and at 2 hours 250 ml of 0.2M tribasic sodium phosphate containing 2% SDS is added to the dissolution medium and the pH is adjusted to pH 6.8" is an in-vitro test carried out in accordance with the USP <711> Dissolution test using Apparatus II (paddle apparatus) operated with a paddle speed of 75 rpm and with the dissolution medium at a temperature of 37° C.±0.5° C. At the start of the test (t=0) the sample is placed in the acidic dissolution medium. After 2 hours an aliquot of the medium is taken for subsequent analysis and immediately (suitably within 5 minutes) the second stage of the dissolution test is initiated. In the second stage of the dissolution test 250 ml of 0.2M tribasic sodium phosphate containing 2% sodium dodecyl sulfate (SDS) is added to the dissolution medium and the pH is adjusted to 6.8±0.05 using 2N NaOH or 2N HCl as required. Samples of the dissolution medium are taken at time points during the second stage of the test, for example at 4, 6, 12 and 24 hours from the start of the test (i.e. from t=0 at the start of the first stage). The samples are analysed for cyclosporin A dissolved in the medium. The "% released" is the amount of cyclosporin A in solution in the respective dissolution medium at a particular time point relative to the amount of cyclosporin A in the composition at the start of the test. The cyclosporin A concentrations in a sample may be measured using standard techniques, such as Reverse Phase HPLC as illustrated in the Examples. References to "two stage dissolution test" herein also refer to this test method.

The in-vitro dissolution profile of the composition according to the invention is described above under the Brief Summary.

Manufacturing Processes

Various methods may be used to prepare the formulations of the invention.

In those embodiments where the formulation comprises an active ingredient in a water-insoluble polymer matrix, a basic method for making the core is to mix a fluid form of the matrix material, for example a hydrogel forming polymer matrix material (e.g. poly(amides), poly(amino-acids), hyaluronic acid; lipoproteins; poly(esters), poly(orthoesters), poly(urethanes) or poly(acrylamides), poly(glycolic acid), poly(lactic acid) and corresponding co-polymers (poly (lactide-co-glycolide acid; PLGA); siloxane, polysiloxane; dimethylsiloxane/methylvinylsiloxane copolymer; poly(dimethylsiloxane/methylvinylsiloxane/methylhydrogensiloxane) dimethylvinyl or trimethyl copolymer; silicone polymers; alkyl silicone; silica, aluminium silicate, calcium silicate, aluminium magnesium silicate, magnesium silicate, diatomaceous silica etc as described more generally elsewhere herein), with an active ingredient to form a mixture that may take the form of a suspension, solution or a colloid. The mixture is processed to form a composition or a core. For example the composition may be shaped into the desired form using a molding or hot-melt extrusion process to form beads.

Methods for preparing a composition and a core comprising the surfactant, cyclosporin, an oil phase and a water-soluble polymer matrix are described below. Generally these cores are coated.

Generally, the manufacturing processes described herein comprise mixing of liquid(s). Such mixing processes must be performed at temperatures at which the substances to be mixed in the liquid state are in liquid form. For example, thermoreversible gelling agents must be mixed at a temperature where they are in the liquid state, for example at a temperature of 50 to 75° C., for example 50 to 70° C., or 55-75° C., e.g. 60-70° C. and in particular embodiments about 55° C. or 65° C. in the case of mixing formulations comprising aqueous gelatin. Similarly other components of the formulation may need to be heated to melt the component for example waxes or surfactants which may be used in the disperse phase.

The liquid composition, composition or the core comprising a surfactant, oil phase, hydrogel-forming polymer and cyclosporin as disclosed herein may be made by mixing materials comprising for example water, a hydrogel-forming polymer and a second surfactant to form an aqueous continuous phase, and mixing a disperse phase. At least one of the aqueous phase and the disperse phase comprises cyclosporin, the cyclosporin may be dissolved in the phase which contains it, for example both phases may be a clear liquid before they are mixed together. Preferably, the disperse phase (the oil phase) may comprise the cyclosporin, (for example a disperse phase comprising an oil, an optional solvent, cyclosporin and a first surfactant) with the aqueous phase to form a colloid. The colloid may have the form of an emulsion or microemulsion wherein the disperse phase is dispersed in the aqueous continuous phase. This colloid may optionally represent the liquid composition of the invention. In order to prepare the composition of the invention or the core, the hydrogel-forming polymer is then caused or allowed to gel to form a hydrogel forming polymer matrix. Suitably, the process includes formulating or processing the composition into a desired form, e.g. a bead (also termed a minibead), which forming process may comprise moulding but preferably comprises ejecting the aqueous colloid through a single orifice nozzle to form droplets which are caused or allowed to pass into a cooling medium, e.g. a water-immiscible cooling liquid, in which the droplets cool to form for e.g. beads.

The mixing of the materials may comprise mixing an aqueous premix (or aqueous phase or continuous phase) and a disperse phase premix (e.g. oil phase premix), wherein the aqueous premix comprises water and water-soluble substances whilst the disperse phase premix may comprise a vehicle containing cyclosporin and the surfactant. The vehicle may be a hydrophobic liquid, for example a liquid lipid, or it may be or comprise a material, for example a surfactant, for forming self-assembly structures. In particular, a disperse phase premix may comprise cyclosporin A, the first surfactant, an oil and other oil soluble components for example an optional solvent. The premixes may contain one or more surfactants suitable for the phase they are to form, as previously mentioned, for example the aqueous premix may comprise a second surfactant.

The aqueous premix comprises, or usually consists of, a solution in water of water-soluble constituents, namely the hydrogel-forming polymer and water-soluble excipient(s). The aqueous premix may include a plasticiser for the hydrogel-forming polymer, as described elsewhere in this specification. The aqueous premix may include a second surfactant, e.g. to increase polymer viscosity and improve emulsification and thereby help prevent precipitation of active agent during processing. SDS is an example of such a surfactant. In any event, the constituents of the aqueous premix may be agitated for a period sufficient to dissolve/melt the components, for example, from 1 hour to 12 hours to form the completed aqueous premix.

The disperse phase pre-mix may comprise the first surfactant and cyclosporin as a dispersion or preferably a solution in a vehicle (for example an oil phase) as described above, for example in a liquid comprising an oil or in a liquid comprising component(s) of self-assembly structures. For example an oil phase pre-mix may therefore be a liquid lipid, for example a medium chain triglyceride (MCT) formulation, the medium chain triglyceride(s) being one or more triglycerides of at least one fatty acid selected from $C_6$-$C_{12}$ fatty acids, and cyclosporin A and the surfactant comprising or being a medium or long chain fatty acid mono- or di-glyceride. Suitably an oil phase pre-mix is stirred at ambient temperature to form a solution of the cyclosporin in the oil and surfactant. In some embodiments, the components of the oil phase premix are mixed (or otherwise agitated) for a period of, for example, 10 minutes to 3 hours to form the premix.

The two premixes may be combined and agitated, for example for a period of a few seconds to an hour, for example from 30 seconds to 1 hour, suitably 5 mins to an hour, to form a dispersion of the disperse phase in an aqueous hydrogel-forming polymer to form the liquid composition of the invention. The dispersion may then be further processed to form the composition or a core. The two premixes may be combined into the dispersion by agitation in a mixing vessel; they may additionally or alternatively be combined in a continuous flow mixer.

The basic method for making a composition or core comprising cyclosporin and hydrogel-forming polymer matrix, therefore, is to mix a liquid form (preferably a solution) of the hydrogel-forming polymer (or mixture of polymers) with the cyclosporin, the surfactant (to avoid any ambiguity the first surfactant) and the oil phase (and any other disperse phase components) to form a dispersion in the polymer, which later in the process forms a hydrogel. The method normally comprises mixing together an aqueous polymer phase premix and a disperse phase premix. Taking account of the final composition required (as described elsewhere herein), the disperse phase pre-mix and the liquid hydrogel-forming polymer (i.e. the solution or suspension of hydrogel-forming polymer, the aqueous phase) may be mixed in a weight ratio of from 1:1 to 1:10, particularly 1:4 to 1:9, e.g. 1:5 to 1:7. In general, only gentle stirring of the components is required using a magnetic or mechanical system, e.g. overhead stirrer, as would be familiar to a person skilled in the art to achieve a dispersion of the disperse phase in the aqueous phase to form a colloid (which may be in the form of for example an emulsion or micro emulsion in which the aqueous hydrogel is the continuous phase). Continuous stirring is preferred. Mixing may also be achieved using an in-line mixing system. Any appropriate laboratory stirring apparatus or industrial scale mixer may be utilized for this purpose for example the Magnetic Stirrer (manufactured by Stuart) or Overhead Stirrer (by KNF or Fisher). It is preferred to set up the equipment in such a way as to minimise evaporation of contents such as, for example, water. In one embodiment of the process of the invention, it is preferred to utilise a closed system for stirring in order to achieve this aim. In-line mixing may be particularly suitable for closed system processing. Suitably mixing of the two components takes place at a temperature of 50 to 70° C., or 55-75° C., e.g. 60-70° C.

The mixing of the two phases results in a colloid wherein the aqueous hydrogel-forming polymer is an aqueous continuous phase and the component(s) not soluble in the aqueous phase are a disperse phase. The colloid may have the form of an emulsion or microemulsion.

In embodiments where the disperse phase is or comprises a second surfactant, the amount of the second surfactant may be selected such that, upon combination of the disperse phase premix with the aqueous pre-mix, the second surfactant concentration in the combined mixture exceeds the CMC for the second surfactant used such that micelles are formed in the aqueous phase comprising the hydrogel-forming polymer. Depending on the concentration of second surfactant used, self-assembly structures other than micelles may also form. The CMC for a particular surfactant may be determined using well known methods, for example as described in Surfactants and Polymers in Aqueous Solutions Second Edition, Chapter 2, Holmberg et al. In embodiments mixing of the aqueous phase and a disperse phase which is or comprises a surfactant may result in the formation of a clear liquid, for example a microemulsion, in which the aqueous phase comprising the hydrogel-forming polymer is the continuous phase. Microemulsions are a thermodynamically stable dispersion of self-assembly structures in the aqueous phase, the size of the self-assembly structures being sufficiently small to give a transparent appearance. The size of the self-assembly structures present as the disperse phase resulting from the mixing of the aqueous and surfactant phases may be from about 0.5 nm to 200 nm, for example about 1 nm to 50 nm, or about 5 nm to 25 nm. The size of the self-assembly structures formed and other characteristics such as the optical isotropicity of the formulation (for example a microemulsion) may be determined using well known techniques such as dynamic light scattering.

Where the polymer matrix substantially consists of gelatin with the addition of sorbitol, the aqueous phase of polymer matrix is prepared by adding the appropriate quantities of sorbitol (and surfactant if desired) to water, heating to approximately 50 to 75° C., for example 60-75° C. until in solution and then adding gelatin, although the precise order and timing of addition is not critical. A typical "gelatin solution" comprises 8 to 35%, (for example 15-25%, preferably 17-18%) gelatin; 65%-85% (preferably 77-82%) of water plus from 1-5% (preferably 1.5 to 3%) sorbitol. When present, a second surfactant (e.g. anionic surfactant) in the aqueous phase premix may be present in an amount of 0.1 to 5% (preferably 0.5 to 4%) wherein all parts are by weight of the aqueous phase.

Optionally the processing temperature required for a standard gelatin can be reduced to a desirable target temperature e.g. 37° C. by use of lower melting-point gelatin (or gelatin derivatives or mixtures of gelatins with melting point reducers) or other polymer matrix material such as, for example, sodium alginate. If gelatin droplets are being formed by machine extrusion and immediately cooled, e.g. in a cooling bath, additional appropriate inlet tubing can be used to introduce an oil phase containing cyclosporin A at ambient temperature into the hotter fluid gelatin solution (and the mixture can be immediately homogenized) very shortly before ejection from a beading nozzle or other droppletting process such that the duration of exposure of the cyclosporin A to the higher temperature gelatin is limited so reducing the degree of any heat-dependent degradation of the active ingredient. This process may use any appropriate device such as, for example, a homogenizer, e.g. a screw homogenizer, in conjunction with an extrusion-type apparatus as described for example in WO 2008/132707 (Sigmoid Pharma) the entirety of which is incorporated herein by reference. Alternatively, the aqueous- and oil-based solutions can be pumped at appropriate rates and passed through a static mixer to form an emulsion prior to dropping.

The colloid is formed by combining of the disperse phase premix with the liquid aqueous phase with stirring as described above. The resultant colloidal dispersion then has the formulation of a solidified core described above but with liquid water still present in the core formulation.

Optionally the cyclosporin may be added after mixing the aqueous phase and other components of a disperse phase of the type comprising a liquid lipid in addition to the cyclosporin, however, it is preferred that the cyclosporin is added together with the other components of the disperse phase as a premix.

The resulting colloid is then poured or introduced into a mould or other vessel or poured onto sheets or between sheets or delivered dropwise (or extruded) into another fluid such that the polymer matrix-containing aqueous phase, on solidification, takes the form of the mould, vessel, sheet or droplet/bead intended. It is preferred to progress to mould-forming e.g. beading without delay.

Solidification (gelling) can occur in a variety of ways depending on the polymer of the matrix, for example by changing the temperature around the mould, vessel, sheet, droplet/bead etc or by applying a solidification fluid or hardening solution so that the moulded shape is gelled or solidified. In certain embodiments both temperature change and application of a solidifying fluid or hardening solution are employed together or simultaneously. For example, when using a dropping method solidification can occur by dropping into cooling oil, air or a combination thereof.

In the preferred embodiment in which the composition or core takes the form of beads, the beads may be formed for example by dropping the colloid dropwise into a fluid which effects solidification. Where the viscosity of the composition to be beaded reaches a certain point, drop formation becomes more difficult and specialised apparatus is then preferred.

By use of the term "dry", it is not sought to imply that a drying step is necessary to produce the dry core (although this is not excluded) rather that the solid or solidified aqueous external phase is substantially free of water or free of available water. Solidification of the aqueous phase (external phase) may have arisen through various means including chemically (e.g. by cross-linking) or physically (e.g. by cooling or heating). In this respect, the term "aqueous phase" is nevertheless employed in this document to denote the external (continuous) phase of the core even though water, in certain embodiments, is largely absent from (or trapped within the cross-linked matrix of) the core. The external phase of the core is however water-soluble and dissolves in aqueous media.

In the case where solidification can be achieved by raising or reducing temperature, the temperature of the solidification fluid can be adapted to achieve solidification of the core at a desired rate. For example, when gelatin is used as the hydrogel-forming polymer, the solidification fluid is at a lower temperature than the temperature of the emulsion thus causing solidification, i.e. gelling, of the polymer matrix. In this case, the solidification fluid is termed a cooling fluid.

In the case where solidification can be achieved chemically, e.g. by induction of cross-linking on exposure to a component of the solidification fluid, the concentration of such component in the solidification fluid and/or its temperature (or other characteristic or content) can be adjusted to achieve the desired rate and degree of solidification. For example, if alginate is chosen as the polymer matrix, one component of the solidification fluid may be a calcium-containing entity (such as, for example, calcium chloride) able to induce cross-linking of the alginate and consequent solidification. Alternatively, the same or similar calcium-containing entity may be included (e.g. disperse) in the aqueous phase of the fluid emulsion prior to beading and triggered to induce cross-linking e.g. by applying a higher or lower pH to a solidification fluid into which droplets of emulsion fall dropwise or are introduced. Such electrostatic cross-linking can be varied as to the resulting characteristics of the bead by control of calcium ion availability (concentration) and other physical conditions (notably temperature). The solidification fluid may be a gas (for example air) or a liquid or both. For example, when gelatin is used as the hydrogel-forming polymer matrix, the solidification fluid can be initially gaseous (e.g. droplets passing through cooling air) and then subsequently liquid (e.g. droplets passing into a cooling liquid). The reverse sequence may also be applied while gaseous or liquid cooling fluids alone may also be used. Alternatively, the fluid may be spray-cooled in which the emulsion is sprayed into a cooling gas to effect solidification.

In the case of gelatin or other water-soluble polymer (or polymer mixture) destined to form an immobilization matrix, it is preferred that the solidification fluid be a non-aqueous liquid (such as, for example, medium chain triglycerides, mineral oil or similar preferably with low HLB to ensure minimal wetting) which can conveniently be placed in a bath (cooling bath) to receive the droplets of the colloid as they solidify to form the beads of the core. Use of a non-aqueous liquid allows greater flexibility in choice of the temperature at which cooling is conducted.

Where a liquid cooling bath is employed, it is generally maintained at less than 20° C., preferably maintained in the range 5-15° C., more preferably 8-12° C. when standard gelatin is used as the hydrogel-forming polymer. If a triglyceride is chosen as the cooling fluid in the cooling bath, a preferred example is Miglyol 840 from Sasol.

If alginate is selected as the polymer matrix, a typical method of making beads involves dropwise addition of a 3% sodium alginate solution in which oil droplets are disperse as described above into a 4° C. crosslinking bath containing 0.1 M calcium chloride to produce calcium alginate (this method can be referred to as "diffusion setting" because the calcium is believed to diffuse into the beads to effect cross-linking or setting). Using a syringe pump, or Inotech machine, droplets can be generated or extruded (egg at 5 mL/h if a pump is used) through a sterile needle or other nozzle (described elsewhere herein) which can be vibrating as discussed elsewhere herein. Airflow of between 15 and 20 L/min through 4.5 mm tubing can be applied downwards over the needle to reduce droplet size if desired. Newly formed beads can then be stirred in the calcium chloride bath for up to an hour. If carrageenan is used as the polymer matrix both salt and reduction in temperature e.g. by dropping into cooling oil may be used to obtain solidification.

An alternative approach when using alginate is internal gelation in which the calcium ions are disperse in the aqueous phase prior to their activation in order to cause gelation of hydrocolloid particles. For example, this can be achieved by the addition of an inactive form of the ion that will cause crosslinking of the alginate, which is then activated by a change in e.g. pH after sufficient dispersion of the ion is complete (see Glicksman, 1983a; Hoefler, 2004 which are both incorporated herein by reference). This approach is particularly useful where rapid gelation is desired and/or where the diffusion approach may lead to loss of API by diffusion thereof into the crosslinking bath.

Where another ionotropic polymer is used than alginate, suitable analogous processes may be used to those described herein in relation to alginate.

Following shape-forming, moulding or beading, the resultant shapes or forms may be washed then dried if appropriate. In the case of beads solidified in a solidification fluid, an optional final step in the method of production described above therefore comprises removal of the solidified beads from the solidification fluid. This may be achieved e.g. by collection in a mesh basket through which the solidification fluid (e.g. medium chain triglycerides) is drained and the beads retained and is preferably conducted without delay e.g. as soon as the beads have formed or within 5, 10, 15, 20, 25 or 30 minutes of their formation. Excess solidification fluid may then be removed using a centrifuge (or other apparatus or machine adapted to remove excess fluid) followed by drying of the beads to remove water or free water and/or removal of some or all of any additional solvent e.g. ethanol or isopropyl alcohol used to dissolve or facilitate dissolution of the active principle in preceding steps optionally followed by washing (e.g. using ethyl acetate) and a subsequent "drying" step to remove excess solvent (e.g. ethyl acetate). Isopropyl alcohol is an example of a solvent which is preferably removed later in processing to reduce residues in the oil or aqueous phase. Drying can be achieved by any suitable process known in the art such as use of a drum drier (e.g. Freund Drum dryer which may be part of the Spherex equipment train if used) with warm air at between 15° C. and 25° C., preferably around 20° C. leading to evaporation or entrainment of the water by the air. Alternatively, drying may be carried out using of a fluid bed drier (e.g. Glatt GPCG 1.1) with warm air between 40° C. and 60° C.; or using a vibrational fluid bed drier. Use of gelatin as the polymer matrix (e.g. as principal constituent of the aqueous immobilisation phase) in most cases requires a drying step and for beads this is preferably achieved by drying in air as above described. Beads can be dried using other techniques, as understood by the person skilled in the art, for example vibrating fluid bed, tray drying or vacuum drying. The resultant formulation (the formulation of the invention) is essentially dry as described in more detail above.

In general, the beads may be generated by the application of surface tension between the liquid dispersion (the mixture of the aqueous and surfactant phases) and an appropriate solidification fluid such as, for example, gas or liquid in order to create the spherical or substantially spherical shape of the ultimate beads.

Alternatively, the beads may be produced through ejection or extrusion of the liquid dispersion (the aqueous phase pre-mix and the disperse phase premix mixture) through an orifice or nozzle with a certain diameter and optionally subject to vibration (using selected vibrational frequencies) and/or gravitational flow. Examples of machines which may be used are encapsulation prilling, drop pelletising, spray cooling or spray congealing machines for example the Freund Spherex, ITAS/Lambo, Globex, Inotech, GEA Niro, Droppo, Buchi, Gelpell, Brace processing equipment processing equipment. Operation of the Spherex machine manufactured by Freund as may be desired to manufacture beads according to the present invention is described in U.S. Pat. No. 5,882,680 (Freund), the entire contents of which are incorporated herein by reference. It is preferred to select a vibrational frequency in the region of 2-200 Hz, suitably 10-50 Hz, although the ultimate choice (and separately the amplitude of vibration selected) depends on the viscosity of the dispersion to be beaded. If the polymer matrix is chosen to solidify at lower temperature, it may be appropriate to maintain the lines to the orifice/nozzle at a certain temperature to maintain the fluidity of the solution. Suitably the colloid is ejected through a single-orifice nozzle, e.g. having a diameter of from 0.1 mm to 5 mm (for example 0.5-5 mm), to form drops which are then caused or allowed to fall into a cooling oil or other hardening medium and allowed to harden to form seeds, after which the seeds are recovered from the cooling oil and dried.

It will be appreciated, therefore, that the invention includes a process for manufacturing a composition of the invention or a core comprising cyclosporin, a first surfactant being or comprising a medium chain or long chain fatty acid mono- or di-glyceride or a combination thereof, wherein the surfactant does not comprise or is not a polyethyleneglycol ether or ester, and an oil phase in a hydrogel forming polymer matrix, which process comprises: forming an aqueous premix which comprises water and water soluble/dispersible materials (including therefore a hydrogel-forming polymer) and a disperse phase premix (e.g. an oil phase premix) which comprises the oil phase, the cyclosporin and the first surfactant optionally other excipients (e.g. oil(s) and oil soluble/dispersible materials), and combining the two premixes to form a colloid (disperse phase) within an aqueous phase comprising the hydrogel-forming polymer. The colloid may then be formed into a shaped unit, for example a bead to provide the core comprising the active ingredient. More particularly the manufacture of a composition or core as defined above may comprise:

(i) forming an aqueous phase pre-mix comprising a solution in water of water-soluble constituents (e.g. of a hydrogel-forming polymer, any water-soluble excipient(s), as described elsewhere herein);

(ii) forming a disperse phase pre-mix typically comprising a dispersion or preferably a solution of cyclospori, in a liquid lipid, and the first surfactant, optionally together with other disperse phase constituents (e.g. surfactant, solvents etc as described elsewhere herein);

(iii) mixing the aqueous phase pre-mix (i) and the disperse phase pre-mix (ii) to form a colloid;

(iv) ejecting the colloid through a nozzle to form droplets;

(v) causing or allowing the a hydrogel-forming polymer to gel or solidify to form a water soluble polymer matrix; and (vi) drying the solid.

The manufacture of a liquid composition of the invention may comprise:

(i) forming an aqueous phase pre-mix comprising a solution in water of water-soluble constituents (e.g. of a hydrogel-forming polymer, any water-soluble excipient(s), as described elsewhere herein);

(ii) forming a disperse phase pre-mix typically comprising a dispersion or preferably a solution of cyclospori, in a liquid lipid, and the first surfactant, optionally together with other disperse phase constituents (e.g. surfactant, solvents etc as described elsewhere herein); and (iii) mixing the aqueous phase pre-mix (i) and the disperse phase pre-mix (ii) to form a colloid.

Some manufacturing processes comprise steps (A) to (D) below or, alternatively, a manufacturing process may comprise a single one or any combination of steps (A) to (D).

(A) Exemplary Preparation of Aqueous Phase:

Aqueous phase components are added to water, e.g. purified water, under agitation e.g. sonication or stirring. The temperature is gradually increased, for example to 60-70° C. and in particular 65° C., to achieve complete dissolution of the solids. The aqueous phase components include a hydrogel-forming polymer, e.g. gelatin or agar and optionally one or more other excipients, for example D-sorbitol (a plasticiser) and surfactant (for example SDS). Possible aqueous phase components are described elsewhere herein.

The gelatin may be Type A gelatin. In some less preferred implementations, the gelatin is Type B. The gelatin may have a Bloom strength of 125-300, optionally of 200-300, for example of 225-300, and in particular 275. The components of the aqueous phase may be agitated for a period of, for example, from 1 hour to 12 hours to complete preparation of the aqueous phase (aqueous premix).

(B) Exemplary Preparation of Disperse Phase:

Cyclosporin is mixed with the first surfactant, an oil and other disperse phase components (for example a co-solvent) under agitation e.g. sonication or stirring, suitably at ambient temperature to disperse or preferably dissolve the active ingredient.

(C) Exemplary Mixing of the Two Phases

The aqueous phase and the disperse phase are mixed. The two phases may be mixed in a desired weight; for example, the weight ratio of disperse phase to aqueous phase may be from 1:1 to 1:10, e.g. from 1:4 to 1:9 and optionally from 1:5 to 1:8 such as about 1:5 or about 1:7. The resulting colloid is agitated, e.g. sonicated or stirred, at a temperature of 60-70° C. and in particular 65° C., to achieve a homogeneous dispersion, then the homogenous dispersion is formed into beads. In particular, the homogenous dispersion is ejected through a single orifice nozzle to form droplets which fall into a cooling medium. The nozzle is suitably vibrated to facilitate droplet formation. The nozzle may be vibrated at a frequency of 2-200 Hz and optionally 15-50 Hz.

The cooling medium may for example be air or an oil; the oil is suitably physiologically acceptable as, for example, in the case of medium chain triglycerides e.g. Miglyol 810N. The cooling medium may be at a cooling temperature often of less than 15° C., for example of less than 10° C. but above 0° C. In some embodiments the cooling temperature is 8-10° C. The nozzle size (diameter) is typically from 0.5 to 7.5 mm, e.g. from 0.5 to 5 mm and optionally from 0.5 to 4 mm. In some embodiments, the nozzle diameter is from 1 to 5 mm for example from 2 to 5 mm, and optionally from 3 to 4 mm, and in particular may be 3.4 mm. The nozzle diameter may be from 1 to 2 mm.

The flow rate through a 3.4 mm nozzle or through a 1.5 mm nozzle is 5 to 35 g/min and optionally 10 to 20 g/min and for nozzles of different sizes may be adjusted suitably for the nozzle area.

(D) Exemplary Processing of Beads

Cooled beads are recovered, for example they may be recovered from cooling oil after a residence time of 15-60 minutes, for example after approximately 30 minutes. Beads recovered from a cooling liquid (e.g. oil) may be centrifuged to eliminate excess cooling liquid, and then dried. Suitably, drying is carried out at room temperature, for example from 15-40° C. and optionally from 20-35° C. The drying may be performed in a drum drier, for example for a period from 6 to 24 hours, e.g. of about 12 hours in the case of beads dried at room temperature. The dried beads may be washed, suitably with a volatile non-aqueous liquid at least partially miscible with water, e.g. they may be washed with ethyl acetate. The washed beads may be dried at room temperature, for example from 15-25° C. and optionally from 20-25° C. The drying may be performed in a drum drier, for example for a period from 6 to 48 hours, e.g. of about 24 hours in the case of beads dried at room temperature. Drying may be achieved by any suitable means, for example using a drum dryer, suitably under vacuum; or by simply passing warm air through the batch of beads, or by fluidising the beads in a suitable equipment with warm air, for example if a fluid bed dryer. Following drying, the beads are passed through a 1 to 10 mm, optionally 2 to 5 mm to remove oversized beads and then through a sieve with a pore size of 0.5 to 9 mm optionally 1 to 4 mm to remove undersized beads.

It can be appreciated that it is possible to recycle the beads that are rejected by the sieving process.

As a further aspect of the invention there is provided a formulation obtainable by (having the characteristic of) any of the processes described herein. It is to be understood that the processes described herein may therefore be used to provide any of the specific cores described in embodiments herein by dispersing the appropriate components which form the disperse phase of the core in the appropriate components which form the aqueous continuous matrix phase of the core.

The preceding paragraphs describe the formation of uncoated compositions or cores. The composition may comprise a coating. Cores may be coated. The composition or the core may be coated with a subcoat and/or coated with a second coating (also referred to as a modified release coating or outer coat). Suitable sub coats and modified release coatings (second coating or outer coat) are any of those described herein and any of the first coating (for the subcoat) or the second coating (for the modified release coating). The coating(s) may be applied using well known methods, for example spray coating as described below to give the desired sub coat and modified release coating weight gains.

With regard to one of the methods described above (ejection of emulsion through an optionally vibrating nozzle) with two concentric orifices (centre and outer), the outer fluid may form a coating (outside the bead) as described herein. The Spherex machine manufactured by Freund (see U.S. Pat. No. 5,882,680 to Freund) is preferably used (the entire contents of this patent is incorporated herein by reference). Other similar ejection or extrusion apparatus may also be used, for example the ejection apparatus described hereinbefore.

Use of the Spherex machine achieves very high monodispersity. For example, in a typical 100 g, batch 97 g of beads were between 1.4 to 2 mm diameter or between 1 and 2 mm. Desired size ranges can be achieved by methods known in the art for rejecting/screening different sized particles. For example, it is possible to reject/screen out the larger/smaller beads by passing a batch first through e.g. a 2 mm mesh and subsequently through a 1.4 mm mesh.

The 1.4 to 2 mm diameter range is a good size if it is desired to spray coat the beads (if smaller, the spray of the coating machine may bypass the bead; if too large, the beads may be harder to fluidise, which is necessary to achieve consistent coating).

Coating Process

The coating process can be carried out by any suitable means such as, for example, by use of a coating machine which applies a solution of a polymer coat (as described above in particular) to the formulation. Polymers for coating are either provided by the manufacturer in ready-made solutions for direct use or can be made up before use following manufacturers' instructions.

Coating is suitably carried out using a fluid bed coating system such as a Wurster column to apply the coating(s) to the composition or the core. Appropriate coating machines are known to persons skilled in the art and include, for example, a perforated pan or fluidized-based system for example the GLATT, Vector (e.g. CF 360 EX), ACCELACOTA, Diosna, O'Hara and/or HICOATER processing equipment. To be mentioned is the MFL/01 Fluid Bed Coater (Freund) used in the "Bottom Spray" configuration.

Typical coating conditions are as follows:

| Process Parameter | Values |
| --- | --- |
| Fluidising airflow (m3/h) | 20-60 (preferably 30-60) |
| Inlet air temperature (° C.) | 20-65 |
| Exhaust air temperature (° C.) | 20-42 |
| Product temperature (° C.) | 20-45 (preferably 40 to 42) |
| Atomizing air pressure (bar) | Up to 1.4 e.g. 0.8-1.2 |
| Spray rate (g/min) | 2-10 and 3-25 RPM |

Suitably the coating is applied as a solution or dispersion of the polymers (and other components) of the coating. Generally the coatings are applied as an aqueous, solution or dispersion, although other solvent systems may be used if required. The coating dispersion is applied to the composition or the core as a spray in the fluid bed coater to give the required coating weight gain.

Generally the coating process is carried out at a temperature which maintains the cores at a temperature of from 35 to 45° C., preferably 40 to 42° C.

After applying the coating, the composition may be dried, for example by drying at 40 to 45° C.

The invention further provides a product having the characteristics of a composition obtained as described herein, a product defined in terms of its characteristics being defined by the characteristics of the composition to the exclusion of the method by which it was made.

As mentioned herein the processes described may be used to provide any of the composition described in the various embodiments herein. By way of example there is provided a composition of the invention comprising a core and a first coating comprising a water-soluble cellulose ether or a water soluble derivative of a cellulose ether and/or a second coating comprising a delayed release polymer wherein the core comprises a hydrogel-forming polymer matrix comprising gelatin, cyclosporin A, medium chain mono- di- and/or tri-glycerides, a first surfactant being or comprising a medium chain or long chain fatty acid mono- or di-glyceride or a combination thereof that does not comprise or is not a polyethyleneglycol ether or ester, a co-solvent and optionally a second surfactant, the core having the characteristics of a core obtained by the process comprising steps (i) to (vi) described above for forming the core, wherein the aqueous phase pre-mix in step (i) of the process comprises gelatin and optionally a second surfactant (suitably an anionic surfactant), and the oil phase pre-mix in step (ii) of the process comprises medium chain mono- di- or tri-glycerides, hydrophobic active ingredient, surfactant (suitably a non-ionic surfactant) and cosolvent; and the wherein the core is optionally coated with a first coating comprising a water-soluble cellulose ether or a water soluble derivative of a cellulose ether and/or a second coating comprising a delayed release polymer; wherein the coatings are any of those described herein. Accordingly, the process may produce a composition as described above comprising a first coating and/or a second coating. The process may additionally produce a composition comprising a first coating and a second coating being outside the first coating.

In the cores described herein to which the following characteristics are applicable, e.g. in the immediately preceding paragraph, the following characteristics may be present:

gelatin may be present in an amount of 300 to 700 mg/g;

the medium chain mono-, di- or tri-glycerides (for example caprylic/capric triglyceride) may be present in an amount of 20 to 200 mg/g;

co-solvent (for example 2-(ethoxyethoxy)ethanol) may be present in an amount of 150 to 250 mg/g;

non-ionic surfactant (for example sorbitan-based surfactants, PEG-fatty acids, or glyceryl fatty acids or poloxamers or particularly a polyethoxylated castor oil for example Kolliphor EL) may be present in an amount of 80 to 200 mg/g;

anionic surfactant (for example, alkyl sulphates, carboxylates or phospholipids (particularly SDS)) may be present in an amount of 15 to 50 mg/g; and cyclosporin A, may be present in an amount of from 60 to 180 mg/g, suitably 60 to 150 mg/g, 90 to 150 mg/g, or 80 to 100 mg/g, for example 81 to 98 mg/g;

wherein all weights are based upon the dry weight of the core before coating.

The composition may comprise or the core may be coated with a first coating (sub-coating) which is or comprises a water-soluble compound selected from cellulose ethers and their derivatives, particularly hydroxypropylmethyl cellulose; the first coating being present in an amount corresponding to a weight gain due to the first coating in a range selected from: (i) from 8% to 12%, for example about 10%; or (ii) from 4% to 6%, for example about 5% by weight based upon the weight of the core prior to applying the first coating. The first coating may have a modified release coating (or second coating) applied to it.

Preferably, any modified release coating (second coating), especially in the embodiments of the immediately preceding paragraphs, is or comprises a pH independent modified release coating, more especially the second coating may be a modified release coating comprising ethyl cellulose (eg Surelease) still more particularly a modified release coating comprising ethyl cellulose and a water-soluble polysaccharide, pectin (e.g. a Surelease-pectin coating as described herein); and wherein the modified release coating is present in an amount corresponding to a weight gain of the formulation due to the second coating selected from (a) from 10% to 12%, for example about 11% or about 11.5%; or (b) from 16% to 18%, for example about 17% by weight based upon the weight of the formulation prior to applying the second coating.

In addition the process to form a composition of the invention may comprise the steps of mixing a first population and a second population, wherein the first population has a coating that is or comprises a water-soluble cellulose ether but having no outer coating, e.g. as described herein; and the second population has a first coating that is or comprises a water-soluble cellulose ether and a second coating that is or comprises a delayed release coating, for example as described herein e.g. a coating that is or comprises a delayed release polymer.

Applications

The composition of the invention may advantageously be used for oral delivery pharmaceutically active ingredients by virtue of the enhanced dissolution profiles achieved.

The compositions of the invention include modified release compositions which comprise cyclosporin A and a modified release coating, for example comprising a pH independent polymer, to target cyclosporin release to the lower intestine. Such compositions result in low systemic exposure to cyclosporin A, whilst providing high levels of cyclosporin A in the lower GI tract, particularly in the colon. Such compositions release the cyclosporin A in an active form for example as a solution, which provides enhanced absorption of cyclosporin A in the local tissue of the lower GI tract. When the composition is used in the form of minibeads, the minibeads are advantageously dispersed along large sections of the GI tract following oral administration and are therefore expected provide a more uniform exposure to cyclosporin to large sections of for example the colon.

Accordingly the modified release compositions according to the invention comprising cyclosporin for local treatment of the lower GI tract are expected to be useful in the treatment or prevention of a condition of the GIT. In particular the composition of the invention may comprise cyclosporin A and/or another immunosuppressant and be useful in the prevention or treatment of inflammatory conditions affecting the lower GI tract, particularly conditions affecting the colon.

The composition of the invention is administered orally. The dose required will vary depending upon the specific condition being treated and the stage of the condition. In the case of compositions containing cyclosporin A, the composition will generally be administered to provide a dose of cyclosporin A of from 0.1 to 100 mg, for example a dose of 1 to 500 mg or particularly a dose of 25 to 250 mg cyclosporin A. The composition is suitably administered as a single daily dose.

In one aspect of the invention there is provided a composition of the invention for use in the treatment or prophylaxis of an inflammatory bowel disease, Crohn's disease, ulcerative colitis, graft-versus-host disease, gastrointestinal graft-versus-host disease, myasthenia gravis, irritable bowel syndrome (e.g. with constipation, diarrhea and/or pain symptoms), celiac disease, stomach ulcers, diverticulitis, pouchitis, proctitis, mucositis, chemotherapy-associated enteritis, radiation-associated enteritis, short bowel disease, or chronic diarrhea, gastroenteritis, duodenitis, jejunitis, peptic ulcer, Curling's ulcer, appendicitis, colitis, diverticulosis, endometriosis, colorectal carcinoma, adenocarcinoma, inflammatory disorders such as diversion colitis, ischemic colitis, infectious colitis, chemical colitis, microscopic colitis (including collagenous colitis and lymphocytic colitis), atypical colitis, pseudomembraneous colitis, fulminant colitis, autistic enterocolitis, interdeminate colitis, jejunoiletis, ileitis, ileocolitis or granulomatous colitis, the prevention of rejection following bone marrow transplantation, psoriasis, atopic dermatitis, rheumatoid arthritis, nephrotic syndrome primary sclerosing cholangitis, familial adenomatous polyposis, or perinanal Crohn's, including perianal fistulae.

In one embodiment the composition of the invention is for use in the treatment of an inflammatory bowel disease. The main forms of inflammatory bowel disease are Crohn's disease and ulcerative colitis. Accordingly the composition of the invention may be useful in the treatment of both of these conditions.

The composition of the invention may be for use in the treatment or prevention of irritable bowel syndrome (e.g. with constipation, diarrhea and/or pain symptoms), celiac disease, stomach ulcers, diverticulitis, pouchitis, proctitis, mucositis, radiation-associated enteritis, short bowel disease, or chronic diarrhea, gastroenteritis, duodenitis, jejunitis, peptic ulcer, Curling's ulcer, appendicitis, colitis, diverticulosis, endometriosis, colorectal carcinoma, adenocarcinoma, inflammatory disorders such as diversion colitis, ischemic colitis, infectious colitis, chemical colitis, microscopic colitis (including collagenous colitis and lymphocytic colitis), atypical colitis, pseudomembraneous colitis, fulminant colitis, autistic enterocolitis, interdeminate colitis, jejunoiletis, ileitis, ileocolitis or granulomatous colitis, fibrosis, graft-versus-host disease, gastrointestinal graft-versus-host disease, HIV prophylaxis and treatment (for example HIV enteropathy) or gastrointestinal enteropathies.

The composition may also be for use in the treatment or prevention of *Clostridium difficile* colitis.

Crohn's disease may affect the entire GI tract including the colon. However, ulcerative colitis is a condition which affects only the colon and the rectum. Accordingly, the release profile provided by the colon-targeted, immunosuppressant-containing (e.g. cyclosporin A-containing), composition according to the invention is expected to be especially beneficial in the treatment of ulcerative colitis.

The colon-targeted, composition of the invention primarily releases cyclosporin A, in the colon. However, cycosporin may also be released higher in the GI tract and accordingly the composition may also provide therapeutic benefit in conditions which affect other parts of the lower GI tract, for example Crohn's disease, irritable bowel syndrome (e.g. with constipation, diarrhea and/or pain symptoms), celiac disease, stomach ulcers, diverticulitis, collagenous colitis, pouchitis, proctitis, mucositis, radiation-associated enteritis, short bowel disease, chronic diarrhea, gastroenteritis, duodenitis, jejunitis, peptic ulcer, Curling's ulcer, appendicitis, diverticulosis, endometriosis, colorectal carcinoma, adenocarcinoma, inflammatory disorders such as, jejunoileitis, ileitis, ileocolitis, celiac disease, fibrosis, graft-versus-host disease, gastrointestinal graft-versus-host disease, HIV prophylaxis and treatment (for example HIV enteropathy) or enteropathies.

Gastrointestinal Graft-Versus-Host-Disease (GI-GVHD) is a life-threatening condition and one of the most common causes for bone marrow and stem cell transplant failure. In patients with GI-GVHD it is the donor cells that begin to attack the patient's body—most frequently the gut, liver and skin. Patients with mild-to-moderate GI-GVHD typically develop symptoms of anorexia, nausea, vomiting and diarrhoea. If left untreated, GI-GVHD can progress to ulcerations in the lining of the GI tract, and in its most severe form, can be fatal. Accordingly, in one embodiment the composition is for use in the treatment or prophylaxis of Gastrointestinal Graft-Versus-Host-Disease (GI-GVHD).

In a further embodiment there is provided a composition of the invention for use in the treatment of celiac disease.

In a further embodiment there is provided a composition of the invention for use in the treatment or prophylaxis of ulcerative colitis.

Also provided is a composition of the invention for use in the treatment of neurodegenerative diseases (for example Parkinson's disease, Alzheimer's disease or vascular dementia) or paediatric diseases, including, but not limited to ulcerative colitis, Crohn's disease and GvHD.

Chronic inflammation of the GI tract may result in cellular transformation and the onset of cancer through tumourigenesis. Cyclosporin has been shown to be effective in inhibiting cell growth in a number of colorectal cancer cell lines (Wereneck et al Cell Cycle 11:21; 2012; 3997-4008). It has also been shown that cyclosporin may be an effective inhibitor of tumourigenesis (Kawahara et al, Cyclosporine A and Tacrolimus Inhibit Urothelial Tumorigenesis; Molecular Carcinogenesis, 2015). Accordingly, cyclosporin may be beneficial in providing a cytostatic anti-cancer effect thereby inhibiting the growth of a tumour. Cyclosporin may be beneficial in preventing or delaying the onset of colorectal cancer in patients with chronic inflammatory conditions affecting the GI tract, particularly the colon, for example the inflammatory conditions described herein such as ulcerative colitis or Crohn's disease. As discussed above the compositions comprising cyclosporin provide high levels of cyclosporin in a solubilised form into the colon and may therefore by particularly beneficial in the treatment of colorectal cancer.

A further aspect of the invention provides a composition comprising cyclosporin as defined herein for use in the treatment of a cancer affecting the GI tract, particularly the lower GI tract and especially the colon. Accordingly the composition comprising cyclosporin may be for use in the treatment of colorectal cancer. The composition comprising cyclosporin may be for use in providing a cytostatic effect in a cancer affecting the GI tract, particularly a colorectal cancer.

Also provided is a composition comprising cyclosporin for use in the preventing or delaying the onset of a cancer of the GI tract in a patient with chronic inflammatory condition affecting the GI tract, particularly the lower GI tract and especially the colon. Accordingly the composition comprising cyclosporin may be for use in inhibiting tumourigenesis in the GI tract, particularly the colon.

The composition comprising cyclosporin may be used alone or together with another anti-cancer agent, for example the composition comprising cyclosporin may be used together with an antineoplastic agent to treat or delay the onset of a cancer affecting the GI tract. The composition comprising cyclosporin may be administered to a subject as a fixed dose combination with one or more additional anticancer agents. The composition comprising cyclosporin may be administered separately, sequentially or substantially simultaneously with another anticancer agent.

Anti-cancer agents which may be suitable for use with the composition comprising cyclosporin include, but are not limited to one or more agents selected from (i) antiproliferative/antineoplastic drugs and combinations thereof, such as alkylating agents (for example cis-platin, oxaliplatin, carboplatin, cyclophosphamide, nitrogen mustard, uracil mustard, bendamustin, melphalan, chlorambucil, chlormethine, busulphan, temozolamide, nitrosoureas, ifosamide, melphalan, pipobroman, triethylene-melamine, triethylenethiophoporamine, carmustine, lomustine, stroptozocin and dacarbazine); antimetabolites (for example gemcitabine and antifolates such as fluoropyrimidines like 5-fluorouracil and tegafur, raltitrexed, methotrexate, pemetrexed, cytosine arabinoside, floxuridine, cytarabine, 6-mercaptopurine, 6-thioguanine, fludarabine phosphate, pentostatine, and gemcitabine and hydroxyurea); antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); proteasome inhibitors, for example carfilzomib and bortezomib; interferon therapy; and topoisomerase inhibitors (for example epipodophyllotoxins like etoposide and teniposide, amsacrine, topotecan, irinotecan, mitoxantrone and camptothecin); bleomcin, dactinomycin, daunorubicin, doxorubicin, epirubicin, idarubicin, ara-C, paclitaxel (Taxol™), nabpaclitaxel, docetaxel, mithramycin, deoxyco-formycin, mitomycin-C, L-asparaginase, interferons (especially IFN-alpha), etoposide, teniposide, DNA-demethylating agents, (for example, azacitidine or decitabine); and histone de-acetylase (HDAC) inhibitors (for example vorinostat, MS-275, panobinostat, romidepsin, valproic acid, mocetinostat (MGCD0103) and pracinostat SB939);

(ii) cytostatic agents such as antiestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride; and navelbene, CPT-11, anastrazole, letrazole, capecitabine, raloxifene, cyclophosphamide, ifosamide, and droloxafine;

(iii) anti-invasion agents, for example dasatinib and bosutinib (SKI-606), and metalloproteinase inhibitors, inhibitors of urokinase plasminogen activator receptor function or antibodies to Heparanase;

(iv) inhibitors of growth factor function: for example such inhibitors include growth factor antibodies and growth factor receptor antibodies, for example the anti-erbB2 antibody trastuzumab [Herceptin™] the anti-EGFR antibody panitumumab, the anti-erbB1 antibody cetuximab, tyrosine kinase inhibitors, for example inhibitors of the epidermal growth factor family (for example EGFR family tyrosine kinase inhibitors such as gefitinib, erlotinib, 6-acrylamido-N-(3-chloro-4-fluorophenyl)-7-(3-morpholinopropoxy)-quinazolin-4-amine (CI 1033), erbB2 tyrosine kinase inhibitors such as lapatinib) and antibodies to costimulatory molecules such as CTLA-4, 4-IBB and PD-I, or antibodies to cytokines (IL-10, TGF-beta); inhibitors of the hepatocyte growth factor family; inhibitors of the insulin growth factor family; modulators of protein regulators of cell apoptosis (for example Bcl-2 inhibitors); inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib, tipifarnib and lonafarnib), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor, kinase inhibitors; aurora kinase inhibitors and cyclin dependent kinase inhibitors such as CDK2 and/or CDK4 inhibitors; and CCR2, CCR4 or CCR6 antagonists;

(v) antiangiogenic agents such as those which inhibit the effects of vascular endothelial growth factor, [for example the anti-vascular endothelial cell growth factor antibody bevacizumab (Avastin™)]; thalidomide; lenalidomide; and for example, a VEGF receptor tyrosine kinase inhibitor such as vandetanib, vatalanib, sunitinib, axitinib and pazopanib;

(vi) gene therapy approaches, including for example approaches to replace aberrant genes such as aberrant p53 or aberrant BRCA1 or BRCA2;

(vii) immunotherapy approaches, including for example antibody therapy such as alemtuzumab, rituximab, ibritumomab tiuxetan (Zevalin®) and ofatumumab; interferons such as interferon α; interleukins such as IL-2 (aldesleukin); interleukin inhibitors for example IRAK4 inhibitors; cancer vaccines including prophylactic and treatment vaccines such as HPV vaccines, for example Gardasil, Cervarix, Oncophage and Sipuleucel-T (Provenge); gp100; dendritic cell-based vaccines (such as Ad.p53 DC); toll-like receptor modulators for example TLR-7 or TLR-9 agonists; PD-1, PD-L1, PD-L2 and CTL4-A modulators (for example Nivolumab), antibodies and vaccines; other IDO inhibitors (such as indoximod); anti-PD-1 monoclonal antibodies (such as MK-3475 and nivolumab); anti-PDL1 monoclonal antibodies (such as MEDI-4736 and RG-7446); anti-PDL2 monoclonal antibodies; and anti-CTLA-4 antibodies (such as ipilumumab; and (viii) cytotoxic agents for example fludaribine (fludara), cladribine, pentostatin (Nipent™);

The coating containing the water-soluble cellulose ether of the present invention may be useful in reducing the variability between release profiles of different batches of minibeads.

A "batch" is a specific quantity of a drug or other material that is intended to have uniform character and quality, within specified limits, and is produced according to a single manufacturing order during the same cycle of manufacture. A "lot" means a batch, or a specific identified portion of a batch, having uniform character and quality within specified limits; or, in the case of a drug product produced by continuous process, it is a specific identified amount produced in a unit of time or quantity in a manner that assures its having uniform character and quality within specified limits. "Lot number", "control number", or "batch number" means any distinctive combination of letters, numbers, or symbols, or any combination of them, from which the complete history of the manufacture, processing, packing, holding, and distribution of a batch or lot of drug product or other material can be determined."

EXAMPLES

Example 1a

Preparation of a Liquid Composition of the Invention

An aqueous phase was prepared by mixing sodium dodecyl sulphate (SDS) and D-sorbitol with purified water under constant stirring. Gelatin was then added to this solution and gentle heat was applied to approximately 60-70° C. to achieve complete melting of gelatin. The composition of the aqueous phase is shown in Table 1 below.

TABLE 1

| Component | w/w % |
| --- | --- |
| water | 79.6 |
| SDS | 1.3 |
| Sorbitol | 2.0 |
| Gelatin | 17.1 |

An oil phase was prepared by mixing together 2-(2-ethoxyethoxy)ethanol (Transcutol HP), glyceryl monooleate/dioleate (Capmul GMO-50) and capric/caprylic triglyceride (Miglyol 810) with stirring at room temperature to form a solution. Ciclosporin A was added and mixed until a clear solution was obtained. The composition of the oil phase is shown below in Table 2.

TABLE 2

| Component | w/w % |
| --- | --- |
| Cyclosporin A | 24.5 |
| Miglyol 810 N | 12.5 |
| Transcutol HP | 37.0 |
| Capmul GMO-50 | 26 |

The oil phase was mixed with the heated aqueous phase in a ratio of approximately 1:5 (oil phase:aqueous phase).

The resulting mixture was stirred at 60-70° C., 250-350 rpm using a magnetic stirrer to achieve homogeneity.

Example 1b

Preparation of a Further Liquid Composition

Following the procedure of Example 1a a further liquid composition with glyceryl caprylate/caprate (Capmul MCM) as the surfactant in the oil phase in place of the glyceryl monooleate/dioleate (Capmul GMO-50) was prepared. The aqueous phase of the composition is shown in Table 3 and the oil phase of the composition is shown in Table 4. The oil phase was mixed with the heated aqueous phase in a ratio of approximately 1:5 (oil phase:aqueous phase).

TABLE 3

| Component | w/w % |
|---|---|
| water | 79.6 |
| SDS | 1.3 |
| Sorbitol | 2.0 |
| Gelatin | 17.1 |

TABLE 4

| Component | w/w % |
|---|---|
| Cyclosporin A | 24.5 |
| Miglyol 810 N | 12.5 |
| Transcutol HP | 37.0 |
| Capmul MCM | 26 |

Example 1c

Preparation of a Further Liquid Composition

Following the procedure of Example 1a a further liquid composition with glycerol linoleate (Maisine 35-1) as the surfactant in the oil phase in place of the glyceryl monooleate/dioleate (Capmul GMO-50) was prepared. The aqueous phase of the composition is shown in Table 5 and the oil phase of the composition is shown in Table 6. The oil phase was mixed with the heated aqueous phase in a ratio of approximately 1:5 (oil phase:aqueous phase).

TABLE 5

| Component | w/w % |
|---|---|
| water | 79.6 |
| SDS | 1.3 |
| Sorbitol | 2.0 |
| Gelatin | 17.1 |

TABLE 6

| Component | w/w % |
|---|---|
| Cyclosporin A | 24.5 |
| Miglyol 810 N | 12.5 |
| Transcutol HP | 37.0 |
| Maisine 35-1 | 26 |

Example 2

Preparation of a Minibead

A minibead as described herein may be a composition of the invention. Alternatively the minibead may be a core. The minibead was generally prepared by forming a minibead according to the following procedure The composition or core in the form of seamless minibeads were prepared using Spherex process as follows.

An aqueous phase and oil phase mixture was prepared following the procedure described in Example 1a.

The mixture was then fed (via temperature controlled tubing) through a vibrating nozzle, with a single nozzle outlet with a diameter of 3 mm. Seamless minibeads were formed as the solution flowed through the vibrating nozzle into a cooling chamber of constantly flowing medium chain triglyceride (Miglyol 810) cooling oil at a temperature of 10° C.

The minibeads were removed from the cooling oil and placed in a centrifuge to remove the excess oil. Following centrifugation, a first drying step was initiated with a set refrigerator temperature of 10° C. and the heater temperature of 20° C. The dryer was rotated at 15 RPM. When the beads were observed to be freely rotating in the drying drum, they were considered to be dry.

The minibeads were washed with ethyl acetate and then dried for a further 24 h under the same drying conditions as those mentioned above in the first drying step. The dried minibeads were then sieved to remove oversize and undersize beads resulting in cores 1 mm-2 mm in diameter. This procedure provided cores with the composition shown in Table 7, the values being the weight percent of the total weight for each component.

TABLE 7

| Component | w/w % |
|---|---|
| Cyclosporin A | 12.1 |
| Miglyol 810 N | 6.2 |
| Transcutol HP | 18.3 |
| Capmul GMO-50 | 12.9 |
| SDS | 3.2 |
| Sorbitol | 4.9 |
| Gelatin | 42.4 |

Example 3

Preparation of a Minibead with a First Coating (Sub-Coat)

A coated minibead can be produced by coating a minibead produced in Example 2 with a dispersion of Opadry White 20A28380 (supplied by Colorcon). The minibeads were loaded into a fluid bed coater (Wurster column) and coated with Opadry White 20A28380 (supplied by Colorcon Limited) as a dispersion. The processing parameters, such as inlet air temperature and inlet air volume, were adjusted to keep the minibead temperature between 40° C. and 42° C. until the required coating weight gain was reached. The resulting subcoated minibeads were dried for 5 minutes at 40° C. in the coater.

Composition of the Coated Minibead

A minibead with the composition shown in Table 8 below was produced by the above procedure. A minibead with an Opadry weight gain of 7.5% relative to the weight of the core is shown in Table 8. Table 9 shows the composition of a minibead coated with an Opadry weight gain of 5% relative to the weight of the core. Table 10 shows the composition of a minibead coated with an Opadry weight gain of 10% relative to the weight of the core.

TABLE 8

| Component | w/w % |
|---|---|
| Cyclosporin A | 11.3 |
| Miglyol 810 N | 5.8 |
| Transcutol HP | 17.0 |
| Capmul GMO-50 | 12.0 |
| SDS | 2.9 |
| Sorbitol | 4.6 |
| Gelatin | 39.4 |
| Opadry | 7.0 |

TABLE 9

| Component | w/w % |
|---|---|
| Cyclosporin A | 11.5 |
| Miglyol 810 N | 5.9 |
| Transcutol HP | 17.4 |
| Capmul GMO-50 | 12.3 |
| SDS | 3.1 |
| Sorbitol | 4.7 |
| Gelatin | 40.3 |
| Opadry | 4.8 |

TABLE 10

| Component | w/w % |
|---|---|
| Cyclosporin A | 11.0 |
| Miglyol 810 N | 5.6 |
| Transcutol HP | 16.7 |
| Capmul GMO-50 | 11.7 |
| SDS | 2.9 |
| Sorbitol | 4.5 |
| Gelatin | 38.5 |
| Opadry | 9.1 |

Example 4a

Preparation of a Minibead with a Second Coating of Ethylcellulose

A minibead coated with Opadry, the first coating (also referred to as a subcoat), was produced following the procedure in Example 3. The minibead produced by the procedure of Example 3 was then further coated with a second coating (also referred to as an overcoat) of Surelease® (an ethylcellulose dispersion).

The Surelease® overcoat was applied by the following procedure. Surelease® was slowly added to a stainless steel vessel and mixed to provide the required coating suspension of Surelease® for the overcoat. The resulting coating suspension was then applied onto the surface of the sub-coated minibeads using an analogous coating method to that described for the Opadry coating in Example 3 until the desired weight gain of Surelease® was reached. The over-coated minibeads were then dried in the coater for an hour at 40-45° C.

The minibead was coated with a 9.5% weight gain of Surelease®.

Minibeads with no Opadry coating may be produced by coating a minibead described in Example 2 with Surelease® as described above.

The minibead with a first and second coating has the composition shown in Table 11.

TABLE 11

| Component | w/w % |
|---|---|
| Cyclosporin A | 10.3 |
| Miglyol 810 N | 5.3 |
| Transcutol HP | 15.5 |
| Capmul GMO-50 | 10.9 |
| SDS | 2.7 |
| Sorbitol | 4.2 |
| Gelatin | 36.0 |
| Opadry | 6.4 |
| Surelease | 8.7 |

Similarly, the composition of minibeads coated with 5% Surelease and 7.5% Opadry are shown in Table 12 and the composition of minibeads coated with 20% Surelease and 7.5% Opadry are shown in Table 13.

TABLE 12

| Component | w/w % |
|---|---|
| Cyclosporin A | 10.7 |
| Miglyol 810 N | 5.5 |
| Transcutol HP | 16.2 |
| Capmul GMO-50 | 11.4 |
| SDS | 2.9 |
| Sorbitol | 4.4 |
| Gelatin | 37.5 |
| Opadry | 6.6 |
| Surelease | 4.8 |

TABLE 13

| Component | w/w % |
|---|---|
| Cyclosporin A | 9.4 |
| Miglyol 810 N | 4.8 |
| Transcutol HP | 14.2 |
| Capmul GMO-50 | 10.0 |
| SDS | 2.5 |
| Sorbitol | 3.8 |
| Gelatin | 32.8 |
| Opadry | 5.8 |
| Surelease | 16.7 |

Example 4b

Preparation of a Minibead with a Second Coating of Ethylcellulose/Pectin

A minibead coated with Opadry, the first coating (also referred to as a subcoat), was produced following the procedure in Example 3. The minibead produced by the procedure of Example 3 was then further coated with a second coating (also referred to as an overcoat) of a mixture of Surelease® (an ethylcellulose dispersion) and Pectin.

The Surelease®/pectin overcoat was applied by an analogous method to the Surelease coating of Example 4a. Pectin was added to purified water in a stainless steel vessel and mixed to obtain a solution. Surelease® was slowly added to the vessel whilst maintaining mixing to provide the required Pectin concentration in the Surelease® for the overcoat. The resulting coating suspension was then applied onto the surface of the sub-coated minibeads using an analogous coating method to that described for the Opadry coating in Example 3 until the desired weight gain of Surelease®/

Pectin was reached. The over-coated minibeads were then dried in the coater for an hour at 40-45° C.

The minibead was coated with a 9.5% weight gain of Surelease®/Pectin.

The minibead with a first and second coating has the composition shown in Table 14.

TABLE 14

| Component | w/w % |
|---|---|
| Cyclosporin A | 10.3 |
| Miglyol 810 N | 5.3 |
| Transcutol HP | 15.5 |
| Capmul GMO-50 | 10.9 |
| SDS | 2.7 |
| Sorbitol | 4.2 |
| Gelatin | 36.0 |
| Opadry | 6.4 |
| Surelease | 8.5 |
| Pectin | 0.2 |

Example 5

Crystallisation Experiments

Comparative Example 1

Three liquid compositions comprising Cremophore EL (also known as Kremophore EL), a polyethoxylated castor oil surfactant with an HLB value of greater than 10 were prepared. The three liquid compositions are different sublots from the same batch. Each of the liquid compositions has an oil phase comprising: cyclosporin A 26.3%, Transcutol HP 40%, Cremophor EL 22.5%, and Miglyol 810 11.2% (% amounts are of the oil phase); and an aqueous phase comprising: gelatin 17.1%, Sorbitol 2.0%, SDS 1.4%, and water 79.5% (% amounts are of the aqueous phase. The liquid composition was prepared by mixing the oil phase and aqueous phases in an oil phase to aqueous phase ratio of 1:7.

Example 5a

Three liquid compositions of Example 1a comprising Capmul GMO-50, replacing the Cremophore EL were prepared. The three liquid compositions are 3 sublots of the same batch. Capmul GMO-50 has an HLB value of 3.

Example 5b

A liquid composition of Example 1b comprising Capmul MCM was prepared Capmul MCM has an HLB value of 6-7.

Example 5c

A liquid composition of Example 1c comprising Maisine 35-1 was prepared. Maisine 35-1 has an HLB value of The crystallisation rate of the liquid compositions of Comparative Example 1, Example 5a, Example 5b and Example 5c were tested to determine the length of time for cyclosporin crystallisation to occur. Each of the liquid compositions was stirred at 250-350 rpm to form an emulsion. Samples of the three emulsions were taken at 30 minute intervals and viewed under a microscope at 50× or 100× magnification. The time when crystals appeared in the sample is shown in Table 15.

TABLE 15

| Example | Surfactant | HLB | Crystallization time (h) | Beads formation |
|---|---|---|---|---|
| 5a | Capmul GMO-50 | 3 | 2 | Yes |
| 5b | Capmul MCM | 5-6 | >7 | No |
| 5c | Maisine 35-1 | 4 | 3 | Yes |
| Comparative Ex. 1 | Cremophor EL | 14 | 0.5 | Yes |

FIG. 1 shows images of the three liquid compositions of Comparative Example 1 comprising Cremophore EL (also known as Kremophore EL), a polyethoxylated castor oil surfactant with an HLB value of greater than 10.

Figure 2:
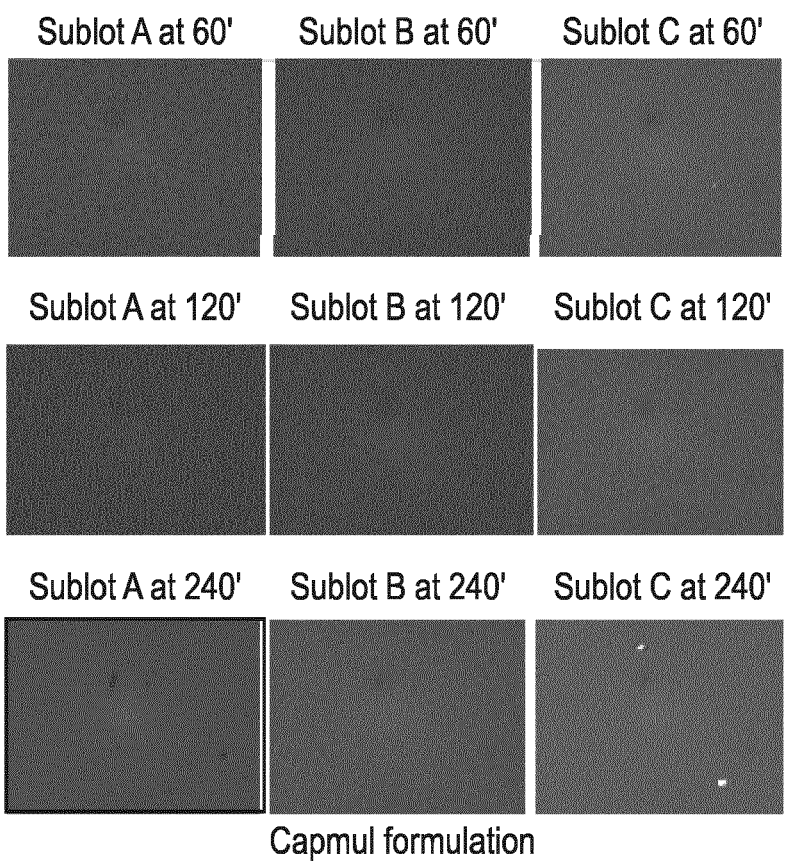
FIG. 2 is an image showing crystal formation over time of a composition of the invention comprising Capmul GMO-50 (glyceryl monooleate/dioleate) as the surfactant (the first surfactant).
Figure 3:
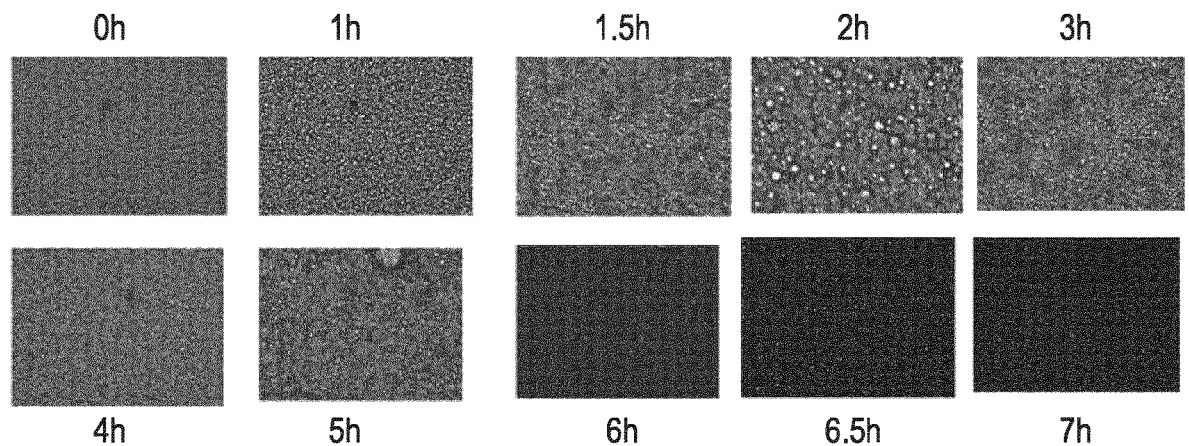
FIG. 3 is an image showing crystal formation over time of a composition of the invention comprising Capmul MCM (glyceryl caprylate/caprate) as the surfactant (the first surfactant).

FIG. 2 shows images of three liquid compositions of Example 5a comprising Capmul GMO-50 which is replacing the Cremophore EL. Capmul GMO-50 has an HLB value of 3. The three compositions comprising Capmul GMO-50 are FIG. 3 shows images of a liquid composition of Example 5b, comprising Capmul MCM.

Figure 4:
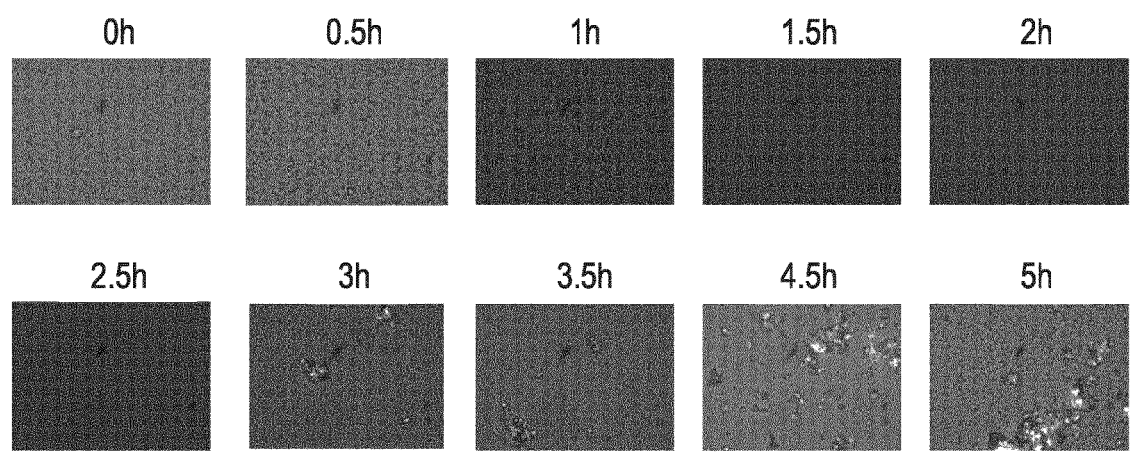
FIG. 4 is an image showing crystal formation over time of a composition of the invention comprising Maisine 35-1 (glycerol monolinoleate) as the surfactant (the first surfactant).

FIG. 4 shows images of a liquid composition of Example 5c comprising Maisine 35-1.

As is evident from the images the liquid compositions of Example 5a, 5b and 5c had a much longer period before crystals appeared. The Capmul GMO-50 and Capmul MCM compositions were essentially free of crystal formation throughout the test period. The Capmul GMO-50 compositions were essentially free of crystal up to 240 min, whereas the Cremophore EL compositions had noticeable crystal formation after 120 min. The Capmul MCM compositions were crystal free for 7 hours. The Maisine 35-1 composition had crystal formation at 3 hours.

Example 6

In-Vitro Dissolution Profile of Minibeads of Example 2

Figure 5:
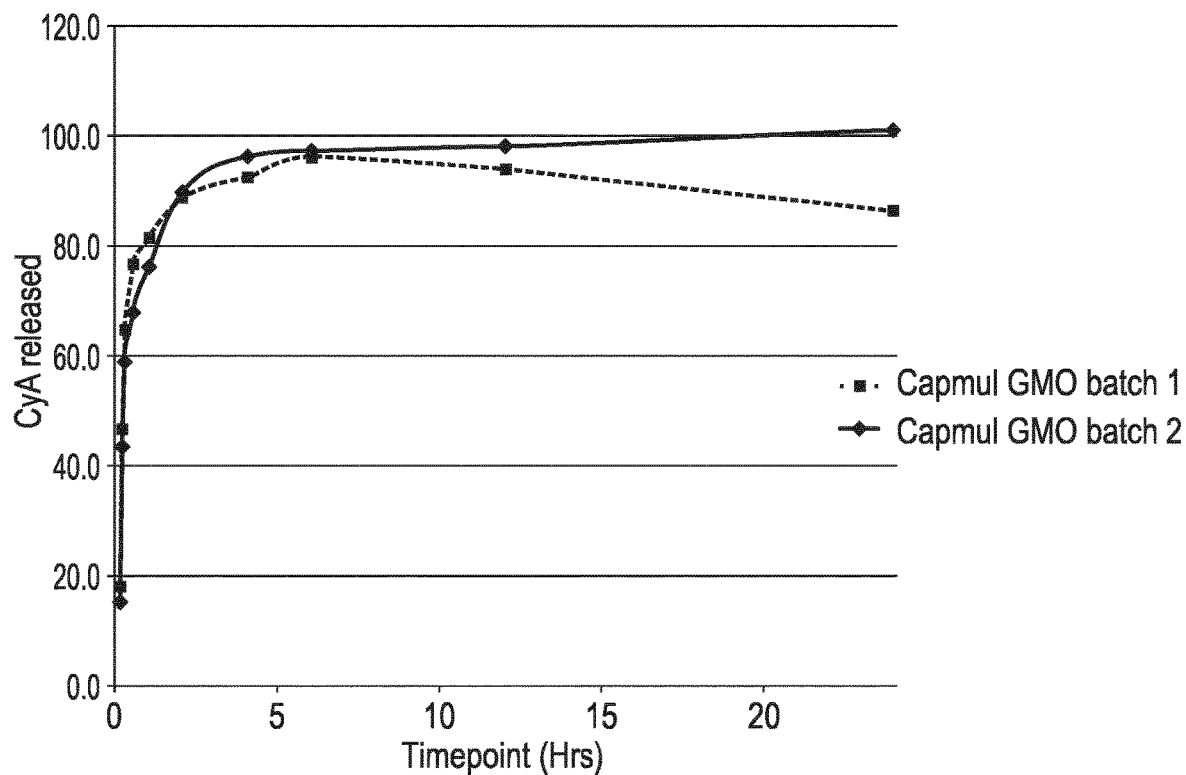
FIG. 5 is a graph plotting % of cyclosporin released against time over 24 hours and showing the release profiles of minibeads of Example 2.

The in-vitro dissolution profiles of a sample of the minibeads produced in Example 2 were measured using the following dissolution test. The dissolution testing was carried out in accordance with USP <711> Dissolution using Apparatus II (paddle apparatus) operated with a paddle speed of 75 rpm and with the dissolution medium at a temperature of 37° C.±0.5° C. The dissolution medium was deionised water. The sample of minibeads were placed in the dissolution medium and at the start of the test (t=0). The dissolution medium was sampled at regular intervals. The obtained dissolution data is shown in the Table 16 and Table 17 below. The dissolution profile for two batches of the minibead of Example 2 is shown in FIG. 5.

TABLE 16

| Timepoint (Hrs) | ESN-740 Pot 1 | ESN-740 Pot 2 | ESN-740 Pot 3 | ESN-740 Pot 4 | ESN-740 Pot 5 | ESN-740 Pot 6 | % RSD |
|---|---|---|---|---|---|---|---|
| 0.08 | 18.7 | 21.7 | 18.3 | 19.7 | 16.5 | 15.4 | 12.2 |
| 0.17 | 49.3 | 51.6 | 49.1 | 49.9 | 45.2 | 36.6 | 11.7 |

TABLE 16-continued

| Timepoint (Hrs) | ESN-740 Pot 1 | ESN-740 Pot 2 | ESN-740 Pot 3 | ESN-740 Pot 4 | ESN-740 Pot 5 | ESN-740 Pot 6 | % RSD |
|---|---|---|---|---|---|---|---|
| 0.25 | 67.0 | 67.0 | 72.6 | 67.4 | 64.2 | 54.0 | 9.5 |
| 0.5 | 76.4 | 77.1 | 79.0 | 76.2 | 89.5 | 63.7 | 10.7 |
| 1 | 81.5 | 82.6 | 84.0 | 85.5 | 77.7 | 77.2 | 4.1 |
| 2 | 92.1 | 90.5 | 87.2 | 95.4 | 82.4 | 87.9 | 5.0 |
| 4 | 101.5 | 95.7 | 85.5 | 97.4 | 82.6 | 93.2 | 7.8 |
| 6 | 99.5 | 97.1 | 91.2 | 98.7 | 96.2 | 94.8 | 3.1 |
| 12 | 98.7 | 94.8 | 94.8 | 90.2 | 91.9 | 95.5 | 3.1 |
| 24 | 100.5 | 99.1 | 52.3 | 85.3 | 93.1 | 88.0 | 20.5 |

TABLE 17

| Timepoint (Hrs) | ESN-760 Pot 1 | ESN-760 Pot 2 | ESN-760 Pot 3 | ESN-760 Pot 4 | ESN-760 Pot 5 | ESN-760 Pot 6 | % RSD |
|---|---|---|---|---|---|---|---|
| 0.08 | 16.1 | 15.5 | 18.2 | 20.2 | 17.5 | 6.4 | 30.8 |
| 0.17 | 47.6 | 44.2 | 52.3 | 51.4 | 44.2 | 24.2 | 23.4 |
| 0.25 | 65.6 | 61.7 | 68.7 | 69.6 | 57.3 | 34.6 | 21.9 |
| 0.5 | 75.7 | 71.2 | 75.2 | 75.9 | 68.0 | 45.7 | 17.0 |
| 1 | 78.9 | 78.0 | 79.0 | 84.8 | 76.4 | 61.6 | 10.2 |
| 2 | 94.6 | 90.7 | 97.9 | 97.9 | 90.7 | 68.9 | 12.1 |
| 4 | 102.7 | 97.5 | 98.2 | 101.0 | 97.9 | 82.3 | 7.6 |
| 6 | 102.2 | 99.1 | 97.5 | 102.1 | 101.0 | 84.0 | 7.1 |
| 12 | 104.5 | 99.1 | 100.0 | 94.9 | 99.5 | 94.9 | 3.6 |
| 24 | 102.0 | 100.2 | 101.0 | 100.0 | 102.7 | 101.2 | 1.0 |

Comparative Example 2

Figure 6:
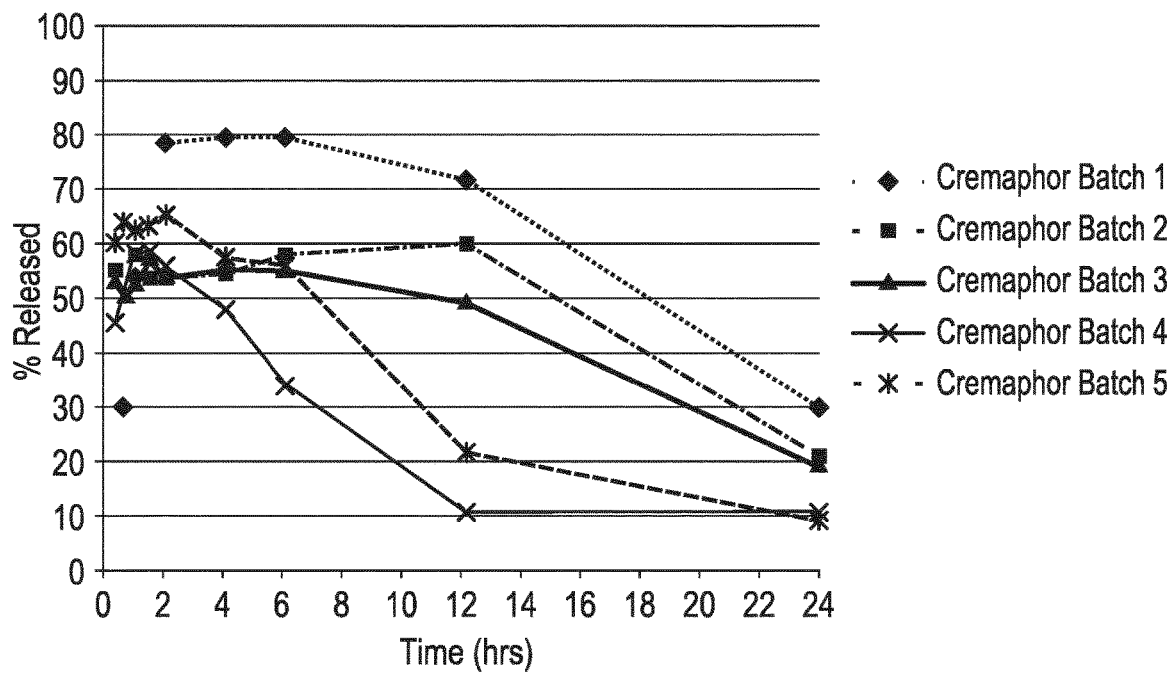
FIG. 6 is a graph plotting % of cyclosporin released against time over 24 hours and showing the release profiles of minibeads of Comparative Example 1.

Minibeads corresponding to those of Example 2 were prepared with Cremophore EL as the surfactant in place of Capmul GMO-50. These minibeads had the composition shown in Table 18. These minibeads were submitted to the same dissolution test in deionised water. The dissolution profile of 5 batches of these minibeads is shown in FIG. 6.

TABLE 18

| Component | w/w % |
|---|---|
| Cyclosporin A | 10.8 |
| Miglyol 810 N | 4.6 |
| Transcutol HP | 16.4 |
| Cremophor EL | 9.2 |
| SDS | 4.0 |
| Sorbitol | 5.8 |
| Gelatin | 49.2 |

Example 6a

As a further comparison with Comparative Example 2, minibeads were prepared using almost identical quantities of each excipient to those of Comparative Example 2, except that the 9.2 w/w % Cremophor was replaced with 9.3% Capmul GMO-50 to give the minibead composition shown in Table 19. The minibeads of Table 19 were prepared in an analogous manner to those of Example 2. The w/w % in Tables 18 and 19 refer to the dry weight of the composition.

TABLE 19

| Component | w/w % |
|---|---|
| Cyclosporin A | 10.9 |
| Miglyol 810 N | 4.6 |

TABLE 19-continued

| Component | w/w % |
|---|---|
| Transcutol HP | 16.6 |
| Capmul GMO-50 | 9.3 |
| SDS | 4.0 |
| Sorbitol | 5.7 |
| Gelatin | 49.0 |
| Cyclosporin A | 10.8 |

These minibeads were submitted to the same dissolution test in deionised water. The dissolution profile of 3 batches of these minibeads is shown in FIG. 7.

Figure 7:
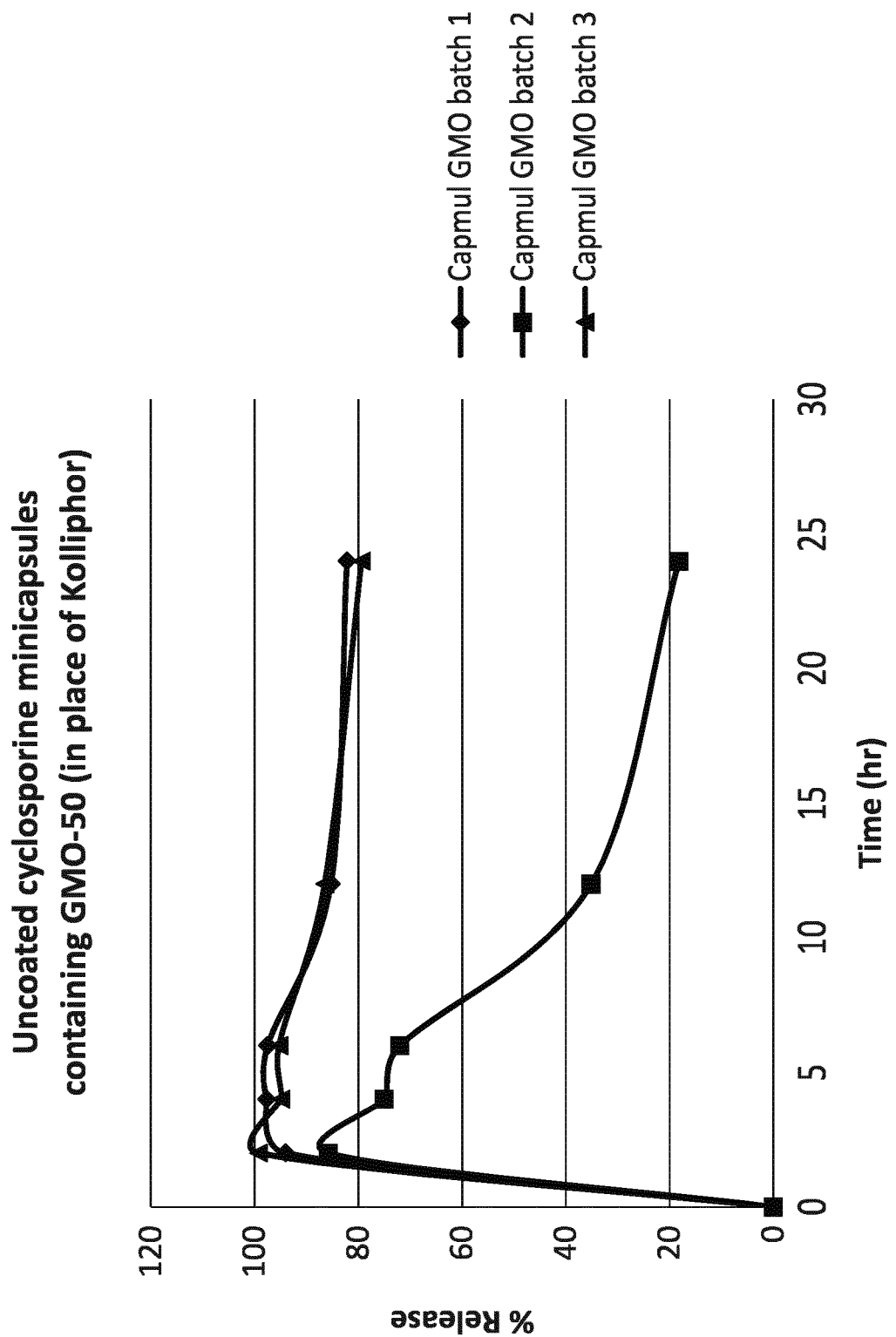

It is apparent from the dissolution profiles shown in FIGS. 5, 6 and 7 that compositions comprising Capmul GMO-50 (FIGS. 5 and 7) have superior dissolution profiles compared to compositions comprising Cremophor EL (FIG. 6). The dissolution profile of the Capmul GMO-50 compositions have a higher maximum release and this maximum release of cyclosporin is generally maintained in solution for longer than that observes with Comparative Example 2, which contained Cremophor. FIG. 6 shows that the % release of cyclosporin from the Cremophor EL compositions is lower and that the cyclosporin concentration reduces over time from a maximum compared to the compositions containing Capmul GMO-50.

Example 7

In-Vitro Dissolution Profile of Minibeads of Example 4a

Minibeads corresponding to those of Example 4a, specifically minibeads with the composition shown in Table 11 (7.5% Opadry subcoat, first coating and 9.5% Surelease overcoat, second coating) were prepared, having Capmul GMO-50 as the surfactant. These minibeads were submitted to a 2 stage dissolution test.

In the first stage of the test the dissolution medium was 750 ml of 0.1N HCl simulating the pH of the gastric environment. At the start of the test (t=0) the sample was placed in the dissolution medium. After 2 hours an aliquot of the medium is taken for subsequent analysis and immediately (suitably within 5 minutes) the second stage of the dissolution test is initiated. In the second stage 250 ml of 0.2M tribasic sodium phosphate containing 2% sodium dodecyl sulphate (SDS) is added to the dissolution medium and the pH adjusted to 6.8±0.05 using 2N NaOH or 2N HCl as required.

Samples of the dissolution medium were taken at the following time points during the second stage of the test: 4 hours; 6 hours; 12 hours; and 24 hours from the start of the test (i.e. from t=0 at the start of the first stage).

The sample taken at the end of the first stage (2 hours) and the samples from the second stage were analysed for cyclosporin A using Reverse Phase HPLC with UV detection at 210 nm.

Figure 8:
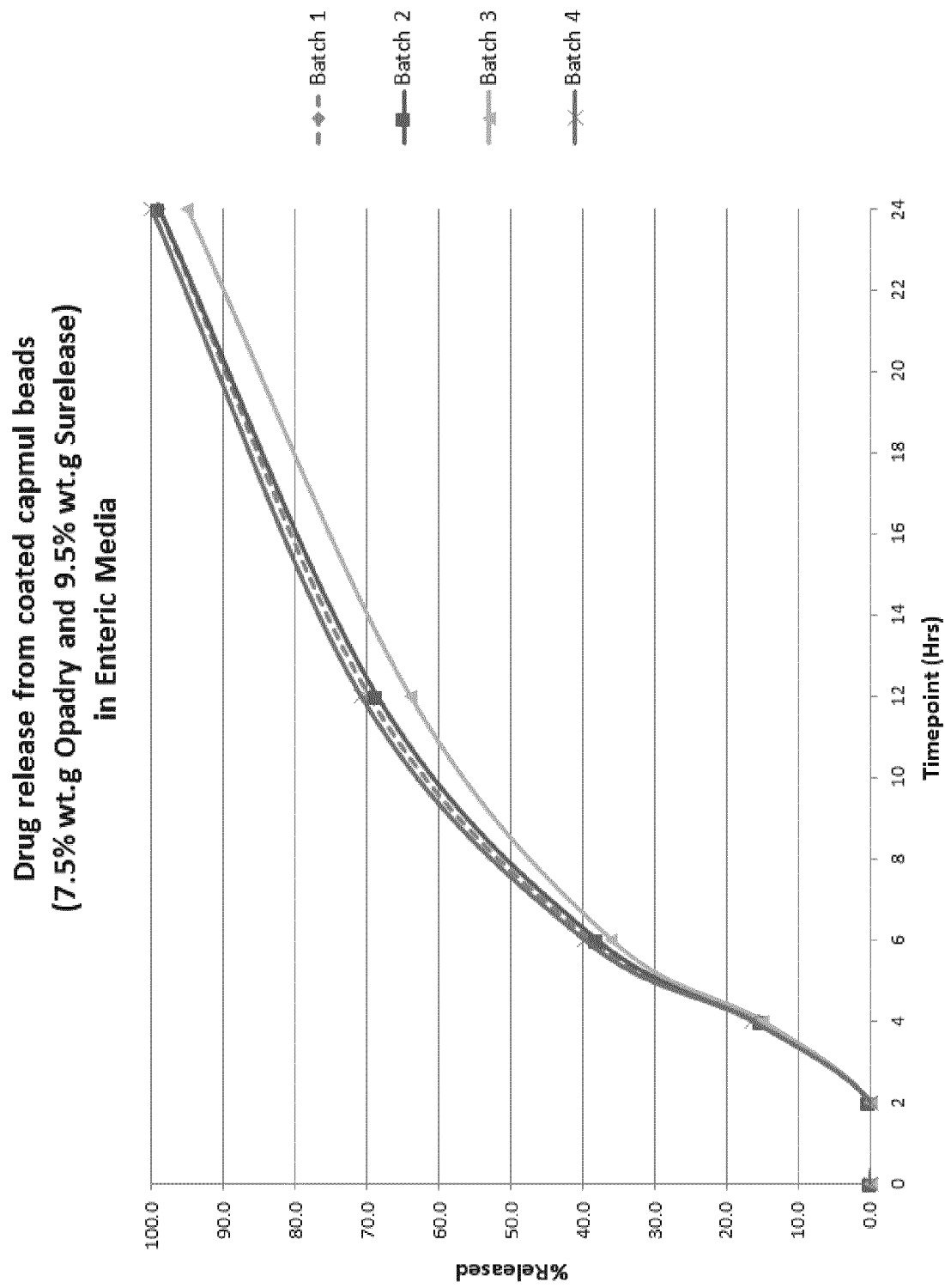
FIG. 8 is a graph plotting % of cyclosporin released against time over 24 hours in the two-stage dissolution test showing the release profiles of beads of Example 4a, specifically those of Table 11.

The amount of dissolved cyclosporin A in the dissolution medium is expressed as a percentage based upon the original cyclosporin content in the test formulation (the % released). The percentage release is given in Table 21 and the dissolution profile of minibeads with the composition shown in Table 11 is shown in FIG. 8.

TABLE 21

| Timepoint | % Drug release | | | |
| --- | --- | --- | --- | --- |
| (hours) | Batch 1 | Batch 2 | Batch 3 | Batch 4 |
| 0 | 0 | 0 | 0 | 0 |
| 2 | 0 | 0 | 0 | 0 |
| 4 | 15 | 15 | 15 | 17 |
| 6 | 39 | 38 | 36 | 40 |
| 12 | 70 | 69 | 64 | 71 |
| 24 | 99 | 99 | 95 | 100 |

Example 8

Droplet Size—Dynamic Light Scattering

The size of the droplets was measured using dynamic light scattering. Coated minibeads of Example 4a, Table 11 (minibeads coated with 7.5% wt gain Opadry and 9.5% wt gain Surelease) (0.5 g) comprising Capmul GMO-50 as the first surfactant were added to a beaker containing 50 g of deionised water. The beaker contents were mixed at 250 rpm throughout the study. Samples of the beaker contents were taken at 0, 1, 2, 3, 4, 5, 6 and 24 hours.

Figure 9:
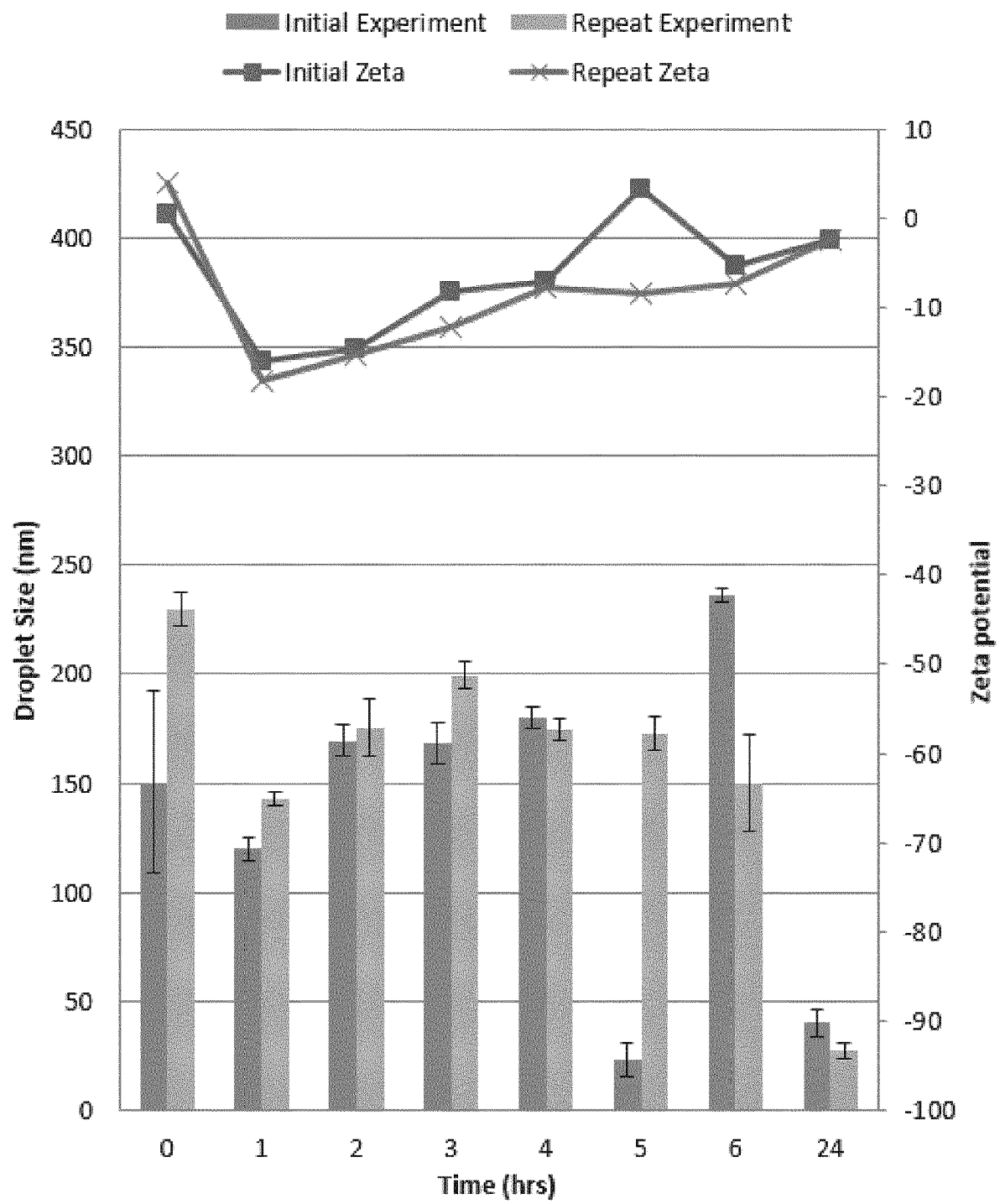
FIG. 9 is a graph showing the droplet size and zeta potential of a coated composition of the invention when the composition has been dissolved in deionised water.

Samples of the beaker contents were filtered using 0.65 μm pore size filters (Merck Millipore Ultrafree-CL Centrifugal Filter). The particle size and zeta potential of each sample was measured and analysed using a Malvern Nano-Zetasiser. The resulting data is shown in FIG. 9.

The coated minibeads tested in this example exhibit very stable droplet release for up to 4 hours with droplet size ranging from 120 to 240 nm in water media. As time passes and further droplets are released from the coated minibeads after 4 hours the droplet size range is broader. Without wishing to be bound by theory, it is possible that as time passes and the dissolution media becomes more saturated with released droplets a re-equilibration between the droplets already present in the media and the ones freshly released may occur. The variability in droplet size after 4 hours is potentially caused by this re-equilibration process rather than a representation of the size of the droplets being released from the minibeads.

Example 9

In-Vivo Study in Healthy Male Volunteers

In the study described below "CyCol®" is a reference to the minibeads of Example 4a, and described in Table 11 (comprising a core with Capmul GMO-50 as the surfactant, a 7.5% weight gain Opadry® first coating on the core, and a 9.5% weight gain of a Surelease® second coating). The minibeads were loaded into HPMC capsules to provide a unit dose of 37.5 mg cyclosporin A per capsule.

| LIST OF ABBREVIATIONS AND DEFINITION OF TERMS | |
| --- | --- |
| Abbreviation | Definition |
| $AUC_{\%extrap}$ | Residual area/Percentage of $AUC_{0-inf}$ extrapolated |
| $AUC_{0-inf}$ | Area under the concentration-time curve from time zero to infinity (extrapolated) |
| $AUC_{0-t}$ | Area under the concentration-time curve from time zero to the last non-zero concentration |
| $AUC_{last}$ | Area under the concentration-time curve from time zero to last quantifiable concentration |
| $C_{av}$ | Average steady state concentration |
| CYP | Cytochrome P-450 |
| $k_{el}$ | Elimination rate constant |
| LLQ | Lower limit of quantification |
| LR | Linearity ratio |
| SD | Standard deviation |
| $t_{1/2}$ | Terminal half-life |
| UC | Ulcerative colitis |

Study Objectives
Primary Objectives:
  To characterise whole blood pharmacokinetics of CyCol® following single and multiple oral doses, and compare to a single Sandimmun® IV administration pharmacokinetic profile in healthy male subjects.
  To evaluate the colonic mucosa (epithelial, mucosal and sub-mucosal tissue) concentrations of cyclosporin and its metabolites following multiple oral doses of CyCol® and compare to concentrations following a single Sandimmun® IV administration.
Secondary Objectives:
  To obtain safety and tolerability information following multiple oral doses of CyCol® at the selected doses in healthy male subjects.
Exploratory Objectives:
  To evaluate the amount of unchanged cyclosporin and its metabolites excreted in the faeces after administration of multiple doses of CyCol® and compare to amounts following a single Sandimmun® IV administration.
Investigational Plan
Overall Study Design and Plan—Description
  This was a Phase I, single centre, multi-stage open study designed to evaluate the safety, tolerability, pharmacokinetics and relative colonic mucosal concentrations of cyclosporin capsules (CyCol®) compared to IV cyclosporin in healthy male volunteers. This study also investigated the amount of unchanged cyclosporin recovered from faecal samples and relative concentrations of its metabolites AM9, AM4N and AM1. The concentrations of cyclosporin metabolites were also examined in faecal and colonic mucosa samples.

In Stage 1 of the study, a total of 24 eligible subjects received either Sandimmun® IV over 24 hours (two consecutive 12 hour infusions) at a dose of 2 mg/kg (2 mg/kg/day), a once daily oral dose of CyCol® 75 mg for 7 days or a twice daily (BID) oral dose of CyCol® 75 mg for 7 days. Subjects who received CyCol® 75 mg BID only received a single dose on Day 7 (morning dose).

At the end of Stage 1 the data were reviewed and based on the evidence available, the protocol allowed for further investigations to be conducted with alternative CyCol® doses and dose frequencies in subsequent stages. Following this review, 8 subjects were recruited to Stage 2 of the study and received a once daily oral dose of CyCol® 37.5 mg for 7 days. A further 8 subjects were recruited to Stage 3 and received a BID oral dose of CyCol® 150 mg for 7 days.

Figure 10:
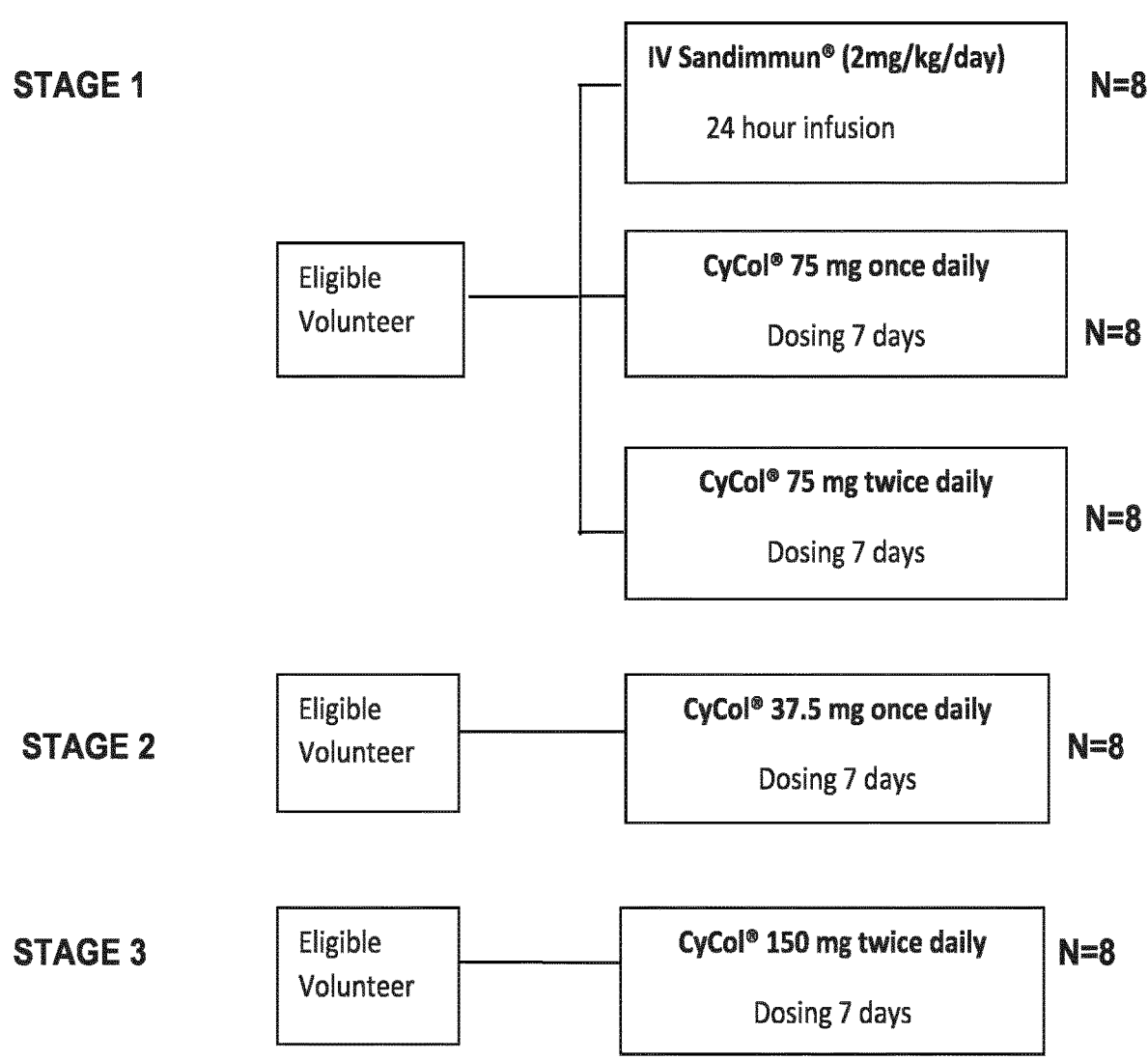
FIG. 10 shows the dosing schedule used in the clinical trial described in Example 9.

Details of the dosing sequence are presented in FIG. 10.

Study Design, Including Choice of Control Groups

A multi stage design was used for this study to reduce the number of dose levels investigated and the number of subjects exposed to cyclosporin and study procedures. The dosing regimens chosen for Stages 2 and 3 were chosen following review of data (safety and tolerability, systemic exposure and colonic mucosa tissue concentrations) observed at other doses.

The study was open-label because of the different mode of administration of the comparator product (IV versus oral for investigational medicinal product), and the objective endpoints of the study (cyclosporin concentrations). The single dose pharmacokinetic profile was examined over a 24 hour period, based on previous experience that demonstrated this duration adequately characterised the concentration-time profile.

The study recruited healthy male volunteers. Females were not included in this study as the Food and Drug Administration pregnancy category for cyclosporin is C.

The comparator chosen for this study was Sandimmun®. The current treatment regimen for UC can often involve the use of several agents administered rectally, orally or intravenously depending on the severity of the disease. Cyclosporin is unlicensed for UC. However, according to the 2013 National Institute for health and Clinical Excellence guidelines for UC, it is recommended that treatment with IV cyclosporin should be considered for subjects with acute severe colitis and not responding to or unsuitable for first line therapy with corticosteroids. An IV dose of 2 to 4 mg/kg/day or an oral dose of 5 to 8 mg/kg/day is recommended for severe ulcerative colitis treatment. The rationale for choosing IV administration of cyclosporin over the oral formulation is based on studies documenting variable absorption and the extensive first pass metabolism following oral ingestion. In addition, an IV dose of 2 to 4 mg/kg/day is known to be efficacious in the treatment of patients with UC and to attain the same concentrations using a currently available oral dose form, approximately 3 times the IV dose would be required. Furthermore, when cyclosporin is administered by IV infusion blood concentrations are constant and metabolites are present in lower concentrations compared to oral administration. CyCol® has been developed to delay the release of active cyclosporin until it reaches the colon, it thereby bypasses the site of absorption in the jejunum and thus limits the amount of metabolism (both pre-systemic metabolism in the gastrointestinal tract and systemic metabolism by the hepatic system) by cytochrome P450 enzymes, including the CYP3A4 enzyme. Therefore, the concentration of metabolites following CyCol® administration is expected to be similar to IV cyclosporin. Furthermore, colon tissue concentrations of cyclosporin are 10 times higher in healthy volunteers given cyclosporin parentally compared to those of healthy volunteers given the drug orally.

Treatments

Treatments Administered

Subjects who met all the eligibility criteria for Stage 1 of the protocol were assigned to one of the following dose groups on Day 1:

Sandimmun® 2 mg/kg IV infusion over 24 hours (2 mg/kg/day).

CyCol® 75 mg (2×37.5 mg CyCol® capsules) once daily orally for 7 days.

CyCol® 75 mg (2×37.5 mg CyCol® capsules) BID orally for 7 days (only a single [morning] dose was administered on Day 7).

Following review of the Stage 1 data, the following CyCol® dosing regimen was explored in Stage 2:

CyCol® 37.5 mg (1×37.5 mg CyCol® capsule) once daily orally for 7 days.

Following review of the data from Stages 1 and 2, the following CyCol® dosing regimen was explored in Stage 3:

CyCol® 150 mg (4×37.5 mg CyCol® capsule) BID orally for 7 days (only a single [morning] dose was administered on Day 7).

The dosing regimens chosen for Stages 2 and 3 were based upon safety and tolerability, systemic exposure and colonic tissue concentrations observed at other doses. To investigate higher doses the lower doses had to have been well tolerated and had to have maximum systemic exposure 250 ng/ml. Providing these criteria were met, doses could have been escalated higher in search of a regimen that yielded colonic tissue concentrations >300 ng/ml.

Identity of Investigational Products

Sandimmun® was provided in commercial packaging of 1 mL ampoules containing 50 mg of cyclosporin. The 1 mL ampoules of Sandimmun® were diluted with normal saline in accordance with the Summary of Product Characteristics (SmPC) and prepared suitably for the two consecutive 12 hour infusions. Each infusion was prepared such that the total dose administered was 2 mg/kg/day.

Methods of Assigning Subjects to Treatment Groups

In Stage 1, subjects were assigned sequentially to study treatment (Sandimmun® IV, CyCol® 75 mg once daily or CyCol® 75 mg BID).

All subjects recruited to Stage 2 received CyCol® 37.5 mg once daily orally for 7 days and all subjects recruited to Stage 3 received CyCol® 150 mg BID orally for 7 days.

Selection and Timing of Dose for each Subject

Sandimmun®

On the morning of Day 1, following an overnight fast, subjects started their IV infusion via an IV catheter. Sandimmun® IV was administered over 24 hours, as two consecutive 12 hour infusions, at a dose of 2 mg/kg/day according to preparation and administration detailed in the Sandimmun® SmPC.

CyCol®

On the morning of Day 1, following an overnight fast, subjects assigned to the CyCol® groups were administered the morning dose with approximately 240 mL of water. A hand and mouth check was performed to ensure ingestion of the study drug. Time of dosing was set to the time the first capsule was administered.

On Day 2, prior to discharge from the study centre, subjects received the morning dose with approximately 240 mL of water. For those subjects assigned to the BID dosing regimen, the pharmacy dispensed the evening dose to the subject with instructions to take the study drug as prescribed and within 10 to 12 hours following the morning dose.

Subjects returned to the study centre daily to receive the morning dose of CyCol® until Day 6 when the subjects were readmitted for an overnight stay. For those subjects assigned to the BID dosing regimen, at each daily visit to the study centre, the pharmacy dispensed the evening dose to subjects with instructions for the evening dose administration.

If the subject was expected to return to the study centre on Day 6 after the scheduled time of the Day 6 morning dose, the pharmacy could have dispensed the Day 6 morning dose to the subject upon discharge from the study centre on Day 5, with instructions for the morning dose administration.

The last dose of CyCol® administration was on the morning of Day 7 for all subjects.

Blinding: This was an open label study.

Pharmacokinetic assessments—Whole Blood

Blood samples for pharmacokinetic analysis were collected from all subjects on Day 1 at 0 (pre dose), 2, 3, 4, 5, 6, 8, 10, 12, 16, 20 and 24 hours post-dose (post start of infusion for the Sandimmun® IV group).

For subjects in the Sandimmun® IV group blood samples were also collected at 2, 4, 6 and 8 hours after completion of the infusion on Day 2.

For subjects in the CyCol® groups trough pharmacokinetic samples were obtained pre morning dose on Day 4. For subjects who received CyCol® once daily additional pharmacokinetic samples were obtained at 6, 12 and 16 hours post morning dose on Day 6. For subjects who received CyCol® BID additional pharmacokinetic samples were obtained at 6 and 12 hours post morning dose (prior to evening dose) on Day 6, and 4 hours post evening dose. On Day 7, all subjects in the CyCol® groups had blood samples for pharmacokinetics obtained at 0 (pre dose), 2, 4, 6 8, and 12 hours post-dose. Actual sampling times were used for statistical analyses and so each time was recorded accurately.

Flexible Sigmoidoscopy and Colon Biopsies

All sigmoidoscopies were performed in an unprepared bowel (except for air and water), unless the subject had not defaecated within 24 hours of sigmoidoscopy.

Subjects who received Sandimmun® IV were required to have the sigmoidoscopy performed within the last hour of their infusion (infusion had to be on-going).

Subjects who received CyCol® were required to have the sigmoidoscopy performed within 4 to 6 hours of the Day 7 morning/last dose.

The sigmoidoscopy was conducted by an appropriately trained endoscopist who was familiar with the study protocol and obtaining biopsies. Per protocol, whenever possible, the same endoscopist was to perform all the sigmoidoscopies. In this study two endoscopists performed the sigmoidoscopies.

For subjects who had not defaecated within 24 hours of the sigmoidoscopy, a rectal enema (Fleet saline, or similar) was administered 15 minutes before the scheduled biopsy time and the time and volume of enema administration was recorded. The time and total weight of the voided gut contents post enema were recorded. A representative sample (approximately 5 g) was obtained from the voided gut for processing as described herein.

The colon biopsies were collected (as described below) as soon as possible and ideally within 10 minutes of the enema being voided.

Standard pinch biopsy forceps were used to obtain the colonic mucosa biopsies. Each biopsy was approximately 5 mm in size (and included mucosa and submucosa layers). A total of 5 biopsies, approximately 1 cm apart were obtained from as close to the sigmoid colon as possible. The time of the biopsy collection and distance from the anal verge to the region where biopsies were obtained were recorded in the CRF.

In the event that access to the sigmoid colon was limited, the 5 biopsies could have been obtained from the rectum.

Each biopsy was rinsed with saline, blot dried and then transferred to a pre-weighed collection tube. The tube was weighed to enable determination of the biopsy weight. The biopsy, without any further preparation or processing was transferred to a cryovial and stored at −70° C. and transported to the bioanalytical laboratory on dry ice.

Concentrations of cyclosporin and its metabolites in the mucosal tissue were assessed by a bioanalytical laboratory. Analysis of the tissue samples was carried out as described below under "Colonic Tissue Analysis"

Faecal Sample Collection

Subjects were recommended to defaecate upon admission to the study centre on Day 0. This sample was collected and one aliquot was collected as a blank matrix.

From Day 0 through to completion of the study, subjects were requested to collect their faeces. For subjects who received Sandimmun® IV, samples collected during the infusion were kept separate from those collected after completion of the infusion.

The time and date of each sample were recorded. Each sample was collected and weighed. Faecal samples were homogenised as soon as possible following collection.

Subjects who produced faecal samples as an outpatient were instructed to collect the samples in the appropriate containers and store the samples at room temperature until return to the study centre.

After homogenisation one aliquot of approximately 5 g was collected from each sample and frozen at −70° C. (with no additives).

The three intracolonic samples (approximately 500 mg to 1 g), if available, were collected and stored in individual containers without any additives at −70° C.

For subjects who were administered a rectal enema, the time and total weight of the voided gut contents post enema were recorded. A representative sample (approximately 5 g) was obtained from the voided gut and transferred to a container without any additives or additional processing.

All samples were stored at −70° C. and transported to a bioanalytical laboratory on dry ice.

Drug Concentration Measurements

Blood samples were collected as described herein for determination of cyclosporin concentrations. The amount of unchanged cyclosporin and relative concentrations of its metabolites (AM9, AM4N and AM1) in faeces were also assessed using faecal samples collected as described herein.

Primary Endpoints

Whole Blood Pharmacokinetics

The following single dose pharmacokinetic parameters were derived after dosing on Day 1 for both the Sandimmun® IV and CyCol® groups using standard non-compartmental methods:

$C_{max}$: maximum observed concentration $T_{max}$: time of observed $C_{max}$ $AUC_{0-t}$: area under the concentration-time curve from time zero to the last non-zero concentration, determined using the linear/log trapezoidal method $AUC_{0-inf}$: area under the concentration-time curve from time zero to infinity (extrapolated) determined by $AUC_{0-t}+(C_{last}/k_{el})$, where $C_{last}$ is the predicted concentration at the last quantifiable time point estimated from the log-linear regression analysis.

$t_{1/2}$: elimination half-life calculated as $\log_e(2)/k_{el}$ $k_{el}$: elimination rate constant (derived to calculate $AUC_{0-inf}$), determined by a linear regression of the log-linear concentration-time curve. Only those data points judged to describe the terminal log-linear decline were used in the regression Residual area (% extrapolated; $AUC_{\%\ extrap}$): calculated as $100*(1-AUC_{0-t}/AUC_{0-inf})$ and derived to quantify the area extrapolated to infinity $AUC_{0-T}$: area under the concentration-time curve over the dosing interval (derived to calculate the accumulation ratio discussed below).

The following steady state parameters were derived for the CyCol® groups:

$C_{max}$, $T_{max}$, $AUC_{0-T}$ and average steady state concentration ($C_{av}$)

Additionally the accumulation ratio was derived to estimate the accumulation over the dosing interval from single dose to steady state.

$$AC = AUC_{0-T}(\text{steady state})/AUC_{0-T}(\text{single dose})$$

The linearity ratio (LR) was derived to estimate the relative exposure per dose with steady state compared to a single dose.

$$LR = AUC_{0-T}(\text{steady state})/AUC_{inf}(\text{single dose})$$

For the Sandimmune IV group simulations to steady state were conducted by the clinical pharmacokineticist to predict the concentration time profile and estimate $C_{max}$, $T_{max}$ and $AUC_{0-T}$ T for the group (i.e., group values, not individual values).

To determine the steady state CyCol® parameters both the Day 6 and Day 7 concentrations were used as summarised below.

| Time post-dose | Days used for once daily | Days used for BID |
|---|---|---|
| 0 | 7 | 7 |
| 2 | 7 | 7 |
| 4 | 7 | 6, 7 |
| 6 | 6, 7 | 6, 7 |
| 8 | 7 | 7 |
| 12 | 6, 7 | 6, 7 |
| 16 | 6 | NA |
| 24 | Day 7 pre-dose | NA |

Actual sampling times were used in the derivation of parameters.

Cyclosporin concentrations were listed and summarised by group, day and nominal time post-dose.

Individual subject and median profiles of the concentration-time data (by day and by group) were plotted by dose group using actual and nominal times respectively. Median profiles were plotted on both linear-linear and log-linear.

Each pharmacokinetic parameter was summarised by group and by day. For the single dose, pharmacokinetic parameters, the Day 1 parameters were summarised combining the once daily and BID groups using the same dose.

To assess the relationship between the pharmacokinetic parameters and dose, dose normalised $AUC_{0-inf}$, $AUC_{last}$ and $C_{max}$ were plotted against dose for Day 1 and dose normalised $C_{av}$ and $C_{max}$ were plotted against dose for Day 7 (using a logarithmic scale). These plots included individual subject values and the geometric means for each dose. The values were dose normalised (to a 1 mg dose) by dividing the individual values and raw geometric means by dose.

Colonic Mucosal Tissue and Mucous Layer Pharmacokinetics

Concentrations of cyclosporin and its metabolites (AM9, AM4N and AM1) in both the colonic mucosal tissue and mucous layer were determined. For the Sandimmun® IV group simulations were conducted by the clinical pharmacokineticist to estimate the steady state concentrations.

Concentrations of cyclosporin and its metabolites (AM9, AM4N and AM1) were listed. Concentrations were also plotted against distance from the anal verge.

The concentration of cyclosporin in the colonic tissue was measured as follows.

Colonic Tissue Analysis

Concentrations of cyclosporin and its metabolites (AM1, AM9 and AM4N) in colonic tissue was determined using the following protocol:

Principle

Liquid-liquid extraction with internal standardisation and HPLC separation using a C18-column, followed by MS/MS detection.

Internal Standard—D12—Cyclosporin A

Sample Matrix—Human Tissue

Calibration standards and quality control samples are prepared in 50% EtOH.

Solutions

The IS stock solution and respective dilutions are prepared by using DMSO/MeOH (1/1). The internal standard (IS) working solution is prepared by dilution of the IS stock solution or one of its dilutions with DMSO/MeOH (1/1), and should have a concentration of ~50 ng/mL Storing of Samples and Solutions Samples/solutions should be stored at −20° C. to −80° C.

Sample Handling and Sample Preparation for Analysis

| Step | Thawing/transfer procedure (step by step) |
|---|---|
| 1 | The following thawing procedures are possible: Thawing at approximately 20 to 25° C. in a water bath for approx. 10 minutes Thawing air exposed at approximately 20 to 25° C. for at least 30 minutes (depends on sample volume) |
| 2 | If applicable: Vortexing for 30 seconds |
| 3a | Cal. Stds. & QCs: Transfer of 1000 µL of each sample into a sample vial |
| 3b | Study sample: weight: approx.. 2-20 mg |
| 4 | Re-freezing of original samples between −20° C. and −80° C. Unless used for immediate preparation -> freezing of transferred samples between −20° C. and −80° C. |

Chromatographic and Auto-Sampler Parameters

| Parameter | Scheduled range/description | |
|---|---|---|
| Mobile phase solvent A | 10 mM Ammonium acetate in water | |
| Mobile phase solvent B | ACN/THF (8/2) | |
| Mobile phase solvent loading pump | 10 mM Ammonium acetate in water | |
| Chromatographic run | 0.0-4.5 min linear gradient: | 40% B → 52% B |
| | 4.5-6.0 min linear gradient: | 52% B → 85% B |
| | 6.0-6.01 min linear gradient: | 85% B → 0% B |
| | 6.01-7.0 min isocratic: | 0% B |

-continued

| Parameter | Scheduled range/description |
|---|---|
| Flow | 0.8 mL/min |
| Injection volume | 10 μL |
| Pre-column/Column | Luna C18, 4 × 2 mm/ACE3AQ; 100 × 2.1 mm, 3 μm (ACT, UK) |
| Column temperature | 80° C. |
| Parameter | Scheduled range/description |
| Cooling set point (T) | 25° C. |

Detection

| Parameter | Scheduled range/description |
|---|---|
| MS Ionisation mode | ESI |
| MS polarity | Positive |
| MS detection mode | MRM |
| Vaporizer temperature | 600° C. |
| Ionisation voltage | 5.5 kV |
| Gas 1 | Pressure = 75 psi |
| Gas 2 | Pressure = 75 psi |
| Curtain gas | pressure = 40 psi |
| Lateral position | 5 units ± 2 units (default) |
| Vertical position | 4 units ± 2 units (ESI default) |
| Quadrupole resolution | low → low |
| Transitions | 1203.0 ± 0.3 → 99.9 ± 0.3 m/z: Cyclosporin A (CE: 125 eV, CXP: 16 V) |
|  | 1215.0 ± 0.3 → 99.9 ± 0.3 m/z: D12-Cyclosporin A (CE: 125 eV, CXP: 16 V) |
|  | 1219.0 ± 0.3 → 224.0 ± 0.3 m/z: AM1 (CE: 65 eV, CXP: 15 V) |
|  | 1219.0 ± 0.3 → 99.9 ± 0.3 m/z: AM9 (CE: 125 eV, CXP: 16 V) |
|  | 1189.0 ± 0.3 → 224.0 ± 0.3 m/z: AM4N (CE: 65 eV, CXP: 15 V) |
| DP (declustering potential) | 130 V ± 20 V |

Acceptance Criteria for Chromatograms

| Parameter | | Scheduled range/ acceptance criteria/ description |
|---|---|---|
| AM1 | Retention time for SST | 4.2 min ± 0.5 min |
| AM4N | Retention time for SST | 5.4 min ± 0.5 min |
| AM9 | Retention time for SST | 4.4 min ± 0.5 min |

Calibration Standards and Quality Conrol Samples:
Preparation of Blank Samples and Processed Matrix:
Preparation as described below, but taking DMSO/MeOH (1/1) instead of IS working solution.

| Step | Preparation procedure (step by step) |
|---|---|
| I | [if not stored/available as 1000 μL aliquots already -> see transfer above] |
| II | [if frozen -> thawing at 20° C. to 25° C. in a water bath for approx.. 5 min] |
| 1 | Addition of 25 μL of internal standard working solution |
| 2 | Addition of 4 mL of DIPE |
| 3 | Conversion Point: Extraction by shaking the test tubes vigorously for approx. 5 minutes using a DVX-2500 Multi-tube Vortexer (1700 rpm; cycle: 5 seconds run, 1 second pause time) |
| 4 | Centrifugation (phase separation) at 4000 rpm for 2 minutes |
| 5 | Storage at −75° C. for about 10 minutes |
| 6 | Decanting of the organic, liquid phase into a centrifuge vial |
| 7 | Evaporation of the organic phase using compressed air (Turbovap) at about 40° C. for 14 minutes |
| 8 | Addition of 50 μL of 50% EtOH |
| 9 | Vortexing for approx. 2 minutes using a DVX-2500 Multi-tube Vortexer (2500 rpm; cycle: 5 seconds run, 1 second pause time) |
| 10 | Centrifugation at 4000 rpm for 1 minute |

Carry-Over Samples:
Transfer of approx. 100 μL 50% EtOH into appropriate auto-sampler vials
Matrix Samples (Human Tissue)—Part A:

| Step | Preparation procedure (step by step) |
|---|---|
| I | [if not stored/available as approx.. 2-20 mg aliquots already -> see transfer above] |
| II | [if frozen -> thawing at 20° C. to 25° C. in a water bath for approx.. 5 min] |
| 1 | Addition of 500 μL 2% N-Acetyl-L-Cysteine in water |
| 2 | Vortexing for approx. 10 min using a DVX-2500 Multi-tube Vortexer (1000 rpm) |
| 3 | Centrifugation (phase separation) at 13000 rpm for 2 minutes using biofuge pico |
| 4 | Decanting of the liquid phase into a sample vial (volume: approx. 10 mL) |
| 4a | Caution: The remaining residue will be prepared separately (described in part B) |
| 5 | Addition of 500 μL EtOH to the liquid phase |
| 9 | Addition of 25 μL of internal standard working solution |
| 10 | Addition of 4 mL of DIPE |
| 11 | Conversion Point: Extraction by shaking the test tubes vigorously for approx. 5 minutes using a DVX-2500 Multi-tube Vortexer (1700 rpm; cycle: 5 seconds run, 1 second pause time) |
| 12 | Centrifugation (phase separation) at 4000 rpm for 2 minutes |
| 13 | Storage at −75° C. for about 10 minutes |
| 14 | Decanting of the organic, liquid phase into a centrifuge vial |
| 15 | Evaporation of the organic phase using compressed air (Turbovap) at about 40° C. for 14 minutes |
| 16 | Addition of 50 μL of 50% EtOH |
| 17 | Vortexing for approx. 2 minutes using a DVX-2500 Multi-tube Vortexer (2500 rpm; cycle: 5 seconds run, 1 second pause time) |
| 18 | Centrifugation at 4000 rpm for 1 minute |

Matrix Samples (Human Tissue)—Part B (Samples are taken from Part A, Step 4a):

| Step | Preparation procedure (step by step) |
|---|---|
| 1 | Addition of 500 µL 50% EtOH to the remaining residue |
| 2 | Addition of 25 µL of internal standard working solution |
| 3 | Destroying of the tissue by using an ultrasonic processor (cycle: 0.5 s, max. amplitude) for 30 s |
| 4 | Decanting of the liquid phase into a sample vial (volume: approx. 10 mL) |
| 5 | Addition of 500 µL 50% EtOH to the remaining residue to the remaining residue |
| 6 | Vortexing for approx. 1 min using a DVX-2500 Multi-tube Vortexer (2500 rpm; cycle: 5 seconds run, 1 second pause time) |
| 7 | Decanting of the liquid phase including all tissue into the same sample vial as used in step 4 |
| 8 | Addition of 4 mL of Diisopropylether (DIPE) |
| 9 | Conversion Point:<br>Extraction by shaking the test tubes vigorously for approx. 5 minutes using a DVX-2500 Multi-tube Vortexer (1700 rpm; cycle: 5 seconds run, 1 second pause time) |
| 10 | Centrifugation (phase separation) at 4000 rpm for 2 minutes |
| 11 | Storage at −75° C. for about 10 minutes |
| 12 | Decanting of the organic, liquid phase into a centrifuge vial |
| 13 | Evaporation of the organic phase using compressed air (Turbovap) at about 40° C. for 14 minutes |
| 14 | Addition of 50 µL of 50% EtOH |
| 15 | Vortexing for approx. 2 minutes using a DVX-2500 Multi-tube Vortexer (2500 rpm; cycle: 5 seconds run, 1 second pause time) |
| 16 | Centrifugation at 4000 rpm for 1 minute |

Faceal Analysis

The concentration of unchanged cyclosporin and the relative concentrations of the metabolites (AM9, AM4N and AM1) were reported for each intracolonic faecal sample and the faeces collected over the duration of the study.

If an enema was used prior to sigmoidoscopy then the appropriate faecal sample had the reported concentrations adjusted for the extra weight of enema used (multiply by [total faecal weight/total-enema]).

Following collection of sigmoidoscopy biopsy samples, three intracolonic faecal samples were taken from the region of the biopsy collection site to test for cyclosporin concentrations.

Amounts of unchanged cyclosporin and the metabolites were plotted for each subject against the collection time. The amount per hour was calculated and plotted for the collection interval. Hence the plot consists of stepped lines where the area under each step equates to the amount of drug measured for the collection interval.

Times since doses taken since the start of the collection interval were listed.

The concentrations from the intracolonic faecal samples taken after the sigmoidoscopy were listed with the colonic mucosal tissue and mucous layer concentrations.

Determination of Cyclosporin-A and its Metabolites, AM1, AM9 and AM4N, in Faecal Samples The faecal samples were analysed by the RP-LC-MS/MS method using the protocol below.

Method:
Preparation of Solutions and Validation Samples
Concentrated Solutions and Dilutions To spike calibration standards, quality control samples and other control samples, concentrates and dilutions were prepared as shown in the following table using the reference items and the internal standard with purities as described above.

Solutions Used for Preparation

| Name/date | Preparation | Conc. [µg/mL] | | | |
|---|---|---|---|---|---|
| | | Cyclosporin A | AM1 | AM4N | AM9 |
| K2718-1640 | 5.27 mg of Cyclosporin A were dissolved in 10.3819 mL of DMSO/MeOH (1/1) | 500.00 | — | — | — |
| K2733-1634 | 2.57 mg of AM1 were dissolved in 10 mL of DMSO/MeOH (1/1) | — | 251.86 | — | — |
| K2731-1649 | 1.76 mg of AM4N were dissolved in 10 mL of DMSO/MeOH (1/1) | — | — | 149.60 | — |
| K2732-1648 | 5.03 mg of AM9 were dissolved in 10 mL of DMSO/MeOH (1/1) | — | — | — | 367.19 |
| V1-B-812 | 420 µL of K2718-1640, 417 µL of K2733-1634, 702 µL of K2731-1649, and 286 µL of K2732-1648 were put together and filled up to 10 mL with DMSO/MeOH (1/1) | 21.000 | 10.503 | 10.502 | 10.502 |
| K2711-1577 | 1.9 mg of D12-Cyclosporin A were dissolved in 10 mL of DMSO/MeOH (1/1) | D12-Cyclosporin A | | | |
| V1-IS-3-811 | 500 µL of K2711-1577 were filled up to 10 mL of DMSO/MeOH 1/1 | 9.2720 | | | |
| IS-WS-1-814-Faeces | 865 µL of V1-IS-3-811 were mixed with 50 mL of DMSO/MeOH 1/1 | 0.16013 | | | |

Calibration Standards and Quality Control Samples

For analytical calibration purposes calibration standards and quality control samples were spiked with either a defined volume of a concentrated solution described above or a higher concentrated calibration standard into 50% Ethanol at eight concentration levels/three concentration levels respectively:

Preparation of Calibration Standards

| Std | Volume of added solution [µL] | Added solution | Matrix | Matrix volume [mL] | Conc. [ng/mL] of Cyclosporin A | AM1 | AM4N | AM9 |
|---|---|---|---|---|---|---|---|---|
| Std0B-812 | — | — | 50% Ethanol | 4 | — | — | — | — |
| Std1B-812 | 102.6 | Std4B-812 | | 4 | 2.00 | 1.00 | 1.00 | 1.00 |
| Std2B-812 | 65.2 | Std5B-812 | | 4 | 4.00 | 2.00 | 2.00 | 2.00 |
| Std3B-812 | 48.6 | Std8B-812 | | 4 | 12.0 | 6.00 | 6.00 | 6.00 |
| Std4B-812 | 348 | Std8B-812 | | 4 | 80.0 | 40.0 | 40.0 | 40.0 |
| Std5B-812 | 48.1 | V1-B-812 | | 4 | 250 | 125 | 125 | 125 |
| Std6B-812 | 97.6 | V1-B-812 | | 4 | 500 | 250 | 250 | 250 |
| Std7B-812 | 148.2 | V1-B-812 | | 4 | 750 | 375 | 375 | 375 |
| Std8B-812 | 200 | V1-B-812 | | 4 | 1000 | 500 | 500 | 500 |
| QC-A2-812 | 187.4 | QC-B2-812 | 50% Ethanol | 6 | 5.00 | 2.50 | 2.50 | 2.50 |
| QC-B2-812 | 63.4 | V1-B-812 | | 8 | 165 | 82.6 | 82.6 | 82.6 |
| QC-C2-812 | 338 | V1-B-812 | | 8 | 851 | 426 | 426 | 426 |

Other Control Samples
Preparation of Other Control Samples (about 1 mg Blank Faeces added per Aliquot)

| Std | Volume of added solution [µL] | Added solution | Matrix | Matrix volume [mL] | Conc. [ng/mL] of Cyclosporin A | AM1 | AM4N | AM9 |
|---|---|---|---|---|---|---|---|---|
| QC-A2-812 | 187.4 | QC-B2-812 | 50% Ethanol | 6 | 5.00 | 2.50 | 2.50 | 2.50 |
| QC-B2-812 | 63.4 | V1-B-812 | | 8 | 165 | 82.6 | 82.6 | 82.6 |
| QC-C2-812 | 338 | V1-B-812 | | 8 | 851 | 426 | 426 | 426 |

Sample Preparation for Analysis (Processing)
Calibration Standards and Quality Control Samples:
Preparation of Blank Samples and (if Applicable) Processed Matrix:

Preparation as described below, but taking DMSO/MeOH (1/1) instead of IS working solution.

| Step | Preparation procedure (step by step) |
|---|---|
| 1 | Addition of 0.4 mL of water |
| 2 | Addition of 25 µL of internal standard working solution |
| 3 | Addition of 4 mL of DIPE |
| 4 | Extraction by shaking the test tubes vigorously for approx. 5 minutes using a DVX-2500 Multi-tube Vortexer (1700 rpm; cycle: 5 seconds run, 1 second pause time) |
| 5 | Centrifugation (phase separation) at 4000 rpm for 2 minutes |
| 6 | Storage at −75° C. for about 10 minutes |
| 7 | Decanting of the organic, liquid phase into a centrifuge vial |
| 8 | Evaporation of the organic phase using compressed air (Turbovap) at about 40° C. for 14 minutes |
| 9 | Addition of 750 µL of 50% EtOH |
| 10 | Vortexing for approx. 2 minutes using a DVX-2500 Multi-tube Vortexer (2500 rpm; cycle: 5 seconds run, 1 second pause time) |
| 11 | Centrifugation at 4000 rpm for 1 minute |
| 12 | Transfer of an volume adequate to injection purposes into appropriate auto-sampler vials |
| 13 | Crimping the vials with appropriate vial caps |

Matrix Samples (Human Faeces):

| Step | Preparation procedure (step by step) |
|---|---|
| I | [if not stored/available as 100 mg aliquots already] |
| II | [if frozen −> thawing at 20° C. to 25° C. in a water bath for approx.. 5 min] |

-continued

| Step | Preparation procedure (step by step) |
|---|---|
| 1 | Fill up the volumetric flask (5 mL) with 50% EtOH |
| 2 | Vortexing for about 1 min using a vortex mixer |
| 3 | Wait (settle down) for 3 min |
| 4 | Transfer of 50 µL into a sample vial |
| 5 | Addition of 950 µL 50% EtOH |
| 6 | Vortexing for approx. 30 s using a DVX-2500 Multi-tube Vortexer (2500 rpm) |
| 7 | Transfer of 50 µL into a sample vial |
| 8 | Addition of 0.4 mL of water |
| 9 | Addition of 25 µL of internal standard working solution |
| 10 | Addition of 4 mL of DIPE |
| 11 | Extraction by shaking the test tubes vigorously for approx. 5 minutes using a DVX-2500 Multi-tube Vortexer (1700 rpm; cycle: 5 seconds run, 1 second pause time) |
| 12 | Centrifugation (phase separation) at 4000 rpm for 2 minutes |
| 13 | Storage at −75° C. for about 10 minutes |
| 14 | Decanting of the organic, liquid phase into a centrifuge vial |

| Step | Preparation procedure (step by step) |
|---|---|
| 15 | Evaporation of the organic phase using compressed air (Turbovap) at about 40° C. for 14 minutes |
| 16 | Addition of 750 μL of 50% EtOH |
| 17 | Vortexing for approx. 2 minutes using a DVX-2500 Multi-tube Vortexer (2500 rpm; cycle: 5 seconds run, 1 second pause time) |
| 18 | Centrifugation at 4000 rpm for 1 minute |
| 19 | Transfer of an volume adequate to injection purposes into appropriate auto-sampler vials |
| 20 | Crimping the vials with appropriate vial caps |

Apparatus
Instruments and Materials

| Instrument/material | Code | Manufacturer |
|---|---|---|
| Work station API 6500 | | |
| Mass Spectrometer | 6500 Q-Trap | AB SCIEX, USA/Canada |

Software

| | |
|---|---|
| Data acquisition | Analyst 1.6.2 (AB SCIEX, USA/Canada) |
| Data processing | Analyst 1.6.2 (AB SCIEX, USA/Canada) |
| Statistics and calculations | Analyst 1.6.2 (AB SCIEX, USA/Canada) |
| Lotus 123 (Lotus Corp, USA) | |

Chromatographic Conditions and Detection Parameters
Chromatographic Conditions

| Parameter | Scheduled range/description |
|---|---|
| Mobile phase solvent A | 10 mM Ammonium acetat in water |
| Mobile phase solvent B | ACN/THF (8/2) |
| Chromatographic run | 0.0-4.5 min linear gradient: 40% B → 52% B<br>4.5-6.0 min linear gradient: 52% B → 85% B<br>6.0-6.01 min linear gradient: 85% B → 0% B<br>6.01-7.0 min isocratic: 0% B |
| Flow | 0.8 mL/min |
| Injection volume | 10 μL |
| Injector flush | DMSO/MeOH/Water (1/1/1) |
| Pre-column/Column | Luna C18, 4 × 2 mm/ACE3AQ; 100 × 2.1 mm, 3 μm (ACT, UK) |
| Column temperature | 80° C. |
| Cooling set point (T) | 25° C. |

Detection Parameters

| Parameter | Scheduled range/description |
|---|---|
| MS Ionisation mode | ESI |
| MS polarity | Positive |
| MS detection mode | MRM |
| Vaporizer temperature | 600° C. |
| Ionisation voltage | 5.5 kV |
| Gas 1 | Pressure = 75 psi |
| Gas 2 | Pressure = 75 psi |
| Curtain gas | pressure = 40 psi |
| Quadrupole resolution | low → low |
| Transitions | 1203.0 → 99.9 m/z: Cyclosporin A (CE: 125 eV, CXP: 16 V)<br>1215.0 → 99.9 m/z: D12-Cyclosporin A (CE: 125 eV, CXP: 16 V)<br>1219.0 → 224.0 m/z: AM1 (CE: 65 eV, CXP: 15 V)<br>1219.0 → 99.9 m/z: AM9 (CE: 125 eV, CXP: 16 V)<br>1189.0 → 224.0 m/z: AM4N (CE: 65 eV, CXP: 15 V) |
| DP (declustering potential) | 130 V |

Data Evaluation

Concentrations were evaluated using an internal standard method.

The concentrations of each analyte were determined using the following regression model, weighting factor and formula:

| Analyte | Regression model | Weighting factor | Formula for concentration |
|---|---|---|---|
| all 4 | $y = ax^2 + bx + c$ | 1/conc. | $\text{concentration} = \dfrac{-b \pm \sqrt{b^2 - 4a(c - \text{peak area ratio})}}{2a}$ |

Based thereon (arithmetic) mean values and relative standard deviations (CV) (formulas shown below) were calculated using the program "Lotus 123".

$$\text{standard deviation} = \sqrt{\frac{1}{N-1} \sum_{i=1}^{N} (x_i - \bar{x})^2}$$

$x_i$ calculated concentration
$\bar{x}$ mean calculated concentration
N number of values
i index of value $$\text{relative standard deviation (\%)} = \frac{\text{standard deviation}}{\text{mean calculated concentration}} * 100$$

The concentration of cyclosporin A and the metabolites AM4N, AM9 in faecal samples collected on day 2 of the study is shown in Table 22.

TABLE 22

| Group | Mean CyA (ng/g) | Mean AM4N (ng/g) | Mean AM9 (ng/g) | Total 1 AM4N + AM9 (ng/g) | Total 2 CyA + AM4N + AM9 (ng/g) | Total 1/Total 2% | Ratio CyA:AM4:AM9 |
|---|---|---|---|---|---|---|---|
| IV Group 1 | 2479.58 | 2194.52 | 3343.21 | 5537.73 | 8017.31 | 69.1% | 0.45 |
| IV Group 2 | 1215.75 | 1110.19 | 2942.91 | 4053.1 | 5268.85 | 77.9% | 0.30 |
| 37.5 mg OD | 351258.5 | 1918.8 | 3687.9 | 5606.7 | 356865.20 | 1.6% | 62.65 |
| 75 mg OD | 122940.4 | 1419.76 | 2384.75 | 3804.51 | 126744.91 | 3.0% | 32.31 |
| 75 mg BID | 159430.6 | 1069.01 | 2431.42 | 3500.43 | 162931.00 | 2.2% | 45.55 |
| 150 mg BID | 1068136 | 4388.83 | 9969.08 | 14357.91 | 1082493.61 | 1.3% | 74.39 |

Pharmacokinetic Evaluation

Demographic and Other Baseline Characteristics

Demographic characteristics are summarised in Table 23. All subjects were male and aged between 19 and 54 years. Demographic characteristics were similar across the treatment groups; any differences were not considered to affect the results of the study.

TABLE 23

Demographics

| | Sandimmun ® IV Group 1 N = 8 | Sandimmun ® IV Group 2 N = 8 | CyCol ® 37.5 mg once daily N = 8 | CyCol ® 75 mg once daily N = 8 | CyCol ® 75 mg BID N = 8 | CyCol ® 150 mg BID N = 8 | Overall N = 48 |
|---|---|---|---|---|---|---|---|
| Age, years | | | | | | | |
| Mean | 30.4 | 29.4 | 37.4 | 38.8 | 32.1 | 31.9 | 33.3 |
| SD | 9.21 | 7.95 | 10.81 | 12.44 | 6.22 | 6.92 | 9.38 |
| Median | 27.0 | 28.5 | 36.5 | 36.5 | 32.5 | 30.0 | 32.0 |
| Min, Max | 23, 50 | 19, 39 | 21, 54 | 20, 54 | 22, 44 | 24, 45 | 19, 54 |
| Age categories, n (%) | | | | | | | |
| 18-30 | 5 (62.5) | 4 (50.0) | 2 (25.0) | 2 (25.0) | 3 (37.5) | 5 (62.5) | 21 (43.8) |
| 31-55 | 3 (37.5) | 4 (50.0) | 6 (75.0) | 6 (75.0) | 5 (62.5) | 3 (37.5) | 27 (56.3) |
| Weight, kg | | | | | | | |
| Mean | 75.0 | 77.3 | 78.4 | 84.5 | 79.4 | 73.9 | 78.1 |
| SD | 9.28 | 12.93 | 15.61 | 13.91 | 11.14 | 11.79 | 12.41 |
| Median | 70.8 | 72.3 | 77.4 | 87.1 | 83.7 | 73.7 | 77.4 |
| Min, Max | 65, 89 | 66, 103 | 58, 100 | 64, 100 | 59, 91 | 54, 91 | 54, 103 |
| Height, cm | | | | | | | |
| Mean | 176.0 | 175.9 | 177.3 | 181.4 | 180.4 | 175.4 | 177.7 |
| SD | 5.76 | 6.75 | 9.33 | 9.47 | 5.07 | 6.05 | 7.27 |
| Median | 176.0 | 173.0 | 179.0 | 180.5 | 179.0 | 176.5 | 177.0 |
| Min, Max | 166, 185 | 169, 188 | 160, 191 | 171, 200 | 174, 188 | 163, 183 | 160, 200 |
| Race, n (%) | | | | | | | |
| Black | 0 | 0 | 1 (12.5) | 1 (12.5) | 2 (25.0) | 1 (12.5) | 5 (10.4) |
| Caucasian | 4 (50.0) | 6 (75.0) | 4 (50.0) | 5 (62.5) | 6 (75.0) | 6 (75.0) | 31 (64.6) |
| Asian/Pacific Islander | 3 (37.5) | 2 (25.0) | 3 (37.5) | 1 (12.5) | 0 | 1 (12.5) | 10 (20.8) |
| Mixed | 1 (12.5) | 0 | 0 | 1 (12.5) | 0 | 0 | 2 (4.2) |
| Ethnicity, n (%) | | | | | | | |
| Not Hispanic | 8 (100.0) | 7 (87.5) | 8 (100.0) | 8 (100.0) | 8 (100.0) | 8 (100.0) | 47 (97.9) |
| Hispanic | 0 | 1 (12.5) | 0 | 0 | 0 | 0 | 1 (2.1) |

TABLE 23-continued

| | Sandimmun® IV Group 1 N = 8 | Sandimmun® IV Group 2 N = 8 | CyCol® 37.5 mg once daily N = 8 | CyCol® 75 mg once daily N = 8 | CyCol® 75 mg BID N = 8 | CyCol® 150 mg BID N = 8 | Overall N = 48 |
|---|---|---|---|---|---|---|---|
| Demographics | | | | | | | |
| Body mass index, kg/m² | | | | | | | |
| Mean | 24.2 | 24.6 | 24.9 | 25.6 | 24.4 | 23.9 | 24.6 |
| SD | 2.89 | 2.71 | 3.84 | 2.80 | 3.11 | 3.21 | 2.99 |
| Median | 23.5 | 23.5 | 25.8 | 26.1 | 24.1 | 23.2 | 24.1 |
| Min, Max | 21, 29 | 22, 29 | 19, 29 | 21, 30 | 20, 29 | 20, 29 | 19, 30 |

BID = twice daily;
IV = intravenous;
Max = maximum;
Min = minimum;
n = number of subjects in assigned category;
N = number of subjects in Safety Population;
SD = standard deviation.
Percentages are based on the number of subjects in the Safety Population.

Pharmacokinetic Results and Tabulations of Individual Subject Data

Analysis of Pharmacokinetics

Cyclosporin Pharmacokinetics

Figure 11:
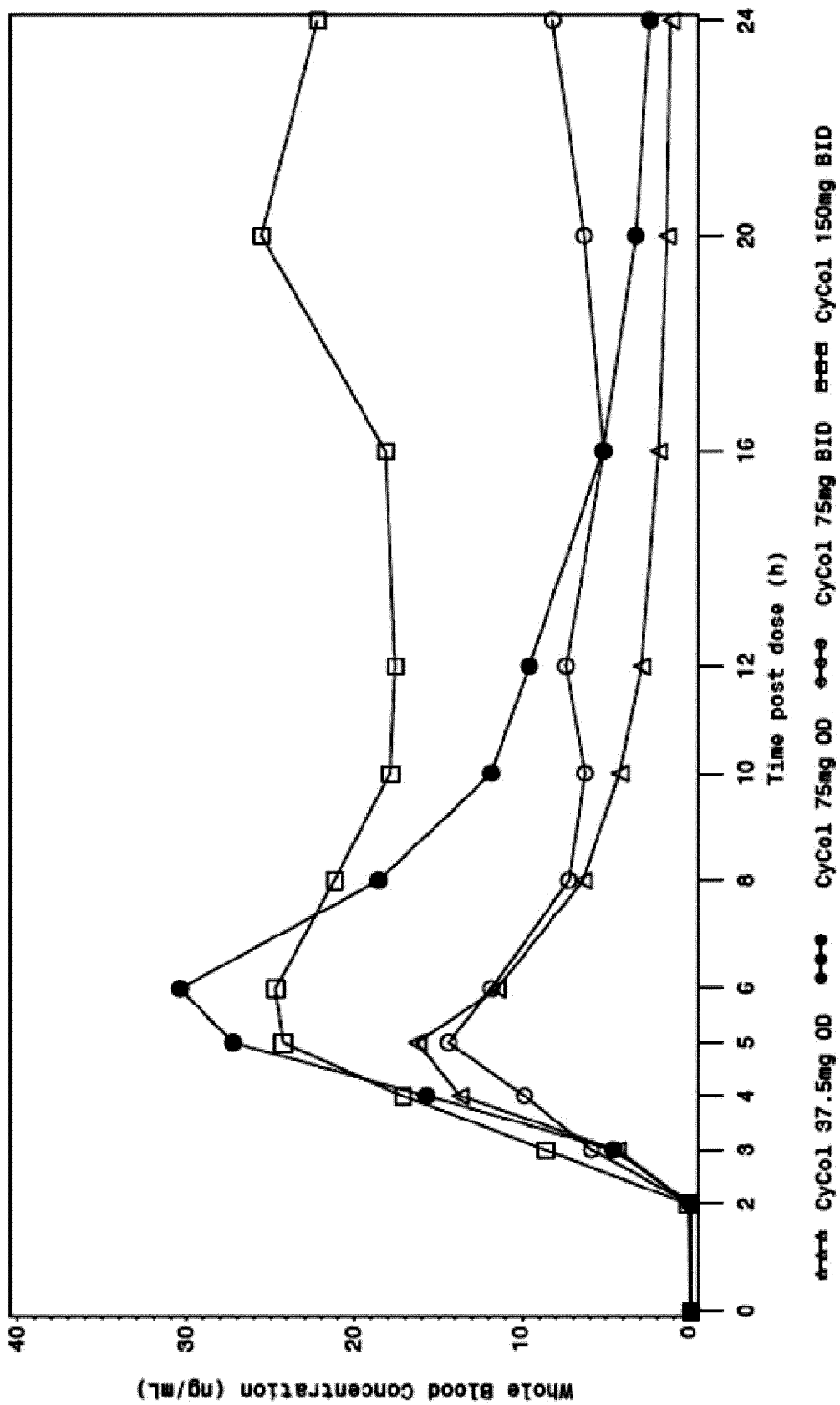
FIG. 11 shows the median whole blood cyclosporin concentration time profiles (linear linear) on day 1 in those subjects treated with CyCol® in the clinical trial described in Example 9.
Figure 12:
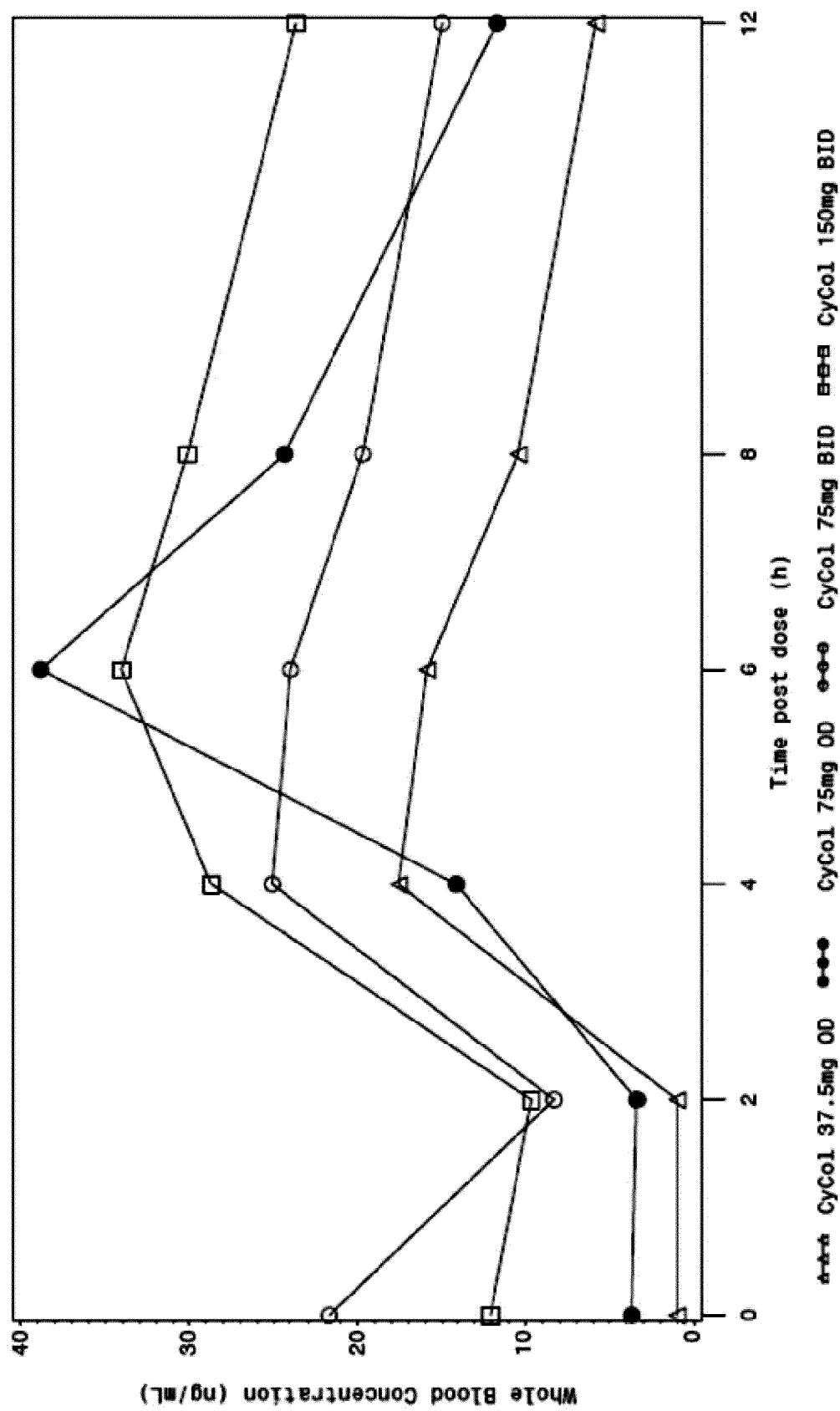
FIG. 12 the median whole blood cyclosporin concentration time profiles (linear linear) on day 7 in those subjects treated with CyCol® in the clinical trial described in Example 9.

Median whole blood cyclosporin concentration-time profiles (linear-linear) for the CyCol® groups on Day 1 and Day 7 are provided in FIGS. 11 and 12 respectively. Cyclosporin concentrations generally increased with increasing dose of CyCol®.

Single Dose Pharmacokinetics

Whole blood cyclosporin pharmacokinetic parameters following a single dose are summarised in Table 24. Exposure ($AUC_{inf}$) was considerably lower following treatment with all doses of CyCol® compared with Sandimmun® IV. Cyclosporin concentrations ($AUC_{last}$ and $AUC_{inf}$) increased with increasing dose of CyCol®. Median $T_{max}$ was similar at all doses of CyCol® (between 5.0 and 5.5 hours).

Median percent extrapolation was low in the two Sandimmun® IV groups (<5%). Median percent extrapolation was highest in the CyCol® 75 mg BID and 150 mg BID groups (24.7% and 28.9%, respectively).

TABLE 24

Summary of Single Dose Whole Blood Cyclosporin Pharmacokinetic Parameters - PK Population

| | Sandimmun® IV Group 1 N = 8 | Sandimmun® IV Group 2 N = 8 | CyCol® 37.5 mg once daily N = 8 | CyCol® 75 mg once daily N = 8 | CyCol® 75 mg BID N = 8 | CyCol® 150 mg BID N = 8 |
|---|---|---|---|---|---|---|
| $AUC_{last}$ (ng · h/mL) | | | | | | |
| n | | | 8 | 8 | 8 | 8 |
| Arithmetic mean | | | 118.1 | 241.2 | 250.5 | 554.3 |
| SD | | | 62.10 | 158.71 | 162.89 | 355.15 |
| Geometric mean | | | 104.7 | 191.7 | 199.1 | 463.7 |
| CV % | | | 52.6 | 65.8 | 65.0 | 64.1 |
| Median | | | 96.9 | 208.5 | 228.0 | 437.5 |
| Minimum, Maximum | | | 46.4, 228 | 55.6, 470 | 64.8, 480 | 146, 1231 |
| $AUC_{inf}$ (ng · h/mL) | | | | | | |
| n | 8 | 8 | 8 | 8 | 8 | 8 |
| Arithmetic mean | 8836.0 | 8397.3 | 132.8 | 265.2 | 329.5 | 821.8 |
| SD | 1180.58 | 1609.76 | 70.81 | 163.83 | 208.07 | 460.76 |
| Geometric mean | 8769.5 | 8274.5 | 117.9 | 218.3 | 265.9 | 700.4 |
| CV % | 13.4 | 19.2 | 53.3 | 61.8 | 63.1 | 56.1 |
| Median | 8649.5 | 8110.5 | 105.9 | 228.0 | 314.5 | 754.0 |
| Minimum, Maximum | 7457, 11088 | 6316, 11845 | 55.0, 263 | 67.9, 502 | 100, 637 | 220, 1661 |
| $C_{max}$ (ng/mL) | | | | | | |
| n | | | 8 | 8 | 8 | 8 |
| Arithmetic mean | | | 18.38 | 41.89 | 28.84 | 59.44 |
| SD | | | 9.810 | 32.574 | 33.206 | 54.306 |
| Geometric mean | | | 15.70 | 29.86 | 17.66 | 40.93 |
| CV % | | | 53.4 | 77.8 | 115.2 | 91.4 |

TABLE 24-continued

Summary of Single Dose Whole Blood Cyclosporin Pharmacokinetic Parameters - PK Population

|  | Sandimmun ® IV Group 1 N = 8 | Sandimmun ® IV Group 2 N = 8 | CyCol ® 37.5 mg once daily N = 8 | CyCol ® 75 mg once daily N = 8 | CyCol ® 75 mg BID N = 8 | CyCol ® 150 mg BID N = 8 |
|---|---|---|---|---|---|---|
| Median | 8649.5 | 8110.5 | 105.9 | 228.0 | 314.5 | 754.0 |
| Minimum, Maximum | 7457, 11088 | 6316, 11845 | 55.0, 263 | 67.9, 502 | 100, 637 | 220, 1661 |
| $C_{max}$ (ng/mL) | | | | | | |
| n | | | 8 | 8 | 8 | 8 |
| Arithmetic mean | | | 18.38 | 41.89 | 28.84 | 59.44 |
| SD | | | 9.810 | 32.574 | 33.206 | 54.306 |
| Geometric mean | | | 15.70 | 29.86 | 17.66 | 40.93 |
| CV % | | | 53.4 | 77.8 | 115.2 | 91.4 |
| Median | | | 17.70 | 30.40 | 14.40 | 36.60 |
| Minimum, Maximum | | | 6.03, 30.8 | 7.20, 86.9 | 3.73, 101 | 10.5, 156 |
| $t_{1/2}$ (h) | | | | | | |
| n | 8 | 8 | | | | |
| Arithmetic mean | 5.04 | 3.83 | | | | |
| SD | 0.753 | 0.556 | | | | |
| CV % | 14.9 | 14.5 | | | | |
| Median | 4.87 | 3.88 | | | | |
| Minimum, Maximum | 4.25, 6.28 | 2.70, 4.42 | | | | |
| $T_{max}$ (h) | | | | | | |
| n | | | 8 | 8 | 8 | 8 |
| Median | | | 5.0 | 5.5 | 5.0 | 5.5 |
| Minimum, Maximum | | | 4, 8 | 4, 12 | 4, 12 | 3, 8 |
| $AUC_{0-T}$ (ng · h/mL) | | | | | | |
| n | 8 | 8 | | | | |
| Arithmetic mean | 8448 | 8122 | | | | |
| SD | 1081.5 | 1562.3 | | | | |
| Geometric mean | 8389 | 8002 | | | | |
| CV % | 12.8 | 19.2 | | | | |
| Median | 8422 | 7867 | | | | |
| Minimum, Maximum | 7119, 10472 | 6054, 11465 | | | | |
| F (%) | | | | | | |
| n | | | 8 | 8 | 8 | 8 |
| Arithmetic mean | | | 6.006 | 6.000 | 3.729 | 4.650 |
| SD | | | 3.2020 | 3.7087 | 2.3575 | 2.6082 |
| Geometric mean | | | 5.336 | 4.938 | 3.007 | 3.962 |
| CV % | | | 53.3 | 61.8 | 63.2 | 56.1 |
| Median | | | 4.790 | 5.150 | 3.560 | 4.265 |
| Minimum, Maximum | | | 2.49, 11.9 | 1.54, 11.4 | 1.13, 7.21 | 1.24, 9.40 |
| $C_{min}$ (ng/mL) | | | | | | |
| n | | | 8 | 8 | 8 | 8 |
| Arithmetic mean | | | 1.21 | 2.67 | 4.23 | 11.32 |
| SD | | | 0.691 | 0.886 | 1.979 | 7.461 |
| Geometric mean | | | 1.04 | 2.53 | 3.73 | 9.69 |
| CV % | | | 57.2 | 33.2 | 46.9 | 65.9 |
| Median | | | 1.12 | 2.44 | 4.26 | 8.74 |
| Minimum, Maximum | | | 0.333, 2.58 | 1.37, 4.00 | 1.17, 7.40 | 5.06, 27.2 |
| Percent extrapolated (%) | | | | | | |
| n | 8 | 8 | 8 | 8 | 8 | 8 |
| Median | 4.5 | 3.3 | 11.6 | 9.0 | 24.7 | 29.8 |
| Minimum, Maximum | 1.64, 6.03 | 2.27, 4.14 | 7.15, 15.6 | 5.75, 23.7 | 10.6, 35.7 | 17.2, 56.6 |

BID = twice daily;
IV = intravenous;
N = number of subjects in Safety Population.

Steady State Pharmacokinetics

Whole blood cyclosporin pharmacokinetic parameters at steady state are summarised in Table 25. Cyclosporin concentrations ($AUC_{0-\tau}$) increased with increasing dose of CyCol®. Median $T_{max}$ was similar at all doses of CyCol® (between 5.5 and 6.0 hours).

TABLE 25

Summary of Steady State Whole Blood Cyclosporin Pharmacokinetic Parameters - PK Population

|  | CyCol® 37.5 mg once daily N = 8 | CyCol® 75 mg once daily N = 8 | CyCol® 75 mg BID N = 8 | CyCol® 150 mg BID N = 8 |
|---|---|---|---|---|
| $AUC_{0-\tau}$ (ng · h/mL) | | | | |
| n | 8 | 8 | 7 | 7 |
| Arithmetic mean | 128 | 225 | 298 | 585 |
| SD | 53.6 | 113.5 | 121.4 | 228.1 |
| Geometric mean | 117 | 190 | 266 | 539 |
| CV % | 41.9 | 50.4 | 40.7 | 39.0 |
| Median | 130 | 257 | 343 | 608 |
| Minimum, | 49.3, | 54.2, | 84.2, | 228, |
| Maximum | 223 | 354 | 410 | 886 |
| $C_{max}$ (ng/mL) | | | | |
| n | 8 | 8 | 7 | 7 |
| Arithmetic mean | 19.47 | 38.57 | 36.67 | 45.30 |
| SD | 10.155 | 24.028 | 13.866 | 25.682 |
| Geometric mean | 16.63 | 28.89 | 33.72 | 37.95 |
| CV % | 52.2 | 62.3 | 37.8 | 56.7 |
| Median | 21.25 | 48.50 | 41.10 | 48.40 |
| Minimum, | 6.23, | 4.94, | 14.1, | 12.9, |
| Maximum | 35.9 | 75.4 | 49.7 | 82.1 |
| Tmax (h) | | | | |
| n | 8 | 8 | 7 | 7 |
| Median | 5.5 | 6.0 | 6.0 | 6.0 |
| Minimum, Maximum | 5, 8 | 2, 6 | 1, 6 | 4, 8 |
| Cmin (ng/mL) | | | | |
| n | 8 | 8 | 7 | 7 |
| Arithmetic mean | 1.11 | 2.68 | 5.69 | 10.06 |
| SD | 0.509 | 1.279 | 3.355 | 1.859 |
| Geometric mean | 1.01 | 2.39 | 4.84 | 9.90 |
| CV % | 46.0 | 47.8 | 58.9 | 18.5 |
| Median | 1.02 | 2.58 | 4.63 | 9.70 |
| Minimum, | 0.56, | 1.17, | 2.28, | 6.90, |
| Maximum | 1.99 | 4.50 | 10.4 | 12.2 |
| F (%) | | | | |
| n | 8 | 8 | 7 | 7 |
| Arithmetic mean | 5.789 | 5.099 | 3.374 | 3.313 |
| SD | 2.4267 | 2.5700 | 1.3748 | 1.2895 |
| Geometric mean | 5.313 | 4.300 | 3.012 | 3.049 |
| CV % | 41.9 | 50.4 | 40.7 | 38.9 |
| Median | 5.840 | 5.810 | 3.880 | 3.440 |
| Minimum, | 2.23, | 1.23, | 0.95, | 1.29, |
| Maximum | 10.1 | 8.01 | 4.64 | 5.01 |
| $C_{av}$ (ng/mL) | | | | |
| n | 8 | 8 | 7 | 7 |
| Arithmetic mean | 5.33 | 9.38 | 24.86 | 48.77 |
| SD | 2.234 | 4.728 | 10.116 | 19.006 |
| Geometric mean | 4.89 | 7.91 | 22.20 | 44.89 |
| CV % | 41.9 | 50.4 | 40.7 | 39.0 |
| Median | 5.40 | 10.69 | 28.58 | 50.67 |
| Minimum, | 2.05, | 2.26, | 7.02, | 19.00, |
| Maximum | 9.29 | 14.75 | 34.17 | 73.83 |
| Linearity Ratio | | | | |
| n | 8 | 8 | 7 | 7 |
| Arithmetic mean | 1.295 | 1.403 | 0.968 | 0.883 |
| SD | 0.7862 | 1.4995 | 0.4929 | 0.3378 |
| Geometric mean | 0.996 | 0.870 | 0.871 | 0.823 |
| CV % | 60.7 | 106.9 | 50.9 | 38.3 |
| Median | 1.5 | 0.9 | 0.7 | 0.8 |
| Minimum, | 0.238, | 0.154, | 0.492, | 0.422, |
| Maximum | 2.309 | 4.786 | 1.762 | 1.300 |

BID = twice daily; IV = intravenous; N = number of subjects in Safety Population.

Colon Tissue Distribution
Cyclosporin Distribution

Tissue, mucous and intracolonic cyclosporin concentrations are summarised in Table 26.

Tissue cyclosporin concentrations generally increased with increasing dose of CyCol® and concentrations were higher in the CyCol® 75 mg BID and 150 mg BID groups than in the Sandimmun® IV groups. There was no relationship between tissue cyclosporin concentrations and distance from anal verge.

Mucous cyclosporin concentrations were higher in the CyCol® 150 mg group compared with the other CyCol® groups and the Sandimmun® IV groups. There was no relationship between mucous cyclosporin concentrations and distance from anal verge.

Intracolonic faecal cyclosporin concentrations generally increased with increasing dose of CyCol® and were considerably higher in all of the CyCol® groups compared with the Sandimmun® IV groups.

TABLE 26

Summary of Tissue, Mucous and Intracolonic Faecal Cyclosporin Concentrations - PK Population

|  | Sandimmun® IV Group 1 N = 8 | Sandimmun® IV Group 2 N = 8 | CyCol® 37.5 mg once daily N = 8 | CyCol® 75 mg once daily N = 8 | CyCol® 75 mg BID N = 7 | CyCol® 150 mg BID N = 7 |
|---|---|---|---|---|---|---|
| Tissue cyclosporin concentrations (ng/g) | | | | | | |
| n | 8 | 8 | 8 | 8 | 7 | 7 |
| Arithmetic mean | 802 | 1100 | 1045 | 1094 | 1579 | 5210 |
| SD | 397.0 | 276.1 | 712.5 | 881.3 | 502.3 | 4417.5 |
| Geometric mean | 717 | 1071 | 863 | 752 | 1493 | 4043 |
| CV % | 49.5 | 25.1 | 68.2 | 80.6 | 31.8 | 84.8 |
| Median | 789 | 974 | 727 | 906 | 1576 | 3114 |

TABLE 26-continued

Summary of Tissue, Mucous and Intracolonic Faecal Cyclosporin Concentrations - PK Population

| | Sandimmun ® IV Group 1 N = 8 | Sandimmun ® IV Group 2 N = 8 | CyCol ® 37.5 mg once daily N = 8 | CyCol ® 75 mg once daily N = 8 | CyCol ® 75 mg BID N = 8 | CyCol ® 150 mg BID N = 8 |
|---|---|---|---|---|---|---|
| Minimum, | 326, | 836, | 352, | 139, | 669, | 1945, |
| Maximum | 1487 | 1541 | 2431 | 2497 | 2279 | 14269 |
| | | | Mucous cyclosporin concentrations (ng/g) | | | |
| n | 8 | 8 | 8 | 8 | 7 | 7 |
| Arithmetic mean | 73.68 | 126.93 | 103.56 | 101.09 | 78.27 | 596.38 |
| SD | 47.311 | 60.086 | 58.416 | 63.478 | 40.067 | 458.366 |
| Geometric mean | 60.46 | 116.36 | 90.72 | 70.42 | 69.93 | 457.16 |
| CV % | 56.0 | 43.6 | 49.0 | 62.2 | 43.1 | 98.2 |
| Median | 1535 | 3230 | 96957 | 277626 | 325550 | 294153 |
| Minimum, | 955, | 1885, | 66664, | 8212, | 142242, | 88100, |
| Maximum | 3748 | 6529 | 234285 | 433770 | 557300 | 1569913 |

Table 26 shows that oral administration of the CyCol™ compositions comprising the surfactant provided similar or higher cyclosporin A concentrations in colonic tissue compared to IV administration of 2 mg/kg cyclosporin. However, the CyCol™ compositions resulted in significantly lower systemic exposure compared to IV administration of cyclosporin (see the AUC and $C_{max}$ values in Tables 24 and 25). Reference to Table 22 also shows that the CyCol™ compositions resulted in much lower cyclosporin metabolism as evidenced by the high ratio of cyclosporin to the AM4+AM9 metabolites in collected faecal samples.

AM1 Concentrations

Tissue, mucous and intracolonic faecal AM1 concentrations are summarised in Table 27.

Tissue AM1 concentrations increased with increasing dose of CyCol® but were slightly lower in the CyCol® 150 mg BID compared with the Sandimmun® IV groups. There was no relationship between tissue AM1 concentrations and distance from anal verge.

Mucous AM1 concentrations were similar in the CyCol® 150 mg BID and Sandimmun® IV groups and lower in the other CyCol® groups. There was no relationship between mucous AM1 concentrations and distance from anal verge.

Intracolonic faecal AM1 concentrations were similar in all treatment groups.

TABLE 27

Summary of Tissue, Mucous and Intracolonic Faecal AM1 Concentrations - PK Population

| | Sandimmun ® IV Group 1 N = 8 | Sandimmun ® IV Group 2 N = 8 | CyCol ® 37.5 mg once daily N = 8 | CyCol ® 75 mg once daily N = 8 | CyCol ® 75 mg BID N = 8 | CyCol ® 150 mg BID N = 8 |
|---|---|---|---|---|---|---|
| | | | Tissue AM1 concentrations (ng/g) | | | |
| n | 8 | 8 | 8 | 8 | 7 | 7 |
| Arithmetic mean | 517.6 | 345.2 | 70.0 | 101.7 | 232.7 | 303.7 |
| SD | 294.49 | 89.95 | 42.48 | 74.12 | 198.53 | 156.50 |
| Geometric mean | 453.4 | 334.5 | 61.8 | 82.5 | 169.3 | 272.5 |
| CV % | 56.9 | 26.1 | 60.7 | 72.9 | 85.3 | 51.5 |
| Median | 534.9 | 320.3 | 63.0 | 75.9 | 155.5 | 330.7 |
| Minimum, | 217, | 205.9, | 34.3, | 27.8, | 38.0, | 132.6, |
| Maximum | 1143.0 | 467.8 | 166.3 | 258.2 | 624.6 | 605.0 |
| | | | Mucous AM1 concentrations (ng/g) | | | |
| n | 8 | 8 | 8 | 8 | 7 | 7 |
| Arithmetic mean | 304.3 | 307.3 | 60.3 | 67.0 | 56.9 | 233.8 |
| SD | 146.10 | 163.66 | 35.63 | 33.47 | 43.74 | 102.73 |
| Geometric mean | 275.6 | 276.5 | 53.7 | 61.0 | 46.1 | 215.7 |
| CV % | 48.0 | 53.3 | 59.1 | 50.0 | 76.8 | 43.9 |
| Median | 268.1 | 245.1 | 48.6 | 61.2 | 44.3 | 203.3 |
| Minimum, | 131.2, | 169.4, | 31.6, | 32.9, | 21.2, | 122.0, |
| Maximum | 566.1 | 568.8 | 141.1 | 138.9 | 145.4 | 378.6 |
| | | | Intracolonic faecal AM1 concentrations (ng/g) | | | |
| n | 8 | 8 | 8 | 8 | 7 | 7 |
| Arithmetic mean | 2472 | 4944 | 2939 | 4719 | 5386 | 5870 |
| SD | 1477.2 | 3375.2 | 645.8 | 2618.3 | 5528.3 | 3249.3 |
| Geometric mean | 2094 | 4029 | 2876 | 3921 | 3564 | 5236 |
| CV % | 59.8 | 68.3 | 22.0 | 55.5 | 102.6 | 55.4 |
| Median | 2160 | 3322 | 2938 | 4424 | 4441 | 4933 |

TABLE 27-continued

Summary of Tissue, Mucous and Intracolonic Faecal AM1 Concentrations - PK Population

| | Sandimmun® IV Group 1 N = 8 | Sandimmun® IV Group 2 N = 8 | CyCol® 37.5 mg once daily N = 8 | CyCol® 75 mg once daily N = 8 | CyCol® 75 mg BID N = 8 | CyCol® 150 mg BID N = 8 |
|---|---|---|---|---|---|---|
| Minimum, Maximum | 1027, 4712 | 1885, 10456 | 2158, 3749 | 1002, 8838 | 948, 16997 | 3041, 12251 |

AM4N Concentrations

Tissue, mucous and intracolonic faecal AM4N concentrations are summarised in Table 28.

Tissue AM4N concentrations generally increased with increasing dose of CyCol®. Concentrations in the CyCol® 150 mg BID were lower compared with the Sandimmun® IV groups. There was no relationship between tissue AM4N concentrations and distance from anal verge.

Mucous AM4N concentrations were higher in the CyCol® 150 mg BID group compared with the other CyCol® groups but concentrations were highest in the Sandimmun® IV groups. There was no relationship between mucous AM4N concentrations and distance from anal verge. Intracolonic faecal AM4N concentrations were similar in all treatment groups.

AM9 Concentrations

Tissue, mucous and intracolonic faecal AM9 concentrations are summarised in Table 29.

Tissue AM9 concentrations generally increased with increasing dose of CyCol®. Concentrations in the CyCol® 150 mg BID were lower compared with the Sandimmun® IV groups. There was no relationship between tissue AM4N concentrations and distance from anal verge.

Mucous AM9 concentrations were higher in the CyCol® 150 mg BID group compared with the other CyCol® groups but concentrations were highest in the Sandimmun® IV groups. There was no relationship between mucous AM9 concentrations and distance from anal verge.

Intracolonic faecal AM9 concentrations were similar in all treatment groups.

TABLE 28

Summary of Tissue, Mucous and Intracolonic Faecal AM4N Concentrations - PK Population

| | Sandimmun® IV Group 1 N = 8 | Sandimmun® IV Group 2 N = 8 | CyCol® 37.5 mg once daily N = 8 | CyCol® 75 mg once daily N = 8 | CyCol® 75 mg BID N = 8 | CyCol® 150 mg BID N = 8 |
|---|---|---|---|---|---|---|
| Tissue AM4N concentrations (ng/g) | | | | | | |
| n | 8 | 8 | 8 | 8 | 7 | 7 |
| Arithmetic mean | 19.816 | 24.272 | 3.013 | 3.862 | 3.657 | 9.686 |
| SD | 23.4043 | 28.1267 | 2.8647 | 3.4242 | 2.8473 | 10.9795 |
| Geometric mean | 11.746 | 11.188 | 2.224 | 2.247 | 2.809 | 6.146 |
| CV % | 118.1 | 115.9 | 95.1 | 88.7 | 77.9 | 113.4 |
| Median | 12.011 | 15.464 | 1.581 | 3.014 | 2.246 | 4.523 |
| Minimum, | 3.49, | 1.36, | 1.12, | 0.40, | 0.78, | 2.30, |
| Maximum | 71.45 | 81.84 | 8.99 | 8.41 | 9.11 | 31.58 |
| Mucous AM4N concentrations (ng/g) | | | | | | |
| n | 8 | 8 | 8 | 8 | 7 | 7 |
| Arithmetic mean | 3.787 | 10.458 | 1.194 | 1.338 | 0.632 | 2.931 |
| SD | 1.7635 | 14.4365 | 0.9826 | 0.8601 | 0.4757 | 1.8756 |
| Geometric mean | 3.440 | 4.332 | 0.913 | 0.974 | 0.513 | 2.510 |
| CV % | 46.6 | 138.0 | 82.3 | 64.3 | 75.2 | 64.0 |
| Median | 3.291 | 5.455 | 0.797 | 1.275 | 0.385 | 2.179 |
| Minimum, | 1.64, | 0.40, | 0.34, | 0.19, | 0.28, | 1.41, |
| Maximum | 6.95 | 43.78 | 2.85 | 2.31 | 1.44 | 5.90 |
| Intracolonic faecal AM4N concentrations (ng/g) | | | | | | |
| n | 8 | 8 | 8 | 8 | 7 | 7 |
| Arithmetic mean | 1390 | 2739 | 2670 | 2143 | 2134 | 2788 |
| SD | 665.9 | 983.7 | 453.1 | 819.3 | 1554.1 | 1123.3 |
| Geometric mean | 1285 | 2599 | 2639 | 1987 | 1768 | 2627 |
| CV % | 47.9 | 35.9 | 17.0 | 38.2 | 72.8 | 40.3 |
| Median | 1119 | 2536 | 2599 | 2282 | 2020 | 2685 |
| Minimum, | 875, | 1785, | 2158, | 895, | 815, | 1842, |
| Maximum | 2863 | 4554 | 3425 | 3171 | 5361 | 5060 |

TABLE 29

Summary of Tissue, Mucous and Intracolonic Faecal AM9 Concentrations - PK Population

|  | Sandimmun ® IV Group 1 N = 8 | Sandimmun ® IV Group 2 N = 8 | CyCol ® 37.5 mg once daily N = 8 | CyCol ® 75 mg once daily N = 8 | CyCol ® 75 mg BID N = 8 | CyCol ® 150 mg BID N = 8 |
|---|---|---|---|---|---|---|
| Tissue AM9 concentrations (ng/g) | | | | | | |
| N | 8 | 8 | 8 | 8 | 7 | 7 |
| Arithmetic mean | 64.41 | 80.81 | 11.81 | 15.80 | 28.53 | 50.28 |
| SD | 57.022 | 74.901 | 8.842 | 12.491 | 36.438 | 44.724 |
| Geometric mean | 45.98 | 53.22 | 9.57 | 11.38 | 18.15 | 36.42 |
| CV % | 88.5 | 92.7 | 74.9 | 79.1 | 127.7 | 88.9 |
| Median | 38.90 | 49.76 | 8.37 | 13.10 | 13.52 | 23.97 |
| Minimum, | 15.21, | 15.18, | 4.49, | 3.17, | 5.38, | 15.92, |
| Maximum | 159.11 | 208.30 | 26.72 | 37.45 | 109.85 | 120.30 |
| Mucous AM9 concentrations (ng/g) | | | | | | |
| N | 8 | 8 | 8 | 8 | 7 | 7 |
| Arithmetic mean | 31.48 | 193.81 | 9.20 | 11.31 | 9.62 | 29.57 |
| SD | 16.406 | 180.450 | 6.570 | 7.819 | 9.460 | 18.643 |
| Geometric mean | 28.40 | 134.27 | 7.70 | 8.88 | 7.37 | 25.14 |
| CV % | 52.1 | 93.1 | 71.4 | 69.1 | 98.3 | 63.0 |
| Median | 27.82 | 100.41 | 6.45 | 9.21 | 6.75 | 20.38 |
| Minimum, | 15.76, | 30.83, | 4.23, | 2.82, | 3.77, | 10.73, |
| Maximum | 66.11 | 558.92 | 21.96 | 25.20 | 30.64 | 61.55 |
| Intracolonic faecal AM9 concentrations (ng/g) | | | | | | |
| N | 8 | 8 | 8 | 8 | 7 | 7 |
| Arithmetic mean | 2254 | 5646 | 3637 | 5479 | 5862 | 6351 |
| SD | 1121.2 | 4390.0 | 1215.2 | 3550.3 | 6721.1 | 4584.7 |
| Geometric mean | 2002 | 4279 | 3464 | 4292 | 3820 | 5296 |
| CV % | 49.7 | 77.8 | 33.4 | 64.8 | 114.7 | 72.2 |
| Median | 2116 | 3226 | 3352 | 6123 | 4023 | 5516 |
| Minimum, | 1032, | 1878, | 2158, | 912, | 953, | 2438, |
| Maximum | 3916 | 11714 | 5396 | 12100 | 20598 | 15941 |

Pharmacokinetic Conclusions
   Systemic exposure to cyclosporin A was lower following treatment with CyCol® at doses up to 150 mg BID once daily for 7 days compared with a single IV infusion of Sandimmun® 2 mg/kg over 24 hours (2 mg/kg/day).
   Tissue and mucous concentrations of cyclosporin A were higher in the CyCol® 75 mg BID and 150 mg BID groups compared with the Sandimmun® IV groups suggesting that these doses should be efficacious. Tissue and mucous concentrations of AM1, AM4N and AM9 were generally higher following treatment with Sandimmun® IV compared with CyCol®.
   Intracolonic faecal concentrations of cyclosporin A were considerably higher in the CyCol® groups compared with the Sandimmun® IV groups indicating that CyCol® is predominantly excreted in faeces.

Discussion And Overall Conclusions
   Systemic exposure to cyclosporin was lower following treatment with CyCol® at doses up to 150 mg BID once daily for 7 days compared with a single IV infusion of Sandimmun® 2 mg/kg over 24 hours (2 mg/kg/day). This may result in a lower incidence of side effects related to cyclosporin following treatment with CyCol® compared with Sandimmun®.
   Tissue and mucous concentrations of cyclosporin were higher in the CyCol® 75 mg BID and 150 mg BID groups compared with the Sandimmun® IV groups suggesting that these doses should be efficacious. Tissue and mucous concentrations of AM1, AM4N and AM9 were generally higher following treatment with Sandimmun® IV compared with CyCol®.
   Intracolonic faecal concentrations of cyclosporin were considerably higher in the CyCol® groups compared with the Sandimmun® IV groups indicating that CyCol® is predominantly excreted in faeces.
   Administration of CyCol® at doses up to 150 mg BID was generally well tolerated; the majority of AEs were mild and no severe or serious AEs were reported. There was a higher incidence of gastrointestinal disorders at the highest dose of CyCol® but none led to discontinuation.

Comparative Example 10

In-Vitro Study Using Minibead Composition Comprising Cremophor

Preparation of Minibead Modified Release Compositions
   Minibead Formulations I and II and a Fast Release Formulation were prepared using an analogous process to that described above.
   Formulation I: "Medium" coating level (10% weight gain Opadry subcoat; 11% weight gain Surelease™/Pectin overcoat)

|  | Component | % |
|---|---|---|
| Core | Cyclosporin A | 8.8 |
|  | Miglyol 810 N | 3.8 |
|  | Transcutol HP | 13.5 |
|  | Kolliphor ™ EL | 7.6 |
|  | SDS | 3.3 |
|  | Sorbitol | 4.7 |

| | Component | % |
|---|---|---|
| Sub-Coat | Gelatin | 40.3 |
| | Opadry | 8.2 |
| Overcoat | Surelease ™ (solid contents) | 9.7 |
| | Pectin | 0.2 |

Formulation II: "High" coating level (10% weight gain Opadry subcoat; 17% weight-gain Surelease™/Pectin overcoat)

| | Component | % |
|---|---|---|
| Core | Cyclosporin A | 8.4 |
| | Miglyol 810 N | 3.6 |
| | Transcutol HP | 12.8 |
| | Kolliphor ™ EL | 7.2 |
| | SDS | 3.1 |
| | Sorbitol | 4.4 |
| | Gelatin | 38.3 |
| Sub-coat | Opadry | 7.8 |
| Overcoat | Surelease ™ (solid contents) | 14.2 |
| | Pectin | 0.3 |

Fast Release Formulation (No Surelease™ Pectin Overcoat)

| | Component | % |
|---|---|---|
| Core | Cyclosporin A | 9.8 |
| | Miglyol 810 N | 4.2 |
| | Transcutol HP | 14.9 |
| | Kolliphor ™ EL | 8.4 |
| | SDS | 3.6 |

| | Component | % |
|---|---|---|
| | Sorbitol | 5.2 |
| | Gelatin | 44.8 |
| Sub-coat | Opadry | 9.1 |

Human Pharmacokinetic Study

Study Objectives:

Objective 1: To compare the rate and extent of absorption of cyclosporin-A following administration of the Fast Release Formulation (fast-release capsule; Test 1), Formulation I (medium-release capsule; Test 2), and Formulation II (slow-release capsule; Test 3) with Neoral™ immediate-release capsule (reference), administered as a single 75 mg dose under fasting conditions.

Objective 2: To evaluate the amount of unchanged cyclosporin-A excreted in the faeces after administration of the Comparative Formulation (fast-release capsule; test 1), Formulation I (medium-release capsule; Test 2), Formulation II (slow-release capsule; Test 3) versus Neoral, administered as a single 75 mg dose under fasting conditions.

Study Design:

A single centre, randomised, single-dose, open-label, 4-period, 4-sequence crossover comparative BA study, performed under fasting conditions.

Subjects:

Enrolled and randomised: 18 (12 females and 6 males)
Withdrew consent: 0
Withdrawal: 1 (was withdrawn) Completed all 4 periods: 16
Safety population: 18
Pharmacokinetic (PK) population: 18

Pharmacokinetic Analysis

The mean pharmacokinetic values obtained in the study are summarized in the Table 30.

TABLE 30

Summary of pharmacokinetic parameters for cyclosporin-A for each treatment

| | Mean ± SD (CV %) Whole Blood Cyclosporin-A | | | |
|---|---|---|---|---|
| | Cyclosporin-A (Test 1) Fast Release Formulation | Cyclosporin-A (Test 2) Formulation I | Cyclosporin-A (Test 3) Formulation II | Neoral |
| N | 17 | 17 | 18 | 17 |
| $AUC_{0-t}$ (ng · hr/mL) | 1212.52 ± 297.62 (24.55) | 609.89 ± 280.15 (45.93) | 408.49 ± 231.01 (56.55) | 1582.20 ± 358.09 (22.63) |
| $AUC_{0-inf}$ (ng · hr/mL) | 1257.83 ± 312.14 (24.82) | 672.07 ± 296.71 (44.15) | 474.37 ± 247.93 (52.27) | 1639.78 ± 371.52 (22.66) |
| $C_{max}$ (ng/mL) | 321.33 ± 87.61 (27.27) | 138.28 ± 63.54 (45.95) | 82.81 ± 48.01 (57.98) | 594.66 ± 117.01 (19.68) |
| Residual Area (%) | 3.55 ± 0.71 (20.12) | 10.72 ± 8.10 (75.50) | 15.38 ± 12.69 (82.52) | 3.52 ± 0.77 (21.87) |
| $T_{max}{}^a$ (hr) | 2.00 (1.25-3.00) | 5.00 (5.00-8.00) | 5.00 (5.00-10.0) | 1.25 (1.00-1.75) |
| $K_{el}$ (1/hr) | 0.1105 ± 0.0113 (10.25) | 0.0863 ± 0.0259 (30.01) | 0.0822 ± 0.0232 (28.20) | 0.1037 ± 0.0103 (9.97) |
| $T_{1/2\ el}$ (hr) | 6.33 ± 0.61 (9.70) | 8.72 ± 2.76 (31.66) | 9.49 ± 4.55 (47.96) | 6.75 ± 0.77 (11.43) |

$^a$Median (Min-Max)

In Table 30 the AUC and Cmax values are the mean value ± standard deviation (SD)

Figure 13:
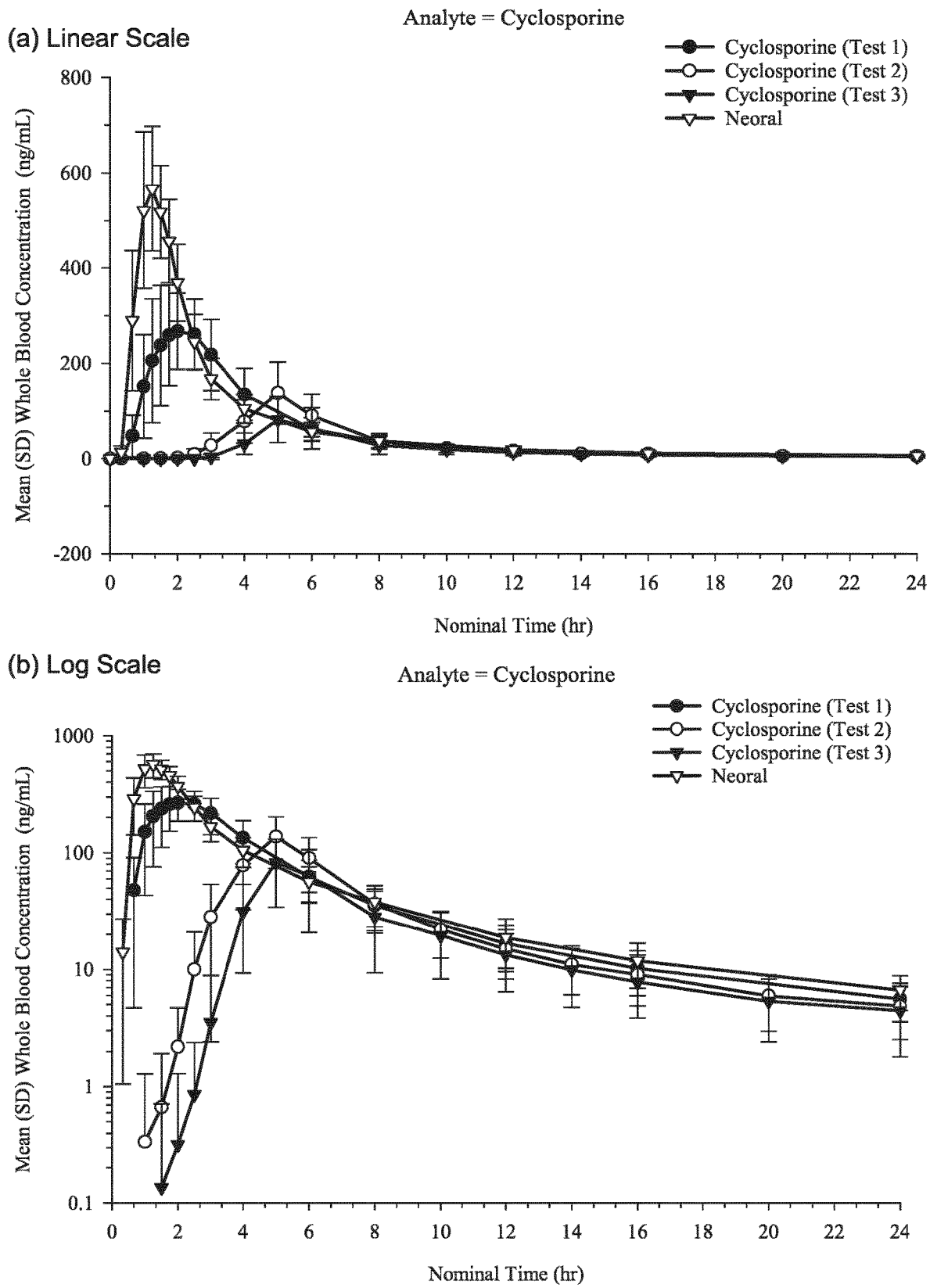
FIG. 13 shows the mean whole blood concentration of cyclosporin A obtained from the comparative clinical trial of Comparative Example 10 on linear and log scales.

The whole blood concentration of cyclosporin A for each of these composition is shown in FIG. 13.

A comparison of FIGS. 11 and 12 using the minibeads of the present invention containing Capmul Capmul GMO-50 (glyceryl monooleate/dioleate) as the surfactant with FIG. 13 (and the corresponding data tables) shows that the Capmul containing composition according to the invention provided lower $C_{max}$ and AUC values indicating lower systemic exposure to cyclosporin A.

Determination of Cyclosporin-A and its Metabolites, AM9 and AM4N, in Faecal Samples Faecal samples collected during the PK trial were analysed by RP-LC-MS/MS as described previously. The results are shown in Table 31.

TABLE 31

| | Mean CSA % | Mean AM4N % | Mean AM9 % | Total 1 AM4N + AM9 % | Total 2 CyA + AM4N + AM9 % | Total 1/Total 2% | Ratio CyA:AM4:AM9 |
|---|---|---|---|---|---|---|---|
| Fast Release | 73.8 | 12 | 14.2 | 26.2 | 100 | 26.20% | 2.82 |
| Formulation I | 86.9 | 5.5 | 7.6 | 13.1 | 100 | 13.10% | 6.63 |
| Formulation II | 91.5 | 3.4 | 5.1 | 8.5 | 100 | 8.50% | 10.76 |
| Neoral | 37.1 | 26.2 | 36.7 | 62.9 | 100 | 62.90% | 0.59 |

A comparison of the faecal data in Table 31 with the faecal data obtained with the Capmul containing compositions of Example 9 (Table 22) shows that the Capmul compositions of Example 9 resulted in much lower cyclosporin metabolism than the comparative compositions containing Cremophor. This is illustrated by the lower relative % of the (AM9+AM4N) metabolites in the collected faeces for the Capmul compositions in Table 22 compared to the Cremophor compositions in Table 31. This difference is clearly illustrated in FIG. 14 which shows the ratio of cyclosporin to (AM4N+AM9) measured in the faecal samples for each of the tested formulations.

The compositions of the invention comprising Capmul GMO-50 resulted in significantly less cyclosporin A metabolism compared to the compositions containing Cremophor. The compositions of the invention therefore provide higher local levels of cyclosporin in the colon as a result of the reduced systemic and non-systemic metabolism of the cyclosporin released from the composition. The compositions of the invention may enable a lower dose of cyclosporin to be administered whilst maintaining a therapeutic effect, thereby further increasing the therapeutic window.

Figure 14:
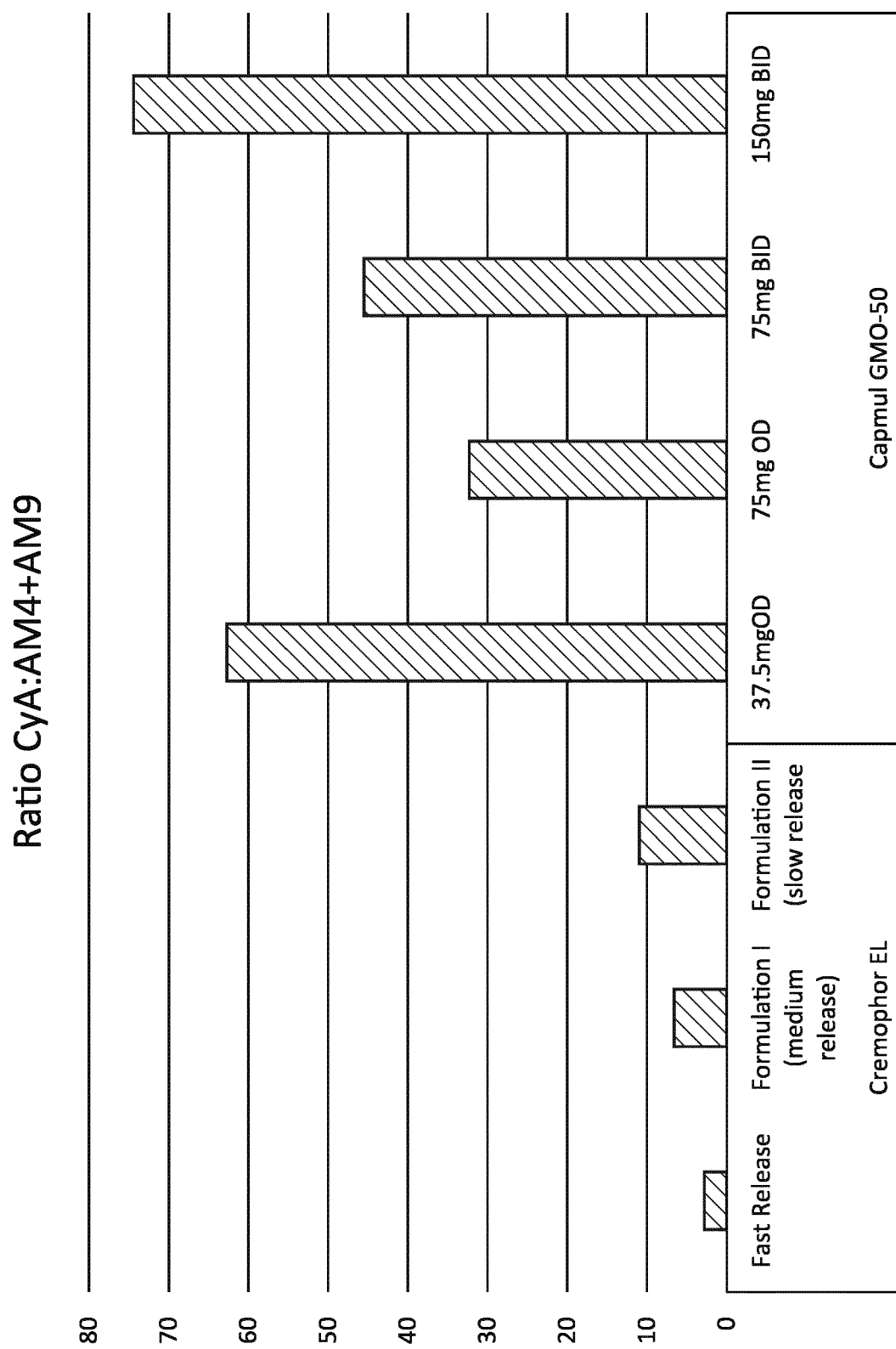
FIG. 14 shows the ratio of cyclosporin A to the concentration of the (AM4N+AM9) cyclosporin metabolites measured in the faecal samples for each of the tested formulations in Example 9 and Comparative Example 10.
Figure 15:
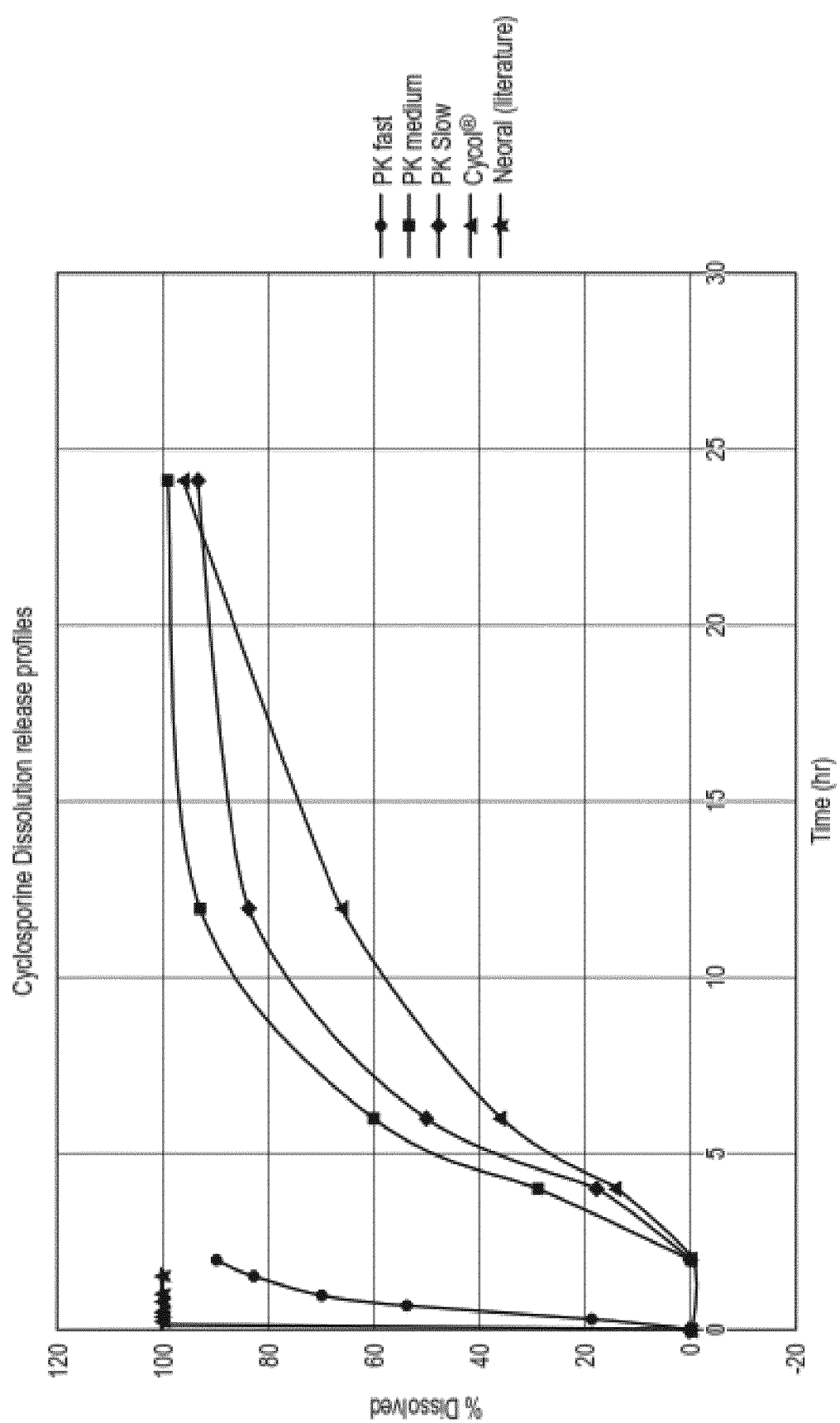
FIG. 15 shows the in-vitro release profiles of the compositions used in Example 9 and Comparative Example 10.
Figure 16A:
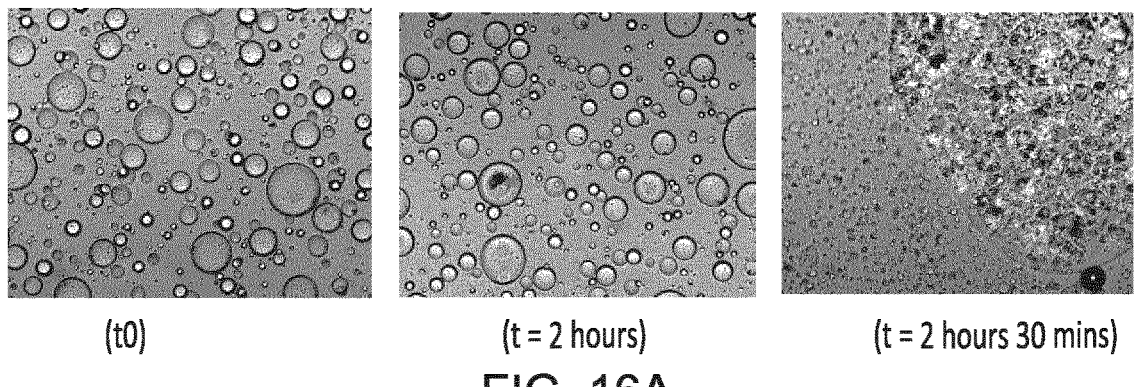
FIGS. 16 to 22 show photomicrographs of the emulsions described in Example 11 comprising surfactants in an aqueous phase at specified time points.
Figure 16B:
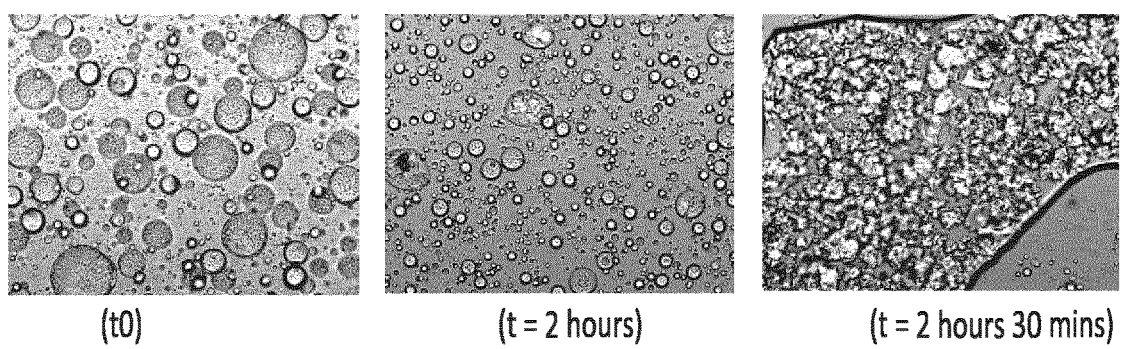
Figure 16C:
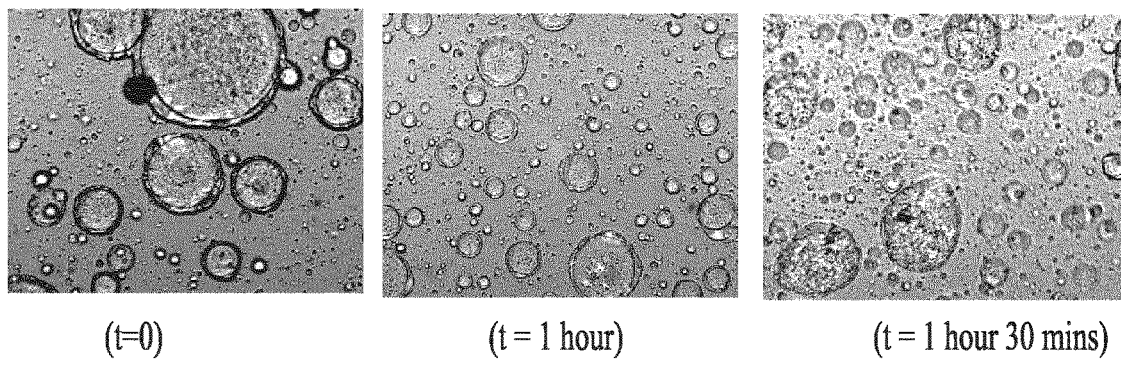
Figure 17A:
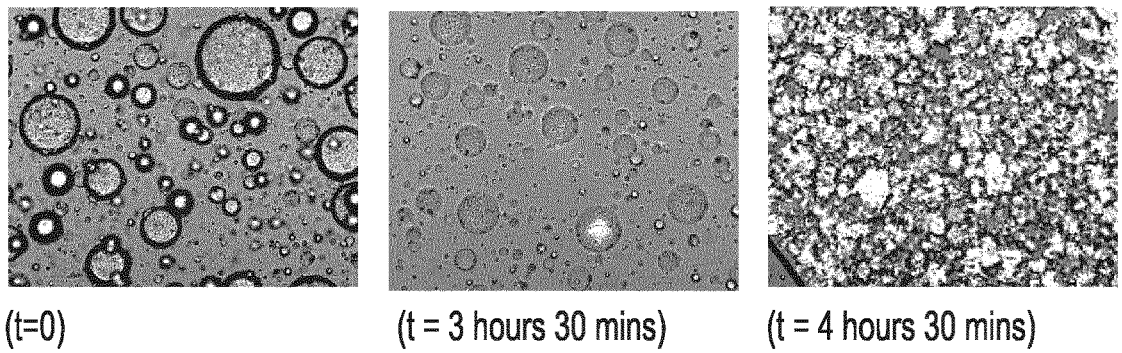
Figure 17B:
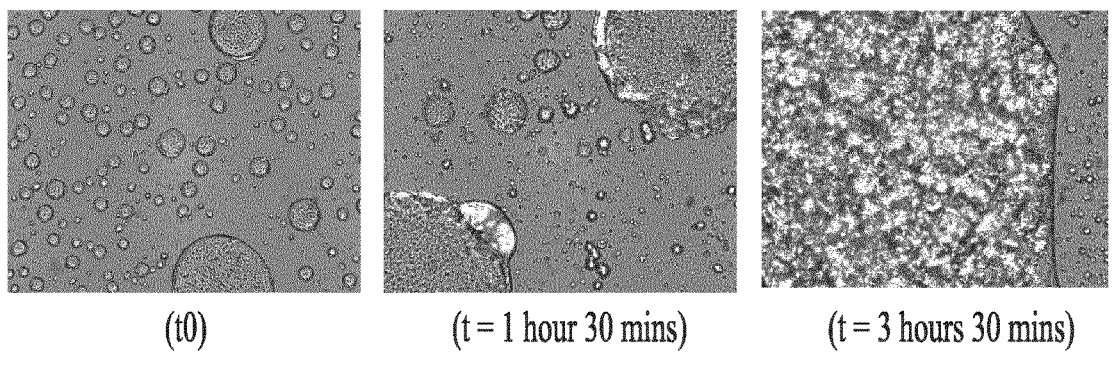
Figure 17C:
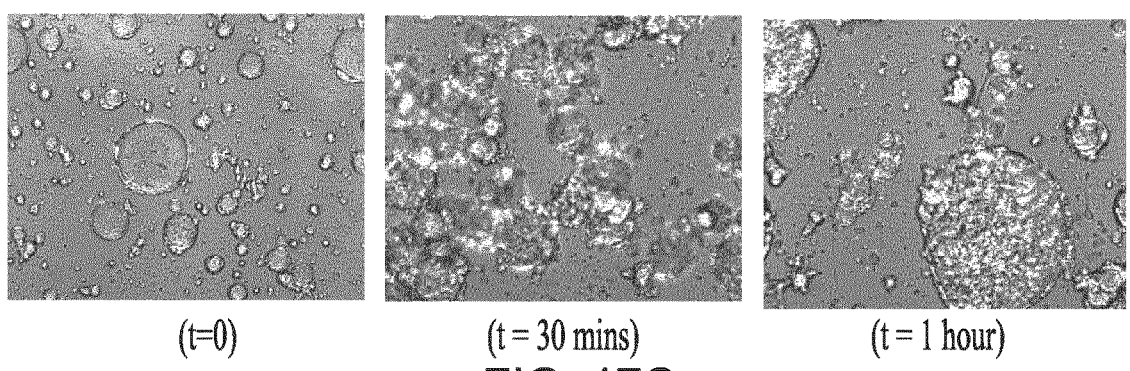
Figure 18A:
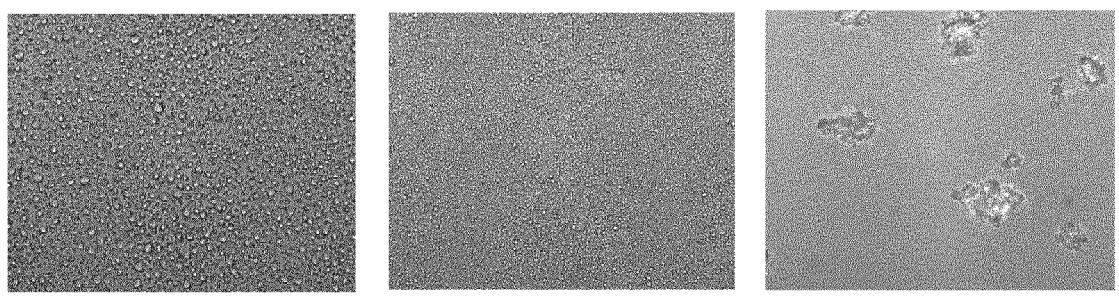
Figure 18B:
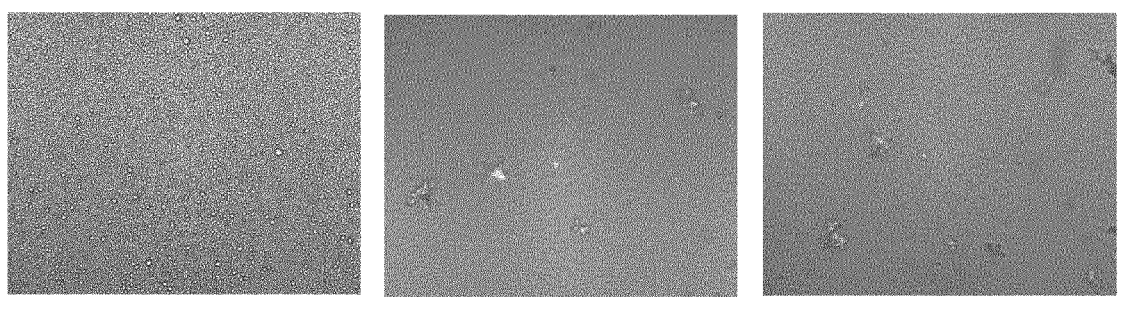
Figure 18C:
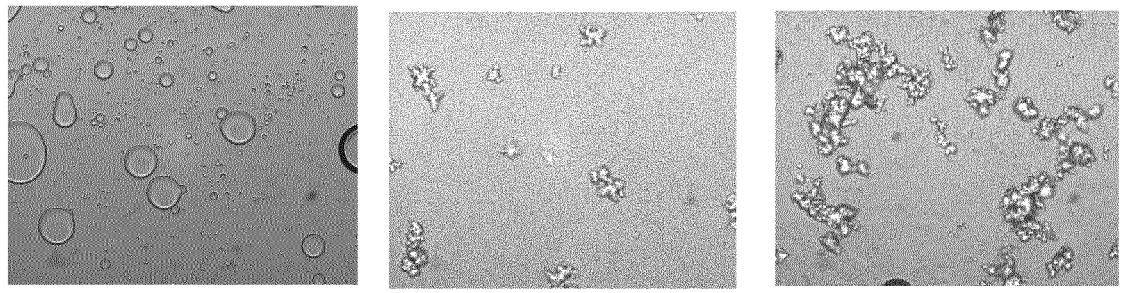
Figure 19A:
Figure 19B:
Figure 19C:
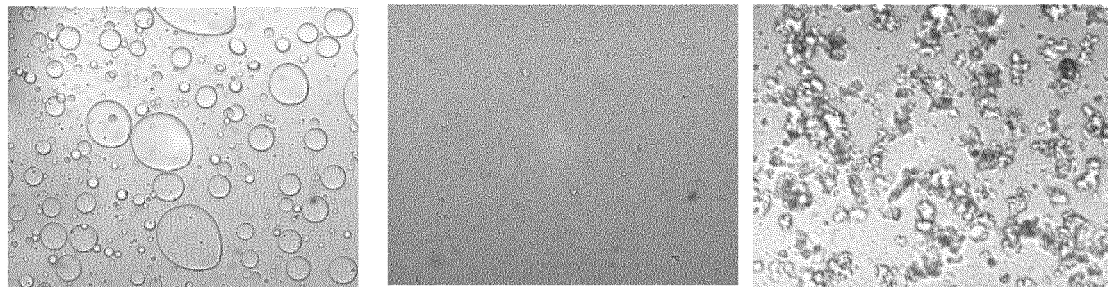
Figure 20A:
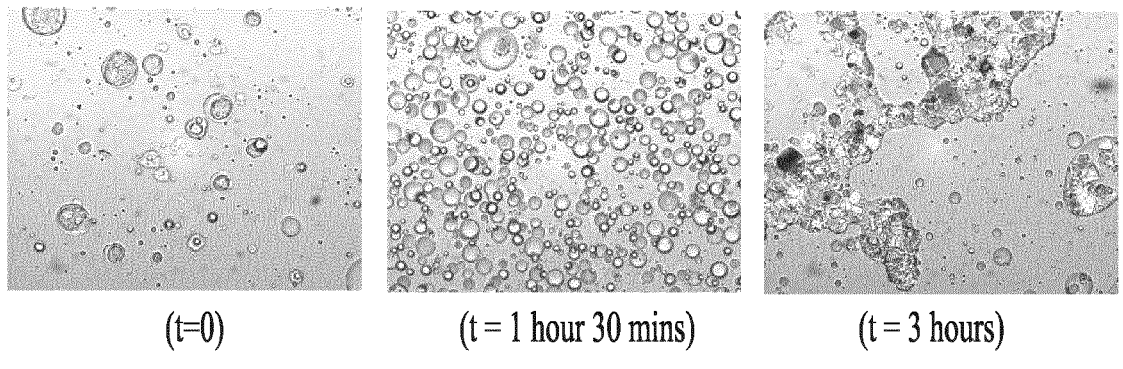
Figure 20B:
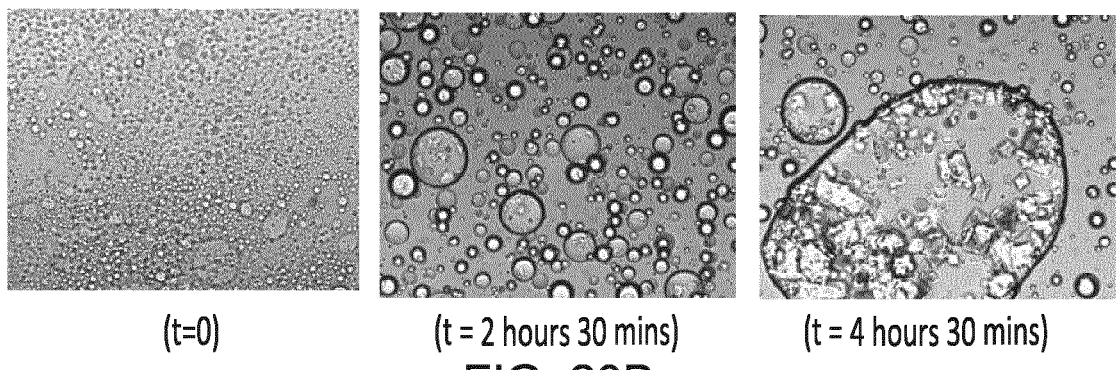
Figure 20C:
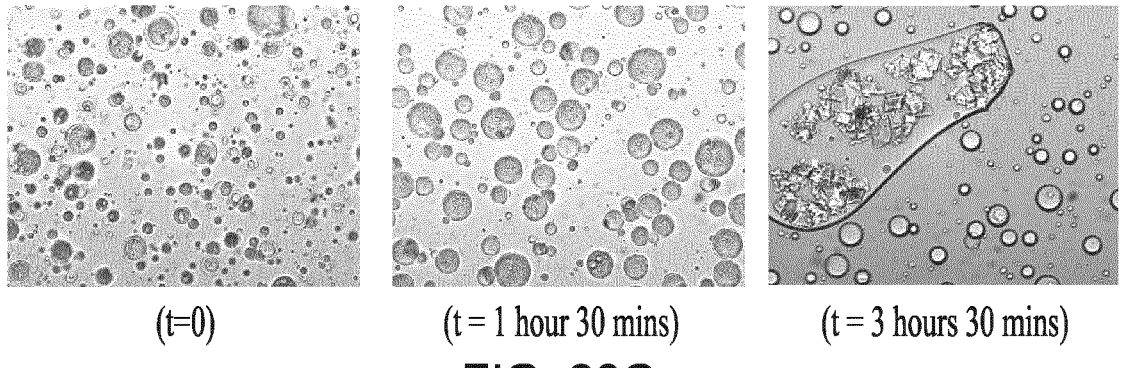
Figure 21A:
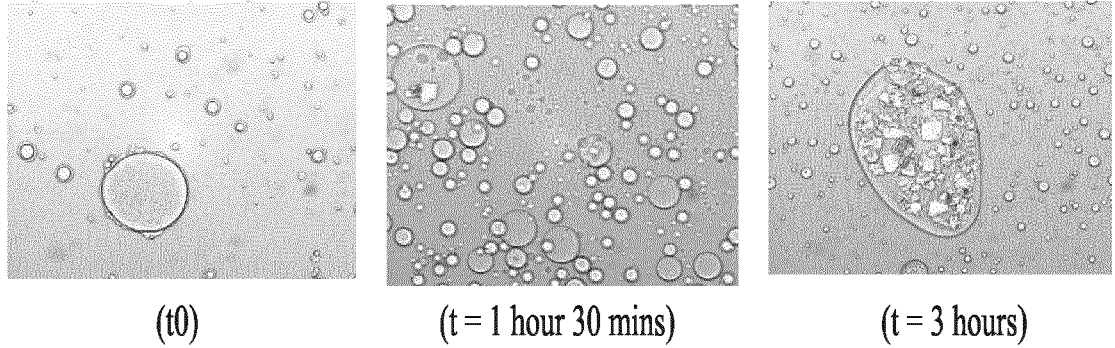
Figure 21B:
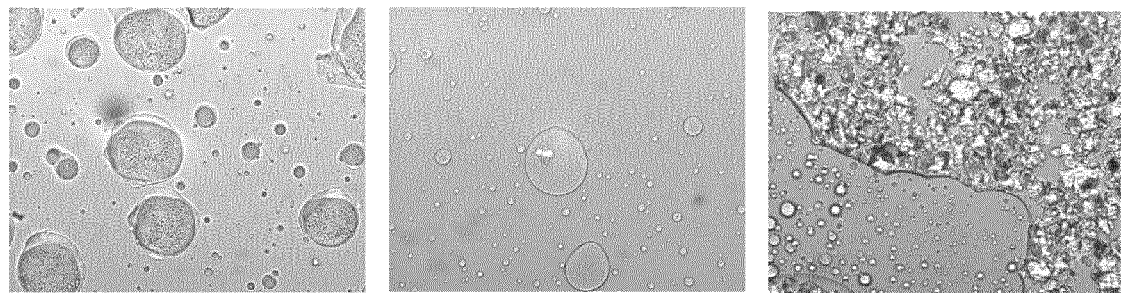
Figure 21C:
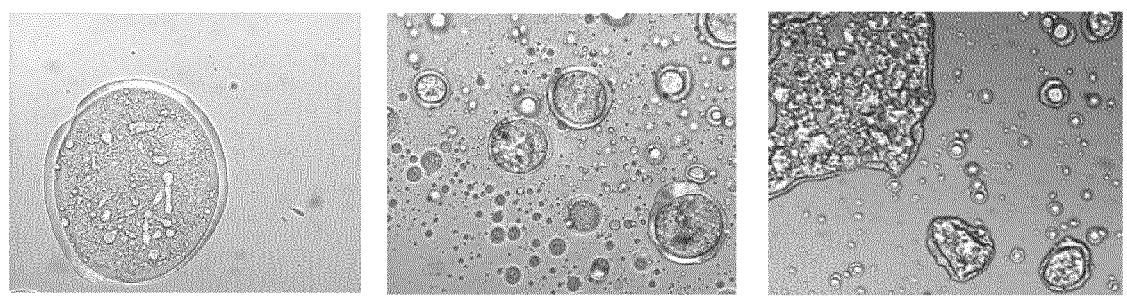
Figure 22A:
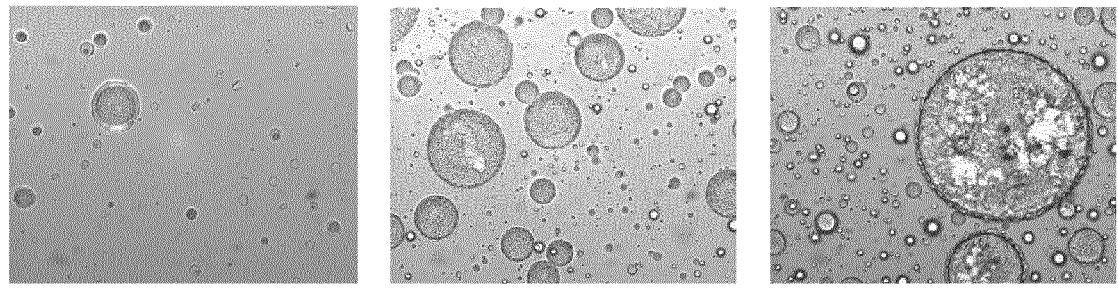
Figure 22B:
Figure 22C:
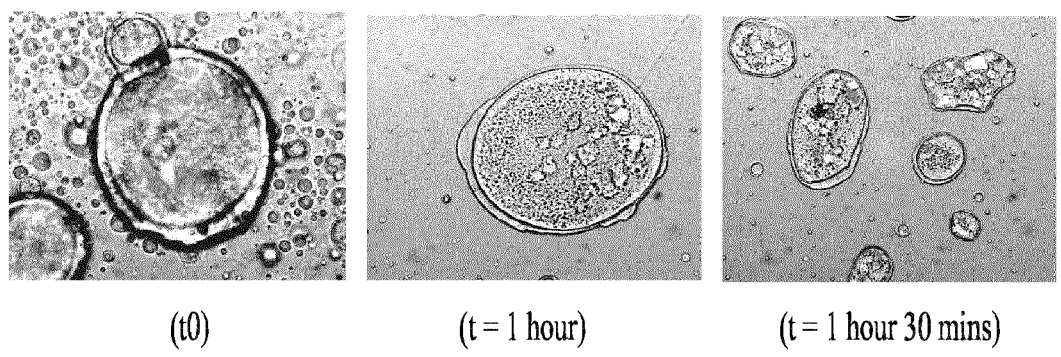

FIG. 15 compares the in-vitro dissolution profile of the Capmul formulation used in Example 9 with the cremophor compositions used in Comparative Example 10 using the two-stage dissolution test described herein. FIG. 15 shows that the release profiles for the Capmul composition, the Slow Release, and the Medium Release are all very similar in the 2 to 5 hour period. During this time the compositions are expected to release cyclosporin in the small intestine and would be prone to both systemic and enteric P450 metabolism of the cyclosporin. Despite the similarities in the in-vitro release profiles, FIG. 14 shows that the Capmul composition of the present invention significantly reduced the metabolism of cyclosporin A compared to the Fast, Medium and Slow compositions containing Cremophor as a surfactant. Additionally the Capmul composition exhibited a lower AUC and Cmax illustrating a lower systemic exposure to cyclosporin than the Cremophor compositions following oral administration (see Tables 24 and 30).

Example 11

Emulsion Stability and Bead Formation: Effect of Surfactant and Surfactant Concentration Compositions with differing aqueous phase surfactants were investigated. The different aqueous phase surfactants were compared to SDS. Three different families of surfactant were chosen to test: Sucrose Fatty Acid Esters, Sodium n-Alkyl Sulfates and Fatty Alcohol Ethoxylates (Brij series).

Emulsions were prepared by mixing an oil phase and an aqueous phase, as described in Example 1. The oil phase was consistent for all emulsions of this example. The emulsion aqueous phase mixed was one of three aqueous mixtures. The three aqueous phases differed in the amount of surfactant, 0.7%, 1.3% and 2.5%, and water. The oil and aqueous phase mixtures are shown in tables 32 to 34.

TABLE 32

| Aqueous Phase | | Oil Phase | |
|---|---|---|---|
| Component | % | Component | % |
| H$_2$O | 79.56% | Transcutol HP | 37.00% |
| Gelatin | 17.14% | Capmul GMO 50 | 26.00% |
| D-Sorbitol | 2.00% | CyA | 24.50% |
| Surfactant | 1.30% | Miglyol | 12.50% |

TABLE 33

| Aqueous Phase | | Oil Phase | |
|---|---|---|---|
| Component | % | Component | % |
| H$_2$O | 79.62% | Transcutol HP | 37.00% |
| Gelatin | 17.14% | Capmul GMO 50 | 26.00% |
| D-Sorbitol | 2.00% | CyA | 24.50% |
| Surfactant | 0.70% | Miglyol | 12.50% |

TABLE 34

| Aqueous Phase | | Oil Phase | |
|---|---|---|---|
| Component | % | Component | % |
| H$_2$O | 78.36% | Transcutol HP | 37.00% |
| Gelatin | 17.14% | Capmul GMO 50 | 26.00% |
| D-Sorbitol | 2.00% | CyA | 24.50% |
| Surfactant | 2.50% | Miglyol | 12.50% |

The emulsion was prepared by mixing the oil phase and aqueous phase in a oil:aqueous phase ratio of 1:5. The experiments were performed in triplicate, N=3. In order to replicate current manufacturing conditions as much as possible the following procedure was carried out:

- Identical size beakers were used to ensure minimal variation between experiments
- Identical submersible magnetic stirrers were placed in each beaker to keep the emulsions under constant magnetic stirring, and the same rpm stir rate used for each
- Hot plates were used to maintain a constant emulsion temperature of 65° C.
- Emulsions were kept covered with aluminium foil during the process Sampling of the emulsion was carried out at various time points using disposable pipettes to avoid cross contamination.

Emulsion Analysis

Samples were withdrawn from each emulsion at half hour time intervals starting at time zero (t0) using a disposable pipette. Drops of emulsion were placed on a glass slide, pre heated on a hot plate. The sample was covered with a cover slip and a small amount of pressure applied to form a thin film of emulsion. The samples were allowed to solidify to room temperature before being viewed at ×50 and ×100 objective lens under polarised light to check for the presence of crystals. Results were recorded as optical photomicrographs with three images taken of each emulsion at each time point. Images documenting crystal growth and size with respect to time within the sample emulsion as well as background oil droplet size were collected. Table 35, shown below, gives the time point when crystallisation was observed.

Photomicrographs of the emulsions enabled the investigation of the droplet size as well as crystal formation. Smaller, more uniform droplet size was preferred. These preferred droplet characteristics were observed in some of the tested emulsions, particularly the emulsions containing Sodium n-Octyl Sulfate and Sodium n-Octadecyl Sulfate.

The photomicrographs of an emulsion for each surfactant at specified time points are shown in FIGS. 16 to 22.

Bead Formation

Bead formation was attempted, to examine how bead formation was affected by the different surfactants. Samples (1 ml) were withdrawn from each emulsion using a Gilson pipette when the emulsion stability experiment had been terminated, before the emulsions were discarded. Beads were formed by dropping the emulsion at a steady rate into a cooling bath of medium chain triglyceride oil which was kept refrigerated. Beads were retrieved using a sieve and placed on tissue paper within a container, gently patted with tissue paper to remove excess surface oil and left to dry overnight on the worktop at room temperature. Bead formation was deemed to have occurred if a spherical or nearly spherical bead was formed by dropping an emulsion into a cooling oil or expelling the emulsion when under the surface of the cooling oil. Formation of oval or elongated beads was not deemed as bead formation. It has to be acknowledged that due to the manual nature of the method of producing beads employed here compared with bead production using the Spherex equipment at a manufacturing scale, formulations which may not form beads at this lab scale study may in fact form beads when processed using the Spherex equipment.

TABLE 35

| Surfactant | Concentration in aqueous phase % w/w | Onset Crystallisation | Beads Formation | Emulsion images in FIG. |
|---|---|---|---|---|
| sodium dodecyl sulphate | 1.4 | (t = 2 hours) | Y | |
| Sucrose Laurate | 0.7 | (t = 2 hours) | Y | 16A |
|  | 1.3 | (t = 1 hour 30 mins) | N | 16B |
|  | 2.5 | (t = 1 hour) | N | 16C |
| Sucrose Palmitate | 0.7 | (t = 2 hours 30 mins) | Y | 17A |
|  | 1.3 | (t = 1 hour 30 mins) | Y | 17B |
|  | 2.5 | (t = 30 mins) | N | 17C |
| Sodium n-Octyl Sulphate | 0.7 | (t = 2 hours 30 mins) | Y | 18A |
|  | 1.3 | (t = 4 hours) | Y | 18B |
|  | 2.5 | (t = 1 hour 30 mins) | Y | 18C |
| Sodium n-Octadecyl Sulfate | 0.7 | (t = 3 hours) | Y | 19A |
|  | 1.3 | (t = 2 hours) | Y | 19B |
|  | 2.5 | (t = 2 hours) | Y | 19C |
| Brij L4 (Polyethylene Glycol Dodecyl Ether) | 0.7 | (t = 1 hour 30 mins) | Y | 20A |
|  | 1.3 | (t = 2 hours 30 mins) | N | 20B |
|  | 2.5 | (t = 1 hour 30 mins) | N | 20C |
| Brij C10 (PEG Hexadecyl Ether) | 0.7 | (t = 1 hour 30 mins) | N | 21A |
|  | 1.3 | (t = 1 hour) | N | 21B |
|  | 2.5 | (t = 1 hour) | N | 21C |
| Brij S10 (PEG Octadecyl Ether) | 0.7 | (t = 1 hour) | Y | 22A |
|  | 1.3 | (t = 1 hour) | N | 22B |
|  | 2.5 | (t = 1 hour) | N | 22C |

The anionic surfactants Sodium n-Octyl Sulfate and Sodium n-Octadecyl Sulfate in particular provided stability that was comparable to that of sodium dodecyl sulfate. Sodium n-Octadecyl Sulfate provided the best stability for each concentration. Non-ionic surfactants provided emulsion stability but with more rapid onset of crystallization compared to SDS, except for Brij L4 at 1.3% aqueous concentration which gave an increase in emulsion stability.

The invention claimed is:

1. An oral composition comprising cyclosporin, a hydrogel forming polymer matrix, a surfactant and an oil phase being dispersed in the hydrogel forming polymer matrix, wherein the oil phase comprises an oil and the surfactant, wherein the surfactant is present in an amount greater than the oil and in an amount of more than 6 wt % of the dry weight of the composition, wherein the surfactant is a combination of glyceryl monooleate and glyceryl dioleate; and wherein the hydrogel-forming polymer is in an amount of at least 25% by weight based upon the dry weight of the composition.

2. The composition of claim 1 wherein the oil phase comprises a solution of the cyclosporin.

3. The composition of claim 1, wherein the oil comprises a liquid lipid, wherein the liquid lipid comprises a medium chain fatty acid triglyceride or a combination thereof, or the liquid lipid comprises a caprylic/capric triglyceride composition.

4. The composition of claim 1, wherein the composition further comprises a solvent, wherein the solvent is miscible with the oil phase and water.

5. The composition of claim 1, wherein the composition further comprises a high HLB surfactant having an HLB value of at least 10.

6. The composition of claim 4, wherein the high HLB surfactant is selected from a fatty acid salt or a bile salt.

7. The composition of claim 1, wherein the hydrogel forming polymer or hydrogel forming polymer matrix comprises a reversible hydrocolloid.

8. The composition of claim 1, wherein the hydrogel forming polymer or hydrogel forming polymer matrix comprises a hydrocolloid selected from carrageenan, gelatin, agar and pectin, or a combination thereof.

9. The composition of claim 1, wherein the composition is a solid composition and is formed by mixing an aqueous phase premix with an oil phase premix to form a mixture, the aqueous phase premix comprising the hydrogel forming polymer matrix and the oil phase premix comprising the oil phase in which the cyclosporin is dissolved and the surfactant.

10. The composition of claim 9, wherein the composition further comprises a surfactant having an HLB value of at least 10 which is present in the aqueous phase premix.

11. The composition of claim 1, wherein the composition is a solid composition and further comprises at least one coating.

12. The composition of claim 11 wherein the at least one coating is adapted to release the cyclosporin in at least the colon.

13. The composition of claim 12 wherein the coating comprises ethylcellulose.

14. The composition of claim 11, wherein the at least one coating is present in an amount corresponding to a weight gain due to the coating of from 2% to 40%.

15. The composition of claim 11, wherein the composition comprises two coatings, a first coating and a second coating.

16. The composition of claim 15, wherein the first coating comprises a water-soluble cellulose ether and the second coating comprises ethylcellulose.

17. The composition of claim 16, wherein the water-soluble cellulose ether is hydroxypropylmethyl cellulose.

18. The composition of claim 1, wherein the composition is a solid composition that is in the form of a minibead having a size of from 0.5 mm to 5 mm.

19. A multiple mini bead formulation, comprising a unit dosage form comprising a multiplicity of mini beads of claim 18.

20. The composition of claim 11, wherein the composition provides a mean whole blood cyclosporin A $AUC_{0\text{-}inf}$ of from about 140 to about 420 ng·hr/ml.

21. The composition of claim 11, wherein the composition provides a $C_{max}$ of cyclosporin A of from about 15 to about 60 ng/ml.

22. The composition of claim 11, wherein the time taken to reach maximum whole blood concentration of cyclosporin A following oral administration of a single dose of the composition ($T_{max}$) is between about 3 hours to about 10 hours.

23. The composition of claim 11, wherein cyclosporin A absolute bioavailability following oral administration of the composition is less than 15%.

24. The composition of claim 11, wherein the composition releases less than 15% of cyclosporin A after 2 hours; releases 10% to 40% of cyclosporin A at 4 hours; and releases from about 30% to 70% of cyclosporin A between 4 hours and 12 hours, when measured in a two stage dissolution test using a USP Apparatus II with a paddle speed of 75 rpm and a dissolution medium temperature of 37° C.; wherein for the first 2 hours of the dissolution test the dissolution medium is 750 ml of 0.1 N HCl, and at 2 hours 250 ml of 0.2M tribasic sodium phosphate containing 2% SDS is added to the dissolution medium and the pH is adjusted to pH 6.8.

25. The composition of claim 11, wherein the composition provides a concentration of cyclosporin A in colonic tissue of at least 250 ng/g following oral administration of the composition to a human.

26. The composition of claim 25, wherein the total daily dose of cyclosporin A administered to the human is in the range of from 1 mg to 500 mg.

27. The composition of claim 1, further comprising a P450 inhibitor or a PgP inhibitor, or a combination thereof.

28. A pharmaceutical formulation comprising the composition of claim 1.

29. The composition of claim 1, wherein the surfactant is present in an amount of up to 20 wt % of the dry weight of the composition.

30. The composition of claim 1, wherein the hydrogel-forming polymer is present in an amount of up to 70% by weight based upon the dry weight of the composition.

31. The composition of claim 1, wherein the surfactant is present in an amount of more than 12 wt % of the oil phase.

32. The composition of claim 9, wherein the surfactant is present in an amount of more than 12% of the oil phase.

33. The composition of claim 18, wherein the surfactant is present in an amount of more than 12% of the oil phase.

* * * * *